US007371381B2

(12) United States Patent
Aaron et al.

(10) Patent No.: US 7,371,381 B2
(45) Date of Patent: May 13, 2008

(54) ANTI-GALANIN ANTIBODIES AND USES THEREOF

(75) Inventors: Wade Aaron, Millbrae, CA (US); Richard J. Austin, San Francisco, CA (US); Cynthia L. Hart, San Francisco, CA (US); Timothy C. Hoey, San Mateo, CA (US); Paul D. Kassner, San Mateo, CA (US); Derek E. Piper, Hayward, CA (US); Anthony J. Slavin, Redwood City, CA (US)

(73) Assignee: Amgen Inc., South San Francisco, CA (US)

( * ) Notice: Subject to any disclaimer, the term of this patent is extended or adjusted under 35 U.S.C. 154(b) by 213 days.

(21) Appl. No.: 11/009,443

(22) Filed: Dec. 10, 2004

(65) Prior Publication Data

US 2005/0152896 A1    Jul. 14, 2005

Related U.S. Application Data

(60) Provisional application No. 60/529,463, filed on Dec. 12, 2003.

(51) Int. Cl.
*C07K 16/28* (2006.01)
*A61K 39/395* (2006.01)

(52) U.S. Cl. ............... 424/143.1; 530/388.22
(58) Field of Classification Search ............. 424/143.1; 530/388.22
See application file for complete search history.

(56) References Cited

U.S. PATENT DOCUMENTS

| | | | |
|---|---|---|---|
| 4,474,893 A | 10/1984 | Reading | |
| 4,631,211 A | 12/1986 | Houghten | |
| 4,676,980 A | 6/1987 | Segal et al. | |
| 4,714,681 A | 12/1987 | Reading | |
| 4,925,648 A | 5/1990 | Hansen et al. | |
| 5,112,946 A | 5/1992 | Maione | |
| 5,122,464 A | 6/1992 | Wilson et al. | |
| 5,223,409 A | 6/1993 | Ladner et al. | |
| 5,336,603 A | 8/1994 | Capon et al. | |
| 5,349,053 A | 9/1994 | Landolfi | |
| 5,359,046 A | 10/1994 | Capon et al. | |
| 5,436,146 A | 7/1995 | Shenk et al. | |
| 5,441,050 A | 8/1995 | Thurston et al. | |
| 5,447,851 A | 9/1995 | Beutler et al. | |
| 5,573,920 A | 11/1996 | Randle | |
| 5,585,089 A | 12/1996 | Queen et al. | |
| 5,601,819 A | 2/1997 | Wong et al. | |
| 5,622,929 A | 4/1997 | Willner et al. | |
| 5,731,168 A | 3/1998 | Carter et al. | |
| 5,807,706 A | 9/1998 | Carter et al. | |
| 5,807,715 A | 9/1998 | Morrison et al. | |
| 5,821,333 A | 10/1998 | Carter et al. | |
| 5,855,886 A | 1/1999 | Randle | |
| 6,005,079 A | 12/1999 | Casterman et al. | |
| 6,019,968 A | 2/2000 | Platz et al. | |
| 6,130,231 A | 10/2000 | Wityak et al. | |
| 6,277,375 B1 | 8/2001 | Ward | |
| 6,331,415 B1 | 12/2001 | Cabilly et al. | |
| 6,333,187 B1 | 12/2001 | Beekwilder et al. | |
| 6,458,933 B1 | 10/2002 | Hansen | |
| 2003/0092042 A1* | 5/2003 | Mu et al. .................. | 435/6 |

FOREIGN PATENT DOCUMENTS

| | | |
|---|---|---|
| EP | 0 367 166 A1 | 5/1990 |
| EP | 0 394 827 A1 | 10/1990 |
| EP | 0 413 622 A1 | 2/1991 |
| EP | 0 307 434 B1 | 9/1993 |
| WO | WO 91/00360 | 1/1991 |
| WO | WO 91/06570 | 5/1991 |
| WO | WO 92/05793 | 4/1992 |
| WO | WO 92/08802 | 5/1992 |
| WO | WO 93/15199 | 8/1993 |
| WO | WO 93/15200 | 8/1993 |
| WO | WO 93/17715 | 9/1993 |
| WO | WO 96/04388 | 2/1996 |
| WO | WO 96/20698 | 7/1996 |
| WO | WO 97/34631 | 9/1997 |
| WO | WO 98/23289 | 6/1998 |
| WO | WO 98/50433 | 11/1998 |
| WO | WO 99/15154 | 4/1999 |
| WO | WO 99/66903 | 12/1999 |
| WO | WO 01/77137 | 10/2001 |
| WO | WO 02/070007 | 9/2002 |
| WO | WO 03/018770 | 3/2003 |

OTHER PUBLICATIONS

ATCC search output for search of murine antibodies 5B4, 1G12, 2F8, 1D7, 4B3, 2H9, 1A1, 2E11, 1D7D1 and 5B4C1 (pp. 19).*
Fundamental Immunology 242 (William E. Paul, M.D. ed., 3d ed. 1993).*
Lundkvist et al. Neuroscience Letters 200:121-124 (1995).*
Floren et al. Neuropeptides 34:331-337 (2000).*
Rudikoff et al (Proc Natl Acad Sci USA 1982 vol. 79 p. 1979-1983).*
Ahmedin, Jemal, et al., "Recent Trends in Lung Cancer Mortality in the United States," *J. Natl. Cancer Inst.*, vol. 93, No. 4, pp. 277-283, Feb. 21, 2001.

(Continued)

*Primary Examiner*—Larry R. Helms
*Assistant Examiner*—Lynn Bristol
(74) *Attorney, Agent, or Firm*—Jones Day

(57) ABSTRACT

The present invention provides antibodies that immunospecifically bind to a galanin peptide and compositions comprising said antibodies. The present invention also provides methods for preventing, treating, managing, and/or ameliorating hyperproliferative disorders or a symptom thereof comprising administering to a subject in need thereof one or more antibodies that immunospecifically bind to a galanin peptide. The invention also encompasses methods and compositions for diagnosing, monitoring, and prognosing hyperproliferative disorders. The present invention further relates to articles of manufacture and kits comprising antibodies that immunospecifically bind to a galanin peptide.

25 Claims, 39 Drawing Sheets

OTHER PUBLICATIONS

Figure 36B:
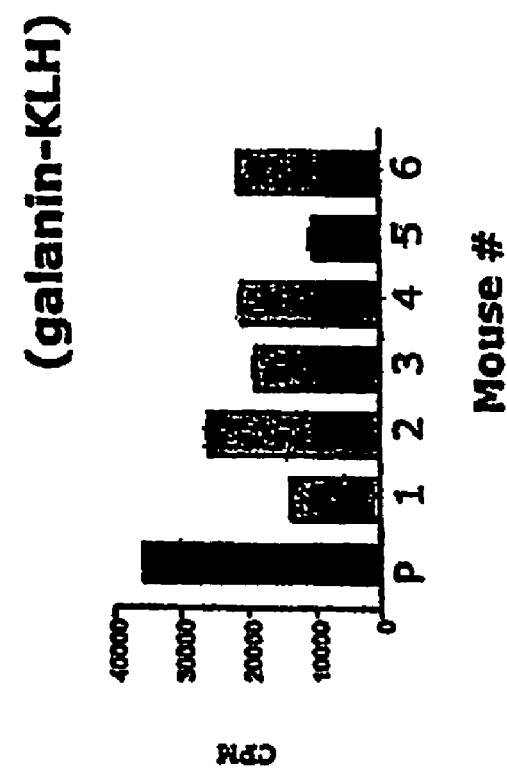

Al-Lazikani, Bissan, et al., "Standard Conformations for the Canonical Structures of Immunoglobulins," *J. Mol. Biol.*, vol. 273, pp. 927-948, (1997).

Altschul, Stephen F., et al. "Basic Local Alignment Search Tool," *J. Mol.Biol.*, vol. 215, pp. 403-410, (1990).

Ashkenazi, Avi, et al., "Protection Against Endotoxic Shock by a Tumor Necrosis Factor Receptor Immunoadhesin," *Proc. Natl. Acad. Sci. USA*, vol. 88, pp. 10535-10539, Dec. 1991.

Bauer, F.E., et al., "Distribution and Molecular Heterogeneity of Galanin in Human, Pig, Guinea Pig, and Rat Gastrointestinal Tracts," *Gastroenterology*, vol. 91, pp. 877-883 (1986).

Berger, Mitchell, et al., "Therapeutic Applications of Monoclonal Antibodies," *Am. J. Med. Sci.*, vol. 324, No. 1, pp. 14-30, Jul. 2002.

Bersani, Maurizio, et al., "Human Galanin: Primary Structure and Identification of Two Molecular Forms," *FEBS Letters*, vol. 283, No. 2, pp. 189-194, Jun. 1991.

Boesen, Jan J.B., et al., "Circumvention of Chemotherapuy-induced Myelosuppression by Transfer of the *mdr1* Gene," *Biotherapy*, vol. 6, pp. 291-302, 1994.

Boulianne, Gabrielle L., et al., "Production of Functional Chimaeric Mouse/Human Antibody," *Nature*, vol. 312, pp. 643-646, Dec. 13, 1984.

Cao, Yihai, et all, "Kringle Domains of Human Angiostatin: Characterization of the Anti-Proliferative Activity on Endothelial Cells," *J. Biol. Chem.*, vol. 271, No. 46, pp. 29461-29467, 1996.

Chothia, Cyrus, and Lesk, Arthur M., "Canonical Structures for the Hypervariable Regions of Immunoglobulins," *J. Mol. Biol.*, vol. 196, pp. 901-917, (1987).

Chothia, Cyrus, et al., "Conformations of Immunoglobulin Hypervariable Regions," *Nature*, vol. 342, pp. 877-883, Dec. 1989.

Chothia, Cyrus, et al., "Domain Association in Immunoglobulin Molecules: The Packing of Variable Domains," *J. Mol. Biol.*, vol. 186, pp. 651-663 (1985).

Crowley, Craig W., et al., "Prevention of Metastasis by Inhibition of the Urokinase Receptor," *Proc. Natl. Acad. Sci. USA*, vol. 90, pp. 5021-5025, Jun. 1993.

Cunningham, Brian C., and Wells, James A., "High-Resolution Epitope Mapping of hGH-Receptor Interactions by Alanine-Scanning Mutagenesis," *Science*, vol. 244, pp. 1081-1085, Jun. 2, 1989.

del Mar Lorenzo, Maria and Blasco, Rafael, "PCR-Based Method for the Introduction of Mutations in Genes Cloned and Expressed in Vaccinia Virus," *BioTechniques*, vol. 24, No. 2, pp. 308-313, (1998).

DeNardo, Gerald L., et al., "Comparison of 1,4,7,10-Tetraazacyclododecane-$N,N',N'',N'''$-tetraacetic acid (DOTA)-Peptide-ChL6, a Novel Immunoconjugate with Catabolizable Linker, to 2-Iminothiolane-2-[*p*-(Bromoacetamido)benzyl]-DOTA-ChL6 in Breast Cancer Xenografts[1]," *Clin. Cancer Res.*, vol. 4, pp. 2483-2490, Oct. 1998.

Depczynski, B., et al., "Distribution and Characterization of the Cell Types Expressing GALR2 mRNA in Brain and Pituitary Gland," *Annals of the New York Academy of Sciences*, vol. 863, pp. 120-128, (1998).

Dillman, Robert O., "Monoclonal Antibodies in the Treatment of Malignancy: Basic Concepts and Recent Developments," *Cancer Investigation*, vol. 19, No. 8, pp. 833-841, (2001).

Fodde, Riccardo and Smits, Ron, "Disease Model: Familial Adenomatous Polyposis," *Trends in Molecular Medicine*, vol. 7, No. 8, pp. 369-373, Aug. 2001.

Gentz, Reiner, et al., "Bioassay for Trans-activation Using Purified Human Immunodeficiency Virus *tat*-encoded Protein: Trans-activation Requires mRNA Synthesis," *Proc. Natl. Acad. Sci. USA*, vol. 86, pp. 821-824, Feb. 1989.

Goldspiel, Barry R., et al., "Human Gene Therapy," *Clinical Pharmacy*, vol. 12, pp. 488-505, Jul. 1993.

Goodson, Robert J., et al., "High-Affinity Urokinase Receptor Antagonists Identified with Bacteriophage Peptide Display," *Proc. Natl. Acad. Sci. USA*, vol. 91, pp. 7129-7133, Jul. 1994.

Hanahan, Douglas and Weinberg, Robert A., "The Hallmarks of Cancer," *Cell*, vol. 100, pp. 57-70, Jan. 7, 2000.

Hosokawa, Yoshitaka, et al., "In vivo Analysis of Mammary and Non-Mammary Tumorigenesis in MMTV-cyclin D1 Transgenic Mice Deficient in p53," *Transgenic Research*, vol. 10, pp. 471-478, (2001).

Jaffers, Gregory J., et al., "Monoclonal Antibody Therapy: Anti-Idiotypic and Non-Anti-Idiotypic Antibodies to OKT3 Arising Despite Intense Immunosuppression," *Transplantation*, vol. 41, No. 5, pp. 572-578, (1986).

Jalkanen, Markku, "Cell Surface Proteoglycan of Mouse Mammary Epithelial Cells is Shed by Cleavage of its Matrix-binding Ectodomain from its Membrane-associated Domain," *J. Cell Biol.*, vol. 105, No. 6, Part 2, pp. 3087-3096, Dec. 1987.

Joliot, A., et al., "Antennapedia Homeobox Peptide Regulates Neural Morphogenesis," *Proc. Natl. Acad. Sci. USA*, vol. 88, pp. 1864-1868, Mar. 1991.

Jones, Peter T., et al., "Replacing the Complementarity-determining Regions in a Human Antibody with Those From a Mouse," *Nature*, vol. 321, pp. 522-525, May 29, 1986.

Kantarjian, Hagop M., et al., "Treatment of Philadelphia Chromosome-positive, Accelerated-phase Chronic Myelogenous Leukemia with Imatinib Mesylate," *Clinical Cancer Research*, vol. 8, pp. 2167-2176, Jul. 2002.

Kilpatrick, Katherine E., et al., "Rapid Development of Affinity Matured Monoclonal Antibodies Using RIMMS," *Hybridoma*, vol. 16, No. 4, pp. 381-389, 1997.

Kostelny, Sheri A., et al., "Formation of a Bispecific Antibody by the Use of Leucine Zippers," *J. Immunol.*, vol. 148, No. 5, pp. 1547-1553, Mar. 1, 1992.

Leung, Betty, et al., "Galanin in Human Pituitary Adenomas: Frequency and Clinical Significance," *Clinical Endocrinology*, vol. 56, pp. 397-403, 2002.

Li, Jing, et al., "Oncogenic Properties of *PPM1D* Located Within a Breast Cancer Amplification Epicenter at 17q23," *Nature Genetics*, vol. 31, pp. 133-134, Jun. 2002.

Loeffler, Jean-Philippe and Behr, Jean-Paul, "Gene Transfer into Primary and Established Mammalian Cell Lines with Lipopolyamine-Coated DNA," *Methods in Enzymology*, vol. 217, pp. 599-618, (1993).

Lonberg, Nils and Huszar, Dennis, "Human Antibodies from Transgenic Mice," *Intern. Rev. Immunol.*, vol. 13, pp. 65-93, (1995).

Margolies, Michael N., et al., "Diversity of Light Chain Variable Region Sequences Among Rabbit Antibodies Elicited by the Same Antigens," *Proc. Nat. Acad. Sci., USA*, vol.. 72, No. 6, pp. 2180-2184, Jun. 1975.

Marrero, Jorge A., et al., "Dextran Sulfate Sodium-Induced Murine Colitis Activates NF-KB and Increases Galanin-1 Receptor Expression," *Am. J. Physiol. Gastrointest. Liver Physiol.*, vol. 278, pp. G797-G804, (2000).

Miller, A. Dusty, et al., "Use of Retroviral Vectors for Gene Transfer and Expression," *Methods in Enzymology*, vol. 217, pp. 581-599 (1993).

Miller, Richard A., et al., "Monoclonal Antibody Therapeutic Trials in Seven Patients with T-Cell Lymphoma," *Blood*, vol. 62, No. 5, pp. 988-995 (Nov. 1983).

Min, Hye Yeong, et al., "Urokinase Receptor Antagonists Inhibit Angiogenesis and Primary Tumor Growth in Syngeneic Mice," *Cancer Research*, vol. 56, pp. 2428-2433, May 15, 1996.

Mohammad, Ramzi M., et al., "Bryostatin 1 Induced Differentiation and Potentiates the Antitumor Effect of Auristatin PE in a Human Pancreatic Tumor (PANC-1) Xenograft Model," *Anti-Cancer Drugs*, vol. 12, pp. 735-740, 2001.

Morrison, Sherie L., et al., "Chimeric Human Antibody Molecules: Mouse Antigen-Binding Domains with Human Constant Region Domains," *Proc. Natl. Acad. Sci., USA*, vol. 81, pp. 6851-6855, Nov. 1984.

Neuberger, M.S., et al., "A Hapten-specific Chimaeric IgE Antibody with Human Physiological Effector Function," *Nature*, vol. 314, pp. 268-270, Mar. 21, 1985.

Peterson, James J. and Meares, Claude F., "Enzymatic Cleavage of Peptide-Linked Radiolabels from Immunoconjugates," *Bioconjugate Chemistry*, vol. 10, No. 4, pp. 553-557, Jul./Aug. 1999.

Pollack, Jonathan R., et al., "Microarray Analysis Reveals a Major Direct Role of DNA Copy Number Alteration in the Transcriptional Program of Human Breast Tumors," *Proc. Natl. Acad. Sci. USA*, vol. 99, No. 20, pp. 12963-12968, Oct. 1, 2002.

Queen, Cary, et al., "A Humanized Antibody that Binds to the Interleukin 2 Receptor," *Proc. Natl. Acad. Sci., USA*, vol. 86, pp. 10029-10033, Dec. 1989.

Riechman, Lutz, et al., "Reshaping Human Antibodies for Therapy," *Nature*, vol. 332, pp. 323-327, Mar. 24, 1988.

Roguska, Michael A., et al., "A Comparison of Two Murine Monoclonal Antibodies Humanized by CDR-Grafting and Variable Domain Resurfacing," *Protein Engineering*, vol. 9, No. 10, pp. 895-904, 1996.

Schroff, Robert W., et al., "Human Anti-Murine Immunoglobulin Responses in Patients Receiving Monoclonal Antibody Therapy," *Cancer Research*, vol. 45, pp. 879-885, Feb. 1985.

Tramontano, Anna, et al., "Framework Residue 71 is a Major Determinant of the Position and Conformation of the Second Hypervariable Region in the $V_H$ Domains of Immunoglobulins," *J. Mol. Biol.*, vol. 215, pp. 175-182, (1990).

Traunecker, André, et al., "Soluble CD4 Molecules Neutralize Human Immunodeficiency Virus Type 1," *Nature*, vol. 331, pp. 84-86, Jan. 7, 1988.

Tutt, Alison, et al, "Trispecific F(ab')$_3$ Derivatives that Use Cooperative Signaling via the TCR/CD3 Complex and CD2 to Activate and Redirect Resting Cytotoxic T Cells," *J. Immunol.*, vol. 147, No. 1, pp. 60-69, Jul. 1, 1991.

van Heyningen, Veronica, "A Simple Method for Ranking the Affinities of Monoclonal Antibodies," *Methods in Enzymology*, vol. 121, pp. 472-481, (1986).

Verhoeyen, Martine, et al., "Reshaping Human Antibodies: Grafting an Antilysozyme Activity," *Science*, vol. 239, pp. 1534-1536, Mar. 25, 1988.

Vié, Henri, et al., "Human Fusion Proteins Between Interleukin 2 and IgM Heavy Chain are Cytotoxic for Cells Expressing the Interleukin 2 Receptor," *Proc. Natl. Acad. Sci. USA*, vol. 89, pp. 11337-11341, Dec. 1992.

Wittau, Norbert, et al., "The Galanin Receptor Type 2 Initiates Multiple Signaling Pathways in Small Cell Lung Cancer Cells by Coupling $G_q$, $G_i$ and $G_{12}$ Proteins," *Oncogene*, vol. 19, pp. 4199-4209 (2000).

Wu, George Y. and Wu, Catherine H., "Receptor-Mediated in Vitro Gene Transformation by a Soluble DNA Carrier System," *J. Biol. Chem.*, vol. 262, No. 10, pp. 4429-4432, Apr. 5, 1987.

Zhang, Wei-Wei and Roth, Jack A., "Anti-Oncogene and Tumor Suppressor Gene Therapy—Examples from a Lung Cancer Animal Model," *In Vivo*, vol. 8, pp. 755-770 (1994).

Zheng, Xin Xiao, et al., "Administration of Noncytolytic IL-10/Fc in Murine Models of Lipopolysaccharide-Induced Septic Shock and Allogeneic Islet Transplantation," *J. Immunol.*, vol. 154, pp. 5590-5600, (1995).

Zöchbauer-Müller, Sabine, et al., "Molecular Pathogenesis of Lung Cancer," *Annu. Rev. Physiol.*, vol. 64, pp. 681-708 (2002).

Ward et al., 1989, "Binding activities of a repertoire of single immunoglobulin variable domains secreted from *Escherichia coli*." Nature 341:544-546.

Dumoulin et al., 2002, "Single-domain antibody fragments with high conformational stability." Protein Sci. 11:500-515.

Davies & Riechmann, 1995, "Antibody VH Domains as a Small Recognition Units." Biotechnol. 13:475-479.

Van Den Beucken et al., 2001, "Building Novel Binding Ligands to B7.1 and B7.2 Based on Human Antibody Single Variable Light Chain Domains." J. Mol. Biol. 310:591-601.

Pereira et al., 1998, "Cardiolipin Binding a Light Chain from Lupus-Prone Mice." Biochem. 37:1430-1437.

Marks et al., 1992, "By-Passing Immunization: Building High Affinity Human Antibodies by Chain Shuffling." Biotechnol. 10:779-783.

Klimka et al., 2000, "Human anti-CD30 recombinant antibodies by guided phage antibody selection using cell panning." Brit. J. of Canc. 83(2):252-260.

Rader et al., 1998, "A phage display approach for rapid antibody humanization: Designed combinatorial V gene libraries." Proc. Natl. Acad. Sci. USA 95:8910-8915.

* cited by examiner m5B4_H
/translation="EVQLQQSGAELVRPGALVKLSCKAS<u>GFNIEDYYMH</u>WVRQRPEEGLEWIG<u>R
IDPENGNTIY</u>DPKFQGKASITADTSSNTAYLQLSSLTSEDTAVYYCVR<u>GYVD</u>WGQGTLV
TVSA"

FIG. 1A m5B4_L
/translation="DVLMTQTPLSLPVSLGDQASISC<u>RSSQSIVHSDGDTYLE</u>WYLQKAGQSPKL
LIY<u>KVSNRFS</u>GVPDRFSGSGSGTDFTLKISRVEAEDLGLYYC<u>FQGSHVPYT</u>FGGGTKLEI
KRA"

FIG. 1B m5B4_H
GAAGTTCAGTTGCAGCAGTCTGGGGCTGAGCTTGTGAGGCCAGGGGCCTTAGTCAA
GTTGTCCTGCAAAGCTTCTGGCTTCAACATTGAAGACTACTATATGCACTGGGTGAG
GCAGAGGCCTGAAGAGGGCCTGGAGTGGATTGGAAGGATTGATCCTGAGAATGGTA
ATACTATATATGACCCGAAGTTCCAGGGCAAGGCCAGTATAACAGCAGACACATCC
TCCAACACAGCCTACCTGCAGCTCAGCAGCCTGACATCTGAGGACACTGCCGTCTAT
TACTGTGTTAGAGGGTATGTTGACTGGGGCCAAGGGACTCTGGTCACTGTCTCTGCA

FIG. 2A m5B4_L
GATGTTTTGATGACCCAGACTCCACTCTCCCTGCCTGTCAGTCTTGGAGATCAAGCCT
CCATCTCTTGCAGATCTAGTCAGAGCATTGTACATAGTGATGGAGACACCTATTTAG
AATGGTACCTGCAGAAAGCAGGCCAGTCTCCTAAGCTCCTGATCTACAAAGTTTCCA
ACCGATTTTCTGGGGTCCCAGACAGGTTCAGTGGCAGTGGATCAGGGACAGATTTCA
CACTCAAGATCAGCAGAGTGGAGGCTGAGGATCTGGGACTTTATTACTGCTTTCAAG
GTTCACATGTTCCGTACACGTTCGGAGGGGGGACCAAGCTGGAAATAAAACGGGCT

FIG. 2B m1G12_H
/translation="EVQLQQSGAELVKPGASVQLSCTAS<u>GFNIKDYYIH</u>WVQQRTEQGLEWIG<u>RIDPEDGEIEY</u>APKFQDKATITADTSSNTAYLQLSSLTSEDSAVYYCTR<u>GYAS</u>WGQGTTLTVSSA"

FIG. 3A m1G12_L
/translation="DVLMTQTPLSLPVSLGDQASISC<u>RSSQTFVHSDGNTYLE</u>WYLQKPGQSPKLLIY<u>KVSNRFS</u>GVPDRFSGSGSGTDFTLKISRVEAEDLGVYYC<u>FQGSHVPYT</u>FGGGTKLEIKRA"

FIG. 3B m1G12_H
GAGGTGCAGTTGCAGCAGTCTGGGGCAGAGCTTGTGAAGCCAGGGGCCTCAGTCCA
GTTGTCCTGCACAGCCTCTGGCTTCAACATTAAAGACTACTATATACACTGGGTGCA
ACAGAGGACTGAACAGGGCCTGGAGTGGATTGGAAGGATTGATCCTGAGGATGGTG
AAATTGAATATGCCCCGAAATTCCAGGACAAGGCCACTATAACAGCAGACACATCC
TCCAACACAGCCTACCTGCAGCTCAGCAGCCTGACATCTGAGGACTCTGCCGTCTAT
TACTGTACTAGAGGCTATGCCTCCTGGGGCCAAGGCACCACTCTCACAGTCTCCTCA
GCC

FIG. 4A m1G12_L
GACGTGCTGATGACTCAGACCCCACTCTCCCTGCCTGTCAGTCTTGGAGATCAAGCC
TCCATCTCTTGCAGATCTAGTCAGACCTTTGTACATAGTGATGGAAACACCTATTTA
GAATGGTACCTGCAGAAACCAGGCCAGTCTCCAAAGCTCCTGATCTACAAAGTTTCC
AACCGATTTTCTGGGGTCCCAGACAGGTTCAGTGGCAGTGGATCAGGGACAGATTTC
ACACTCAAGATCAGCAGAGTGGAGGCTGAGGATCTGGGAGTTTATTACTGCTTTCAA
GGWTCACATGTTCCGTACACGTTCGGAGGGGGGACCAAGCTGGAAATAAAACGGGC
T

FIG. 4B m2F8_H
/translation="EVQLQQSGAELVRPGALVKLSCKASGFNIEDYYIHWVRQRPEEGLEWI
GRIDPENGNTIYDPKFQGKASLTADTSSNTAYLQLSSLTSEDTAVYFCARGYVDWGQ
GTLVTVSAA"

FIG. 5A m2F8_L
/translation="DVLMTQTPLSLPVSLGDQASISCRSSQSIVHSDGDTYLEWYLQKP
GQSPKLLIYKVSNRFSGVPDRFSGSGSGTDFTLKIIRVEAEDLGLYFCFQGSHVPYTFG
GGTKLEIKRA

FIG. 5B m2F8_H
GAGGTACAGTTGCAGCAGTCTGGGGCTGAGCTTGTGAGGCCAGGGGCCTTAGTCAA
GTTGTCCTGCAAAGCTTCTGGCTTCAACATTGAAGACTACTATATACACTGGGTGAG
GCAGAGGCCTGAAGAGGGCCTGGAGTGGATTGGAAGGATTGATCCTGAGAATGGTA
ATACTATATATGACCCGAAGTTCCAGGGCAAGGCCAGTCTAACAGCAGACACATCC
TCCAACACAGCCTACCTGCAGCTCAGCAGCCTGACATCTGAGGACACTGCCGTCTAT
TTCTGTGCTAGAGGGTATGTTGACTGGGGCCAAGGGACTCTGGTCACTGTCTCTGCA
GCC

FIG. 6A m2F8_L
GACGTGTTGATGACTCAGACCCCGCTCTCCCTGCCTGTCAGTCTTGGAGATCAAGCC
TCCATCTCTTGCAGATCTAGTCAGAGCATTGTACATAGTGATGGAGACACCTATTTA
GAATGGTACCTGCAGAAACCAGGCCAGTCTCCTAAGCTCCTGATCTACAAAGTTTCC
AACCGATTTTCTGGGGTCCCAGACAGGTTCAGTGGCAGTGGATCAGGGACAGATTTC
ACACTCAAGATCATCAGAGTGGAGGCTGAGGATCTGGGACTTTATTTCTGCTTTCAA
GGWTCACATGTTCCGTACACGTTCGGAGGGGGGACCAAGCTGGAAATAAAACGGGC
T

FIG. 6B m1D7_H
/translation="EIQLQQSEAELVKPGASVRLSCATS<u>GFNIKDYYIH</u>WVKQTTEQGLEWIG<u>RI
DPEDGETEY</u>APKFQGKATIAADTSSNTAYLLLNSLSSEDTAVYYCTR<u>GYAS</u>WGQGTTLT
VSSA"

FIG. 7A m1D7_L
/translation="DVLMTQTPLSLSVSLGDQASISC<u>RSSQSFVHSDGNTYLE</u>WYLQKSGQSPKL
LIY<u>KVSNRFS</u>GVPDRFSGSGSGTDFTLKINRVEAEDLGVYYC<u>FQGSHVPYT</u>FGGGTKLEI
KRA"

FIG. 7B m1D7_H
GAAATTCAGTTGCAGCAGTCTGAGGCAGAGCTTGTGAAGCCAGGGGCCTCAGTCAG
GTTGTCCTGCGCTACTTCTGGCTTCAACATTAAAGACTACTATATACACTGGGTGAA
GCAGACGACTGAACAGGGCCTGGAGTGGATTGGAAGGATTGATCCTGAGGATGGTG
AAACTGAGTATGCCCCGAAATTCCAGGGCAAGGCCACTATAGCAGCAGACACATCT
TCCAATACAGCCTACCTTCTACTCAACAGCCTGTCATCTGAGGACACTGCCGTCTAT
TACTGTACTAGAGGCTATGCCTCCTGGGGCCAAGGCACCACTCTCACAGTCTCCTCA
GCC

FIG. 8A m1D7_L
GACGTACTGATGACCCAGACTCCACTCTCCCTGTCTGTCAGTCTTGGAGATCAAGCC
TCCATCTCTTGTAGATCTAGTCAGAGTTTtGTACATAGTGATGGAAACACCTATTTAG
AATGGTACCTGCAGAAATCAGGCCAGTCTCCAAAGCTCCTGATCTACAAAGTTTCCA
ACCGATTTTCTGGGGTCCCAGACAGGTTCAGTGGCAGTGGATCAGGGACAGATTTCA
CACTCAAGATCAACAGAGTGGAGGCTGAGGATCTGGGAGTTTATTACTGCTTTCAAG
GTTCACATGTTCCGTACACGTTCGGAGGGGGGACCAAGTTGGAAATAAAACGGGCT

FIG. 8B m4B3_H
/translation="EIQLQQSEAELVKPGASVRLSCATS<u>GFNIKDYYIH</u>WVKQTTEQGLEWIG<u>RI
DPEDGETE</u>YAPKFQGKATIAADTSSNTAYLLLNSLSSEDTAVYYCTR<u>GYAS</u>WGQGTTLT
VSS"

FIG. 9A m4B3_L
/translation="DVLMTQTPLSLSVSLGDQASISC<u>RSSQSFVHSDGNTYLE</u>WYLQKSGQSPKL
LIY<u>KVSNRFS</u>GVPDRFSGSGSGTDFTLKINRVEAEDLGVYYC<u>FQGSHVPYT</u>FGGGTKLEI
KRA"

FIG. 9B m4B3_H
GAAATTCAGTTGCAGCAGTCCGAGGCAGAGCTTGTGAAGCCAGGGGCCTCAGTC
AGGTTGTCCTGCGCTACTTCT<u>GGCTTCAACATTAAAGACTACTATATACACT</u>GGG
TGAAGCAGACGACTGAACAGGGCCTGGAGTGGATTGGA<u>AGGATTGATCCTGAGG
ATGGTGAAACTGAGT</u>ATGCCCCGAAATTCCAGGGCAAGGCCACTATAGCAGCAG
ACACATCTTCCAATACAGCCTACCTTCTACTCAACAGCCTGTCATCTGAGGACAC
TGCCGTCTATTACTGTACTAGA<u>GGCTATGCCTCC</u>TGGGGCCAAGGCACCACTCTC
ACAGTCTCCTCA

FIG. 10A m4B3_L
GACGTACTGATGACTCAGACTCCGCTCTCCCTGTCTGTCAGTCTTGGAGATCAAG
CCTCCaTCTCTTGT<u>AGATCTAGTCAGAGTTTTGTACATAGTGATGGAAACACCTAT
TTAGAA</u>TGGTACCTGCAGAAATCAGGCCAGTCTCCAAAGCTCCTGATCTAC<u>AAAG
TTTCCAACCGATTTTCT</u>GGGGTCCCAGACAGGTTCAGTGGCAGTGGATCAGGGAC
AGATTTCACACTCAAGATCAACAGAGTGGAGGCTGAGGATCTGGGAGTTTATTA
CTGC<u>TTTCAAGGWTCACATGTTCCGTACAC</u>GTTCGGAGGGGGGACCAAGTTGGA
AATAAAACGGGCT

FIG. 10B m2H9_H
/translation="EIQLQQSEAELVKPGASVRLSCATS<u>GFNIKDYYIH</u>WVKQTTEQGLEWIG
<u>RIDPEDGETEY</u>APKFQGKATIAADTSSNTAYLLLNSLSSEDTAVYYCTR<u>GYA</u>SWGQG
TTLTVSS"

FIG. 11A m2H9_L
/translation="DVLMTQTPLSLSVSLGDQASISC<u>RSSQSFVHSDGNTYLE</u>WYLQKSGQSP
KLLIY<u>KVSNRFS</u>GVPDRFSGSGSGTDFTLKINRVEAEDLGVYYC<u>FQGSHVPYT</u>FGGGT
KLEIKRA"

FIG. 11B m2H9_H
GAAATTCAGTTGCAGCAGTCCGAGGCAGAGCTTGTGAAGCCAGGGGCCTCAGTC
AGGTTGTCCTGCGCTACTTCTGGCTTCAACATTAAAGACTACTATATACACTGGG
TGAAGCAGACGACTGAACAGGGCCTGGAGTGGATTGGAAGGATTGATCCTGAGG
ATGGTGAAACTGAGTATGCCCCGAAATTCCAGGGYAAGGCCACTATAGCAGCAG
ACACATCTTCCAATACAGCCTACCTTCTACTCAACAGCCTGTCATCTGAGGACAC
TGCCGTCTATTACTGTACTAGAGGCTATGCCTCCTGGGGCCAAGGCACCACTCTC
ACAGTCTCCTCA

FIG. 12A m2H9_L
GACGTTTTGATGACCCAGACTCCACTCTCCCTGTCTGTCAGTCTTGGAGATCAAG
CCTCCATCTCTTGTAGATCTAGTCAGAGTTTTGTACATAGTGATGGAAACACCTA
TTTAGAATGGTACCTGCAGAAATCAGGCCAGTCTCCAAAGCTCCTGATCTACAAA
GTTTCCAACCGATTTTCTGGGGTCCCAGACAGGTTCAGTGGCAGTGGATCAGGGA
CAGATTTCACACTCAAGATCAACAGAGTGGAGGCTGAGGATCTGGGAGTTTATT
ACTGCTTTCAAGGTTCACATGTTCCGTACACGTTCGGAGGGGGGACCAAGTTGGA
AATAAAACGGGCT

FIG. 12B m1A1_H
/translation="EIQLQQSEAELVRPGALVKLSCKTS<u>GFNIKDYYMH</u>WVKQRPEQGLEWI
G<u>RIDPENDNSI</u>YDPNFQGKASITADTSSNTAYLQLSSLTSEDTAVYYCVR<u>GYVD</u>WGQ
GTLVTVSA"

FIG. 13A m1A1_L
/translation="DVLMTQTPLSLPVSLGDQASISC<u>RSSQSIVHSDGDTYLE</u>WYLQKPGQSP
KLLIF<u>KVSNRFS</u>GVPDRFSGSGSGTDFTLKISRVEAEDLGVYYC<u>FQGSHVPYT</u>FGGGT
KLEIKRA"

FIG. 13B m1A1_H
GAGATCCAGTTGCAGCAGTCTGAGGCTGAGCTTGTGAGGCCAGGGGCCTTAGTC
AAGTTGTCCTGCAAAACTTCTGGCTTCAACATTAAAGACTACTATATGCACTGGG
TGAAGCAGAGGCCTGAACAGGGCCTGGAGTGGATAGGACGGATTGATCCTGAGA
ATGATAATAGTATATGACCCGAACTTCCAGGGCAAGGCCAGTATAACAGCAG
ACACATCCTCCAACACAGCCTATCTGCAGCTCAGCAGCCTGACATCTGAGGACAC
TGCCGTCTATTATTGTGTTAGAGGGTATGTTGACTGGGGCCAAGGGACTCTGGTC
ACTGTCTCTGCA

FIG. 14A m1A1_L
GATGTTCTGATGACCCAGACTCCACTCTCCCTGCCTGTCAGTCTTGGAGATCAAG
CCTCCATCTCTTGCAGATCTAGTCAGAGCATTGTACATAGTGATGGAGACACCTA
TTTAGAATGGTACCTGCAGAAACCAGGCCAGTCTCCAAAACTCCTGATCTTCAAA
GTTTCCAACCGATTTTCTGGGGTCCCAGACAGGTTCAGTGGCAGTGGATCAGGGA
CAGATTTCACACTCAAGATCAGCAGAGTGGAGGCTGAGGATCTGGGAGTTTATT
ACTGCTTTCAAGGTTCACATGTTCCGTACACGTTCGGAGGGGGGACTAAGCTGGA
AATAAAACGGGCT

FIG. 14B m2E11_H
/translation="EIQLQQSGAEVMKPGASVKISCKAT<u>GYTFSNYWIE</u>WIKQRPGHGLEWIG
<u>EILPGSESTK</u>YNEKFKGKATFTTDTSSNTAYMQLSSLTSEDSAVYYCAT<u>FYGGFDY</u>W
GQGTTLTVSSA"

FIG. 15A m2E11_L
/translation="DVLMTQTPLTLSVTIGQPASISC<u>KSSQSLLYSDGKIYLN</u>WLLQRPGQSPK
RLIY<u>LVSKLDS</u>GVPDRFTGSGSGTDFTLKISRVEAEDLGVYYC<u>VQGTHFPRT</u>FGGGTK
LEIKRA"

FIG. 15B m2E11_H
GAGATCCAGTTGCAGCAGTCTGGAGCTGAGGTGATGAAGCCTGGGGCCTCAGTG
AAGATATCCTGCAAGGCTACTGGCTACACATTCAGTAACTACTGGATAGAGTGG
ATAAAACAGAGGCCTGGACATGGCCTTGAGTGGATTGGAGAGATTTTACCTGGA
AGTGAAAGTACTAAATATAATGAGAAGTTCAAGGGCAAGGCCACATTTACTACA
GATACATCCTCCAACACAGCGTACATGCAACTCAGCAGCCTGACATCTGAGGACT
CTGCCGTCTATTACTGTGCAACCTTCTACGGAGGTTTTGACTACTGGGGCCAAGG
CACCACTCTCACAGTCTCCTCAGCC

FIG. 16A m2E11_L
GACGTTCTGATGACCCAGACTCCACTGACTTTGTCGGTTACCATTGGACAACCAG
CCTCTATCTCTTGCAAGTCAAGTCAGAGCCTCCTATATAGTGATGGAAAAATCTA
TTTGAATTGGTTATTACAGAGGCCAGGCCAGTCTCCAAAGCGCCTAATTTATCTG
GTGTCTAAATTGGACTCTGGAGTCCCTGACAGGTTCACTGGCAGTGGATCAGGAA
CAGATTTTACACTGAAAATCAGCAGAGTGGAGGCTGAGGATTTGGGAGTTTATTA
CTGCGTGCAAGGTACACATTTTCCTCGGACGTTCGGTGGAGGCACCAAGCTGGAA
ATCAAACGGGCT

FIG. 16B

Zu5B4_H_v02
/translation="EVQLVQSGAEVKKPGATVKISCKVSGFNIEDYYMHWVQQAPGKGLEW
MGRIDPENGNTIYDPKFQGRVTITADTSTDTAYMDLSSLRSEDTAVYYCATGYVDW
GQGTLVTVSS"

FIG. 17A

Zu5B4_L_v02
/translation="DVVMTQSPLSLPVTLGQPASISCRSSQSIVHSDGDTYLEWFQQRP
GQSPMSLIYKVSNRFSGVPDRFSGSGSGTDFTLKITRVEAEDVGVYYCFQGSHVPYTF
GGGTKVEIKRT

FIG. 17B

Zu5B4_H_v02
GAGGTCCAGCTGGTACAGTCTGGGGCTGAGGTGAAGAAGCCTGGGGCTACAGTG
AAAATCTCCTGCAAGGTTTCT<u>GGATTCAACATCGAGGACTACTACATGCAC</u>TGGG
TGCAACAGGCCCCTGGAAAAGGGCTTGAGTGGATGGGA<u>CGTATCGATCCTGAAA
ATGGTAATACAATC</u>TACGACCCGAAGTTCCAGGGCAGAGTCACCATAACCGCGG
ACACGTCTACAGACACAGCCTACATGGACCTGAGCAGCCTGAGATCTGAGGACA
CGGCCGTGTATTACTGTGCAACA<u>GGATATGTCGAC</u>TGGGGCCAGGGAACCCTGG
TCACCGTCTCCTCA

FIG. 18A

Zu5B4_L_v02
GATGTAGTAATGACTCAGTCTCCACTCTCCCTGCCCGTCACCCTTGGACAGCCGG
CCTCCATCTCCTGC<u>AGGTCTAGTCAAAGCATCGTACACAGTGATGGAGACACCTA
CTTGGAGT</u>GGTTTCAGCAGAGGCCAGGCCAATCTCCAATGAGCCTAATTTAT<u>AAG
GTTTCTAACCGGTTCTCT</u>GGGGTCCCAGACAGATTCAGCGGCAGTGGTCAGGCA
CTGACTTCACACTGAAAATCACCAGGGTGGAGGCTGAGGATGTTGGGGTTTATTA
CTGC<u>TTCCAAGGTAGCCACGTGCCGTACACT</u>TTCGGCGGAGGTACCAAGGTGGA
AATCAAACGAACT

FIG. 18B

Zu5B4_H_v04
/translation="EVQLVQSGAEVKKPGATVKISCKVSGFNIEDYYMHWVQQAPGKGLEW
MGRIDPENGNTIYDPKFQGRVTITADTSTNTAYLDLSSLRSEDTAVYYCARGYVDWG
QGTLVTVSS"

FIG. 19A

Zu5B4_L_v04
/translation="DVVMTQSPLSLPVTLGQPASISCRSSQSIVHSDGDTYLEWYLQRPGQSP
MLLIYKVSNRFSGVPDRFSGSGSGTDFTLKITRVEAEDVGVYYCFQGSHVPYTFGGG
TKVEIKRT"

FIG. 19B

Zu5B4_H_v04
gaggtccagctggtacagtctggggctgaggtgaagaagcctggggctacagtgaaaatctcctgcaaggtttctggattcaacatcg
aggactactacatgcactgggtgcaacaggcccctggaaaagggctCgagtggatgggacgtatcgatcctgaaaatggtaataca
atctacgacccgaagttccagggcagagtcaccataaccgcggacacgtctacaAacacagcctacCtggacctgagcagcctga
gatctgaggacacggccgtgtattactgtgcaaGaggatatgtcgactggggccagggaaccctggtcaccgtctcctca

FIG. 20A

Zu5B4_L_v04
gatgtagtaatgactcagtctccactctccctgcccgtcacccttggacagccggcctccatctcctgcaggtctagtcaaagcatcgta
cacagtgatggagacacctacttggagtggtAtcTgcagaggccCggGcaatctccaatgTTGctaatttataaggtttctaaccg
gttctctggggtcccagacagattcagcggcagtgggtcaggcactgacttcacactgaaaatcaccagggtggaggctgaggatgtt
ggggtttattactgcttccaaggtagccacgtgccgtacactttcggcggaggtaccaaggtggaaatcaaacgaact

FIG. 20B zu5B4_H_v05
/translation="EVQLVQSGAEVKKPGATVKISCKVSGFNIEDYYMHWVQQAPGKGLEW
MGRIDPENGNTIYDPKFQGRVTITADTSTNTAYMDLSSLRSEDTAVYYCARGYVDW
GQGTLVTVSS"

FIG. 21A zu5B4_L_v05
/translation="DVVMTQSPLSLPVTLGQPASISCRSSQSIVHSDGDTYLEWYQQRPGQSP
MSLIYKVSNRFSGVPDRFSGSGSGTDFTLKITRVEAEDVGVYYCFQGSHVPYTFGGG
TKVEIKRT"

FIG. 21B

Zu5B4_H_v05
gaggtccagctggtacagtctggggctgaggtgaagaagcctggggctacagtgaaaatctcctgcaaggtttctggattcaacatcg
aggactactacatgcactgggtgcaacaggcccctggaaaagggctCgagtggatgggacgtatcgatcctgaaaatggtaataca
atctacgacccgaagttccagggcagagtcaccataaccgcggacacgtctacaAacacagcctacatggacctgagcagcctgag
atctgaggacacggccgtgtattactgtgcaaGaggatatgtcgactgggggccagggaaccctggtcaccgtctcctca

FIG. 22A

Zu5B4_L_v05
gatgtagtaatgactcagtctccactctccctgcccgtcacccttggacagccggcctccatctcctgcaggtctagtcaaagcatcgta
cacagtgatggagacacctacttggagtggtAtcagcagaggccCggGcaatctccaatgTCGctaatttataaggtttctaaccg
gttctctggggtcccagacagattcagcggcagtgggtcaggcactgacttcacactgaaaatcaccagggtggaggctgaggatgtt
ggggtttattactgcttccaaggtagccacgtgccgtacactttcggcggaggtaccaaggtggaaatcaaacgaact

FIG. 22B zu5B4_H_v06
/translation="EVQLVQSGAEVKKPGATVKISCKVS<u>GFNIEDYYMH</u>WVQQAPGKGLEW IG<u>RIDPENGNTI</u>YDPKFQGRATITADTSTNTAYLDLSSLRSEDTAVYYCAR<u>GYVD</u>WG QGTLVTVSS"

FIG. 23A zu5B4_L_v06
/translation="DVVMTQSPLSLPVTLGQPASISC<u>RSSQSIVHSDGDTYLE</u>WYQQRP GQSPMSLIY<u>KVSNRFS</u>GVPDRFSGSGSGTDFTLKITRVEAEDVGVYYC<u>FQGSHVPYT</u>F GGGTKVEIKRT ZuSB4_H_v06
gaggtccagctggtacagtctggggctgaggtgaagaagcctggggctacagtgaaaatctcctgcaaggtttctggattcaacatcg
aggactactacatgcactgggtgcaacaggcccctggaaaagggctCgagtggatCggacgtatcgatcctgaaaatggtaataca
atctacgacccgaagttccagggcagagCcaccataaccgcggacacgtctacaAacacagcctacCtggacctgagcagcctg
agatctgaggacacggccgtgtattactgtgcaaGaggatatgtcgactggggccagggaaccctggtcaccgtctcctca

FIG. 24A

ZuSB4_L_v06
gatgtagtaatgactcagtctccactctccctgcccgtcacccttggacagccggcctccatctcctgcaggtctagtcaaagcatcgta
cacagtgatggagacacctacttggagtggtAtcagcagaggccCggGcaatctccaatgTCGctaatttataaggtttctaaccg
gttctctggggtcccagacagattcagcggcagtgggtcaggcactgacttcacactgaaaatcaccagggtggaggctgaggatgtt
ggggtttattactgcttccaaggtagccacgtgccgtacactttcggcggaggtaccaaggtggaaatcaaacgaact

FIG. 24B zu5B4_H_v07
/translation="EVQLVQSGAEVKKPGATVKISCKVS<u>GFNIEDYYMH</u>WVQQAPGKGLEW
MG<u>RIDPENGNTIY</u>DPKFQGRVTITADTSTNTAYLDLSSLRSEDTAVYYCAR<u>GYVD</u>WG
QGTLVTVSS"

FIG. 25A zu5B4_L_v07
/translation="DVVMTQSPLSLPVTLGQPASISC<u>RSSQSIVHSDGDTYLE</u>WYQQRPGQSP
MSLIY<u>KVSNRFS</u>GVPDRFSGSGSGTDFTLKITRVEAEDVGVYYC<u>FQGSHVPYT</u>FGGG
TKVEIKRT"

FIG. 25B

Zu5B4_H_v07
gaggtccagctggtacagtctggggctgaggtgaagaagcctggggctacagtgaaaatctcctgcaaggtttctggattcaacatcg
aggactactacatgcactgggtgcaacaggcccctggaaaagggctCgagtggatgggacgtatcgatcctgaaaatggtaataca
atctacgacccgaagttccagggcagagtcaccataaccgcggacacgtctacaAacacagcctacCtggacctgagcagcctga
gatctgaggacacggccgtgtattactgtgcaaGaggatatgtcgactggggccagggaacCctggtcaccgtctcctca

FIG. 26A zu5B4_L_v07
gatgtagtaatgactcagtctccactctccctgcccgtcacccttggacagccggcctccatctcctgcaggtctagtcaaag
catcgtacacagtgatggagacacctacttggagtggtAtcagcagaggccCggGcaatctccaatgTCGctaatttataaggttt
ctaaccggttctctggggtcccagacagattcagcggcagtgggtcaggcactgacttcacactgaaaatcaccagggtggaggctg
aggatgttggggtttattactgcttccaaggtagccacgtgccgtacactttcggcggaggtaccaaggtggaaatcaaacgaact

FIG. 26B zu5B4_H_v08
/translation="EVQLVQSGAEVKKPGATVKISCKVSGFNIEDYYMHWVQQAPGKGLEW
MGRIDPENGNTIYDPKFQGRATITADTSTDTAYLDLSSLRSEDTAVYYCARGYVDWG
QGTLVTVSS"

FIG. 27A zu5B4_L_v08
/translation="DVVMTQSPLSLPVTLGQPASISCRSSQSIVHSDGDTYLEWYQQRPGQSP
MSLIYKVSNRFSGVPDRFSGSGSGTDFTLKITRVEAEDVGVYYCFQGSHVPYTFGGG
TKVEIKRT"

FIG. 27B zu5B4_H_v08 gaggtccagctggtacagtctggggctgaggtgaagaagcctggggctacagtgaaaatctcctgcaaggtttctggattcaacatcg
aggactactacatgcactgggtgcaacaggcccctggaaaagggctCgagtggatgggacgtatcgatcctgaaaatggtaataca
atctacgacccgaagttccagggcagagCcaccataaccgcggacacgtctacagacacagcctacCtggacctgagcagcctga
gatctgaggacacggccgtgtattactgtgcaaGaggatatgtcgactggggccagggaaccctggtcaccgtctcctca

FIG. 28A zu5B4_L_v08 gatgtagtaatgactcagtctccactctccctgcccgtcacccttggacagccggcctccatctcctgcaggtctagtcaaag
catcgtacacagtgatggagacacctacttggagtggtAtcagcagaggccCggGcaatctccaatgTCGctaatttataaggttt
ctaaccggttctctggggtcccagacagattcagcggcagtgggtcaggcactgacttcacactgaaaatcaccagggtggaggctg
aggatgttggggtttattactgcttccaaggtagccacgtgccgtacactttcggcggaggtaccaaggtggaaatcaaacgaact

FIG. 28B zu5B4_H_v09
/translation="EVQLVQSGAEVKKPGATVKISCKVS<u>GFNIEDYYMH</u>WVQQAPGKGLEW
IG<u>RIDPENGNT</u>IYDPKFQGRVTITADTSTNTAYMDLSSLRSEDTAVYYCAR<u>GYVD</u>WG
QGTLVTVSS"

FIG. 29A zu5B4_L_v09
/translation="DVVMTQSPLSLPVTLGQPASISC<u>RSSQSIVHSDGDTYLE</u>WYQQRPGQSP
MSLIY<u>KVSNRFS</u>GVPDRFSGSGSGTDFTLKITRVEAEDVGVYYC<u>FQGSHVPYT</u>FGGG
TKVEIKRT"

FIG. 29B zu5B4_H_v09
gaggtccagctggtacagtctgggggctgaggtgaagaagcctggggctacagtgaaaatctcctgcaaggtttct<u>ggattcaacatcg</u>
<u>aggactactacatgcac</u>tgggtgcaacaggcccctggaaaagggctCgagtggatCgga<u>cgtatcgatcctgaaaatggtaataca</u>
<u>atc</u>tacgacccgaagttccagggcagagtcaccataaccgcggacacgtctacaAacacagcctacatggacctgagcagcctgag
atctgaggacacggccgtgtattactgtgcaaGa<u>ggatatgtcgactggggc</u>cagggaaccctggtcaccgtctcctca

FIG. 30A zu5B4_L_v09
gatgtagtaatgactcagtctccactctccctgcccgtcacccttggacagccggcctccatctcctgc<u>aggtctagtcaaagcatcgta</u>
<u>cacagtgatggagacacctacttggagtggt</u>AtcagcagaggccCggGcaatctccaatgTCGctaatttat<u>aaggtttctaaccg</u>
<u>gttctctggggtccca</u>gacagattcagcggcagtgggtcaggcactgacttcacactgaaaatcaccagggtggaggctgaggatgtt
ggggtttattactgcttc<u>caaggtagccacgtgccgtacactttc</u>ggcggaggtaccaaggtggaaatcaaacgaact

FIG. 30B zu5B4_H_v10
/translation="EVQLVQSGAEVKKPGATVKISCKVS<u>GFNIEDYYMH</u>WVQQAPGKGLEW
IGR<u>IDPENGNTI</u>YDPKFQGRATITADTSTNTAYLDLSSLRSEDTAVYYCAR<u>GYVD</u>WG
QGTLVTVSS"

FIG. 31A zu5B4_L_v10
/translation="DVVMTQSPLSLPVTLGQPASISC<u>RSSQSIVHSDGDTYLE</u>WYQQRPGQSP
MLLIY<u>KVSNRFS</u>GVPDRFSGSGSGTDFTLKITRVEAEDVGVYYC<u>FQGSHVPYT</u>FGGG
TKVEIKRT"

FIG. 31B zu5B4_H_v10
gaggtccagctggtacagtctgggggctgaggtgaagaagcctggggctacagtgaaaatctcctgcaaggtttctggattcaacatcg
aggactactacatgcactgggtgcaacaggcccctggaaaagggctCgagtggatCggacgtatcgatcctgaaaatggtaataca
atctacgacccgaagttccagggcagagCcaccataaccgcggacacgtctacaAacacagcctacCtggacctgagcagcctg
agatctgaggacacggccgtgtattactgtgcaaGaggatatgtcgactggggccagggaaccctggtcaccgtctcctca

FIG. 32A zu5B4_L_v10
gatgtagtaatgactcagtctccactctccctgcccgtcacccttggacagccggcctccatctcctgcaggtctagtcaaag
catcgtacacagtgatggagacacctacttggagtggtAtcagcagaggccCggGcaatctccaatgTTGctaatttataaggttt
ctaaccggttctctggggtcccagacagattcagcggcagtgggtcaggcactgacttcacactgaaaatcaccagggtggaggctg
aggatgttggggtttattactgcttccaaggtagccacgtgccgtacactttcggcggaggtaccaaggtggaaatcaaacgaact

FIG. 32B zu5B4_H_v11
/translation="EVQLVQSGAEVKKPGATVKISCKVS<u>GFNIEDYYMH</u>WVQQAPGKGL
EWMG<u>RIDPENGNTI</u>YDPKFQGRVTITADTSTNTAYMDLSSLRSEDTAVYYCAR<u>G</u>
<u>YVD</u>WGQGTLVTVSS"

FIG. 33A zu5B4_L_v11
/translation="DVVMTQSPLSLPVTLGQPASISC<u>RSSQSIVHSDGDTYLE</u>WYQQRPG
QSPMLLIY<u>KVSNRFS</u>GVPDRFSGSGSGTDFTLKITRVEAEDVGVYYC<u>FQGSHVPY</u>
<u>T</u>FGGGTKVEIKRT"

FIG. 33B zu5B4_H_v12

/translation="EVQLVQSGAEVKKPGATVKISCKVS<u>GFNIEDYYMH</u>WVQQAPGKGL
EWMG<u>RIDPENGNTIY</u>DPKFQGRATITADTSTDTAYLDLSSLRSEDTAVYYCAR<u>G
YVD</u>WGQGTLVTVSS"

FIG. 34A zu5B4_L_v12

/translation="DVVMTQSPLSLPVTLGQPASISC<u>RSSQSIVHSDGDTYLE</u>WYLQRPGQ
SPMLLIY<u>KVSNRFS</u>GVPDRFSGSGSGTDFTLKITRVEAEDVGVYYC<u>FQGSHVPYT</u>
FGGGTKVEIKRT"

FIG. 34B zu5B4_H_v13

/translation="EVQLVQSGAEVKKPGATVKISCKVS<u>GFNIEDYYMH</u>WVQQAPGKGL EWIG<u>RIDPENGNTI</u>YDPKFQGRVTITADTSTNTAYMDLSSLRSEDTAVYYCAR<u>GY VD</u>WGQGTLVTVSS"

FIG. 35A zu5B4_L_v13

/translation="DVVMTQSPLSLPVTLGQPASISC<u>RSSQSIVHSDGDTYLE</u>WYQQRPG QSPMLLIY<u>KVSNRFS</u>GVPDRFSGSGSGTDFTLKITRVEAEDVGVYYC<u>FQGSHVPY T</u>FGGGTKVEIKRT"

FIG. 35B

ANTI-GALANIN ANTIBODIES AND USES THEREOF

CROSS-REFERENCE TO RELATED APPLICATION

This application is related to and claims the benefit of U.S. Application Ser. No. 60/529,463, filed Dec. 12, 2003, the disclosure of which is incorporated by reference herein.

BACKGROUND OF THE INVENTION

1. Field of the Invention

The present invention provides antibodies that immunospecifically bind to a galanin peptide and compositions comprising said antibodies. The invention also provides prophylactic and therapeutic protocols to prevent, treat, manage, and/or ameliorate disorders associated with aberrant expression and/or activity of galanin and/or a galanin receptor, including, without limitation hyperproliferative disorders, Alzheimer's disease, depression and eating disorders, or one or more symptoms thereof, said protocols comprising the administration of antibodies that immunospecifically bind to a galanin peptide alone or in combination with other therapies. The invention also encompasses methods and compositions for diagnosing, monitoring, and prognosing hyperproliferative disorders. The present invention further relates to articles of manufacture and kits comprising antibodies that immunospecifically bind to a galanin peptide.

2. Background of the Invention

2.1 Cancer

Cancer is a leading cause of death in the world and lung cancer is one of the most common types. In the United States, 28% of all cancer deaths are due to lung cancer (Jomal et al, 2001, *J. Natl. Cancer Inst.* 93: 277-283). Thus, there is a critical need for improved cancer therapies, particularly for lung cancer. Prognosis of lung cancer patients is poor with a 5 year survival rate of 14% (Zochbauer-Muller et al. 2002, *Annu. Rev. Physiol.* 64: 681-708).

Although cancer is a diverse set of diseases there are certain features that are common to cancer cells. These include increased proliferation, resistance to apoptosis, resistance to anti-growth signals, and ability to metastasize (Hanahan and Weinberg, 2000 Cell 100: 57-70).

Cancer is a disease that is largely caused by somatic mutations, and it is thought that a cell must accumulate multiple genetic alterations to make the transition from a normal cell to a fully malignant cell (Hanahan and Weinberg, 2000, *Cell* 100: 57-70). Genes that promote cancer through increased activity caused by mutation or overexpression are known as oncogenes, while genes whose loss of function promotes cancer are referred to as tumor suppressors.

Gene amplifications are important genetic alterations in the development and progression of human cancers by increasing the expression of oncogenes (Pollack et al. 2002, Proc. Natl. Acad. Sci. (USA) 99: 12963-12968: Li et al, 2002, Nature Genetics 31, 133-134). Many known oncogenes are found to be amplified and identifying novel amplified genes in a tumor is an efficient method for oncogene discovery.

Currently, cancer therapy may involve surgery, chemotherapy, hormonal therapy and/or radiation treatment to eradicate neoplastic cells in a patient (see, for example, Stockdale, 1998, "Principles of Cancer Patient Management", in Scientific American: Medicine, vol. 3, Rubenstein and Federman, eds., Chapter 12, Section IV). Recently, cancer therapy can also involve biological therapy or immunotherapy. All of these approaches pose significant drawbacks for the patient. Surgery, for example, may be contraindicated due to the health of the patient or may be unacceptable to the patient. Additionally, surgery may not completely remove the neoplastic tissue. Radiation therapy is only effective when the neoplastic tissue exhibits a higher sensitivity to radiation than normal tissue, and radiation therapy can also often elicit serious side effects. Hormonal therapy is rarely given as a single agent and although it can be effective, is often used to prevent or delay recurrence of cancer after other treatments have removed the majority of the cancer cells.

With respect to chemotherapy, there are a variety of chemotherapeutic agents available for treatment of cancer. Many cancer chemotherapeutics act by inhibiting DNA synthesis, either directly, or indirectly by inhibiting the biosynthesis of the deoxyribonucleotide triphosphate precursors, to prevent DNA replication and concomitant cell division (see, for example, Gilman et al., Goodman and Gilman's: The Pharmacological Basis of Therapeutics, Eighth Ed. (Pergamom Press, New York, 1990)). These agents, which include alkylating agents, such as nitrosourea, anti-metabolites, such as methotrexate and hydroxyurea, and other agents, such as etoposides, campathecins, bleomycin, doxorubicin, daunorubicin, etc., although not necessarily cell cycle specific, kill cells during S phase because of their effect on DNA replication. Other agents, specifically colchicine and the vinca alkaloids, such as vinblastine and vincristine, interfere with microtubule assembly resulting in mitotic arrest. Chemotherapy protocols generally involve administration of a combination of chemotherapeutic agents to increase the efficacy of treatment.

Despite the availability of a variety of chemotherapeutic agents, chemotherapy has many drawbacks (see, for example, Stockdale, 1998, "Principles Of Cancer Patient Management" in Scientific American Medicine, vol. 3, Rubenstein and Federman, eds., ch. 12, sect. 10). Almost all chemotherapeutic agents are toxic, and chemotherapy causes significant, and often dangerous, side effects, including severe nausea, bone marrow depression, immunosuppression, etc. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even those agents that act by mechanisms different from the mechanisms of action of the drugs used in the specific treatment; this phenomenon is termed pleiotropic drug or multidrug resistance. Thus, because of drug resistance, many cancers prove refractory to standard chemotherapeutic treatment protocols.

There is a significant need for alternative cancer treatments, particularly for treatment of cancer that has proved refractory to standard cancer treatments, such as surgery, radiation therapy, chemotherapy, and hormonal therapy. Further, it is uncommon for cancer to be treated by only one method. Thus, there is a need for development of new therapeutic agents for the treatment of cancer and new, more effective, therapy combinations for the treatment of cancer.

Biological therapies/immunotherapies such as monoclonal antibody therapies are becoming increasingly important as new therapeutics in a variety of diseases including cancer (Berger et al. 2002, *Am J. Med. Sci.* 324: 14-30). Widely used therapeutic antibodies include Rituxan (IDEC) for lymphoma and Herceptin (Genentech) for breast cancer (Dillman, 2001, *Cancer Invest.* 19: 833-841). Although biological therapies/immunotherapies may produce side effects such as rashes or swellings, flu-like symptoms, including fever, chills and fatigue, digestive tract problems or allergic reactions, in general they are better tolerated than conventional cancer chemotherapies. Therapeutic antibodies for use in the treatment are few in number and there is a need to identify more therapeutically useful targets for biological therapies.

2.2 Galanin and Galanin Receptors

Galanin is a 29- or 30-amino acid peptide suggested to play a role in pain processing, learning and memory, prolactin secretion and other biological processes. Several galanin receptor subtypes are present in dorsal root ganglia and spinal cord with a differential distribution. The galanin receptor type 1 (GALR1) is known to normally be expressed predominantly in basal forebrain, hypothalamus, as well as spinal cord. On the other hand, the galanin receptor type 2 (GALR2) has been found to normally be widely distributed in brain and is also present in the pituitary gland and peripheral tissues (Depczynski et al., 1998, *Annals of the New York Academy of Sciences* 863: 120-128). GALR2 has been found to initiate multiple signaling pathways in small cell lung cancer cells by coupling to G(q), G(i) and G(12) proteins (Wittau et al., 2000, *Oncogene* 19(37): 4199-209). The galanin receptor type 3 (GALR3) has been found to normally be expressed in the periphery and at the lower levels of the central nervous system.

Amplification is an important means of increasing gene expression in tumor cells and many known oncogenes are over-replicated in cancer cells. It has been previously discovered that the genes encoding galanin and two of its receptors, GALR2 and GALR3, are amplified in lung cancer (Mu and Powers, International Publication No. WO 03/018770). Galanin is amplified in greater than 50% of lung cancer samples. Strikingly, the genes encoding GALR2 and/or GALR3 are frequently co-amplified with galanin. Since the three genes are located on different chromosomes, their co-amplification provides compelling genetic evidence that the activity of this pathway is being selected for its role in the establishment and progression of lung cancer. The genes encoding galanin and its receptors are over-expressed at a higher frequency than they are amplified indicating that other mechanisms in addition to DNA copy number changes can regulate expression of these genes. In addition to lung cancer, the genes encoding galanin, GALR2 and GALR3 were found to be amplified and/or over-expressed in several other cancers including breast, prostate, stomach, esophagus, bladder, liver, melanoma, and lymphoma.

2.3. Antibodies

The use of antibodies to block the activity of foreign and/or endogenous polypeptides provides an effective and selective strategy for treating the underlying cause of disease. Naturally occurring antibodies (immunoglobulins) have two heavy chains linked together by disulfide bonds and two light chains, one light chain being linked to each of the heavy chains by disulfide bonds. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains, see e.g. Chothia et al., J. Mol. Biol. 186:651-663 (1985).

The variable domains of each pair of light and heavy chains are involved directly in binding the antibody to the antigen, whereas the constant domains are not involved directly in the antibody-antigen binding, but are involved in various effector functions, such as participation of the antibody in antibody-dependent cellular cytotoxicity. Each domain of natural light and heavy chains contains four framework (FR) regions, whose sequences are somewhat conserved, connected by three hyper-variable regions called Complementarity Determining Regions (CDRs) (see Kabat, E. A. et al., Sequences of Proteins of Immunological Interest, National Institutes of Health, Bethesda, Md., (1987)). The four framework regions largely adopt a β-sheet conformation and the CDRs form loops connecting, and in some cases forming part of, the β-sheet structure. Thus, the antigen binding site is formed by the CDRs in each chain that are held in close proximity by the framework regions, together with the CDRs from the other chain.

The discovery of monoclonal antibody technology in the mid-1970's heralded a new age of medicine. Unfortunately, the development of therapeutic products based on monoclonal antibodies has been severely hindered by a host of drawbacks inherent in antibody production. Since most monoclonal antibodies are rodent-derived, they do not fix human complement well and they are frequently antigenic in human clinical use. For example, a major limitation in the clinical use of rodent monoclonal antibodies is an antiglobulin response during therapy (Miller, R. A. et al., Blood 62:988-995 (1983); Schroff, R. W. et al., Cancer Res. 45:879-885 (1985)). A number of studies have shown that after injection of a foreign immunoglobulin, the immune response in a patient's body can be quite strong, essentially eliminating the antibody's therapeutic utility after an initial treatment.

The production of "chimeric" antibodies in which an animal antigen-binding variable domain is coupled to a human constant domain has proven somewhat successful (Morrison, S. L. et al., Proc. Natl. Acad. Sci. USA 81:6851-6855 (1984); Boulianne, G. L. et al., Nature 312:643-646 (1984); Neuberger, M. S. et al., Nature 314:268-270 (1985)), however, significant immunogencity problems remained. For example, in the case of the murine anti-CD3 antibody, OKT3, much of the resulting anti-globulin response is directed against the variable region rather than the constant region (Jaffers, G. J. et al., Transplantation 41:572-578 (1986)).

More recently, recombinant DNA technology has been employed to produce immunoglobulins which have human framework regions combined with CDRs from a donor mouse or rat immunoglobulins (See Jones, P. T. et al., Nature 321:522-525 (1986); Riechmann, L. et al., Nature 332:323-327 (1988); Verhoeyen, M. et al., Science 239:1534-1536 (1988)). In practice, humanized antibodies are typically human antibodies in which some CDR residues and possibly some FR residues are substituted by residues from analogous sites in rodent antibodies.

A major problem with humanization procedures has been a loss of affinity for the antigen (Jones, P. T. et al., Nature 321:522-525 (1986)), in some cases as much as 10-fold or more. In some instances, substituting CDRs from rodent antibodies for the human CDRs in human frameworks was sufficient to transfer high antigen binding affinity (Verhoeyen, M. et al., Science 239:1534-1536 (1988)), whereas in other cases it has been necessary to additionally replace one (Riechmann, L. et al., Nature 332:323-327 (1988)) or several (Queen, C. et al., Proc. Natl. Acad. Sci. USA 86:10029-10033 (1989)) framework region residues. A number of FR residues have been suggested as critically affecting the conformation of particular CDRs and thus their contribution to antigen binding (Chothia, C. & Lesk, A. M., J. Mol. Biol. 196:901-917 (1987); Chothia, C. et al., Nature 342:877-883 (1989); Tramontano, A. et al., J. Mol. Biol. 215:175-182 (1990); Margolies et al., Proc. Natl. Acad. Sci. USA 72:2180-2184 (1975)). Furthermore, it is known that the function of an antibody is dependent on its three-dimensional structure, and that amino acid substitutions can change the three-dimensional structure of an antibody. It has previously been shown that the antigen binding affinity of a humanized antibody can be increased by mutagenesis based upon molecular modeling (Riechmann, L. et al., Nature 332:323-327 (1988); Queen, C. et al., Proc. Natl. Acad. Sci. USA 86:10029-10033 (1989)).

Thus, there is a need to provide antibodies that specifically bind to a galanin peptide (for example, a human galanin) for treatment of various types of cancer where the genes encoding galanin and its receptors are amplified and/or overexpressed. There is a need to provide humanized immunoglobulins that bind a galanin peptide with strong affinity and thereby inhibit binding of galanin to its receptors. These humanized antibodies should be substantially non-immunogenic in humans, and be easily and economically produced in a manner suitable for therapeutic formulation and other uses.

Citation or discussion of a reference herein shall not be construed as an admission that such is prior art to the present invention.

3. SUMMARY OF THE INVENTION

The present invention provides antibodies that immunospecifically bind to a galanin peptide (in one aspect, a human galanin). In particular, the present invention provides antibodies that immunospecifically bind to the carboxy terminus of a galanin peptide (for example, a human galanin). In one aspect, the present invention provides antibodies that immunospecifically bind to an epitope comprising amino acid residues 21 through 27 of murine or human galanin, amino acid residues 21 through 26 of murine or human galanin, amino acid residues 22 through 27 of murine or human galanin, or amino acid residues 22 through 26 of murine or human galanin. In another aspect, the present invention provides high affinity and/or high avidity antibodies that immunospecifically bind to an epitope comprising amino acid residues 21 through 27 of murine or human galanin, amino acid residues 21 through 26 of murine or human galanin, amino acid residues 22 through 27 of murine or human galanin, or amino acid residues 22 through 26 of murine or human galanin.

The present invention provides antibodies that immunospecifically bind to a galanin peptide (in one aspect, a human galanin) with a $K_a$ of at least $1 \times 10^8$ $M^{-1}$. The present invention also provides antibodies that immunospecifically bind to a galanin peptide (in one aspect, a human galanin) with a $K_d$ of less than $1 \times 10^{-9}$ M. In one aspect, the invention provides antibodies that immunospecifically bind to the carboxy-terminus of a galanin peptide (for example, a human galanin) with a $K_a$ of at least $1 \times 10^8$ $M^{-1}$. In another aspect, the invention provides antibodies that immunospecifically bind to the carboxy-terminus of a galanin peptide (in one aspect, a human galanin peptide) with a $K_d$ of less than $1 \times 10^{-9}$ M.

The invention provides murine hybridoma clones 1D7D1 and 5B4C1 (ATCC accession numbers PTA-5650 and PTA-5651, respectively). The invention also provides monoclonal antibodies produced by the murine hybridoma clones 1D7D1 and 5B4C1 (ATCC accession numbers PTA-5650 and PTA-5651, respectively). The invention further provides antibodies that compete with the monoclonal antibodies produced by the murine hybridoma clones 1D7D1 and 5B4C1 (ATCC accession numbers PTA-5650 and PTA-5651, respectively).

The invention provides antibodies that immunospecifically bind to a galanin peptide, said antibodies comprising a variable heavy domain and/or variable light domain or an antigen-binding fragment thereof of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13. The present invention also provides antibodies that immunospecifically bind to a galanin peptide, said antibodies comprising a variable heavy ("VH") domain having the amino acid sequence of the VH domain of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13. The present invention also provides antibodies that immunospecifically bind to a galanin peptide, said antibodies comprising a variable light ("VL") domain having the amino acid sequence of the VL domain of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13. The present invention also provides for antibodies that immunospecifically bind to a galanin peptide, said antibodies comprising a VH domain and VL domain having the amino acid sequence of the VH and VL domains of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13. The invention further provides antibodies that immunospecifically bind to a galanin peptide, said antibodies comprising one or more VH complementarity determining regions ("CDRs") and/or one or more VL CDRs having the amino acid sequence of one or more of the VH CDRs of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 and/or the amino acid sequence of one or more of the VL CDRs of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13, respectively. In one aspect, the VH CDRs comprise the amino acid sequences as set forth in SEQ ID NO:1, 2, or 3. In one aspect, the VL CDRs comprise the amino acid sequences as set forth in SEQ ID NO:4, 5, or 6.

The present invention provides for mixtures of antibodies that immunospecifically bind to a galanin peptide, wherein the mixture comprises at least one, two, three, four, five or more different antibodies of the invention. The present invention also provides for panels or a series of antibodies that immunospecifically bind to a galanin peptide, wherein the panel or series has at least one, two, three, four, five or more different antibodies of the invention. In particular, the invention provides for panels or a series of different antibodies that immunospecifically bind a galanin peptide in the milieu (i.e., not bound to a galanin receptor), the receptor-bound form of a galanin peptide, and/or both the receptor-bound form of a galanin peptide and a galanin peptide in the milieu. For example, the invention provides for panels or a series of antibodies that have different affinities for a galanin peptide, different specificities for a galanin peptide, and/or different dissociation rates. The invention provides panels or a series of at least 10, preferably at least 25, at least 50, at least 75, at least 100, at least 125, at least 150, at least 175, at least 200, at least 250, at least 300, at least 350, at least 400, at least 450, at least 500, at least 550, at least 600, at least 650, at least 700, at least 750, at least 800, at least 850, at least 900, at least 950, or at least 1000, antibodies. Panels or a series of antibodies can be used, for example, in multi-well plates for assays such as ELISAs.

In one aspect, the antibodies of the invention are human or humanized antibodies. In another aspect, the antibodies of the invention are conjugated to a detectable agent or therapeutic moiety. In an alternative aspect, the antibodies of the invention are not conjugated to a detectable agent or a therapeutic moiety.

The present invention encompasses treatment protocols for disorders associated with or characterized by aberrant expression and/or activity of a galanin peptide, disorders associated with or characterized by aberrant expression and/or activity of a galanin receptor or hyperproliferative disorders (e.g., cancer), or one or more symptoms thereof. In one aspect, the present invention encompasses treatment protocols that provide better prophylactic or therapeutic profiles than current single agent therapies or combination therapies for disorders associated with or characterized by aberrant expression and/or activity of a galanin peptide, disorders associated with or characterized by aberrant expression and/or activity of a galanin receptor or hyperproliferative disorders (e.g., cancer), or one or more symptoms thereof. In particular, the invention provides prophylactic and therapeutic protocols for the prevention, treatment, management, and/or amelioration of disorders associated with or characterized by aberrant expression and/or activity of a galanin peptide, disorders associated with or characterized by aberrant expression and/or activity of a galanin receptor or hyperproliferative disorders (e.g., cancer), or one or more symptoms thereof, comprising administering to a subject an effective amount of one or more of the antibodies of the invention. The invention also provides prophylactic and therapeutic protocols for the prevention, treatment, management, and/or amelioration of disorders associated with or characterized by aberrant expression and/or activity of a galanin peptide, disorders associated with or characterized by aberrant expression and/or activity of a galanin receptor or hyperproliferative disorders (e.g., cancer), or one or more symptoms thereof, comprising administering to a subject an effective amount of one or more antibodies of the invention and an effective amount of at least one therapy (e.g., a prophylactic or therapeutic agent) other than an antibody of the invention.

In one aspect, the present invention provides methods of preventing, treating, managing, and/or ameliorating cancer or one or more symptoms thereof, said method comprising administering an effective amount of one or more galanin antibodies of the invention alone or in combination with an effective amount of one or more therapies (e.g., one or more prophylactic or therapeutic agents) other than antibodies of the invention. In one aspect, the cancer is associated with or characterized by aberrant expression and/or activity of galanin and/or a galanin receptor. In another aspect, the cancer is lung, breast, colon, prostate or ovarian cancer, which can be associated with or characterized by aberrant expression and/or activity of a galanin peptide. Non-limiting examples of the therapies (e.g., prophylactic or therapeutic agents) for the prevention, treatment, management, and/or amelioration of a cancer include anti-angiogenic agents, immunomodulatory agents, anti-cancer agents, and anti-inflammatory agents.

The present invention provides a method of diagnosing, prognosing, or monitoring a disorder characterized by aberrant expression and/or activity of a galanin peptide, a disorder characterized by aberrant expression and/or activity of a galanin receptor or a hyperproliferative disease, comprising assaying the level of galanin in cells or a tissue sample of a subject using a galanin antibody of the invention and comparing the assayed level of galanin with a control level. An increase or decrease in the assayed level of galanin compared to the control level of galanin is indicative of a disorder characterized by aberrant expression and/or activity of a galanin peptide or a disorder characterized by aberrant expression and/or activity of a galanin receptor. The invention also provides for pharmaceutical compositions, kits, and articles of manufacture comprising one or more antibodies that immunospecifically bind to a galanin peptide with or without one or more therapies (e.g., one or more prophylactic or therapeutic agents) other than antibodies of the invention, for use in the prevention, treatment, management, and/or amelioration of a disorder characterized by aberrant expression and/or activity of a galanin peptide, a disorder characterized by aberrant expression and/or activity of a galanin receptor or a hyperproliferative disease, or one or more symptoms thereof. The kits or articles of manufacture may further comprise instructions.

3.1 Terminology

As used herein the term "aberrant" refers to a deviation from the norm, e.g., the average healthy subject and/or a population of average healthy subjects. The term "aberrant expression," as used herein, refers to abnormal expression of a gene product (e.g., RNA, protein, polypeptide, or peptide) by a cell or subject relative to a normal, healthy cell or subject and/or population of normal, healthy cells or subjects. Such aberrant expression may be the result of the amplification of the gene. In one aspect, the term "aberrant expression" refers to abnormal expression of galanin and/or a galanin receptor by a cell or subject relative to the expression of the gene product by a normal, healthy cell or subject and/or population of normal, healthy cells or subjects and encompasses the expression of a galanin gene product and/or galanin receptor gene product at an unusual location within the cell or subject, the expression of a galanin gene product at an altered level in the cell or subject, the expression of a mutated galanin gene product and/or a mutated galanin receptor gene product, or a combination thereof. In another aspect, the term "aberrant expression" refers to the overexpression of a galanin gene product and/or a galanin receptor gene product by a cell or subject relative to the expression of a galanin gene product and/or a galanin receptor gene product by a normal, healthy cell or subject and/or population of normal, healthy cells or subjects. In accordance with this aspect, the overexpression may be the result of gene amplification. The term "aberrant activity," as used herein, refers to an altered level of a gene product, the increase of an activity by a gene product, or the loss of an activity of a gene product in a cell or subject relative to a normal, healthy cell or subject and/or population of normal, healthy cells or subjects. In one aspect, the term "aberrant activity" refers to a galanin activity and/or galanin receptor activity that deviates from that normally found in a healthy cell or subject and/or population of healthy cells or subjects (e.g., an increase in galanin's ability to form a bond with one or more of its receptors). In another aspect, the term "aberrant activity" refers to an increase in a galanin activity and/or galanin receptor activity relative to that normally found in a healthy cell or subject and/or population of healthy cells or subjects. Examples of galanin activity include, but are not limited to, the inhibition of acetylcholine release, the increase in the levels of growth hormone, prolactin and luteinizing hormone, the inhibition of glucose induced insulin release, the increase in $Ca^{2+}$ signaling, the activation of Erk, the increase in cell proliferation, and the resistance to apoptosis.

As used herein, the term "analog" in the context of a proteinaceous agent (e.g., proteins, polypeptides, peptides, and antibodies) refers to a proteinaceous agent that possesses an identical function(s) as a second proteinaceous agent but does not necessarily comprise a similar or identical amino acid sequence of the second proteinaceous agent, or possess a similar or identical structure of the second proteinaceous agent. A proteinaceous agent that has a similar amino acid sequence refers to a second proteinaceous agent that satisfies at least one of the following: (a) a proteinaceous agent having the amino acid sequence that is at least 30%, preferably at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of a second proteinaceous agent; (b) a proteinaceous agent encoded by a nucleotide sequence that hybridizes under stringent conditions to a nucleotide sequence encoding a second proteinaceous agent of at least 5 contiguous amino acid residues, preferably at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues or more; and (c) a proteinaceous agent encoded by a nucleotide sequence that is at least 30%, preferably at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding a second proteinaceous agent. A proteinaceous agent with similar structure to a second proteinaceous agent refers to a proteinaceous agent that has a similar secondary, tertiary or quaternary structure to the second proteinaceous agent. The structure of a proteinaceous agent can be determined by methods known to those skilled in the art, including but not limited to, peptide sequencing, X-ray crystallography, nuclear magnetic resonance, circular dichroism, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/ total number of positions×100%). In one aspect, the two sequences are the same length.

The determination of percent identity between two sequences can also be accomplished using a mathematical algorithm. One non-limiting example of a mathematical algorithm utilized for the comparison of two sequences is the algorithm of Karlin and Altschul, 1990, *Proc. Natl. Acad. Sci. U.S.A.* 87: 2264-2268, modified as in Karlin and Altschul, 1993, *Proc. Natl. Acad. Sci. U.S.A.* 90: 5873-5877. Such an algorithm is incorporated into the NBLAST and XBLAST programs of Altschul et al., 1990, *J. Mol. Biol.* 215: 403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, *Nucleic Acids Res.* 25: 3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another non-limiting example of a mathematical algorithm utilized for the comparison of sequences is the algorithm of Myers and Miller, 1988, *CABIOS* 4: 11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "analog" in the context of a non-proteinaceous analog refers to a second organic or inorganic molecule which possesses a similar or identical function as a first organic or inorganic molecule and is structurally similar to the first organic or inorganic molecule.

As used herein, the terms "antagonist" and "antagonists" refer to any protein, polypeptide, peptide, peptidomimetic, glycoprotein, antibody, carbohydrate, nucleic acid, organic molecule, inorganic molecule, large molecule, or small molecule that blocks, inhibits, reduces or neutralizes the function, activity and/or expression of another molecule. In various aspects, an antagonist reduces the function, activity and/or expression of another molecule by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 99% relative to a control such as phosphate buffered saline (PBS).

As used herein, the terms "antibody" and "antibodies" refer to monoclonal antibodies, multispecific antibodies, human antibodies, humanized antibodies, camelised antibodies, chimeric antibodies, single-chain Fvs (scFv), single chain antibodies, single domain antibodies, Fab fragments, F(ab') fragments, disulfide-linked Fvs (sdFv), and anti-idiotypic (anti-Id) antibodies (including, e.g., anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

As used herein, the terms "anti-galanin antibodies," "galanin antibodies," "antibodies of the invention," and "antibodies of the present invention" refer to the antibodies described in section 5.1.

As used herein, the term "chimeric antibody" refers to a polypeptide comprising at least the antigen binding portion of an antibody molecule linked to at least part of another protein (typically an immunoglobulin constant domain).

As used herein, the terms "C-terminus of a galanin peptide" and "carboxy terminus of a galanin peptide" refer to amino acid residues 19 through the carboxy terminal amino acid residue of the mature processed form of galanin from any species.

As used herein, the term "derivative" in the context of a proteinaceous agent (e.g., proteins, polypeptides, peptides, and antibodies) refers to a proteinaceous agent that comprises the amino acid sequence which has been altered by the introduction of amino acid residue substitutions, deletions, and/or additions. The term "derivative" as used herein also refers to a proteinaceous agent which has been modified, i.e., by the covalent attachment of a type of molecule to the proteinaceous agent. For example, but not by way of limitation, a derivative of a proteinaceous agent may be produced, e.g., by glycosylation, acetylation, pegylation, phosphorylation, amidation, derivatization by known protecting/blocking groups, proteolytic cleavage, linkage to a cellular ligand or other protein, etc. A derivative of a proteinaceous agent may also be produced by chemical modifications using techniques known to those of skill in the art, including, but not limited to specific chemical cleavage, acetylation, formylation, metabolic synthesis of tunicamycin, etc. Further, a derivative of a proteinaceous agent may contain one or more non-classical amino acids. A derivative of a proteinaceous agent possesses an identical function(s) as the proteinaceous agent from which it was derived.

As used herein, the term "derivative" in the context of a non-proteinaceous derivative refers to a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl, nitryl, or amine group. An organic molecule may also, for example, be esterified, alkylated and/or phosphorylated.

As used herein, the terms "disease" and "disorder" are used interchangeably to refer to a condition in a subject.

As used herein, the term "effective amount" refers to the amount of a therapy (e.g., a prophylactic or therapeutic agent) which is sufficient to reduce and/or ameliorate the severity and/or duration of a disorder associated with aberrant expression and/or activity of galanin and/or a galanin receptor (e.g., a hyperproliferative disorder, Alzheimer's disease, depression and eating disorders) or a symptom thereof, prevent the advancement of said disorder, cause regression of said disorder, prevent the recurrence, development, or onset of one or more symptoms associated with said disorder, or enhance or improve the prophylactic or therapeutic effect(s) of another therapy (e.g., prophylactic or therapeutic agent).

As used herein, the term "epitopes" refers to sites or fragments of a polypeptide or protein having antigenic or immunogenic activity in an animal, in one aspect, in a mammal, and, in one aspect, in a human. An epitope having immunogenic activity is a site or fragment of a polypeptide or protein that elicits an antibody response in an animal. An epitope having antigenic activity is a site or fragment of a polypeptide or protein to which an antibody immunospecifically binds as determined by any method well-known to one of skill in the art, for example by immunoassays.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, at least 200 contiguous amino acid residues, or at least 250 contiguous amino acid residues of the polypeptide or protein. In another aspect, a fragment of a protein or polypeptide retains at least one function of the protein or polypeptide. In another aspect, a fragment of a polypeptide or protein retains at least two, three, four, or five functions of the polypeptide or protein. In one aspect, a fragment of an antibody that immunospecifically binds to galanin peptide retains the ability to immunospecifically bind to galanin peptide.

As used herein, the term "fusion protein" refers to a polypeptide or protein that comprises the amino acid sequence of a first polypeptide or protein or fragment, analog or derivative thereof, and the amino acid sequence of a heterologous polypeptide or protein (i.e., a second polypeptide or protein or fragment, analog or derivative thereof different than the first polypeptide or protein or fragment, analog or derivative thereof, or not normally part of the first polypeptide or protein or fragment, analog or derivative thereof). In one aspect, a fusion protein comprises a prophylactic or therapeutic agent fused to a heterologous protein, polypeptide or peptide. In accordance with this aspect, the heterologous protein, polypeptide or peptide may or may not be a different type of prophylactic or therapeutic agent. For example, two different proteins, polypeptides, or peptides with immunomodulatory activity may be fused together to form a fusion protein. In one aspect, fusion proteins retain or have improved activity relative to the activity of the original polypeptide or protein prior to being fused to a heterologous protein, polypeptide, or peptide.

As used herein, the term "galanin peptide" refers to galanin, an analog, derivative or a fragment thereof, or a fusion protein comprising galanin, an analog, derivative or a fragment thereof. The galanin peptide may be from any species. In certain aspects, the term "galanin peptide" refers to the mature, processed form of galanin. In other aspects, the term "galanin peptide" refers to an immature form of galanin (e.g., preproprotein and preprotein galanin). In accordance with this aspect, the antibodies of the invention immunospecifically bind to the portion of the immature form of galanin that corresponds to the mature, processed form of galanin.

The nucleotide and/or amino acid sequences of galanin peptides can be found in the literature or public databases, or the nucleotide and/or amino acid sequences can be determined using cloning and sequencing techniques known to one of skill in the art. For example, the nucleotide sequence of human galanin can be found in the GenBank database (see, e.g., Accession Nos. A28025 and NM_015973). The amino acid sequence of human galanin can be found in the GenBank database (see, e.g., Accession Nos. CAA01907, NP_057057, P22466. and AAH30241). Additional non-limiting examples of amino acid sequences of galanin are listed in Table 1, infra. In a specific aspect, a galanin peptide is galanin from any species. In another aspect, a galanin peptide is human galanin.

TABLE 1

| Species of Galanin | Accession No. |
|---|---|
| Bos taurus (precursor protein; mature form of galanin consists of amino acid residues 33-61) | NP_776339 |
| Homo sapiens (preproprotein) | AAH30241 |
| Homo sapiens | AAB20740 (SEQ ID NO:150) |
| Rattus norvegicus (precursor protein; mature form of galanin consists of amino acid residues 33-62) | NP_150240 |
| Rattus norvegicus (precursor protein) | RHRTN |
| Mus musculus (precursor protein) | NP_034383 |
| Mus musculus (precursor protein) | S34301 |
| Rana ridibunda | P47216 |
| Alligator mississippiensis | P47215 |
| Sus scrofa domestica (precursor protein; mature form of galanin consists of amino acid residues 33-61) | RHPGN |
| Bovine (precursor protein; mature form of galanin consists of amino acid residues 33-61) | RHBOG |
| Ovis aries | P31234 |
| Gallus gallus | P30802 |
| Amia calva | P47214 |
| Oncorhynchus mykiss | P47213 |

As used herein, the terms "galanin receptor" and "GALR" refer to a galanin receptor (e.g., GALR1, GALR2 and/or GALR3) or an analog, derivative, or fragment thereof, or a fusion protein comprising a galanin receptor, an analog, derivative, or a fragment thereof. The GALR may be from any species. The nucleotide and/or amino acid sequences of the GALR can be found in the literature or in public databases, or the nucleotide and/or amino acid sequences can be determined using cloning and sequencing techniques known to one of skill in the art. For example, the nucleotide sequence of human GALR1, human GALR2 and human GALR3 can be found in the GenBank database (see, e.g., Accession Nos. NM_001480, AF080586 and NM_003857, respectively). The amino acid sequence of human GALR1, human GALR2 and human GALR3 can be found in the GenBank database (see, e.g., Accession Nos. NP_001471, NP_003848, and O60755, respectively). Additional non-limiting examples of amino acid sequences of galanin receptors are listed in Table 2, infra. In one aspect, a galanin receptor is a galanin receptor from any species. In one aspect, a GALR is a human GALR.

TABLE 2

| Galanin Receptor | Accession No. |
|---|---|
| Homo sapiens galanin receptor 1 | I59336 |
| Homo sapiens galanin receptor 2 | O43603 |
| Homo Sapiens Galanin receptor 2 | JC5949 |
| Homo Sapiens Galanin receptor 3 | O60755 |
| Homo Sapiens Galanin receptor 3 | NP_003605 |
| Rattus norvegicus Galanin receptor 1 | NP_037090 |
| Rattus norvegicus Galanin receptor 2 | NP_062045 |
| Rattus norvegicus Galanin receptor 3 | XP_346808 |
| Rattus norvegicus Galanin receptor 3 | NP_062046 |
| Mus musculus Galanin receptor 1 | P56479 |
| Mus musculus Galanin receptor 1 | NP_032108 |
| Mus musculus Galanin receptor 2 | AAC36589 |
| Mus musculus Galanin receptor 3. | NP_056553 |

As used herein, the term "host cell" includes a particular subject cell transfected or transformed with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

As used herein, the term "human adult" or "adult" refers to a human 18 years of age or older.

As used herein, the terms "human child" or "child" or variations thereof refer to a human between 24 months of age and 18 years of age.

As used herein, the terms "elderly human," "elderly," or variations thereof refer to a human 65 years old or older, preferably 70 years old or older.

As used herein, the terms "human infant" or "infant" or variations thereof refer to a human less than 24 months of age, preferably less than 12 months, less than 6 months, less than 3 months, less than 2 months, or less than 1 month of age.

As used herein, the terms "human infant born prematurely," "preterm infant," or "premature infant," or variations thereof refer to a human born at less than 40 weeks of gestational age, preferably less than 35 weeks gestational age, who is less than 6 months old, preferably less than 3 months old, more preferably less than 2 months old, and most preferably less than 1 month old.

As used herein, the term "humanized" antibody refers to an immunoglobulin variant or fragment thereof, which is capable of binding to a predetermined antigen and which comprises FR regions having substantially the amino acid sequence of a human immunoglobulin and CDRs having substantially the amino acid sequence of a non-human immunoglobulin. Ordinarily, a humanized antibody has one or more amino acid residues introduced into it from a source that is non-human. In general, the humanized antibody will include substantially all of at least one, and typically two, variable domains (Fab, Fab', F(ab')$_2$, Fabc, Fv) in which all or substantially all of the CDR regions correspond to those of a non-human immunoglobulin and all or substantially all of the FR regions are those of a human immunoglobulin consensus sequence. The humanized antibody optimally comprises at least a portion of an immunoglobulin constant region (Fc), typically that of a human immunoglobulin. Generally, the antibody will contain both the light chain as well as at least the variable domain of a heavy chain. The humanized antibody can be selected from any class of immunoglobulins, including IgM, IgG, IgD, IgA and IgE, and any isotype, including IgG$_1$, IgG$_2$, IgG$_3$ and IgG$_4$. The humanized antibody may comprise sequences from more than one class or isotype, and selecting particular constant domains to optimize desired effector functions is within the ordinary skill in the art.

As used herein, the term "hybridizes under stringent conditions" describes conditions for hybridization and washing under which nucleotide sequences at least 30% (preferably, 35%, 40%, 45%, 50%, 55%, 60%, 65%, 70%, 75%, 80%, 85%, 90%, 95% or 98%) identical to each other typically remain hybridized to each other. Such stringent conditions are known to those skilled in the art and can be found in *Current Protocols in Molecular Biology*, John Wiley & Sons, N.Y. (1989), 6.3.1-6.3.6.

Generally, stringent conditions are selected to be about 5 to 10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (for example, 10 to 50 nucleotides) and at least about 60° C. for long probes (for example, greater than 50 nucleotides). Stringent conditions may also be achieved with the addition of destabilizing agents, for example, formamide. For selective or specific hybridization, a positive signal is at least two times background, preferably 10 times background hybridization.

In one, non-limiting example stringent hybridization conditions are hybridization at 6x sodium chloride/sodium citrate (SSC) at about 45° C., followed by one or more washes in 0.1xSSC, 0.2% SDS at about 68° C. In one non-limiting example stringent hybridization conditions are hybridization in 6xSSC at about 45° C., followed by one or more washes in 0.2xSSC, 0.1% SDS at 50-65° C. (i.e., one or more washes at 50° C., 55° C., 60° C. or 65° C.). It is understood that the nucleic acids of the invention do not include nucleic acid molecules that hybridize under these conditions solely to a nucleotide sequence consisting of only A or T nucleotides.

As used herein, the term "immunomodulatory agent" and variations of the term, including, but not limited to, "immunomodulatory agents," "immunomodulants" or "immunomodulatory drugs," refer to an agent that modulates a host's immune system. In one aspect, an immunomodulatory agent is an agent that alters one aspect of a subject's immune response. In certain aspects, an immunomodulatory agent is an agent that inhibits or reduces a subject's immune system (i.e., an immunosuppressant agent). In certain other aspects, an immunomodulatory agent is an agent that activates or increases a subject's immune system (i.e., an immunostimulatory agent). In accordance with the invention, an immunomodulatory agent used in the combination therapies of the invention does not include an antibody of the invention. Immunomodulatory agents include, but are not limited to, small molecules, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides), antibodies, synthetic or natural inorganic molecules, mimetic agents, and synthetic or natural organic molecules.

As used herein, the term "immunospecifically binds to an antigen" and analogous terms refer to peptides, polypeptides, proteins, fusion proteins and antibodies that specifically bind to an antigen or a fragment and do not specifically bind to other antigens. A peptide, polypeptide, protein, or antibody that immunospecifically binds to an antigen may bind to other peptides, polypeptides, or proteins with lower affinity as determined by, e.g., immunoassays, BIAcore, or other assays known in the art. In one aspect, a peptide, polypeptide, protein or antibody that immunospecifically binds to an antigen of interest binds to other antigens with an affinity constant of less than $10^6$ $M^{-1}$ as determined by a BIAcore assay under standard assay conditions, and in particular the BIAcore kinetic assay described in Section 5.6.1. Antibodies that immunospecifically bind to an antigen may be cross-reactive with related antigens. In one aspect, antibodies that immunospecifically bind to an antigen do not cross-react with other antigens. An antibody binds specifically to an antigen when it binds to an antigen with higher affinity than to any cross-reactive antigen as determined using experimental techniques, such as radioimmunoassays (RIA) and enzyme-linked immunosorbent assays (ELISAs). See, e.g., Paul, ed., 1989, Fundamental Immunology, 2nd ed., Raven Press, New York at pages 332-336 for a discussion regarding antibody specificity. In one aspect, an antibody binds specifically to an antigen when it has an affinity constant for the antigen of at least $10^7$ $M^{-1}$ as determined by a BIAcore assay under standard assay conditions, and in particular the BIAcore kinetic assay described in Section 5.6.1.

As used herein, the term "immunospecifically binds to a galanin peptide" and analogous terms refer to peptides, polypeptides, proteins, fusion proteins, and antibodies that specifically bind to a galanin peptide and do not specifically bind to other peptides. The term "immunospecifically binds to a galanin receptor" and analogous terms refer to peptides, polypeptides, proteins, fusion proteins, and antibodies that specifically bind to one or more galanin receptors and do not specifically bind to other receptors. A peptide, polypeptide, protein, or antibody that immunospecifically binds to a galanin peptide or a galanin receptor may bind to other peptides, polypeptides, or proteins with lower affinity as determined by, e.g., immunoassays, BIAcore, or other assays known in the art. In one aspect, a peptide, polypeptide, protein or antibody that immunospecifically binds to a galanin peptide or a galanin receptor binds to other antigens with an affinity constant of less than $10^6$ $M^{-1}$ as determined by a BIAcore assay under standard assay conditions, and in particular the BIAcore kinetic assay described in Section 5.6.1. Antibodies that immunospecifically bind to a galanin peptide or a galanin receptor may be cross-reactive with related antigens. In one aspect, antibodies that immunospecifically bind to a galanin peptide or a galanin receptor thereof do not cross-react with other antigens. Antibodies or antibody fragments that immunospecifically bind to a galanin peptide or a galanin receptor can be identified, for example, by immunoassays, BIAcore, or other techniques known to those of skill in the art. An antibody binds specifically to a galanin peptide or a galanin receptor when it binds to a galanin peptide or a galanin receptor with higher affinity than to any cross-reactive antigen as determined using experimental techniques, such as radioimmunoassays (RIA) and enzyme-linked immunosorbent assays (ELISAs). See, e.g., Paul, ed., 1989, Fundamental Immunology, 2nd ed., Raven Press, New York at pages 332-336 for a discussion regarding antibody specificity. In one aspect, an antibody binds specifically to a galanin peptide or a galanin receptor when it has an affinity constant for the galanin peptide or galanin receptor, respectively, of at least $10^7$ $M^{-1}$ as determined by a BIAcore assay under standard assay conditions, and in particular the BIAcore kinetic assay described in Section 5.6.1. In one aspect, an antibody that immunospecifically binds to a galanin receptor specifically binds to one type of galanin receptor and does not bind or cross-react with the other types of galanin receptors. In another aspect, an antibody that immunospecifically binds to a galanin peptide that is a fusion protein specifically binds to the portion of the fusion protein that is galanin. In another aspect, an antibody that immunospecifically binds to a galanin receptor that is a fusion protein specifically binds to the portion of the fusion protein that is a GALR1, GALR2 and/or GALR3.

As used herein, the term "in combination" refers to the use of more than one therapy (e.g., more than one prophylactic agent and/or therapeutic agent). The use of the term "in combination" does not restrict the order in which therapies (e.g., prophylactic and/or therapeutic agents) are administered to a subject with a disorder associated with aberrant expression and/or activity of galanin and/or a galanin receptor (e.g., a hyperproliferative disorder, Alzheimer's disease, depression and eating disorders). A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a second prophylactic or therapeutic agent) to a subject with a disorder associated with aberrant expression and/or activity of galanin and/or a galanin receptor (e.g., a hyperproliferative disorder, Alzheimer's disease, depression and eating disorders).

As used herein, the term "isolated" in the context of an organic or inorganic molecule (whether it be a small or large molecule), other than a proteinaceous agent or a nucleic acid, refers to an organic or inorganic molecule substantially free of a different organic or inorganic molecule. In one aspect, an organic or inorganic molecule is 60%, 65%, 70%, 75%, 80%, 85%, 90%, 95%, or 99% free of a second, different organic or inorganic molecule. In one aspect, an organic and/or inorganic molecule is isolated.

As used herein, the term "isolated" in the context of a proteinaceous agent (e.g., a peptide, polypeptide, fusion protein, or antibody) refers to a proteinaceous agent which is substantially free of cellular material or contaminating proteins from the cell or tissue source from which it is derived, or substantially free of chemical precursors or other chemicals when chemically synthesized. The language "substantially free of cellular material" includes preparations of a proteinaceous agent in which the proteinaceous agent is separated from cellular components of the cells from which it is isolated or recombinantly produced. Thus, a proteinaceous agent that is substantially free of cellular material includes preparations of a proteinaceous agent having less than about 30%, 20%, 10%, or 5% (by dry weight) of heterologous protein, polypeptide, peptide, or antibody (also referred to as a "contaminating protein"). When the proteinaceous agent is recombinantly produced, it is also can be substantially free of culture medium, i.e., culture medium represents less than about 20%, 10%, or 5% of the volume of the proteinaceous agent preparation. When the proteinaceous agent is produced by chemical synthesis, it can be substantially free of chemical precursors or other chemicals, i.e., it is separated from chemical precursors or other chemicals which are involved in the synthesis of the proteinaceous agent. Accordingly, such preparations of a proteinaceous agent have less than about 30%, 20%, 10%, 5% (by dry weight) of chemical precursors or compounds other than the proteinaceous agent of interest. In one aspect, proteinaceous agents disclosed herein are isolated. In another aspect, an antibody of the invention is isolated.

As used herein, the term "isolated" in the context of nucleic acid molecules refers to a nucleic acid molecule which is separated from other nucleic acid molecules which are present in the natural source of the nucleic acid molecule. Moreover, an "isolated" nucleic acid molecule, such as a cDNA molecule, it can be substantially free of other cellular material, or culture medium when produced by recombinant techniques, or substantially free of chemical precursors or other chemicals when chemically synthesized. In one aspect, nucleic acid molecules are isolated. In another aspect, a nucleic acid molecule encoding an antibody of the invention is isolated.

As used herein, the terms "manage," "managing," and "management" refer to the beneficial effects that a subject derives from a therapy (e.g., a prophylactic or therapeutic agent), which does not result in a cure of the disease. In certain aspects, a subject is administered one or more therapies (e.g., one or more prophylactic or therapeutic agents) to "manage" a disease so as to prevent the progression or worsening of the disease.

As used herein, the terms "non-responsive" and "refractory" describe patients treated with a currently available therapy (e.g., prophylactic or therapeutic agent) for a disorder associated with aberrant expression and/or activity of galanin and/or a galanin receptor (e.g., a hyperproliferative disorder, Alzheimer's disease, depression and eating disorders) which is not clinically adequate to relieve one or more symptoms associated with the disorder. Typically, such patients suffer from severe, persistently active disease and require additional therapy to ameliorate the symptoms associated with the disease.

As used herein, the phrase "pharmaceutically acceptable" means approved by a regulatory agency of the federal or a state government, or listed in the U.S. Pharmacopeia, European Pharmacopeia, or other generally recognized pharmacopeia for use in animals, and more particularly, in humans.

As used herein, the terms "prevent," "preventing," and "prevention" refer to the inhibition of the development or onset of a disorder associated with aberrant expression and/or activity of galanin and/or a galanin receptor (e.g., a hyperproliferative disorder, Alzheimer's disease, depression and eating disorders) or the prevention of the recurrence, onset, or development of one or more symptoms of a disorder associated with aberrant expression and/or activity of galanin and/or a galanin receptor (e.g., a hyperproliferative disorder, Alzheimer's disease, depression and eating disorders) in a subject resulting from the administration of a therapy (e.g., a prophylactic or therapeutic agent), or the administration of a combination of therapies (e.g., a combination of prophylactic or therapeutic agents).

As used herein, the terms "prophylactic agent" and "prophylactic agents" refer to any agent(s) which can be used in the prevention of a disorder associated with aberrant expression and/or activity of galanin and/or a galanin receptor (e.g., a hyperproliferative disorder, Alzheimer's disease, depression and eating disorders) or one or more of the symptoms thereof. In certain aspects, the term "prophylactic agent" refers to an antibody that immunospecifically binds to a galanin peptide. In certain other aspects, the term "prophylactic agent" refers to an agent other than an antibody that immunospecifically binds to a galanin peptide. In one aspect, a prophylactic agent is an agent which is known to be useful to or has been or is currently being used to the prevent or impede the onset, development, progression and/or severity of a disorder associated with aberrant expression and/or activity of galanin and/or a galanin receptor (e.g., a hyperproliferative disorder, Alzheimer's disease, depression and eating disorders) or one or more symptoms thereof.

As used herein, the term "prophylactically effective amount" refers to the amount of a therapy (e.g., prophylactic agent) which is sufficient to result in the prevention of the development, recurrence, or onset of a disorder associated with aberrant expression and/or activity of galanin and/or a galanin receptor (e.g., a hyperproliferative disorder, Alzheimer's disease, depression and eating disorders) or one or more symptoms thereof, or to enhance or improve the prophylactic effect(s) of another therapy (e.g., a prophylactic agent).

As used herein, the term "prophylactic protocol" refers to a regimen for dosing and timing the administration of one or more therapies (e.g., one or more prophylactic agents) that has a prophylactic effect.

As used herein, a "protocol" includes dosing schedules and dosing regimens. The protocols herein are methods of use and include prophylactic and therapeutic protocols.

As used herein, the phrase "side effects" encompasses unwanted and adverse effects of a prophylactic or therapeutic agent. Side effects are always unwanted, but unwanted effects are not necessarily adverse. An adverse effect from a therapy (e.g., a prophylactic or therapeutic agent) might be harmful, uncomfortable, or risky.

As used herein, the term "small molecules" and analogous terms include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such agents.

As used herein, the terms "subject" and "patient" are used interchangeably. As used herein, the terms "subject" and "subjects" refer to an animal, in one aspect, a mammal including a non-primate (e.g., a cow, pig, horse, cat, dog, rat, and mouse) and a primate (e.g., a monkey, such as a cynomolgous monkey, chimpanzee, and a human), and, in one aspect, a human. In one aspect, the subject is a mammal, for example, a human, with a hyperproliferative disorder. In another aspect, the subject is a farm animal (e.g., a horse, pig, or cow), a pet (e.g., a guinea pig, dog or cat), or a laboratory animal (e.g., an animal model) with a hyperproliferative disorder. In another aspect, the subject is a mammal, for example, a human, at risk of developing a hyperproliferative disorder (e.g., an immunocompromised or immunosuppressed mammal, or a genetically predisposed mammal). In another aspect, the subject is not an immunocompromised or immunosuppressed mammal, for example, a human. In another aspect, the subject is a mammal, for example, a human, with a lymphocyte count that is not under approximately 500 cells/mm$^3$. In another aspect, the subject is a human infant or a human infant born prematurely. In another aspect, the subject is a human child or a human adult. In another aspect, the subject is a human child. In another aspect, the subject is an elderly human. In yet another aspect, the subject is a human in an institution or group home, such as, but not limited to, a nursing home.

As used herein, the term "synergistic" refers to a combination of therapies (e.g., prophylactic or therapeutic agents) which is more effective than the additive effects of any two or more single therapies (e.g., one or more prophylactic or therapeutic agents). A synergistic effect of a combination of therapies (e.g., a combination of prophylactic or therapeutic agents) permits the use of lower dosages of one or more of therapies (e.g., one or more prophylactic or therapeutic agents) and/or less frequent administration of said therapies to a subject with a disorder associated with aberrant expression and/or activity of galanin and/or a galanin receptor (e.g., a hyperproliferative disorder, Alzheimer's disease, depression and eating disorders). The ability to utilize lower dosages of therapies (e.g., prophylactic or therapeutic agents) and/or to administer said therapies less frequently reduces the toxicity associated with the administration of said therapies to a subject without reducing the efficacy of said therapies in the prevention or treatment of a disorder associated with aberrant expression and/or activity of galanin and/or a galanin receptor (e.g., a hyperproliferative disorder, Alzheimer's disease, depression and eating disorders). In addition, a synergistic effect can result in improved efficacy of therapies (e.g., prophylactic or therapeutic agents) in the prevention or treatment of a disorder associated with aberrant expression and/or activity of galanin and/or a galanin receptor (e.g., a hyperproliferative disorder, Alzheimer's disease, depression and eating disorders). Finally, synergistic effect of a combination of therapies (e.g., prophylactic or therapeutic agents) may avoid or reduce adverse or unwanted side effects associated with the use of any single therapy.

As used herein, the terms "therapeutic agent" and "therapeutic agents" refer to any agent(s) which can be used in the prevention, treatment, management, or amelioration of a disorder associated with aberrant expression and/or activity of galanin and/or a galanin receptor (e.g., a hyperproliferative disorder, Alzheimer's disease, depression and eating disorders) or one or more symptoms thereof. In certain aspects, the term "therapeutic agent" refers to an antibody that immunospecifically binds to a galanin peptide. In certain other aspects, the term "therapeutic agent" refers an agent other than an antibody that immunospecifically binds to a galanin peptide. In one aspect, a therapeutic agent is an agent which is known to be useful for, or has been or is currently being used for the prevention, treatment, management, or amelioration of a disorder associated with aberrant expression and/or activity of galanin and/or a galanin receptor (e.g., a hyperproliferative disorder, Alzheimer's disease, depression and eating disorders) or one or more symptoms thereof.

As used herein, the term "therapeutically effective amount" refers to the amount of a therapy (e.g., an antibody that immunospecifically binds to a galanin peptide), which is sufficient to reduce the severity of a disorder associated with aberrant expression and/or activity of galanin and/or a galanin receptor (e.g., a hyperproliferative disorder, Alzheimer's disease, depression and eating disorders), reduce the duration of a disorder associated with aberrant expression and/or activity of galanin and/or a galanin receptor (e.g., a hyperproliferative disorder, Alzheimer's disease, depression and eating disorders), ameliorate one or more symptoms of a disorder associated with aberrant expression and/or activity of galanin and/or a galanin receptor (e.g., a hyperproliferative disorder, Alzheimer's disease, depression and eating disorders), prevent the advancement of a disorder associated with aberrant expression and/or activity of galanin and/or a galanin receptor (e.g., a hyperproliferative disorder, Alzheimer's disease, depression and eating disorders), cause regression of a disorder associated with aberrant expression and/or activity of galanin and/or a galanin receptor (e.g., a hyperproliferative disorder, Alzheimer's disease, depression and eating disorders), or enhance or improve the therapeutic effect(s) of another therapy.

As used herein, the terms "therapies" and "therapy" can refer to any protocol(s), method(s), and/or agent(s) that can be used in the prevention, treatment, management, or amelioration of a disorder associated with aberrant expression and/or activity of galanin and/or a galanin receptor (e.g., a hyperproliferative disorder, Alzheimer's disease, depression and eating disorders) or one or more symptoms thereof. In certain aspects, the terms "therapies" and "therapy" refer to anti-cancer therapy, biological therapy, supportive therapy, and/or other therapies useful in treatment, management, prevention, or amelioration of a hyperproliferative disorder or one or more symptoms thereof known to one of skill in the art such as medical personnel.

As used herein, the term "therapeutic protocol" refers to a regimen for dosing and timing the administration of one or more therapies (e.g., therapeutic agents) that has a therapeutic effect.

As used herein, the terms "treat," "treatment," and "treating" refer to the eradication, removal, modification, or control of primary, regional, or metastatic cancer tissue, or the reduction or amelioration of the progression, severity, and/or duration of a disorder associated with aberrant expression and/or activity of galanin and/or a galanin receptor (e.g., a hyperproliferative disorder, Alzheimer's disease, depression and eating disorders) or amelioration of one or more symptoms thereof resulting from the administration of one or more therapies (including, but not limited to, the administration of one or more prophylactic or therapeutic agents). In certain aspects, such terms in the context of a hyperproliferative disorder (e.g., cancer) refer to a reduction in the growth of hyperproliferative cells (e.g., cancerous cells), a decrease in number of hyperproliferative cells (e.g., cancerous cells and/or a reduction in the growth, formation and/or volume of a tumor. In accordance with this aspect, a reduction in the growth or numbers of hyperproliferative cells can be determined by contacting the cells with a therapy of interest (e.g., a galanin antibody of the invention) or a control (e.g., PBS) and measuring in vitro the effect of the therapy relative to the control on the growth or proliferation of the cells by, e.g., $^3$H-thymidine assays or trypan blue assays. Further, in accordance with this aspect, a reduction of growth, formation and/or volume of a tumor can be determined by contacting a tumor with a therapy of interest (e.g., a galanin antibody of the invention) or a control (e.g., PBS) and measuring the effect of the therapy relative to the control on the size or volume of the tumor using standard assays known in the art or described herein. In other aspects, such terms refer to the minimizing or delay of the spread of cancer resulting from the administration of one or more therapies to a subject with such a disease.

4. BRIEF DESCRIPTION OF THE DRAWINGS

FIGS. 1A-B show the amino acid sequences of the (A) variable heavy domain (SEQ ID NO:18) of murine 5B4 with the VH CDR1 (SEQ ID NO:1), the VH CDR2 (SEQ ID NO:2), and the VH CDR3 (SEQ ID NO:3) underlined, starting in order from VH CDR1 at the far left; and (B) variable light domain (SEQ ID NO:19) of murine 5B4 with the VL CDR1 (SEQ ID NO:4), the VL CDR2 (SEQ ID NO:5), and the VL CDR3 (SEQ ID NO:6) underlined, starting in order from VL CDR1 at the far left.

FIGS. 2A-B show the nucleic acid sequences of the (A) variable heavy domain (SEQ ID NO:142) of murine 5B4 with the VH CDR1 (SEQ ID NO:143), the VH CDR2 (SEQ ID NO:144), and the VH CDR3 (SEQ ID NO:145) underlined, starting in order from VH CDR1 at the far left; and (B) variable light domain (SEQ ID NO:146) of murine 5B4 with the VL CDR1 (SEQ ID NO:147), the VL CDR2 (SEQ ID NO:148), and the VL CDR3 (SEQ ID NO:149) underlined, starting in order from VL CDR1 at the far left.

FIGS. 3A-B show the amino acid sequences of the (A) variable heavy domain (SEQ ID NO:28) of murine 1G12 with the VH CDR1 (SEQ ID NO:7), the VH CDR2 (SEQ ID NO:8), and the VH CDR3 (SEQ ID NO:9) underlined, starting in order from VH CDR1 at the far left; and (B) variable light domain (SEQ ID NO:29) of murine 1G12 with the VL CDR1 (SEQ ID NO:10), the VL CDR2 (SEQ ID NO:5), and the VL CDR3 (SEQ ID NO:6) underlined, starting in order from VL CDR1 at the far left.

FIGS. 4A-B show the nucleic acid sequences of the (A) variable heavy domain (SEQ ID NO:30) of murine 1G12 with the VH CDR1 (SEQ ID NO:31), the VH CDR2 (SEQ ID NO:32), and the VH CDR3 (SEQ ID NO:33) underlined, starting in order from VH CDR1 at the far left; and (B) variable light domain (SEQ ID NO:34) of murine 1G12 with the VL CDR1 (SEQ ID NO:35), the VL CDR2 (SEQ ID NO:36), and the VL CDR3 (SEQ ID NO:37) underlined, starting in order from VL CDR1 at the far left.

FIGS. 5A-B show the amino acid sequences of the (A) variable heavy domain (SEQ ID NO:38) of murine 2F8 with the VH CDR1 (SEQ ID NO:11), the VH CDR2 (SEQ ID NO:2), and the VH CDR3 (SEQ ID NO:3) underlined, starting in order from VH CDR1 at the far left; and (B) variable light domain (SEQ ID NO:105) of murine 2F8 with the VL CDR1 (SEQ ID NO:4), the VL CDR2 (SEQ ID NO:5), and the VL CDR3 (SEQ ID NO:6) underlined, starting in order from VL CDR1 at the far left.

FIGS. 6A-B show the nucleic acid sequences of the (A) variable heavy domain (SEQ ID NO:39) of murine 2F8 with the VH CDR1 (SEQ ID NO:40), the VH CDR2 (SEQ ID NO:41), and the VH CDR3 (SEQ ID NO:42) underlined, starting in order from VH CDR1 at the far left; and (B) variable light domain (SEQ ID NO:43) of murine 2F8 with the VL CDR1 (SEQ ID NO:44), the VL CDR2 (SEQ ID NO:45), and the VL CDR3 (SEQ ID NO:46) underlined, starting in order from VL CDR1 at the far left.

FIGS. 7A-B show the amino acid sequences of the (A) variable heavy domain (SEQ ID NO:47) of murine 1D7 with the VH CDR1 (SEQ ID NO:7), the VH CDR2 (SEQ ID NO:12), and the VH CDR3 (SEQ ID NO:9) underlined, starting in order from VH CDR1 at the far left; and (B) variable light domain (SEQ ID NO:48) of murine 1D7 with the VL CDR1 (SEQ ID NO:13), the VL CDR2 (SEQ ID NO:5), and the VL CDR3 (SEQ ID NO:6) underlined, starting in order from VL CDR1 at the far left.

FIGS. 8A-B show the nucleic acid sequences of the (A) variable heavy domain (SEQ ID NO:49) of murine 1D7 with the VH CDR1 (SEQ ID NO:50), the VH CDR2 (SEQ ID NO:51), and the VH CDR3 (SEQ ID NO:52) underlined, starting in order from VH CDR1 at the far left; and (B) variable light domain (SEQ ID NO:53) of murine 1D7 with the VL CDR1 (SEQ ID NO:54), the VL CDR2 (SEQ ID NO:55), and the VL CDR3 (SEQ ID NO:56) underlined, starting in order from VL CDR1 at the far left.

FIGS. 9A-B show the amino acid sequences of the (A) variable heavy domain (SEQ ID NO:104) of murine 4B3 with the VH CDR1 (SEQ ID NO:7), the VH CDR2 (SEQ ID NO:12), and the VH CDR3 (SEQ ID NO:9) underlined, starting in order from VH CDR1 at the far left; and (B) variable light domain (SEQ ID NO:106) of murine 4B3 with the VL CDR1 (SEQ ID NO:13), the VL CDR2 (SEQ ID NO:5), and the VL CDR3 (SEQ ID NO:6) underlined, starting in order from VL CDR1 at the far left.

FIGS. 10A-B show the nucleic acid sequences of the (A) variable heavy domain (SEQ ID NO:57) of murine 4B3 with the VH CDR1 (SEQ ID NO:58), the VH CDR2 (SEQ ID NO:59), and the VH CDR3 (SEQ ID NO:60) underlined, starting in order from VH CDR1 at the far left; and (B) variable light domain (SEQ ID NO:61) of murine 4B3 with the VL CDR1 (SEQ ID NO:62), the VL CDR2 (SEQ ID NO:63), and the VL CDR3 (SEQ ID NO:64) underlined, starting in order from VL CDR1 at the far left.

FIGS. 11A-B show the amino acid sequences of the (A) variable heavy domain (SEQ ID NO:65) of murine 2H9 with the VH CDR1 (SEQ ID NO:7), the VH CDR2 (SEQ ID NO:14), and the VH CDR3 (SEQ ID NO:9) underlined, starting in order from VH CDR1 at the far left; and (B) variable light domain (SEQ ID NO:107) of murine 2H9 with the VL CDR 1 (SEQ ID NO:13), the VL CDR2 (SEQ ID NO:5), and the VL CDR3 (SEQ ID NO:6) underlined, starting in order from VL CDR1 at the far left.

FIGS. 12A-B show the nucleic acid sequences of the (A) variable heavy domain (SEQ ID NO:66) of murine 2H9 with the VH CDR1 (SEQ ID NO:67), the VH CDR2 (SEQ ID NO:68), and the VH CDR3 (SEQ ID NO:69) underlined, starting in order from VH CDR1 at the far left; and (B) variable light domain (SEQ ID NO:70) of murine 2H9 with the VL CDR1 (SEQ ID NO:71), the VL CDR2 (SEQ ID NO:72), and the VL CDR3 (SEQ ID NO:73) underlined, starting in order from VL CDR1 at the far left.

FIGS. 13A-B show the amino acid sequences of the (A) variable heavy domain (SEQ ID NO:74) of murine 1A1 with the VH CDR1 (SEQ ID NO:15), the VH CDR2 (SEQ ID NO:16), and the VH CDR3 (SEQ ID NO:3) underlined, starting in order from VH CDR1 at the far left; and (B) variable light domain (SEQ ID NO:75) of murine 1A1 with the VL CDR1 (SEQ ID NO:4), the VL CDR2 (SEQ ID NO:17), and the VL CDR3 (SEQ ID NO:6) underlined, starting in order from VL CDR1 at the far left.

FIGS. 14A-B show the nucleic acid sequences of the (A) variable heavy domain (SEQ ID NO:76) of murine 1A1 with the VH CDR1 (SEQ ID NO:77), the VH CDR2 (SEQ ID NO:78), and the VH CDR3 (SEQ ID NO:79) underlined, starting in order from VH CDR1 at the far left; and (B) variable light domain (SEQ ID NO:80) of murine 1A1 with the VL CDR1 (SEQ ID NO:81), the VL CDR2 (SEQ ID NO:82), and the VL CDR3 (SEQ ID NO:83) underlined, starting in order from VL CDR1 at the far left.

FIGS. 15A-B show the amino acid sequences of the (A) variable heavy domain (SEQ ID NO:84) of murine 2E11 with the VH CDR1 (SEQ ID NO:85), the VH CDR2 (SEQ ID NO:86), and the VH CDR3 (SEQ ID NO:87) underlined, starting in order from VH CDR1 at the far left; and (B) variable light domain (SEQ ID NO:88) of murine 2E11 with the VL CDR1 (SEQ ID NO:89), the VL CDR2 (SEQ ID NO:90), and the VL CDR3 (SEQ ID NO:91) underlined, starting in order from VL CDR1 at the far left.

FIGS. 16A-B show the nucleic acid sequences of the (A) variable heavy domain (SEQ ID NO:92) of murine 2E11 with the VH CDR1 (SEQ ID NO:93), the VH CDR2 (SEQ ID NO:94), and the VH CDR3 (SEQ ID NO:95) underlined, starting in order from VH CDR1 at the far left; and (B) variable light domain (SEQ ID NO:96) of murine 2E11 with the VL CDR1 (SEQ ID NO:97), the VL CDR2 (SEQ ID NO:98), and the VL CDR3 (SEQ ID NO:99) underlined, starting in order from VL CDR1 at the far left.

FIGS. 17A-B show the amino acid sequences of the (A) variable heavy domain (SEQ ID NO:100) of humanized 5B4-v2 with the VH CDR1 (SEQ ID NO:1), the VH CDR2 (SEQ ID NO:2), and the VH CDR3 (SEQ ID NO:3) underlined, starting in order from VH CDR1 at the far left; and (B) variable light domain (SEQ ID NO:101) of humanized 5B4-v2 with the VL CDR1 (SEQ ID NO:4), the VL CDR2 (SEQ ID NO:5), and the VL CDR3 (SEQ ID NO:6) underlined, starting in order from VL CDR1 at the far left.

FIGS. 18A-B show the nucleic acid sequences of the (A) variable heavy domain (SEQ ID NO:102) of humanized 5B4-v2 with the VH CDR1 (SEQ ID NO:21), the VH CDR2 (SEQ ID NO:22), and the VH CDR3 (SEQ ID NO:23) underlined, starting in order from VH CDR1 at the far left; and (B) variable light domain (SEQ ID NO:103) of humanized 5B4-v2 with the VL CDR1 (SEQ ID NO:25), the VL CDR2 (SEQ ID NO:26), and the VL CDR3 (SEQ ID NO:27) underlined, starting in order from VL CDR1 at the far left.

FIGS. 19A-B show the amino acid sequences of the (A) variable heavy domain (SEQ ID NO:108) of humanized 5B4-v4 with the VH CDR1 (SEQ ID NO:1), the VH CDR2 (SEQ ID NO:2), and the VH CDR3 (SEQ ID NO:3) underlined, starting in order from VH CDR1 at the far left; and (B) variable light domain (SEQ ID NO:109) of humanized 5B4-v4 with the VL CDR1 (SEQ ID NO:4), the VL CDR2 (SEQ ID NO:5), and the VL CDR3 (SEQ ID NO:6) underlined, starting in order from VL CDR1 at the far left.

FIGS. 20A-B show the nucleic acid sequences of the (A) variable heavy domain (SEQ ID NO:110) of humanized 5B4-v4 with the VH CDR1 (SEQ ID NO:21), the VH CDR2 (SEQ ID NO:22), and the VH CDR3 (SEQ ID NO:23) underlined, starting in order from VH CDR1 at the far left; and (B) variable light domain (SEQ ID NO:111) of humanized 5B4-v4 with the VL CDR1 (SEQ ID NO:25), the VL CDR2 (SEQ ID NO:26), and the VL CDR3 (SEQ ID NO:27) underlined, starting in order from VL CDR1 at the far left.

FIGS. 21A-B show the amino acid sequences of the (A) variable heavy domain (SEQ ID NO:112) of humanized 5B4-v5 with the VH CDR1 (SEQ ID NO:1), the VH CDR2 (SEQ ID NO:2), and the VH CDR3 (SEQ ID NO:3) underlined, starting in order from VH CDR1 at the far left; and (B) variable light domain (SEQ ID NO:113) of humanized 5B4-v5 with the VL CDR1 (SEQ ID NO:4), the VL CDR2 (SEQ ID NO:5), and the VL CDR3 (SEQ ID NO:6) underlined, starting in order from VL CDR1 at the far left.

FIGS. 22A-B show the nucleic acid sequences of the (A) variable heavy domain (SEQ ID NO:114) of humanized 5B4-v5 with the VH CDR1 (SEQ ID NO:21), the VH CDR2 (SEQ ID NO:22), and the VH CDR3 (SEQ ID NO:23) underlined, starting in order from VH CDR1 at the far left; and (B) variable light domain (SEQ ID NO:115) of humanized 5B4-v5 with the VL CDR1 (SEQ ID NO:25), the VL CDR2 (SEQ ID NO:26), and the VL CDR3 (SEQ ID NO:27) underlined, starting in order from VL CDR1 at the far left.

FIGS. 23A-B show the amino acid sequences of the (A) variable heavy domain (SEQ ID NO:116) of humanized 5B4-v6 with the VH CDR1 (SEQ ID NO:1), the VH CDR2 (SEQ ID NO:2), and the VH CDR3 (SEQ ID NO:3) underlined, starting in order from VH CDR1 at the far left; and (B) variable light domain (SEQ ID NO:117) of humanized 5B4-v6 with the VL CDR1 (SEQ ID NO:4), the VL CDR2 (SEQ ID NO:5), and the VL CDR3 (SEQ ID NO:6) underlined, starting in order from VL CDR1 at the far left.

FIGS. 24A-B show the nucleic acid sequences of the (A) variable heavy domain (SEQ ID NO:118) of humanized 5B4-v6 with the VH CDR1 (SEQ ID NO:21), the VH CDR2 (SEQ ID NO:22), and the VH CDR3 (SEQ ID NO:23) underlined, starting in order from VH CDR1 at the far left; and (B) variable light domain (SEQ ID NO:119) of humanized 5B4-v6 with the VL CDR1 (SEQ ID NO:25), the VL CDR2 (SEQ ID NO:26), and the VL CDR3 (SEQ ID NO:27) underlined, starting in order from VL CDR1 at the far left.

FIGS. 25A-B show the amino acid sequences of the (A) variable heavy domain (SEQ ID NO:120) of humanized 5B4-v7 with the VH CDR1 (SEQ ID NO:1), the VH CDR2 (SEQ ID NO:2), and the VH CDR3 (SEQ ID NO:3) underlined, starting in order from VH CDR1 at the far left; and (B) variable light domain (SEQ ID NO:121) of humanized 5B4-v7 with the VL CDR1 (SEQ ID NO:4), the VL CDR2 (SEQ ID NO:5), and the VL CDR3 (SEQ ID NO:6) underlined, starting in order from VL CDR1 at the far left.

FIGS. 26A-B show the nucleic acid sequences of the (A) variable heavy domain (SEQ ID NO:122) of humanized 5B4-v7 with the VH CDR1 (SEQ ID NO:21), the VH CDR2 (SEQ ID NO:22), and the VH CDR3 (SEQ ID NO:23) underlined, starting in order from VH CDR1 at the far left; and (B) variable light domain (SEQ ID NO:123) of humanized 5B4-v7 with the VL CDR1 (SEQ ID NO:25), the VL CDR2 (SEQ ID NO:26), and the VL CDR3 (SEQ ID NO:27) underlined, starting in order from VL CDR1 at the far left.

FIGS. 27A-B show the amino acid sequences of the (A) variable heavy domain (SEQ ID NO:124) of humanized 5B4-v8 with the VH CDR1 (SEQ ID NO:1), the VH CDR2 (SEQ ID NO:2), and the VH CDR3 (SEQ ID NO:3) underlined, starting in order from VH CDR1 at the far left; and (B) variable light domain (SEQ ID NO:125) of humanized 5B4-v8 with the VL CDR1 (SEQ ID NO:4), the VL CDR2 (SEQ ID NO:5), and the VL CDR3 (SEQ ID NO:6) underlined, starting in order from VL CDR1 at the far left.

FIGS. 28A-B show the nucleic acid sequences of the (A) variable heavy domain (SEQ ID NO:126) of humanized 5B4-v8 with the VH CDR1 (SEQ ID NO:21), the VH CDR2 (SEQ ID NO:22), and the VH CDR3 (SEQ ID NO:23) underlined, starting in order from VH CDR1 at the far left; and (B) variable light domain (SEQ ID NO:127) of humanized 5B4-v8 with the VL CDR1 (SEQ ID NO:25), the VL CDR2 (SEQ ID NO:26), and the VL CDR3 (SEQ ID NO:27) underlined, starting in order from VL CDR1 at the far left.

FIGS. 29A-B show the amino acid sequences of the (A) variable heavy domain (SEQ ID NO:128) of humanized 5B4-v9 with the VH CDR1 (SEQ ID NO:1), the VH CDR2 (SEQ ID NO:2), and the VH CDR3 (SEQ ID NO:3) underlined, starting in order from VH CDR1 at the far left; and (B) variable light domain (SEQ ID NO:129) of humanized 5B4-v9 with the VL CDR1 (SEQ ID NO:4), the VL CDR2 (SEQ ID NO:5), and the VL CDR3 (SEQ ID NO:6) underlined, starting in order from VL CDR1 at the far left.

FIGS. 30A-B show the nucleic acid sequences of the (A) variable heavy domain (SEQ ID NO:130) of humanized 5B4-v9 with the VH CDR1 (SEQ ID NO:21), the VH CDR2 (SEQ ID NO:22), and the VH CDR3 (SEQ ID NO:23) underlined, starting in order from VH CDR1 at the far left; and (B) variable light domain (SEQ ID NO:131) of humanized 5B4-v9 with the VL CDR1 (SEQ ID NO:25), the VL CDR2 (SEQ ID NO:26), and the VL CDR3 (SEQ ID NO:27) underlined, starting in order from VL CDR1 at the far left.

FIGS. 31A-B show the amino acid sequences of the (A) variable heavy domain (SEQ ID NO:132) of humanized 5B4-v10 with the VH CDR1 (SEQ ID NO:1), the VH CDR2 (SEQ ID NO:2), and the VH CDR3 (SEQ ID NO:3) underlined, starting in order from VH CDR1 at the far left; and (B) variable light domain (SEQ ID NO:133) of humanized 5B4-v10 with the VL CDR1 (SEQ ID NO:4), the VL CDR2 (SEQ ID NO:5), and the VL CDR3 (SEQ ID NO:6) underlined, starting in order from VL CDR1 at the far left.

FIGS. 32A-B show the nucleic acid sequences of the (A) variable heavy domain (SEQ ID NO:134) of humanized 5B4-v10 with the VH CDR1 (SEQ ID NO:21), the VH CDR2 (SEQ ID NO:22), and the VH CDR3 (SEQ ID NO:23) underlined, starting in order from VH CDR1 at the far left; and (B) variable light domain (SEQ ID NO:135) of humanized 5B4-v10 with the VL CDR1 (SEQ ID NO:25), the VL CDR2 (SEQ ID NO:26), and the VL CDR3 (SEQ ID NO:27) underlined, starting in order from VL CDR1 at the far left.

FIGS. 33A-B show the amino acid sequences of the (A) variable heavy domain (SEQ ID NO:136) of humanized 5B4-v 11 with the VH CDR1 (SEQ ID NO:1), the VH CDR2 (SEQ ID NO:2), and the VH CDR3 (SEQ ID NO:3) underlined, starting in order from VH CDR1 at the far left; and (B) variable light domain (SEQ ID NO:137) of humanized 5B4-v11 with the VL CDR1 (SEQ ID NO:4), the VL CDR2 (SEQ ID NO:5), and the VL CDR3 (SEQ ID NO:6) underlined, starting in order from VL CDR1 at the far left.

FIGS. 34A-B show the amino acid sequences of the (A) variable heavy domain (SEQ ID NO:138) of humanized 5B4-v12 with the VH CDR1 (SEQ ID NO:1), the VH CDR2 (SEQ ID NO:2), and the VH CDR3 (SEQ ID NO:3) underlined, starting in order from VH CDR1 at the far left; and (B) variable light domain (SEQ ID NO:139) of humanized 5B4-v12 with the VL CDR1 (SEQ ID NO:4), the VL CDR2 (SEQ ID NO:5), and the VL CDR3 (SEQ ID NO:6) underlined, starting in order from VL CDR1 at the far left.

FIGS. 35A-B show the amino acid sequences of the (A) variable heavy domain (SEQ ID NO:140) of humanized 5B4-v13 with the VH CDR1 (SEQ ID NO:1), the VH CDR2 (SEQ ID NO:2), and the VH CDR3 (SEQ ID NO:3) underlined, starting in order from VH CDR1 at the far left; and (B) variable light domain (SEQ ID NO:141) of humanized 5B4-v13 with the VL CDR1 (SEQ ID NO:4), the VL CDR2 (SEQ ID NO:5), and the VL CDR3 (SEQ ID NO:6) underlined, starting in order from VL CDR1 at the far left.

Figure 36A:
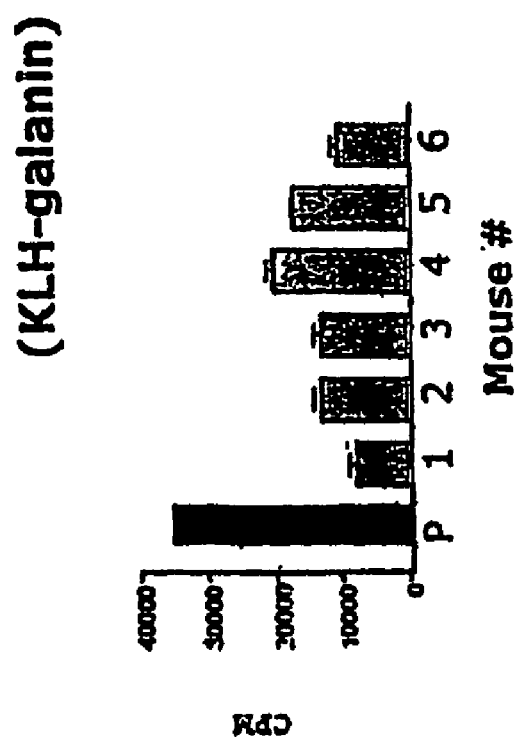

FIGS. 36A-B show the results from a GALR2 filtration binding assay. Membrane preparations from A9 cells engineered to overexpress GALR2 were incubated with $^{125}$I-labeled human galanin and pre-immune (designated P) or mouse anti-galanin anti-sera (designated 1-6) and harvested onto a GF/B Unifilter plate. All 12 mouse anti-sera selectively inhibited binding of human galanin to GALR2 in the filtration binding assay.

Figure 37:
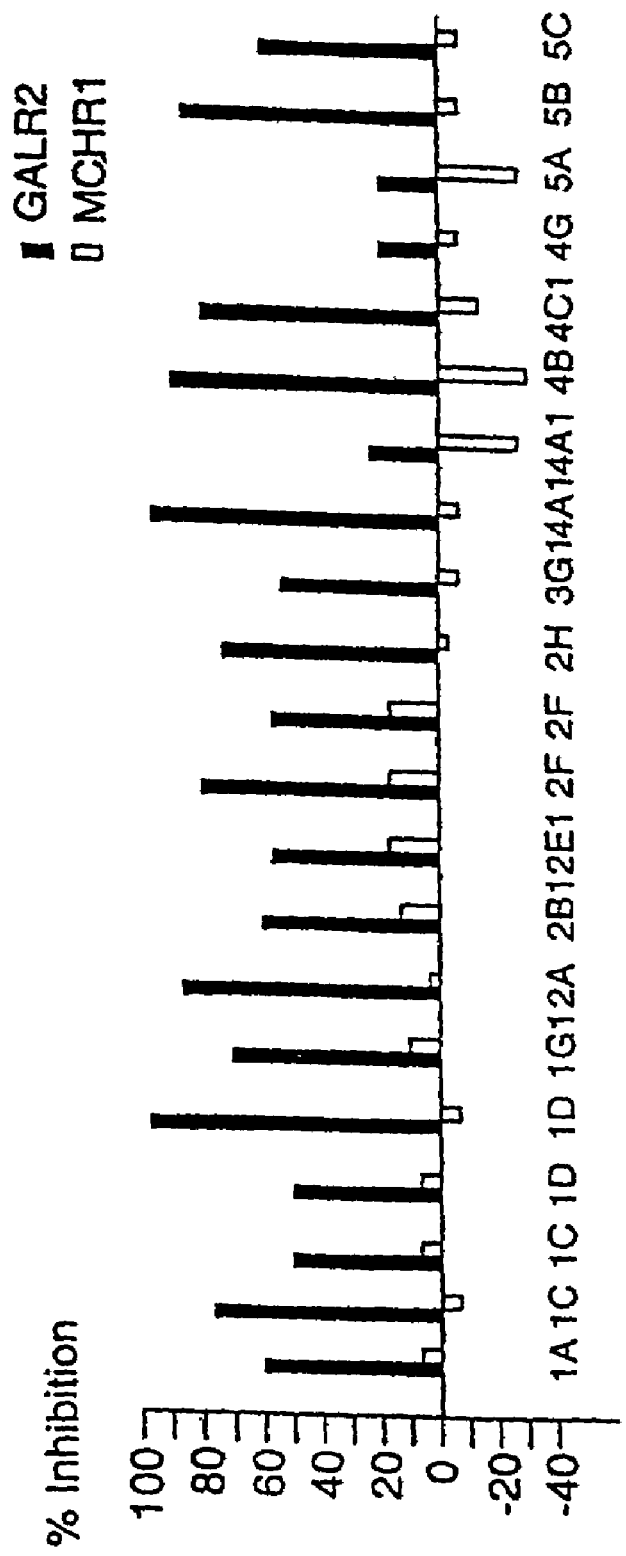

FIG. 37 shows the results from a GALR2 filtration assay. Membrane preparations from A9 cells engineered to overexpress GALR2 were incubated with $^{125}$I-labeled human galanin and mouse anti-galanin hybridomas supernatants and harvested onto a GF/B Unifilter plate. Twenty-one hybridomas were able to inhibit binding of human galanin to GALR2.

Figure 38:
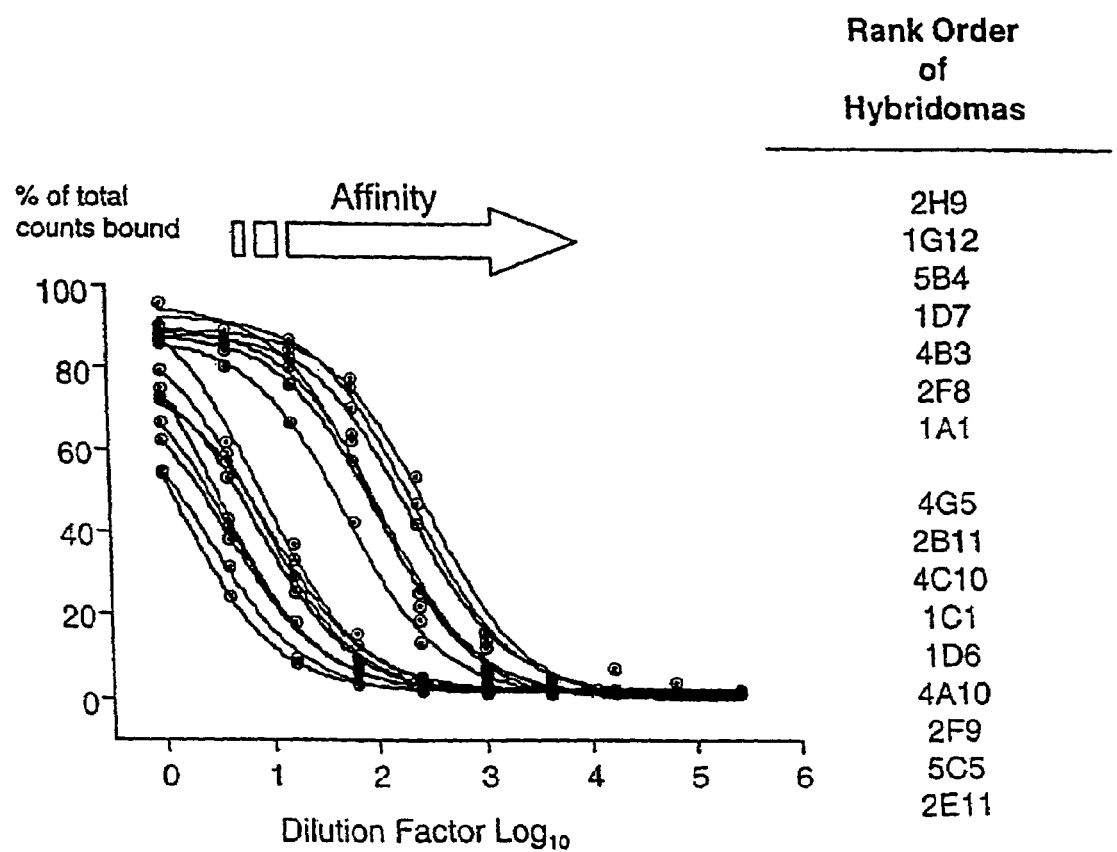

FIG. 38 shows the results from an affinity assay. Hybridoma supernatants from confluent cultures were serially diluted, pre-incubated with $^{125}$I-labeled human galanin, and precipitated with an excess of Protein G Sepharose. The monoclonal antibodies produced by the hybridomas were ranked according to affinity. The following seven monoclonal antibodies were ranked high affinity: 2H9, 1G12, 5B4, 1D7, 4B3, 2F8 and 1A1. The following monoclonal antibodies were ranked low affinitiy: 4G5, 2B11, 4C10, 1C1, 1D6, 4A10, 2F9, 5C5 and 2E11.

Figure 39:
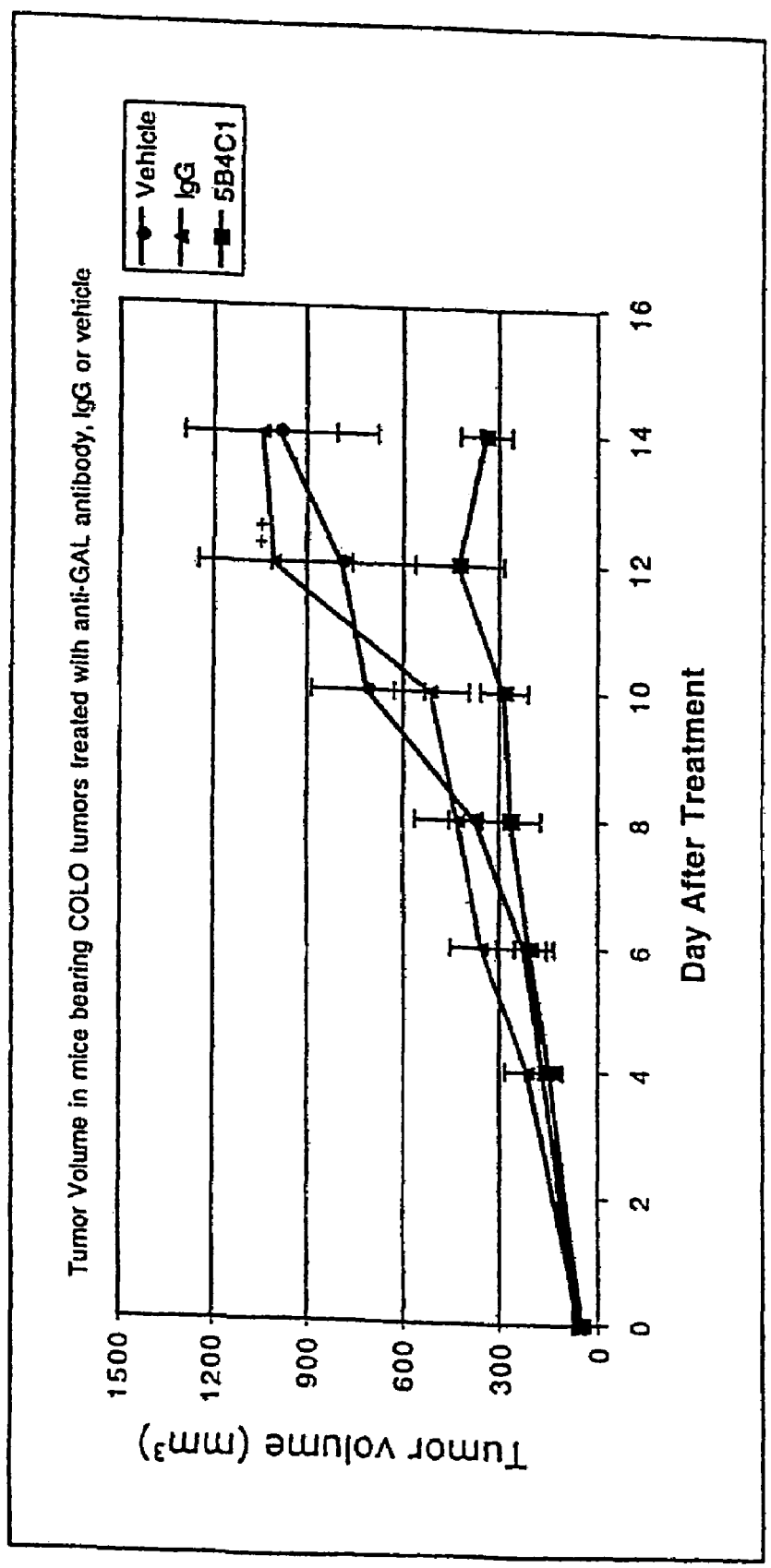

FIG. 39 shows that the administration of anti-galanin antibodies reduce tumor growth in established tumors. Athymic nude mice injected with 5 million COLO-677 cells were administered 200 μg of anti-galanin IgG or vehicle approximately 10-14 days after tumor volume reached approximately 50-100 mm³.

5. DETAILED DESCRIPTION OF THE INVENTION

The present invention provides antibodies that immunospecifically bind to a galanin peptide (for a example, a human galanin peptide). In particular, the invention provides the following antibodies that immunospecifically bind to a galainin peptide: murine antibody 4B3, 1D7, 1G12, 5B4, 2F8, 1A1 and 2E11, and the humanized antibody 5B4-v2, 5B4-v4, 5B4-v5, 5B4-v6, 5B4-v7, 5B4-v8, 5B4-v9, 5B4-v10, 5B4-v11, 5B4-v12, and 5B4-v13. The invention also provides the antibodies that are produced by the murine hybridoma 1D7D1 (ATCC accession number PTA-5650) and the murine hybridoma 5B4C1 (ATCC accession number PTA-5651). The present invention also provides for antibodies comprising a variable heavy ("VH") domain and/or a variable light ("VL") domain having the amino acid sequence of the VH domain and/or VL domain, respectively, of the murine antibody 4B3, 1D7, 1G12, 5B4, 2F8, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13. In addition, the present invention provides for antibodies comprising one or more complementarity determining regions ("CDR") of the murine antibody 4B3, 1D7, 1G12, 5B4, 2F8, 1A1 and/or 2E11, and/or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13.

The present invention encompasses treatment protocols that provide better prophylactic or therapeutic profiles than current single agent therapies or combination therapies for a disorder associated with aberrant expression and/or activity of galanin and/or a galanin receptor (e.g., a hyperproliferative disorder, Alzheimer's disease, depression and eating disorders) or one or more symptoms thereof. In particular, the invention provides prophylactic and therapeutic protocols for the prevention, treatment, management, and/or amelioration of a disorder associated with aberrant expression and/or activity of galanin and/or a galanin receptor (e.g., a hyperproliferative disorder, Alzheimer's disease, depression and eating disorders) or one or more symptoms thereof, comprising administering to a subject an effective amount of one or more of the antibodies of the invention alone or in combination with an effective amount of at least one therapy (e.g., a prophylactic or therapeutic agent) other than an antibody of the invention.

The present invention provides for pharmaceutical compositions, kits, and articles of manufacture comprising one or more antibodies that immunospecifically binds to a galanin peptide for use in the prevention, treatment, management, and/or amelioration of a disorder associated with aberrant expression and/or activity of galanin and/or a galanin receptor (e.g., a hyperproliferative disorder, Alzheimer's disease, depression and eating disorders) or one or more symptoms thereof. The present invention also provides for pharmaceutical compositions, kits, and articles of manufacture comprising one or more antibodies that immunospecifically bind to a galanin peptide and one or more prophylactic or therapeutic agents other than antibodies of the invention for use in the prevention, treatment, management, or amelioration of a disorder associated with aberrant expression and/or activity of galanin and/or a galanin receptor (e.g., a hyperproliferative disorder, Alzheimer's disease, depression and eating disorders) or one or more symptoms thereof.

5.1 Galanin Antibodies

The present invention provides antibodies that immunospecifically bind to a galanin peptide (for example, human galanin). In particular, the present invention provides for antibodies that have a high binding affinity for a galanin peptide. In one aspect, an antibody that immunospecifically binds to a galanin peptide has an association rate constant or $k_{on}$ rate

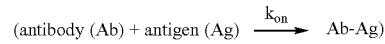

$$\text{(antibody (Ab)} + \text{antigen (Ag))} \xrightarrow{k_{on}} \text{Ab-Ag}$$

of at least $5 \times 10^2$ $M^{-1}s^{-1}$, at least $10^3$ $M^{-1}s^{-1}$, at least $5 \times 10^3$ $M^{-1}s^{-1}$, at least $10^4$ $M^{-1}s^{-1}$, at least $10^5$ $M^{-1}s^{-1}$, at least $5 \times 10^5$ $M^{-1}s^{-1}$, at least $10^6$ $M^{-1}s^{-1}$, at least $5 \times 10^6$ $M^{-1}s^{-1}$, at least $10^7$ $M^{-1}s^{-1}$, at least $5 \times 10^7$ $M^{-1}s^{-1}$, or at least $10^8$ $M^{-1}s^{-1}$, or a $k_{on}$ ranging from $5 \times 10^2$ $M^{-1}s^{-1}$ to $10^8$ $M^{-1}s^{-1}$. In another aspect, an antibody that immunospecifically binds to a galanin peptide has a $k_{on}$ of at least $5 \times 10^3$ $M^{-1}s^{-1}$, at least $10^4$ $M^{-1}s^{-1}$, at least $10^5$ $M^{-1}s^{-1}$, at least $5 \times 10^5$ $M^{-1}s^{-1}$, at least $10^6$ $M^{-1}s^{-1}$, at least $5 \times 10^6$ $M^{-1}s^{-1}$, at least $10^7$ $M^{-1}s^{-1}$ or at least $5 \times 10^7$ $M^{-1}s^{-1}$, or at least $10^8$ $M^{-1}s^{-1}$, or a $k_{on}$ ranging from $5 \times 10^2$ $M^{-1}s^{-1}$ to $10^6$ $M^{-1}s^{-1}$.

In another aspect, an antibody that immunospecifically binds to a galanin polypeptide has a $k_{off}$ rate

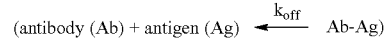

$$\text{(antibody (Ab)} + \text{antigen (Ag))} \xleftarrow{k_{off}} \text{Ab-Ag}$$

of less than $10^{-3}$ $s^{-1}$, less than $5 \times 10^{-3}$ $s^{-1}$, less than $10^{-4}$ $s^{-1}$, less than $5 \times 10^{-4}$ $s^{-1}$, less tshan $10^{-5}$ $s^{-1}$, less than $5 \times 10^{-5}$ $s^{-1}$, less than $10^{-6}$ $s^{-1}$, less than $5 \times 10^{-6}$ $s^{-1}$, less than $10^{-7}$ $s^{-1}$, less than $5 \times 10^{-7}$ $s^{-1}$, less than $10^{-8}$ $s^{-1}$ or less than $5 \times 10^{-8}$ $s^{-1}$, or a $k_{off}$ ranging from $10^{-3}$ $s^{-1}$ to $5 \times 10^{-8}$ $s^{-1}$. In another aspect, an antibody that immunospecifically binds to a galanin peptide has a $k_{off}$ of less than $5 \times 10^{-4}$ $s^{-1}$, less than $10^{-5}$ $s^{-1}$, less than $5 \times 10^{-5}$ $s^{-1}$, less than $10^{-6}$ $s^{-1}$, less than $5 \times 10^{-6}$ $s^{-1}$, less than $10^{-7}$ $s^{-1}$ or less than $5 \times 10^{-7}$ $s^{-1}$, or a $k_{off}$ ranging from $5 \times 10^{-4}$ $s^{-1}$ to $5 \times 10^{-7}$ $s^{-1}$.

In another aspect, an antibody that immunospecifically binds to a galanin peptide has an affinity constant or $K_a$ ($k_{on}/k_{off}$) of at least $10^7$ $M^{-1}$, at least $5 \times 10^7$ $M^{-1}$, at least $10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ $M^{-1}$, at least $10^{12}$ $M^{-1}$, at least $5 \times 10^{12}$ $M^{-1}$, at least $10^{13}$ $M^{-1}$, at least $5 \times 10^{13}$ $M^{-1}$ or at least $10^{14}$ $M^{-1}$, or a $K_a$ ranging from $10^7$ $M^{-1}$ to $10^{14}$ $M^{-1}$. In another aspect, an antibody that immunospecifically binds to a galanin peptide has a $K_a$ of at least $10^8$ $M^{-1}$, at least $5 \times 10^8$ $M^{-1}$, at least $10^9$ $M^{-1}$, at least $5 \times 10^9$ $M^{-1}$, at least $10^{10}$ $M^{-1}$, at least $5 \times 10^{10}$ $M^{-1}$, at least $10^{11}$ $M^{-1}$, at least $5 \times 10^{11}$ $M^{-1}$, at least $10^{12}$ $M^{-1}$ or at least $5 \times 10^{12}$ $M^{-1}$, or a $K_a$ ranging from $10^8$ $M^{-1}$ to $10^{12}$ $M^{-1}$.

In another aspect, an antibody that immunospecifically binds to a galanin peptide has a dissociation constant or $K_d$ ($k_{off}/k_{on}$) of less than $10^{-8}$ M, less than $5 \times 10^{-8}$ M, less than $10^{-9}$ M, less than $5 \times 10^{-9}$ M, less than $10^{-10}$ M, less than $5 \times 10^{-10}$ M, less than $10^{-11}$ M, less than $5 \times 10^{-11}$ M, less than $10^{-12}$ M, less than $5 \times 10^{-12}$ M, less than $10^{-13}$ M, less than $5 \times 10^{-13}$ M, less than $10^{-14}$ M or less than $5 \times 10^{-14}$ M, or a $K_d$ ranging from $10^{-8}$ M to $5 \times 10^{-14}$ M. In yet another aspect, an antibody that immunospecifically binds to a galanin peptide has a $K_d$ of less than $5 \times 10^{-8}$ M, less than $10^{-9}$ M, less than $5 \times 10^{-9}$ M, less than $10^{-10}$ M, less than $5 \times 10^{-10}$ M, less than $10^{-11}$ M, less than $5 \times 10^{-11}$ M, less than $10^{-12}$ M or less than $5 \times 10^{-12}$ M, or a $K_d$ ranging from $10^{-8}$ M to $5 \times 10^{-12}$ M.

In some aspects, antibodies of the invention immunospecifically bind antigenic epitope-bearing peptides and polypeptides of galanin, and said antigenic epitope-bearing peptides and polypeptides comprise or consist of an amino acid sequence of at least 4, at least 5, at least 6, at least 7, more preferably at least 8, at least 9, at least 10, at least 11, at least 12, at least 13, at least 14, at least 15, at least 20, at least 25 or at least 30 contiguous amino acid residues, and, preferably, between about 15 to about 30 contiguous amino acids of galanin found in any species. In one aspect, antibodies of the invention immunospecifically bind to the C-terminus of a galanin peptide. In another aspect, antibodies of the invention immunospecifically bind to an epitope comprising amino acid residues 21 through 27 of murine or human galanin, amino acid residues 21 through 26 of murine or human galanin, amino acid residues 22 through 27 of murine or human galanin, or amino acid residues 22 through 26 of murine or human galanin. In certain aspects, the antibodies of the invention do not include antibodies known in the art that immunospecifically bind to a galanin peptide. Non-limiting examples of known antibodies include anti-galanin polyclonal antibody (catalog number RDI-PRO16023; Research Diagnostics, Inc.), rabbit anti-galanin (Linco), rabbit anti-galanin antibody (catalog number PS228; Monosan), and anti-galanin polyclonal antibody (TCS Cell Works). In yet other aspects, the antibodies of the invention do not include antibodies that immunospecifically bind to an epitope of galanin not found in the C-terminus of a galanin peptide.

In one aspect, an antibody of the invention immunospecifically binds to the C-terminus of a galanin peptide with a $K_a$ of at least $10^7$ M$^{-1}$, at least $5 \times 10^7$ M$^{-1}$, at least $10^8$ M$^{-1}$, at least $5 \times 10^8$ M$^{-1}$, at least $10^9$ M$^{-1}$, at least $5 \times 10^9$ M$^{-1}$, at least $10^{10}$ M$^{-1}$, at least $5 \times 10^{10}$ M$^{-1}$, at least $10^{11}$ M$^{-1}$, at least $5 \times 10^{11}$ M$^{-1}$, at least $10^{12}$ M$^{-1}$, at least $5 \times 10^{12}$ M$^{-1}$, at least $10^{13}$ M$^{-1}$, at least $5 \times 10^{13}$ M$^{-1}$ or at least $10^{14}$ M$^{-1}$. In another aspect, an antibody of the invention immunospecifically binds to an epitope comprising amino acid residues 21 through 27 of murine or human galanin, amino acid residues 21 through 26 of murine or human galanin, amino acid residues 22 through 27 of murine or human galanin, or amino acid residues 22 through 26 of murine or human galanin, with a $K_a$ of at least $10^7$ M$^{-1}$, at least $5 \times 10^7$ M$^{-1}$, at least $10^8$ M$^{-1}$, at least $5 \times 10^8$ M$^{-1}$, at least $10^9$ M$^{-1}$, at least $5 \times 10^9$ M$^{-1}$, at least $10^{10}$ M$^{-1}$, at least $5 \times 10^{10}$ M$^{-1}$, at least $10^{11}$ M$^{-1}$, at least $5 \times 10^{11}$ M$^{-1}$, at least $10^{12}$ M$^{-1}$, at least $5 \times 10^{12}$ M$^{-1}$, at least $10^{13}$ M$^{-1}$, at least $5 \times 10^{13}$ M$^{-1}$ or at least $10^{14}$ M$^{-1}$.

In another aspect, an antibody of the invention immunospecifically binds to the C-terminus of a galanin peptide and the antibody has a $K_d$ of $10^{-8}$ M, less than $5 \times 10^{-8}$ M, less than $10^{-9}$ M, less than $5 \times 10^{-9}$ M, less than $10^{-10}$ M, less than $5 \times 10^{-10}$ M, less than $10^{-11}$ M, less than $5 \times 10^{-11}$ M, less than $10^{-12}$ M, less than $5 \times 10^{-12}$ M, less than $10^{-13}$ M, less than $5 \times 10^{-13}$ M, less than $10^{-14}$ M or less than $5 \times 10^{-14}$ M. In another aspect, an antibody of the invention immunospecifically binds to an epitope comprising amino acid residues 21 through 27 of murine or human galanin, amino acid residues 21 through 26 of murine or human galanin, amino acid residues 22 through 27 of murine or human galanin, or amino acid residues 22 through 26 of murine or human galanin, and the antibody has a $K_d$ of $10^{-8}$ M, less than $5 \times 10^{-8}$ M, less than $10^{-9}$ M, less than $5 \times 10^{-9}$ M, less than $10^{-10}$ M, less than $5 \times 10^{-10}$ M, less than $10^{-11}$ M, less than $5 \times 10^{-11}$ M, less than $10^{-12}$ M, less than $5 \times 10^{-12}$ M, less than $10^{-13}$ M, less than $5 \times 10^{-13}$ M, less than $10^{-14}$ M or less than $5 \times 10^{-14}$ M.

Galanin epitope-bearing peptides, polypeptides, and fragments thereof may be produced by any conventional means. See, e.g., Houghten, R. A. (1985) "General method for the rapid solid-phase synthesis of large numbers of peptides: specificity of antigen-antibody interaction at the level of individual amino acids," Proc. Natl. Acad. Sci. USA 82:5 13 1-5 135; this "Simultaneous Multiple. Peptide Synthesis (SMPS)" process is further described in U.S. Pat. No. 4,631,211 to Houghten et al. (1986).

The invention provides the antibodies produced by the murine hybridoma 1D7D1 (ATCC accession number PTA-5650) and the murine hybridoma 5B4C1 (ATCC accession number PTA-5651). The invention also provides antibodies that immunospecifically bind to a galanin peptide that comprise the variable heavy domain and/or variable light domain or antigen-binding fragment thereof (e.g., one or more CDRs) of one or more of the following: murine 4B3 (FIGS. 9A-B), murine 1D7 (FIGS. 7A-B), murine 1G12 (FIGS. 3A-B), murine 5B4 (FIGS. 1A-B), murine 2F8 (FIGS. 5A-B), murine 1A1 (FIGS. 13A-B), murine 2E11 (FIGS. 15A-B), and murine 2H9 (FIGS. 11A-B). The antibodies may further comprise any constant region (for example, any murine constant region) known in the art. In one aspect, an antibody that immunospecifically binds to a galanin peptide comprises the variable heavy domain and/or variable light domain or antigen-binding fragment thereof (e.g., one or more CDRs) of humanized 5B4-v2 (FIGS. 17A-B), humanized 5B4-v4 (FIGS. 19A-B), humanized 5B4-v5 (FIGS. 21A-B), humanized 5B4-v6 (FIGS. 23A-B), humanized 5B4-v7 (FIGS. 25A-B), humanized 5B4-v8 (FIGS. 27A-B), humanized 5B4-v9 (FIGS. 29A-B), humanized 5B4-v10 (FIGS. 31A-B), humanized 5B4-v11, humanized 5B4-v12, and humanized 5B4-v13. In accordance with this aspect, the antibody may further comprise any human constant region known in the art, including, but not limited to, human light (kappa (κ)) chain ($C_L$), human light lambda (λ) chain, the constant region 1 of human IgG$_2$ heavy chain ($C_H1$), the constant region of IgG$_1$, the constant region of IgG$_3$, and the constant region of IgG$_4$. In another aspect, an antibody that immunospecifically binds to a galanin peptide comprises the variable heavy domain and/or variable light domain or antigen-binding fragment thereof (e.g., one or more CDRs) of the antibody produced by the murine hybridoma 1D7D1 (ATCC accession number PTA-5650) and/or the murine hybridoma 5B4C1 (ATCC accession number PTA-5651).

The present invention provides antibodies that immunospecifically bind a galanin peptide, said antibodies comprising a VH domain having the amino acid sequence of the VH domain of the murine 5B4 (FIG. 1A; SEQ ID NO:18), 1G12 (FIG. 3A; SEQ ID NO:28), 2F8 (FIG. 5A; SEQ ID NO:38), 1D7 (FIG. 7A; SEQ ID NO:47), 4B3 (FIG. 9A; SEQ ID NO:104), 2H9 (FIG. 11A; SEQ ID NO:65), 1A1 (FIG. 13A; SEQ ID NO:84) or 2E11 (FIG. 15A; SEQ ID NO:76). In one aspect, an antibody that immunospecifically binds to a galanin peptide comprises a VH domain having the amino acid sequence of the VH domain of the humanized antibody 5B4-v2 (FIG. 17A; SEQ ID NO:100), the humanized antibody 5B4-v4 (FIG. 19A; SEQ ID NO:108), the humanized antibody 5B4-v5 (FIG. 21A; SEQ ID NO:112), the humanized antibody 5B4-v6 (FIG. 23A; SEQ ID NO:116), the humanized antibody 5B4-v7 (FIG. 25A; SEQ ID NO:120), the humanized antibody 5B4-v8 (FIG. 27A; SEQ ID NO:124), the humanized antibody 5B4-v9 (FIG. 29A; SEQ ID NO:128), the humanized antibody 5B4-v10 (FIG. 31A; SEQ ID NO:132), the humanized antibody 5B4-v11 (FIG. 33A, SEQ ID NO:136), the humanized antibody 5B4-v12 (FIG. 34A, SEQ ID NO:138), or the humanized antibody 5B4-v13 (FIG. 35A, SEQ ID NO:140). In another aspect, an antibody that immunospecifically binds to a galanin peptide comprises a VH domain having the amino acid sequence of the VH domain of the antibody produced by the murine hybridoma 1D7D1 (ATCC accession number PTA-5650) or the murine hybridoma 5B4C1 (ATCC accession number PTA-5651).

The present invention provides antibodies that immunospecifically bind to a galanin peptide, said antibodies comprising a VH domain having a nucleic acid sequence of the VH domain for 5B4 (FIG. 2A; SEQ ID NO:142), 1G12 (FIG. 4A; SEQ ID NO:30), 2F8 (FIG. 6A; SEQ ID NO:39), 1D7 (FIG. 8A; SEQ ID NO:49), 4B3 (FIG. 10A; SEQ ID NO:57), 2H9 (FIG. 12A; SEQ ID NO:66), 1A1 (FIG. 14A; SEQ ID NO:76) or 2E11 (FIG. 16A; SEQ ID NO:92). In one aspect, an antibody that immunospecifically binds to a galanin peptide comprises a VH domain encoded by a nucleotide sequence having a nucleic acid sequence of the VH domain for VH domain of the humanized antibody 5B4-v2 (FIG. 18A; SEQ ID NO:102), the humanized antibody 5B4-v4 (FIG. 20A; SEQ ID NO:110), the humanized antibody 5B4-v5 (FIG. 22A; SEQ ID NO:114), the humanized antibody 5B4-v6 (FIG. 24A; SEQ ID NO:118), the humanized antibody 5B4-v7 (FIG. 26A; SEQ ID NO:122), the humanized antibody 5B4-v8 (FIG. 28A; SEQ ID NO:126), the humanized antibody 5B4-v9 (FIG. 30A; SEQ ID NO:130), the humanized antibody 5B4-v10 (FIG. 32A; SEQ ID NO:134), the humanized antibody 5B4-v11, the humanized antibody 5B4-v12, or the humanized antibody 5B4-v13. In another aspect, an antibody that immunospecifically binds to a galanin peptide comprises a VH domain encoded by a nucleotide sequence having a nucleic acid sequence of the VH domain of the antibody produced by the murine hybridoma 1D7D1 (ATCC accession number PTA-5650) or the murine hybridoma 5B4C1 (ATCC accession number PTA-5651).

The present invention provides antibodies that immunospecifically bind to a galanin peptide, said antibodies comprising a VH CDR having the amino acid sequence of any one of the VH CDRs listed in Table 3, infra, and/or the amino acid sequence of any one of the VH CDRs of the antibody produced by the murine hybridoma 1D7D1 (ATCC accession number PTA-5650) or the murine hybridoma 5B4C1 (ATCC accession number PTA-5651). In particular, the invention provides antibodies that immunospecifically bind to a galanin peptide, said antibodies comprising (or alternatively, consisting of) one, two, three, four, five or more VH CDRs having the amino acid sequence of any of the VH CDRs listed in Table 3, infra. In one aspect, an antibody that immunospecifically binds to a galanin peptide comprises a VH CDR1 having the amino acid sequence of SEQ ID NO:1, SEQ ID NO:7, SEQ ID NO:11, SEQ ID NO:15 or SEQ ID NO:85. In another aspect, an antibody that immunospecifically binds to a galanin peptide comprises a VH CDR2 having the amino acid sequence of SEQ ID NO:2, SEQ ID NO:5, SEQ ID NO:8, SEQ ID NO:12, SEQ ID NO:14, SEQ ID NO:16 or SEQ ID NO:86. In another aspect, an antibody that immunospecifically binds to a galanin peptide comprises a VH CDR3 having the amino acid sequence of SEQ ID NO:3, SEQ ID NO:9 or SEQ ID NO:87.

In another aspect, an antibody that immunospecifically binds to a galanin peptide comprises a VH CDR1 having the amino acid sequence of SEQ ID NO:1, SEQ ID NO:7, SEQ ID NO:1, SEQ ID NO:15 or SEQ ID NO:85 and a VH CDR2 having the amino acid sequence of SEQ ID NO:2, SEQ ID NO:8, SEQ ID NO:12, SEQ ID NO:14, SEQ ID NO:16 or SEQ ID NO:86. In another aspect, an antibody that immunospecifically binds to a galanin peptide comprises a VH CDR1 having the amino acid sequence of SEQ ID NO:1, SEQ ID NO:7, SEQ ID NO:11, SEQ ID NO:15 or SEQ ID NO:85 and a VH CDR3 having the amino acid sequence of SEQ ID NO:3, SEQ ID NO:9 or SEQ ID NO:87. In another aspect, an antibody that immunospecifically binds to a galanin peptide comprises a VH CDR2 having the amino acid sequence of SEQ ID NO:2, SEQ ID NO:8, SEQ ID NO:12, SEQ ID NO:14, SEQ ID NO:16 or SEQ ID NO:86 and a VH CDR3 having the amino acid sequence of SEQ ID NO:3, SEQ ID NO:9 or SEQ ID NO:87. In yet another aspect, an antibody that immunospecifically binds to a galanin peptide comprises a VH CDR1 having the amino acid sequence of VH CDR1 of SEQ ID NO:1, SEQ ID NO:7, SEQ ID NO:11, SEQ ID NO:15 or SEQ ID NO:85, a VH CDR2 having the amino acid sequence of SEQ ID NO:2, SEQ ID NO:8, SEQ ID NO:12, SEQ ID NO:14, SEQ ID NO:16 or SEQ ID NO:86, and a VH CDR3 having the amino acid sequence of SEQ ID NO:3, SEQ ID NO:9 or SEQ ID NO:87.

The present invention provides antibodies that immunospecifically bind to a galanin peptide, said antibodies comprising a VH CDR encoded by a nucleotide sequence having a nucleic acid sequence of any one of the VH CDRs of 5B4, 1G12, 2F8, 1D7, 4B3, 2H9, 1A1 or 2E11. In particular, the invention provides antibodies that immunospecifically bind to a galanin peptide, said antibodies comprising (or alternatively, consisting of) one, two, three, four, five or more VH CDRs encoded by a nucleotide sequence having a nucleic acid sequence of any of the VH CDRs 5B4, 1G12, 2F8, 1D7, 4B3, 2H9, 1A1 or 2E11. In one aspect, an antibody that immunospecifically binds to a galanin peptide comprises a VH CDR1 encoded by a nucleotide sequence having the nucleic acid sequence of SEQ ID NO:21, SEQ ID NO:31, SEQ ID NO:40, SEQ ID NO:50, SEQ ID NO:66, SEQ ID NO:77 or SEQ ID NO:93. In another aspect, an antibody that immunospecifically binds to a galanin peptide comprises a VH CDR2 encoded by a nucleotide sequence having the nucleic acid sequence of SEQ ID NO:22, SEQ ID NO:32, SEQ ID NO:41, SEQ ID NO:51, SEQ ID NO:59, SEQ ID NO:67, SEQ ID NO:78 or SEQ ID NO:94. In another aspect, an antibody that immunospecifically binds to a galanin peptide comprises a VH CDR3 encoded by a nucleotide sequence having the nucleic acid sequence of SEQ ID NO:23, SEQ ID NO:33, SEQ ID NO:42, SEQ ID NO:52, SEQ ID NO:60, SEQ ID NO:68, SEQ ID NO:79 or SEQ ID NO:95.

In another aspect an antibody that immunospecifically binds to a galanin peptide comprises a VH CDR1 encoded by a nucleotide sequence having the nucleic acid sequence of SEQ ID NO:21, SEQ ID NO:31, SEQ ID NO:40, SEQ ID NO:50, SEQ ID NO:66, SEQ ID NO:77 or SEQ ID NO:93 and a VH CDR2 encoded by a nucleotide sequence having the nucleic acid sequence of SEQ ID NO:22, SEQ ID NO:32, SEQ ID NO:41, SEQ ID NO:51, SEQ ID NO:59, SEQ ID NO:67, SEQ ID NO:78 or SEQ ID NO:94. In another aspect, an antibody that immunospecifically binds to a galanin peptide comprises a VH CDR1 encoded by a nucleotide sequence having the nucleic acid sequence of SEQ ID NO:21, SEQ ID NO:31, SEQ ID NO:40, SEQ ID NO:50, SEQ ID NO:66, SEQ ID NO:77 or SEQ ID NO:93 and a VH CDR3 encoded by a nucleotide sequence having the nucleic sequence of SEQ ID NO:23, SEQ ID NO:33, SEQ ID NO:42, SEQ ID NO:52, SEQ ID NO:60, SEQ ID NO:68, SEQ ID NO:79 or SEQ ID NO:95. In another aspect, an antibody that immunospecifically binds to a galanin peptide comprises a VH CDR2 encoded by a nucleotide sequence having the nucleic acid sequence of SEQ ID NO:22, SEQ ID NO:32, SEQ ID NO:41, SEQ ID NO:51, SEQ ID NO:59, SEQ ID NO:67, SEQ ID NO:78 or SEQ ID NO:94 and a VH CDR3 encoded by a nucleotide sequence having the nucleic acid sequence of SEQ ID NO:23, SEQ ID NO:33, SEQ ID NO:42, SEQ ID NO:52, SEQ ID NO:60, SEQ ID NO:68, SEQ ID NO:79 or SEQ ID NO:95. In yet another aspect, an antibody that immunospecifically binds to a galanin peptide comprises a VH CDR1 encoded by a nucleotide sequence having the nucleic acid sequence of SEQ ID NO:21, SEQ ID NO:31, SEQ ID NO:40, SEQ ID NO:50, SEQ ID NO:66, SEQ ID NO:77 or SEQ ID NO:93, a VH CDR2 encoded by a nucleotide sequence having the nucleic acid sequence of SEQ ID NO:22, SEQ ID NO:32, SEQ ID NO:41, SEQ ID NO:51, SEQ ID NO:59, SEQ ID NO:67, SEQ ID NO:78 or SEQ ID NO:94, and a VH CDR3 encoded by a nucleotide sequence having the nucleic acid sequence of SEQ ID NO:23, SEQ ID NO:33, SEQ ID NO:42, SEQ ID NO:52, SEQ ID NO:60, SEQ ID NO:68, SEQ ID NO:79 or SEQ ID NO:95.

The present invention provides antibodies that immunospecifically bind to a galanin peptide, said antibodies comprising a VL domain having the amino acid sequence of the VL domain of the murine 5B4 (FIG. 1B; SEQ ID NO:19), 1G12 (FIG. 3B; SEQ ID NO:29), 2F8 (FIG. 5B; SEQ ID NO:105), 1D7 (FIG. 7B; SEQ ID NO:48), 4B3 (FIG. 9B; SEQ ID NO:106), 2H9 (FIG. 11B; SEQ ID NO:107), 1A1 (FIG. 13B; SEQ ID NO:75) or 2E11 (FIG. 15B; SEQ ID NO:88). In a specific aspect, an antibody that immunospecifically binds to a galanin peptide comprises a VL domain having the amino acid of the VL domain of the humanized antibody 5B4-v2 (FIG. 17B; SEQ ID NO:101), the humanized antibody 5B4-v4 (FIG. 19B; SEQ ID NO:109), the humanized antibody 5B4-v5 (FIG. 21B; SEQ ID NO:113), the humanized antibody 5B4-v6 (FIG. 23B; SEQ ID NO:117), the humanized antibody 5B4-v7 (FIG. 25B; SEQ ID NO:121), the humanized antibody 5B4-v8 (FIG. 27B; SEQ ID NO:125), the humanized antibody 5B4-v9 (FIG. 29B; SEQ ID NO:129), the humanized antibody 5B4-v10 (FIG. 31B; SEQ ID NO:133), the humanized antibody 5B4-v11, the humanized antibody 5B4-v12, or the humanized antibody 5B4-v11. In another aspect, an antibody that immunospecifically binds to a galanin peptide comprises a VL domain having the amino acid sequence of the VL domain of the antibody produced by the murine hybridoma 1D7D1 (ATCC accession number PTA-5650) or the murine hybridoma 5B4C1 (ATCC accession number PTA-5651).

The present invention provides antibodies that immunospecifically bind to a galanin peptide, said antibodies comprising a VL domain encoded by a nucleotide sequence having a nucleic acid sequence of the VL domain for 5B4-v2 (FIG. 2B; SEQ ID NO:24), 1G12 (FIG. 4B; SEQ ID NO:34), 2F8 (FIG. 6B; SEQ ID NO:43), 1D7 (FIG. 8B; SEQ ID NO:53), 4B3 (FIG. 10B; SEQ ID NO:61), 2H9 (FIG. 12B; SEQ ID NO:70), 1A1 (FIG. 14B; SEQ ID NO:80) or 2E11 (FIG. 16B; SEQ ID NO:96). In one aspect, an antibody that immunospecifically binds to a galanin peptide comprises a VL domain encoded by a nucleotide sequence having a nucleic acid sequence of the VL domain for humanized 5B4-v2 (FIG. 18B; SEQ ID NO:103), the humanized antibody 5B4-v4 (FIG. 20B; SEQ ID NO:111), the humanized antibody 5B4-v5 (FIG. 22B; SEQ ID NO:115), the humanized antibody 5B4-v6 (FIG. 24B; SEQ ID NO:119), the humanized antibody 5B4-v7 (FIG. 26B; SEQ ID NO:123), the humanized antibody 5B4-v8 (FIG. 28B; SEQ ID NO:127), the humanized antibody 5B4-v9 (FIG. 30B; SEQ ID NO:131), the humanized antibody 5B4-v10 (FIG. 32B; SEQ ID NO:135), the humanized antibody 5B4-v11, the humanized antibody 5B4-v12, or the humanized antibody 5B4-v13. In another aspect, an antibody that immunospecifically binds to a galanin peptide comprises a VL domain encoded by a nucleotide sequence having a nucleic acid sequence of the VL domain of the antibody produced by the murine hybridoma 1D7D1 (ATCC accession number PTA-5650) or the murine hybridoma 5B4C1 (ATCC accession number PTA-5651).

The present invention also provides antibodies that immunospecifically bind to a galanin peptide, said antibodies comprising a VL CDR having the amino acid sequence of any one of the VL CDRs listed in Table 3, infra, and/or the amino acid sequence of the VL CDRs of the antibody produced by the murine hybridoma 1D7D1 (ATCC accession number PTA-5650) or the murine hybridoma 5B4C1 (ATCC accession number PTA-5651). The present invention also provides antibodies that immunospecifically bind to a galanin peptide, said antibodies comprising a VL CDR having the amino acid sequence of any one of the VL CDRs listed in Table 3, infra. In particular, the invention provides antibodies that immunospecifically bind to a galanin peptide, said antibodies comprising (or alternatively, consisting of) one, two, three or more VL CDRs having the amino acid sequence of any of the VL CDRs listed in Table 3, infra. In one aspect, an antibody that immunospecifically binds to a galanin peptide comprises a VL CDR1 having the amino acid sequence of SEQ ID NO:4, SEQ ID NO:10, SEQ ID NO:13 or SEQ ID NO:89. In another aspect, an antibody that immunospecifically binds to a galanin peptide comprises a VL CDR2 having the amino acid sequence of SEQ ID NO:5, SEQ ID NO:17 or SEQ ID NO:90. In another aspect, an antibody that immunospecifically binds to a galanin peptide comprises a VL CDR3 having the amino acid sequence of SEQ ID NO:6 or SEQ ID NO:91.

In another aspect, an antibody of that immunospecifically binds to a galanin peptide comprises a VL CDR1 having the amino acid sequence of SEQ ID NO:4, SEQ ID NO:10, SEQ ID NO:13 or SEQ ID NO:89 and a VL CDR2 having the amino acid sequence of SEQ ID NO:5, SEQ ID NO:17 or SEQ ID NO:90. In another aspect of an antibody that immunospecifically binds to a galanin peptide comprises a VL CDR1 having the amino acid sequence of SEQ ID NO:4, SEQ ID NO:10, SEQ ID NO:13 or SEQ ID NO:89 and a VL CDR3 having the amino acid sequence of SEQ ID NO:6 or SEQ ID NO:91. In another aspect, an antibody of that immunospecifically binds to a galanin peptide comprises a VL CDR2 having the amino acid sequence of SEQ ID NO:5, SEQ ID NO:17 or SEQ ID NO:90 and a VL CDR3 having the amino acid sequence of SEQ ID NO:6 or SEQ ID NO:91.

TABLE 3

| Antibody Name | VH CDR1 | VH CDR2 | VH CDR3 | VL CDR1 | VL CDR2 | VL CDR3 |
|---|---|---|---|---|---|---|
| 5B4 | GFNIEDYYMH (SEQ ID NO:1) | RIDPENGNTI (SEQ ID NO:2) | GYVD (SEQ ID NO:3) | RSSQSIVHSDGDTYLE (SEQ ID NO:4) | KVSNRFS (SEQ ID NO:5) | FQGSHVPYT (SEQ ID NO:6) |
| 1G12 | GFNIKDYYIH (SEQ ID NO:7) | RIDPEDGEIE (SEQ ID NO:8) | GYAS (SEQ ID NO:9) | RSSQTFVHSDGNTYLE (SEQ ID NO:10) | KVSNRFS (SEQ ID NO:5) | FQGSHVPYT (SEQ ID NO:6) |
| 2F8 | GFNIEDYYIH (SEQ ID NO:11) | RIDPENGNTI (SEQ ID NO:2) | GYVD (SEQ ID NO:3) | RSSQSIVHSDGDTYLE (SEQ ID NO:4) | KVSNRFS (SEQ ID NO:5) | FQGSHVPYT (SEQ ID NO:6) |
| 1D7 | GFNIKDYYIH (SEQ ID NO:7) | RIDPEDGETE (SEQ ID NO:12) | GYAS (SEQ ID NO:9) | RSSQSFVHSDGNTYLE (SEQ ID NO:13) | KVSNRFS (SEQ ID NO:5) | FQGSHVPYT (SEQ ID NO:6) |
| 4B3 | GFNIKDYYIH (SEQ ID NO:7) | RIDPEDGETE (SEQ ID NO:12) | GYAS (SEQ ID NO:9) | RSSQSFVHSDGNTYLE (SEQ ID NO:13) | KVSNRFS (SEQ ID NO:5) | FQGSHVPYT (SEQ ID NO:6) |
| 2H9 | GFNIKDYYIH (SEQ ID NO:7) | RIDPEDGETE (SEQ ID NO:14) | GYAS (SEQ ID NO:9) | RSSQSFVHSDGNTYLE (SEQ ID NO:13) | KVSNRFS (SEQ ID NO:5) | FQGSHVPYT (SEQ ID NO:6) |
| 1A1 | GFNIKDYYMH (SEQ ID NO:15) | RIDPENDNSI (SEQ ID NO:16) | GYVD (SEQ ID NO:3) | RSSQSIVHSDGDTYLE (SEQ ID NO:4) | KVSNRFS (SEQ ID NO:17) | FQGSHVPYT (SEQ ID NO:6) |
| 2E11 | GYTFSNYWIE (SEQ ID NO:86) | EILPGSESTK (SEQ ID NO:87) | FYGGFDY (SEQ ID NO:88) | KSSQSLLYSDGKIYLN (SEQ ID NO:89) | LVSKLDS (SEQ ID NO:90) | VQGTHFPRT (SEQ ID NO:91) |

Bold amino acid residues: The amino acid residues in bold may be substituted with another amino acid residue.

The present invention provides antibodies that immunospecifically bind to a galanin peptide, said antibodies comprising a VL CDR encoded by a nucleotide sequence having a nucleic acid sequence of any one of the VL CDRs of 5B4, 1G12, 2F8, 1D7, 4B3, 2H9, 1A1 or 2E11. In particular, the invention provides antibodies that immunospecifically bind to a galanin peptide, said antibodies comprising (or alternatively, consisting of) one, two, three, four, five or more VL CDRs encoded by a nucleotide sequence having a nucleic acid sequence of any of the VL CDRs 5B4, 1G12, 2F8, 1D7, 4B3, 2H9, 1A1 or 2E11. In one aspect, an antibody that immunospecifically binds to a galanin peptide comprises a VL CDR1 encoded by a nucleotide sequence having the nucleic acid sequence of SEQ ID NO:25, SEQ ID NO:35, SEQ ID NO:44, SEQ ID NO:54, SEQ ID NO:62, SEQ ID NO:71, SEQ ID NO:81 or SEQ ID NO:96. In another aspect, an antibody that immunospecifically binds to a galanin peptide comprises a VL CDR2 encoded by a nucleotide sequence having the nucleic acid sequence of SEQ ID NO:26, SEQ ID NO:36, SEQ ID NO:45, SEQ ID NO:55, SEQ ID NO:63, SEQ ID NO:72, SEQ ID NO:82 or SEQ ID NO:97. In another aspect, an antibody that immunospecifically binds to a galanin peptide comprises a VL CDR3 encoded by a nucleotide sequence having the nucleic acid sequence of SEQ ID NO:27, SEQ ID NO:37, SEQ ID NO:46, SEQ ID NO:56, SEQ ID NO:64, SEQ ID NO:73, SEQ ID NO:83 or SEQ ID NO:98.

In another aspect, an antibody that immunospecifically binds to a galanin peptide comprises a VL CDR1 encoded by a nucleotide sequence having the nucleic acid sequence of SEQ ID NO:25, SEQ ID NO:35, SEQ ID NO:44, SEQ ID NO:54, SEQ ID NO:62, SEQ ID NO:71, SEQ ID NO:81 or SEQ ID NO:96 and a VL CDR2 encoded by a nucleotide sequence having the nucleic acid sequence of SEQ ID NO:26, SEQ ID NO:36, SEQ ID NO:45, SEQ ID NO:55, SEQ ID NO:63, SEQ ID NO:72, SEQ ID NO:82 or SEQ ID NO:97. In another aspect, an antibody that immunospecifically binds to a galanin peptide comprises a VL CDR1 encoded by a nucleotide sequence having the nucleic acid sequence of SEQ ID NO:25, SEQ ID NO:35, SEQ ID NO:44, SEQ ID NO:54, SEQ ID NO:62, SEQ ID NO:71, SEQ ID NO:81 or SEQ ID NO:96 and a VL CDR3 encoded by a nucleotide sequence having the nucleic acid sequence of SEQ ID NO:27, SEQ ID NO:37, SEQ ID NO:46, SEQ ID NO:56, SEQ ID NO:64, SEQ ID NO:73, SEQ ID NO:83 or SEQ ID NO:98. In another aspect, an antibody that immunospecifically binds to a galanin peptide comprises a VL CDR2 encoded by a nucleotide sequence having the nucleic acid sequence of SEQ ID NO:26, SEQ ID NO:36, SEQ ID NO:45, SEQ ID NO:55, SEQ ID NO:63, SEQ ID NO:72, SEQ ID NO:82 or SEQ ID NO:97 and a VH CDR3 encoded by a nucleotide sequence having the nucleic acid sequence of SEQ ID NO:27, SEQ ID NO:37, SEQ ID NO:46, SEQ ID NO:56, SEQ ID NO:64, SEQ ID NO:73, SEQ ID NO:83 or SEQ ID NO:98. In yet another aspect, an antibody that immunospecifically binds to a galanin peptide comprises a VL CDR1 encoded by a nucleotide sequence having the nucleic acid sequence of SEQ ID NO:25, SEQ ID NO:35, SEQ ID NO:44, SEQ ID NO:54, SEQ ID NO:62, SEQ ID NO:71, SEQ ID NO:81 or SEQ ID NO:96, a VL CDR2 encoded by a nucleotide sequence having the nucleic acid sequence of SEQ ID NO:26, SEQ ID NO:36, SEQ ID NO:45, SEQ ID NO:55, SEQ ID NO:63, SEQ ID NO:72, SEQ ID NO:82 or SEQ ID NO:97, and a VL CDR3 encoded by a nucleotide sequence having the nucleic acid sequence of SEQ ID NO:27, SEQ ID NO:37, SEQ ID NO:46, SEQ ID NO:56, SEQ ID NO:64, SEQ ID NO:73, SEQ ID NO:83 or SEQ ID NO:98.

The present invention provides antibodies that immunospecifically bind to a galanin peptide, said antibodies comprising a VH domain disclosed herein combined with a VL domain disclosed herein, or other VL domain. The present invention also provides antibodies that immunospecifically bind to a galanin peptide, said antibodies comprising a VL domain disclosed herein combined with a VH domain disclosed herein, or other VH domain.

The present invention provides antibodies that immunospecifically bind to a galanin peptide, said antibodies comprising one or more VH CDRs and one or more VL CDRs of 5B4, 1G12, 2F8, 1D7, 4B3, 2H9, 1A1 and/or 2E11. In particular, the present invention provides antibodies that immunospecifically bind to a galanin peptide, said antibodies comprising one or more VH CDRs and one or more VL CDRs listed in Table 3, supra, or one or more VH CDRs and one or more VL CDRs of the antibody produced by the murine hybridoma 1D7D1 (ATCC accession number PTA-5650) or the murine hybridoma 5B4C1 (ATCC accession number PTA-5651). More specifically, the invention provides an antibody that immunospecifically binds to a galanin peptide, said antibody comprising (or alternatively, consisting of) a VH CDR1 and a VL CDR1; a VH CDR1 and a VL CDR2; a VH CDR1 and a VL CDR3; a VH CDR2 and a VL CDR1; VH CDR2 and VL CDR2; a VH CDR2 and a VL CDR3; a VH CDR3 and a VH CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1, a VH CDR2, a VH CDR3 and a VL CDR2; a VH CDR2, a VH CDR2 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR3, a VL CDR1 and a VL CDR2; a VH CDR1, a VH CDR3, a VL CDR1 and a VL CDR3; a VH CDR2, a VH CDR3, a VL CDR1 and a VL CDR2; a VH CDR2, a VH CDR3, a VL CDR1 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; or any combination thereof of the VH CDRs and VL CDRs listed in Table 3, supra.

The present invention provides for a nucleic acid molecule, generally isolated, encoding an antibody of the present invention that immunospecifically binds to a galanin peptide. In particular, the invention provides an isolated nucleic acid molecule encoding an antibody that immunospecifically binds to a galanin peptide, said antibody having the amino acid sequence of the variable heavy domain and/or variable light domain or an antigen-binding fragment thereof of the murine antibody 5B4, 1G12, 2F8, 1D7, 4B3, 2H9, 1A1 or 2E11. In one aspect, an isolated nucleic acid molecule encodes an antibody that immunospecifically binds to a galanin peptide, said antibody having the amino acid sequence of the variable heavy domain and/or variable light domain or an antigen-binding fragment thereof of the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13.

The invention provides an isolated nucleic acid molecule encoding an antibody that immunospecifically binds to a galanin peptide, said nucleic acid molecule comprising the nucleic acid sequence of the variable heavy domain and/or variable light domain or antigen-binding fragment thereof of the murine antibody 5B4, 1G12, 2F8, 1D7, 4B3, 2H9, 1A1 or 2E11. In one aspect, an isolated nucleic acid molecule encodes an antibody that immunospecifically binds to a galanin peptide, said nucleic acid molecule comprising the nucleic acid sequence of the variable heavy domain and/or variable light domain or antigen-binding fragment of the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13.

The invention provides an isolated nucleic acid molecule encoding an antibody that immunospecifically binds to a galanin peptide, said antibody comprising (alternatively, consisting of) a VH domain having the amino acid sequence of a VH domain of the murine antibody 5B4, 1G12, 2F8, 1D7, 4B3, 2H9, 1A1 or 2E11. In a specific aspect, an isolated nucleic acid molecule encodes an antibody that immunospecifically binds to a galanin peptide, said antibody comprising a VH domain having the amino acid sequence of the VH domain of the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13.

The invention provides an isolated nucleic acid molecule encoding an antibody that immunospecifically binds to a galanin peptide, said antibody comprising (alternatively, consisting of) a VH domain encoded by a nucleotide sequence having a nucleic acid sequence of a VH domain of murine 5B4, 1G12, 2F8, 1D7, 4B3, 2H9, 1A1 or 2E11. In one aspect, an isolated nucleic acid molecule encodes an antibody that immunospecifically binds to a galanin peptide, said antibody comprising a VH domain encoded by a nucleotide sequence having a nucleic acid sequence of the VH domain of humanized 5B4-v2, 5B4-v4, 5B4-v5, 5B4-v6, 5B4-v7, 5B4-v8, 5B4-v9, 5B4-v10, 5B4-v11, 5B4-v12, or 5B4-v13.

The invention provides an isolated nucleic acid molecule encoding an antibody that immunospecifically binds to a galanin peptide, said antibody comprising (alternatively, consisting of) a VH CDR having the amino acid sequence of any of the VH CDRs of the murine antibody 5B4, 1G12, 2F8, 1D7, 4B3, 2H9, 1A1 or 2E11. In particular, the invention provides an isolated nucleic acid molecule encoding an antibody that immunospecifically binds to a galanin peptide, said antibody comprising (alternatively, consisting of) a VH CDR having the amino acid sequence of any of the VH CDRs listed in Table 3, supra. More specifically, the invention provides an isolated nucleic acid molecule encoding an antibody that immunospecifically binds to a galanin peptide, said antibody comprising one, two, three, four, five or more VH CDRs having the amino acid sequence of any of the VH CDRs listed in Table 3, supra.

In one aspect, an isolated nucleic acid molecule encodes an antibody that immunospecifically binds to a galanin peptide, said antibody comprising a VH CDR1 having the amino acid sequence of the VH CDR1 listed in Table 3, supra. In another aspect, an isolated nucleic acid molecule encodes an antibody that immunospecifically binds to a galanin peptide, said antibody comprising a VH CDR2 having the amino acid sequence of the VH CDR2 listed in Table 3, supra. In another aspect, an isolated nucleic acid molecule encodes an antibody that immunospecifically binds to a galanin peptide, said antibody comprising a VH CDR3 having the amino acid sequence of the VH CDR3 listed in Table 3, supra.

The invention provides an isolated nucleic acid molecule encoding an antibody that immunospecifically binds to a galanin peptide, said antibody comprising (alternatively, consisting of) a VL domain having the amino acid sequence of a VL domain of the murine antibody 5B4, 1G12, 2F8, 1D7, 4B3, 2H9, 1A1 or 2E11. In one aspect, an isolated nucleic acid molecule encodes an antibody that immunospecifically binds to a galanin peptide, said antibody comprising a VL domain having the amino acid sequence of the VL domain of the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13.

The invention provides an isolated nucleic acid molecule encoding an antibody that immunospecifically binds to a galanin peptide, said antibody comprising (alternatively, consisting of) a VL domain encoded by a nucleotide sequence having a nucleic acid sequence of a VL domain of murine antibody 5B4, 1G12, 2F8, 1D7, 4B3, 2H9, 1A1 or 2E11. In one aspect, an isolated nucleic acid molecule encodes an antibody that immunospecifically binds to a galanin peptide, said antibody comprising a VL domain encoded by a nucleotide sequence having a nucleic acid sequence of the VL domain of humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13.

The invention also provides an isolated nucleic acid molecule encoding an antibody that immunospecifically binds to a galanin peptide, said antibody comprising (alternatively, consisting of) a VL CDR having the amino acid sequence of any of the VL CDRs of the murine antibody 5B4, 1G12, 2F8, 1D7, 4B3, 2H9, 1A1 or 2E11. In particular, the invention provides an isolated nucleic acid molecule encoding an antibody that immunospecifically binds to a galanin peptide, said antibody comprising (alternatively, consisting of) a VL CDR having the amino acid sequence of any of the VL CDRs listed in Table 3, supra. More specifically, the invention provides an isolated nucleic acid molecule encoding an antibody that immunospecifically binds to a galanin peptide, said antibody comprising one, two, three or more VL CDRs having the amino acid sequence of any of the VL CDRs listed in Table 3, supra.

In one aspect, an isolated nucleic acid molecule encodes an antibody that immunospecifically binds to a galanin peptide, said antibody comprising a VL CDR1 having the amino acid sequence of the VH CDR1 listed in Table 3, supra. In another aspect, an isolated nucleic acid molecule encodes an antibody that immunospecifically binds to a galanin peptide, said antibody comprising a VL CDR2 having the amino acid sequence of the VL CDR2 listed in Table 3, supra. In another aspect, an isolated nucleic acid molecule encodes an antibody that immunospecifically binds to a galanin peptide, said antibody comprising a VL CDR3 having the amino acid sequence of the VL CDR3 listed in Table 3, supra.

The present invention provides nucleic acid molecules encoding antibodies that immunospecifically bind to a galanin peptide, said antibodies comprising one or more VH CDRs and one or more VL CDRs of murine antibody 5B4, 1G12, 2F8, 1D7, 4B3, 2H9, 1A1 and/or 2E11. In particular, the present invention provides nucleic acid molecules encoding antibodies that immunospecifically bind to a galanin peptide, said antibodies comprising one or more VH CDRs and one or more VL CDRs listed in Table 3, supra. More specifically, the invention provides an isolated nucleic acid molecule encoding an antibody that immunospecifically binds to a galanin peptide, said antibody comprising (or alternatively, consisting of) a VH CDR1 and a VL CDR1; a VH CDR1 and a VL CDR2; a VH CDR1 and a VL CDR3; a VH CDR2 and a VL CDR1; VH CDR2 and VL CDR2; a VH CDR2 and a VL CDR3; a VH CDR3 and a VH CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1, a VH CDR2, a VH CDR3 and a VL CDR2; a VH CDR2, a VH CDR3 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR3, a VL CDR1 and a VL CDR2; a VH CDR1, a VH CDR3, a VL CDR1 and a VL CDR3; a VH CDR2, a VH CDR3, a VL CDR1 and a VL CDR2; a VH CDR2, a VH CDR3, a VL CDR1 and a VL CDR3; a VH CDR2, a VH CDR3, a VL CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; or any combination thereof of the VH CDRs and VL CDRs listed in Table 3, supra.

The present invention provides antibodies that immunospecifically bind to a galanin peptide, said antibodies comprising derivatives of the VH domains, VH CDRs, VL domains, or VL CDRs described herein that immunospecifically bind to a galanin peptide. Standard techniques known to those of skill in the art can be used to introduce mutations (e.g., deletions, additions, and/or substitutions) in the nucleotide sequence encoding an antibody of the invention, including, for example, site-directed mutagenesis and PCR-mediated mutagenesis which results in amino acid substitutions. In one aspect, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In one aspect, the derivatives have conservative amino acid substitutions are made at one or more predicted non-essential amino acid residues (i.e., amino acid residues which are not critical for the antibody to immunospecifically bind to a galanin peptide). A "conservative amino acid substitution" is one in which the amino acid residue is replaced with the amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded antibody can be expressed and the activity of the antibody can be determined.

The present invention provides for antibodies that immunospecifically bind to a galanin peptide, said antibodies comprising the amino acid sequence of the variable heavy domain and/or variable light domain or an antigen-binding fragment thereof of murine antibody 5B4, 1G12, 2F8, 1D7, 4B3, 2H9, 1A1 or 2E11, or humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 with one or more amino acid residue substitutions in the variable heavy domain and/or variable light domain or antigen-binding fragment. The present invention also provides for antibodies that immunospecifically bind to a galanin peptide, said antibodies comprising the amino acid sequence of the variable heavy domain and/or variable light domain or an antigen-binding fragment thereof of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 with one or more amino acid residue substitutions in one or more VH CDRs and/or one or more VL CDRs. Non-limiting examples of amino acid residues in the VH CDRs and VL CDRs of the murine antibodies 5B4, 1G12, 2F8, 1D7, 4B3, 2H9, 1A1 and 2E11 which may be substituted are shown in bold in Table 3, supra. The present invention also provides for antibodies that immunospecifically bind to a galanin peptide, said antibodies comprising the amino acid sequence of the variable heavy domain and/or variable light domain or an antigen-binding fragment thereof of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 with one or more amino acid residue substitutions in one or more VH frameworks and/or one or more VL frameworks. The antibody generated by introducing substitutions in the VH domain, VH CDRs, VL domain, VL CDRs and/or frameworks of murine 5B4, 1G12, 2F8, 1D7, 4B3, 2H9, 1A1 or 2E11, or humanized 5B4 can be tested in vitro and/or in vivo, for example, for its ability to bind to a galanin peptide, or for its ability to prevent, treat and/or ameliorate a hyperproliferative disorder or one or more symptoms thereof.

In one aspect, the invention provides for antibodies comprising the variable heavy domain and/or variable light domain or an antigen-binding fragment thereof of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 with an amino acid residue substitution in one or more of the following framework residues: VH amino acid residue 77, VH amino acid residue 81, VH amino acid residue 98, VL amino acid residue 41, VL amino acid residue 42 and/or VL amino acid residue 51. In another aspect, the invention provides for antibodies comprising the variable heavy domain and/or variable light domain or an antigen-binding fragment thereof of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 with an amino acid residue substitution in one or more of the following CDR residues: VL amino acid residue 31 and/or variable amino acid residue 39. In accordance with this aspect, a histidine at amino acid residue 31 of the VL domain may be substituted with lysine and/or a glutamic acid acid residue 39 of the VL domain may be substituted with a glutamine residue. In yet another aspect, the invention provides for antibodies comprising the variable heavy domain and/or variable light domain or an antigen-binding fragment thereof of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 with an amino acid residue substitution in one or more of the following framework residues and/or CDR residues: VH amino acid residue 77, VH amino acid residue 81, VH amino acid residue 98, VL amino acid residue 41, VL amino acid residue 42, VL amino acid residue 51, VL amino acid residue 31 and/or variable amino acid residue 39.

In one aspect, an antibody that immunospecifically binds to a galanin peptide comprises an amino acid sequenece encoded by a nucleic acid sequence comprising a nucleotide sequence that hybridizes to the nucleotide sequence encoding the variable heavy domain and/or variable light domain or an antigen-binding fragment thereof of murine antibody 5B4, 1G12, 2F8, 1D7, 4B3, 2H9, 1A1 or 2E11, or humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 under stringent conditions, e.g., hybridization to filter-bound DNA in 6× sodium chloride/sodium citrate (SSC) at about 45° C. followed by one or more washes in 0.2×SSC/0.1% SDS at about 50-65° C., under highly stringent conditions, e.g., hybridization to filter-bound nucleic acid in 6×SSC at about 45° C. followed by one or more washes in 0.1×SSC/ 0.2% SDS at about 68° C., or under other stringent hybridization conditions which are known to those of skill in the art (see, for example, Ausubel, F. M. et al., eds., 1989, *Current Protocols in Molecular Biology*, Vol. I, Green Publishing Associates, Inc. and John Wiley & Sons, Inc., New York at pages 6.3.1-6.3.6 and 2.10.3).

In another aspect, an antibody that immunospecifically binds to a galanin peptide comprises the amino acid sequence of a VH domain and/or the amino acid sequence a VL domain encoded by a nucleotide sequence that hybridizes to the nucleotide sequence encoding the VH and/or VL domains of murine antibody 5B4, 1G12, 2F8, 1D7, 4B3, 2H9, 1A1 or 2E11, or humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 under stringent conditions described herein or under other stringent hybridization conditions which are known to those of skill in the art. In another aspect, an antibody that immunospecifically binds to a galanin peptide comprises the amino acid sequence of a VH CDR or the amino acid sequence of a VL CDR encoded by a nucleotide sequence that hybridizes to the nucleotide sequence encoding any one of the VH CDRs or VL CDRs listed in Table 3, supra under stringent conditions described herein or under other stringent hybridization conditions which are known to those of skill in the art. In another aspect, an antibody that immunospecifically binds to a galanin peptide comprises the amino acid sequence of a VH CDR and the amino acid sequence of a VL CDR encoded by nucleotide sequences that hybridize to the nucleotide sequences encoding any one of the VH CDRs listed in Table 3, supra, and any one of the VL CDRs listed Table 3, supra, under stringent conditions described herein or under other stringent hybridization conditions which are known to those of skill in the art.

In another aspect, an antibody that immunospecifically binds to a galanin peptide comprises an amino acid sequence encoded by a nucleic acid sequence comprising a nucleotide sequence that hybridizes to the nucleotide sequence encoding the variable heavy domain and/or variable light domain or an antigen-binding fragment thereof of the antibody produced by the murine hybridoma 1D7D1 or the murine hybridoma 5B4C1 under stringent conditions described herein or under other stringent hybridization conditions which are known to those of skill in the art. In another aspect, an antibody that immunospecifically binds to a galanin peptide comprises the amino acid sequence of a VH CDR and/or the amino acid sequence of a VL CDR encoded by a nucleotide sequence that hybridizes to the nucleotide sequence encoding any one of the VH CDRs and/or VL CDRs of the antibody produced by the murine hybridoma 1D7D1 and/or the murine hybridoma 5B4C1 under stringent conditions described herein or under other stringent hybridization conditions which are known to those of skill in the art.

In one aspect, an antibody that immunospecifically binds to a galanin peptide comprises an amino acid sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy domain and/or variable light domain or an antigen-binding fragment thereof of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13. In another aspect, an antibody that immunospecifically binds to a galanin peptide comprises the amino acid sequence of a VH domain that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of VH domain of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13. In another aspect, an antibody that immunospecifically binds to a galanin peptide comprises an amino acid sequence of a VL domain that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of VL domain of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13.

In one aspect, an antibody that immunospecifically binds to a galanin peptide comprises an amino acid sequence encoded by a nucleic acid sequence comprising a nucleotide sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the nucleic acid sequence encoding the variable heavy domain and/or variable light domain or antigen-binding fragment thereof of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13. In another aspect, an antibody that immunospecifically binds to a galanin peptide comprises an amino acid sequence encoded by a nucleic acid sequence comprising a nucleotide sequence of a VH domain that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the nucleic acid sequence encoding the VH domain of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13. In another aspect, an antibody that immunospecifically binds to a galanin peptide comprises an amino acid sequence encoded by a nucleic acid sequence comprising a nucleotide sequence of a VL domain that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the nucleic acid sequence encoding the VL domain of the murine 5B4, 1G12, 2F8, 1D7, 4B3, 2H9, 1A1 or 2E11, or the humanized 5B4-v2, 5B4-v4, 5B4-v5, 5B4-v6, 5B4-v7, 5B4-v8, 5B4-v9, 5B4-v10, 5B4-v11, 5B4-v12, or 5B4-v13.

In another aspect, an antibody that immunospecifically binds to a galanin peptide comprises an amino acid sequence of one or more VH CDRs that are at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to any of the VH CDRs listed in Table 3, supra. In another aspect, an antibody that immunospecifically binds to a galanin peptide comprises an amino acid sequence of one or more VL CDRs that are at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to any of the VL CDRs listed in Table 3, supra. In another aspect, an antibody that immunospecifically binds to a galanin peptide comprises an amino acid sequence of one or more VH CDRs and one or more of VL CDRs that are at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to any of the VH CDRs and VL CDRs listed in Table 3, supra. In another aspect, an antibody that immunospecifically binds to a galanin peptide comprises an amino acid sequence encoded by a nucleic acid sequence comprising a nucleotide sequence of one or more VH CDRs and/or one or more VL CDRs that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to any of the VH CDRs and/or VL CDRs listed in Table 3, supra.

In one aspect, an antibody that immunospecifically binds to a galanin peptide comprises an amino acid sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy domain and/or variable light domain or an antigen-binding fragment thereof of the antibody produced by the murine hybridoma 1D7D1 (ATCC accession number PTA-5650) or the murine hybridoma 5B4C1 (ATCC accession number PTA-5651). In another aspect, an antibody that immunospecifically binds to a galanin peptide comprises the amino acid sequence of a VH domain that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of VH domain of the antibody produced by the murine hybridoma 1D7D1 (ATCC accession number PTA-5650) or the murine hybridoma 5B4C1 (ATCC accession number PTA-5651). In another aspect, an antibody that immunospecifically binds to a galanin peptide comprises an amino acid sequence of a VL domain that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the amino acid sequence of VL domain of the antibody produced by the murine hybridoma 1D7D1 (ATCC accession number PTA-5650) or the murine hybridoma 5B4C1 (ATCC accession number PTA-5650).

In one aspect, an antibody that immunospecifically binds to a galanin peptide comprises an amino acid sequence encoded by a nucleic acid sequence comprising a nucleotide sequence that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the nucleic acid sequence encoding the variable heavy domain and/or variable light domain or antigen-binding fragment thereof of the antibody produced by the murine hybridoma 1D7D1 (ATCC accession number PTA-5650) or the murine hybridoma 5B4C1 (ATCC accession number PTA-5651). In another aspect, an antibody that immunospecifically binds to a galanin peptide comprises an amino acid sequence encoded by a nucleic acid sequence comprising a nucleotide sequence of a VH domain that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the nucleic acid sequence encoding the VH domain of the antibody produced by the murine hybridoma 1D7D1 (ATCC accession number PTA-5650) or the murine hybridoma 5B4C1 (ATCC accession number PTA-5651). In another aspect, an antibody that immunospecifically binds to a galanin peptide comprises an amino acid sequence encoded by a nucleic acid sequence comprising a nucleotide sequence of a VL domain that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to the nucleic acid encoding the VL domain of the antibody produced by the murine hybridoma 1D7D1 (ATCC accession number PTA-5650) or the murine hybridoma 5B4C1 (ATCC accession number PTA-5651).

In another aspect, an antibody that immunospecifically binds to a galanin peptide comprises an amino acid sequence of one or more VH CDRs that are at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to any of the VH CDRs of the antibody produced by the murine hybridoma 1D7D1 (ATCC accession number PTA-5650) or the murine hybridoma 5B4C1 (ATCC accession number PTA-5651). In another aspect, an antibody that immunospecifically binds to a galanin peptide comprises an amino acid sequence of one or more VL CDRs that are at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to any of one of the VL CDRs of the antibody produced by the murine hybridoma 1D7D1 (ATCC accession number PTA-5650) or the murine hybridoma 5B4C1 (ATCC accession number PTA-5651). In another aspect, an antibody that immunospecifically binds to a galanin peptide comprises an amino acid sequence encoded by a nucleic acid sequence comprising a nucleotide sequence of one or more VH CDRs and/or one or more VL CDRs that is at least 35%, preferably at least 40%, at least 45%, at least 50%, at least 55%, at least 60%, at least 65%, at least 70%, at least 75%, at least 80%, at least 85%, at least 90%, at least 95%, or at least 99% identical to any of the VH CDRs and/or VL CDRs of the antibody produced by the murine hybridoma 1D7D1 (ATCC accession number PTA-5650) or the murine hybridoma 5B4C1 (ATCC accession number PTA-5651).

The present invention encompasses antibodies that compete with an antibody described herein for binding to a galanin peptide. In particular, the present invention encompasses antibodies that compete with antibodies comprising the variable heavy domain and/or variable light domain or an antigen-binding fragment thereof of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 for binding to the galanin peptide. In one aspect, the invention encompasses an antibody that reduces the binding of an antibody comprising the variable heavy domain and/or variable light domain or an antigen-binding fragment thereof of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 to a galanin peptide by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, or 5 to 15%, 10 to 25%, 25% to 50%, 45 to 75%, or 75 to 99% relative to a control such as PBS in a competition assay described herein or well-known to one of skill in the art. In another aspect, the invention encompasses an antibody that reduces the binding of an antibody comprising the variable heavy domain and/or variable light domain or an antigen-binding fragment thereof of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 to a galanin peptide by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, or 5 to 15%, 10 to 25%, 25% to 50%, 45 to 75%, or 75 to 99% relative to a control such as PBS in an ELISA competition assay or an IGEN assay. See, e.g., Obenauer-Kutner et al., 1997, J. Immunol. Methods 206:25-33 and Swanson et al., 1999, Dev. Biol. Stand. 97:135-147 for a description of an IGEN assay.

In one aspect, the present invention encompasses antibodies that compete with the antibody produced by the murine hybridoma 1D7D1 (ATCC accession number PTA-5650) or the murine hybridoma 5B4 (ATCC accession number PTA-5651), or an antigen-binding fragment thereof for binding to a galanin peptide. In another aspect, the invention encompasses an antibody that reduces the binding of an antibody comprising the variable heavy domain and/or variable light domain or an antigen-binding fragment thereof of the antibody produced by the murine hybridoma 1D7D1 (ATCC accession number PTA-5650) or the murine hybridoma 5B4C1 (ATCC accession number PTA-5651) to a galanin peptide by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, or 5 to 15%, 10 to 25%, 25% to 50%, 45 to 75%, or 75 to 99% relative to a control such as PBS in a competition assay described herein or well-known to one of skill in the art. In another aspect, the invention encompasses an antibody that reduces the binding of an antibody comprising the variable heavy domain and/or variable light domain or an antigen-binding fragment thereof of the antibody produced by the murine hybridoma 1D7D1 (ATCC accession number PTA-5650) or the murine hybridoma 5B4C1 (ATCC accession number PTA-5651) to a galanin peptide by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or more, or 5 to 15%, 10 to 25%, 25% to 50%, 45 to 75%, or 75 to 99% relative to a control such as PBS in an ELISA competition assay or an IGEN assay.

The present invention encompasses proteins comprising (alternatively, consisting of) a VH domain that competes with a protein comprising (alternatively, consisting of) the VH domain of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9 or 5B4-v10 for binding to a galanin peptide. The present invention also encompasses proteins comprising (alternatively, consisting of) a VL domain that competes with a protein comprising (alternatively, consisting of) a VL domain of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 for binding to a galanin peptide.

The present invention encompasses proteins comprising (alternatively, consisting of) a VH CDR that competes with a protein comprising (alternatively, consisting of) a VH CDR listed in Table 3, supra, for binding to a galanin peptide. The present invention also encompasses proteins comprising (alternatively, consisting of) a VL CDR that competes with a protein comprising (alternatively, consisting of) a VL CDR listed in Table 3, supra for binding to a galanin peptide.

The antibodies that immunospecifically bind to a galanin peptide include derivatives that are modified, i.e., by the covalent attachment of a type of molecule to the antibody such that covalent attachment. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

The present invention also provides antibodies that immunospecifically bind to a galanin peptide, said antibodies comprising a framework region known to those of skill in the art (e.g., a human or non-human framework). The framework regions may be naturally occurring or consensus framework regions. In one aspect, the fragment region of an antibody of the invention is human (see, e.g., Chothia et al., 1998, J. Mol. Biol. 278:457-479 for a listing of human framework regions, which is incorporated herein by reference in its entirety).

In one aspect, the present invention provides for antibodies that immunospecifically bind to a galanin peptide, said antibodies comprising the amino acid sequence of the CDRs of the murine antibody 5B4, 1G12, 2F8, 1D7, 4B3, 2H9, 1A1 or 2E11 and human framework regions with one or more amino acid substitutions at one, some or all of the following residues: (a) rare framework residues that differ between the murine antibody framework (i.e., donor antibody framework) and the human antibody framework (i.e., acceptor antibody framework); (b) Venier zone residues when differing between donor antibody framework and acceptor antibody framework; (c) interchain packing residues at the VH/VL interface that differ between the donor antibody framework and the acceptor antibody framework; (d) canonical residues which differ between the donor antibody framework and the acceptor antibody framework sequences, particularly the framework regions crucial for the definition of the canonical class of the murine antibody CDR loops; (e) residues that are adjacent to a CDR; (g) residues capable of interacting with the antigen; (h) residues capable of interacting with the CDR; and (i) contact residues between the VH domain and the VL domain.

The present invention encompasses antibodies that immunospecifically bind to a galanin peptide, said antibodies comprising the amino acid sequence of the variable heavy domain and/or variable light domain or an antigen-binding fragment thereof of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 with mutations (e.g., one or more amino acid substitutions) in the framework regions. In certain aspects, antibodies that immunospecifically bind to a galanin peptide comprise the amino acid sequence of the variable heavy domain and/or variable light domain or an antigen-binding fragment thereof of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 with one or more amino acid residue substitutions in the framework regions of the VH and/or VL domains. In one aspect, the amino acid substitutions in the framework region improve binding of the antibody to a galanin peptide. Non-limiting examples of amino acid residues in the frameworks that may be substituted include, VH amino acid residue 77, VH amino acid residue 81, VH amino acid residue 98, VL amino acid residue 41, VL amino acid residue 42 and VL amino acid residue 51.

The present invention also encompasses antibodies that immunospecifically bind to a galanin peptide, said antibodies comprising the amino acid sequence of the variable heavy domain and/or variable light domain of the murine antibody 5B4, 1G12, 2F8, 1D7, 4B3, 2H9, 1A1 or 2E11, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 with mutations (e.g., one or more amino acid residue substitutions) in the hypervariable and framework regions. In one aspect, the amino acid substitutions in the hypervariable and framework regions improve binding of the antibody to a galanin peptide.

The present invention also provides antibodies of the invention that comprise constant regions known to those of skill in the art. In one aspect, the constant regions of an antibody of the invention are human.

The invention encompasses antibodies that immunospecifically bind to a galanin peptide found in the milieu, i.e., not bound to a galanin receptor (e.g., GALR1, GALR2 and/or GALR3). The invention also encompasses antibodies that immunospecifically bind to a galanin peptide bound to a cellular membrane-bound galanin receptor (e.g., GALR1, GALR2 and/or GALR3).

In one aspect, antibodies that immunospecifically bind to a galanin peptide inhibit and/or reduce the interaction between the galanin peptide and one or more galanin receptors by approximately 25%, preferably approximately 30%, approximately 35%, approximately 45%, approximately 50%, approximately 55%, approximately 60%, approximately 65%, approximately 70%, approximately 75%, approximately 80%, approximately 85%, approximately 90%, approximately 95%, or approximately 98% relative to a control such as PBS in an in vivo and/or in vitro assay described herein or well-known to one of skill in the art (for example, an immunoassay such as an ELISA or the BIAcore assay described Section 5.6.1). In another aspect, antibodies that immunospecifically bind to a galanin peptide do not inhibit or reduce the interaction between a galanin peptide and one or more galanin receptors in an in vivo and/or in vitro assay described herein or well-known to one of skill in the art (for example, an immunoassay such as an ELISA or the BIAcore assay described Section 5.6.1). In another aspect, antibodies that immunospecifically bind to a galanin peptide inhibit and/or reduce the interaction between the galanin peptide and one or more galanin receptors by less than 20%, less than 15%, less than 10%, or less than 5% relative to a control such as PBS using, in an in vivo and/or in vitro assay described herein or well-known to one of skill in the art (for example, an immunoassay such as an ELISA or the BIAcore assay described Section 5.6.1). In another aspect, antibodies that immunospecifically bind to a galanin peptide inhibit and/or reduce the interaction between the galanin peptide and only one galanin receptor by approximately 25%, preferably approximately 30%, approximately 35%, approximately 45%, approximately 50%, approximately 55%, approximately 60%, approximately 65%, approximately 70%, approximately 75%, approximately 80%, approximately 85%, approximately 90%, approximately 95%, or approximately 98% relative to a control such as PBS in an in vivo and/or in vitro assay described herein or well-known to one of skill in the art (for example, an immunoassay such as an ELISA or the BIAcore assay described Section 5.6.1). In yet another aspect, antibodies that immunospecifically bind to a galanin peptide inhibit and/or reduce the interaction between the galanin peptide and one galanin receptor more than another galanin receptor by approximately 25%, preferably approximately 30%, approximately 35%, approximately 45%, approximately 50%, approximately 55%, approximately 60%, approximately 65%, approximately 70%, approximately 75%, approximately 80%, approximately 85%, approximately 90%, approximately 95%, or approximately 98% relative to a control such as PBS in an in vivo and/or in vitro assay described herein or well-known to one of skill in the art (for example, an immunoassay such as an ELISA or the BIAcore assay described Section 5.6.1). Non-limiting examples of assays that can be used to measure the inhibition and/or reduction in the interaction between a galanin peptide and a galanin receptor include assays that measure $Ca^{2+}$ flux (e.g., fluorescence imaging plate reader (FLIPR) and aequorin assays), cyclic AMP detection assays, proliferation assays, apoptosis assays, $^{125}$I-galanin binding assays and ERK phosphorylation assays.

In one aspect, antibodies that immunospecifically bind to a galanin peptide inhibit or reduce the proliferation of cancerous cells, inhibit or reduce the growth of a tumor, and/or inhibit or reduce the spread of cancer by approximately 25%, preferably approximately 30%, approximately 35%, approximately 45%, approximately 50%, approximately 55%, approximately 60%, approximately 65%, approximately 70%, approximately 75%, approximately 80%, approximately 85%, approximately 90%, approximately 95%, or approximately 98% relative to a control such as PBS in an in vivo and/or in vitro assay described herein or well-known to one of skill in the art. Non-limiting examples of assays that can be used to measure proliferation of cancer cells in vitro include a $^3$H-thymidine assay and trypan blue cell counts.

The antibodies of the present invention that immunospecifically bind to a galanin peptide may be monospecific, bispecific, trispecific or of greater multispecificity. Multispecific antibodies may be specific for different epitopes of a galanin peptide or may be specific for both a galanin peptide as well as for a heterologous epitope, such as a heterologous polypeptide or solid support material. See, e.g PCT publications WO 93/17715, WO 92/08802, WO 91/00360, and WO 92/05793; Tutt, et al., 1991, J. Immunol. 147:60-69; U.S. Pat. Nos. 4,474,893, 4,714,681, 4,925,648, 5,573,920, 5,855,886, 5,821,333, 5,807,706, 5,731,168, 5,601,819, and 6,458,933, and Kostelny et al., 1992, J. Immunol. 148:1547-1553.

The present invention provides peptides, polypeptides and/or proteins comprising one or more variable or hypervariable regions of the antibodies described herein. In one aspect, peptides, polypeptides or proteins comprising one or more variable or hypervariable regions of antibodies of the invention further comprise a heterologous amino acid sequence. In certain aspects, such a heterologous amino acid sequence comprises at least 5 contiguous amino acid residues, at least 10 contiguous amino acid residues, at least 15 contiguous amino acid residues, at least 20 contiguous amino acid residues, at least 25 contiguous amino acid residues, at least 30 contiguous amino acid residues, at least 40 contiguous amino acid residues, at least 50 contiguous amino acid residues, at least 75 contiguous amino acid residues, at least 100 contiguous amino acid residues or more contiguous amino acid residues. Such peptides, polypeptides and/or proteins may be referred to as fusion proteins.

In one aspect, peptides, polypeptides or proteins comprising one or more variable or hypervariable regions of the antibodies of the invention are about 10 amino acid residues, about 15 amino acid residues, about 20 amino acid residues, about 25 amino acid residues, about 30 amino acid residues, about 35 amino acid residues, about 40 amino acid residues, about 45 amino acid residues, about 50 amino acid residues, about 75 amino acid residues, about 100 amino acid residues, about 125 amino acid residues, about 150 amino acid residues or more amino acid residues in length. In certain aspects, peptides, polypeptides, or proteins comprising one or more variable or hypervariable regions of an antibody of the invention immunospecifically bind to a galanin peptide. In other aspects, peptides, polypeptides, or proteins comprising one or more variable or hypervariable regions of an antibody of the invention do not immunospecifically bind to a galanin peptide.

In one aspect, the present invention provides peptides, polypeptides and/or proteins comprising a VH domain and/or VL domain of one of the antibodies described herein. In one aspect, the present invention provides peptides, polypeptides and/or proteins comprising one or more CDRs having the amino acid sequence of any of the CDRs listed in Table 3, supra. In accordance with these aspects, the peptides, polypeptides or proteins may further comprise a heterologous amino acid sequence.

Peptides, polypeptides or proteins comprising one or more variable or hypervariable regions have utility, e.g., in the production of anti-idiotypic antibodies which in turn may be used to prevent, treat, and/or ameliorate one or more symptoms associated with a disorder (e.g., a hyperproliferative disorder or an infection). The anti-idiotypic antibodies produced can also be utilized in immunoassays, such as, e.g., ELISAs, for the detection of antibodies which comprise a variable or hypervariable region contained in the peptide, polypeptide or protein used in the production of the anti-idiotypic antibodies.

5.1.1 Antibodies Having Increased Half-Lives

The present invention provides for antibodies that immunospecifically bind to a galanin peptide which have an extended half-life in vivo. In particular, the present invention provides antibodies that immunospecifically bind to a galanin peptide which have a half-life in a subject, in one aspect, a mammal and, in one aspect, a human, of greater than 3 days, greater than 7 days, greater than 10 days, preferably greater than 15 days, greater than 25 days, greater than 30 days, greater than 35 days, greater than 40 days, greater than 45 days, greater than 2 months, greater than 3 months, greater than 4 months, or greater than 5 months.

To prolong the serum circulation of antibodies (e.g., monoclonal antibodies, single chain antibodies and Fab fragments) in vivo, for example, inert polymer molecules such as high molecular weight polyethyleneglycol (PEG) can be attached to the antibodies with or without a multifunctional linker either through site-specific conjugation of the PEG to the N- or C-terminus of the antibodies or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein.

Antibodies having an increased half-life in vivo can also be generated by introducing one or more amino acid modifications (i.e., substitutions, insertions or deletions) into an IgG constant domain, or FcRn binding fragment thereof (in one aspect, a Fc or hinge-Fc domain fragment). See, e.g., International Publication No. WO 98/23289; International Publication No. WO 97/34631; and U.S. Pat. No. 6,277,375, each of which is incorporated herein by reference in its entirety.

Further, antibodies can be conjugated to albumin in order to make the antibody more stable in vivo or have a longer half life in vivo. The techniques are well-known in the art, see, e.g., International Publication Nos. WO 93/15199, WO 93/15200, and WO 01/77137; and European Patent No. EP 413,622, all of which are incorporated herein by reference.

5.1.2 Antibody Conjugates

The present invention provides antibodies that immunospecifically bind to a galanin peptide, wherein said antibodies are recombinantly fused or chemically conjugated (including both covalent and non-covalent conjugations) to a heterologous protein or polypeptide (or fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antigen-binding fragment of an antibody described herein (e.g., a Fab fragment, Fd fragment, Fv fragment, F(ab)$_2$ fragment, a VH domain, a VH CDR, a VL domain or a VL CDR) and a heterologous protein, polypeptide, or peptide. In one aspect, the heterologous protein, polypeptide, or peptide that the antibody is fused to is useful for targeting the antibody to a particular cell type. For example, an antibody that immunospecifically binds to a cell surface receptor expressed by a particular cell type (e.g., an immune cell) may be fused or conjugated to an antibody of the invention. Methods for fusing or conjugating proteins, polypeptides, or peptides to an antibody are known in the art. See, e.g., U.S. Pat. Nos. 5,336,603, 5,622,929, 5,359,046, 5,349,053, 5,447,851, and 5,112,946; European Patent Nos. EP 307,434 and EP 367,166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341 (said references are incorporated herein by reference in their entireties).

Additional fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of antibodies or antibody fragments of the invention (e.g., antibodies or antibody fragments with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies, or the encoded antibodies, may be altered by being subjected to random mutagenesis by error-prone PCR, random nucleotide insertion or other methods prior to recombination. A polynucleotide encoding an antibody that immunospecifically binds to a galanin peptide may be recombined with one or more components, motifs, sections, parts, domains, fragments, etc. of one or more heterologous molecules.

Moreover, the antibodies can be fused to marker sequences, such as a peptide to facilitate purification. In some aspects, the marker amino acid sequence is a hexa-histidine peptide, such as the tag provided in a pQE vector (QIAGEN, Inc.), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In other aspects, antibodies of the present invention are conjugated to a diagnostic or detectable agent. Such antibodies can be useful for monitoring or prognosing the onset, development, progression and/or severity of a disorder associated with aberrant expression and/or activity of galanin and/or a galanin receptor (e.g., a hyperproliferative disorder, Alzheimer's disease, depression and eating disorders) as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}I$, $^{125}I$, $^{123}I$, and $^{121}I$), carbon ($^{14}C$), sulfur ($^{35}S$), tritium ($^{3}H$), indium ($^{115}In$, $^{113}In$, $^{112}In$, and $^{111}In$), technetium ($^{99}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, $^{97}Ru$, $^{68}Ge$, $^{57}Co$, $^{65}Zn$, $^{85}Sr$, $^{32}P$, $^{153}Gd$, $^{169}Yb$, $^{51}Cr$, $^{54}Mn$, $^{75}Se$, $^{113}Sn$, and $^{117}Tin$; and positron emitting metals using various positron emission tomographies, and non-radioactive paramagnetic metal ions.

The present invention further encompasses uses of antibodies conjugated to a therapeutic moiety. An antibody may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, antimetabolites (e.g., methotrexate, 6-mercaptopurine, 6-thioguanine, cytarabine, 5-fluorouracil decarbazine); alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP), and cisplatin); anthracyclines (e.g., daunorubicin (formerly daunomycin) and doxorubicin); antibiotics (e.g., dactinomycin (formerly actinomycin), bleomycin, mithramycin, and anthramycin (AMC)); Auristatin molecules (e.g., auristatin PHE, bryostatin 1, and solastatin 10; see Woyke et al., Antimicrob. Agents Chemother. 46:3802–8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun. 266:76-80 (1999), Mohammad et al., Int. J. Oncol. 15:367-72 (1999), all of which are incorporated herein by reference); hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantarjian et al., Clin Cancer Res. 8(7):2167-76 (2002)); cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucorticoids, procaine, tetracaine, lidocaine, propranolol, and puromycin and analogs or homologs thereof and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); farnesyl transferase inhibitors (e.g., R115777, BMS-214662, and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); topoisomerase inhibitors (e.g., camptothecin; irinotecan; SN-38; topotecan; 9-aminocamptothecin; GG-211 (GI 147211); DX-895 1f; IST-622; rubitecan; pyrazoloacridine; XR-5000; saintopin; UCE6; UCE1022; TAN-1518A; TAN-1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin); antisense oligonucleotides (e.g., those disclosed in the U.S. Pat. Nos. 6,277,832, 5,998,596, 5,885,834, 5,734,033, and 5,618,709); adenosine deaminase inhibitors (e.g., Fludarabine phosphate and 2-Chlorodeoxyadenosine); ibritumomab tiuxetan (Zevalin®); tositumomab (Bexxar®)) and pharmaceutically acceptable salts, solvates, clathrates, and prodrugs thereof.

Further, an antibody may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, pseudomonas exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567-1574), and VEGF (see, International Publication No. WO 99/23105), an anti-angiogenic agent, e.g., angiostatin, endostatin or a component of the coagulation pathway (e.g., tissue factor); or, a biological response modifier such as, for example, a lymphokine (e.g., interferon gamma ("IFN-γ"), interleukin-1 ("IL-1"), interleukin-2 ("IL-2"), interleukin-5 ("IL-5"), interleukin-6 ("IL-6"), interleuking-7 ("IL-7"), interleukin-10 ("IL-10"), interleukin-12 ("IL-12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid. fibrinopeptides A and B from the α and β chains of fibrinogen, fibrin monomer).

Moreover, an antibody can be conjugated to therapeutic moieties such as a radioactive metal ion, such as alph-emiters such as $^{213}Bi$ or macrocyclic chelators useful for conjugating radiometal ions, including but not limited to, $^{131}$In, $^{131}$LU, $^{131}$Y, $^{131}$Ho, $^{131}$Sm, to polypeptides. In certain aspects, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4(10): 2483-90; Peterson et al., 1999, Bioconjug. Chem. 10(4): 553-7; and Zimmerman et al., 1999, Nucl. Med. Biol. 26(8):943-50, each incorporated by reference in their entireties.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Alternatively, an antibody can be conjugated to a second antibody to form an antibody heteroconjugate as described by Segal in U.S. Pat. No. 4,676,980, which is incorporated herein by reference in its entirety.

The therapeutic moiety or drug conjugated to an antibody that immunospecifically binds to a galanin peptide should be chosen to achieve the desired prophylactic or therapeutic effect(s) for a particular hyperproliferative disorder in a subject. A clinician or other medical personnel should consider the following when deciding on which therapeutic moiety or drug to conjugate to an antibody that immunospecifically binds to a galanin peptide: the nature of the disease, the severity of the disease, and the condition of the subject.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

5.2 Therapies Useful in Combination with Galanin Antibodies

The present invention also provides methods for preventing, managing, treating, and/or ameliorating diseases and disorders including, but not limited to, disorders characterized by aberrant expression and/or activity galanin and disorders characterized by aberrant expression and/or activity of a galanin receptor comprising administering to a subject in need thereof an effective amount of one or more antibodies that immunospecifically bind to a galanin peptide and an effective amount of one or more therapies (e.g., prophylactic or therapeutic agents) other than antibodies that immunospecifically bind to a galanin peptide. The present invention also provides compositions comprising one or more antibodies that immunospecifically bind to a galanin peptide and one or more prophylactic or therapeutic agents other than antibodies that immunospecifically bind to a galanin peptide and methods of preventing, managing, treating, and/or ameliorating a disorder utilizing said compositions. Therapeutic or prophylactic agents include, but are not limited to, small molecules, synthetic drugs, peptides, polypeptides, proteins, nucleic acids (e.g., DNA and RNA nucleotides including, but not limited to, antisense nucleotide sequences, triple helices, RNAi, and nucleotide sequences encoding biologically active proteins, polypeptides or peptides) antibodies, synthetic or natural inorganic molecules, mimetic agents, and synthetic or natural organic molecules.

Any therapy (e.g., prophylactic or therapeutic agents) which is known to be useful, or which has been used or is currently being used for the prevention, management, treatment, or amelioration of a disorder characterized by aberrant expression and/or activity of galanin and/or a disorder characterized by aberrant expression and/or activity of a galanin receptor can be used in combination with an antibody that immunospecifically binds to a galanin peptide in accordance with the invention described herein. See, e.g., Gilman et al., *Goodman and Gilman's: The Pharmacological Basis of Therapeutics*, Tenth Ed., McGraw-Hill, New York, 2001; The *Merck Manual of Diagnosis and Therapy*, Berkow, M. D. et al. (eds.), 17th Ed., Merck Sharp & Dohme Research Laboratories, Rahway, N.J., 1999; and *Cecil Textbook of Medicine,* 20th Ed., Bennett and Plum (eds.), W. B. Saunders, Philadelphia, 1996 for information regarding therapies, in particular prophylactic or therapeutic agents, which have been or are currently being used for preventing, treating, managing, and/or ameliorating disorders associated with aberrant expression and/or activity of galanin and/or disorders associated with aberrant expression and/or activity of a galanin receptor. Examples of prophylactic and therapeutic agents include, but are not limited to, immunomodulatory agents, anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steroids, non-steriodal anti-inflammatory drugs (e.g., aspirin, ibuprofen, diclofenac, and COX-2 inhibitors), antibodies that immunospecifically bind to one or more galanin receptors (e.g., GALR1, GALR2 and/or GALR3) anti-malarial agents (e.g., hydroxychloroquine), anti-cancer agents; anti-viral agents, and antibiotics (e.g., dactinomycin (formerly actinomycin), bleomycin, erythomycin, penicillin, mithramycin, and anthramycin (AMC)).

5.2.1 Immunomodulatory Therapies

Any immunomodulatory agent well known to one of skill in the art may be used in the methods and compositions of the invention. Immunomodulatory agents can affect one or more or all aspects of the immune response in a subject. Aspects of the immune response include, but are not limited to, the inflammatory response, the complement cascade, leukocyte and lymphocyte differentiation, proliferation, and/or effector function, and the cellular communication among cells of the immune system. In certain aspects of the invention, an immunomodulatory agent modulates one aspect of the immune response. In other aspects, an immunomodulatory agent modulates more than one aspect of the immune response. In one aspect of the invention, the administration of an immunomodulatory agent to a subject inhibits or reduces one or more aspects of the subject's immune response capabilities. In one aspect of the invention, the immunomodulatory agent inhibits or suppresses the immune response in a subject. In accordance with the invention, an immunomodulatory agent is not antibody that immunospecifically binds to a galanin peptide. In certain aspects, an immunomodulatory agent is not an anti-inflammatory agent. In certain aspects, an immunomodulatory agent is not an anti-angiogneic agent. In certain aspects, an immunomodulatory agent is a chemotherapeutic agent. In certain aspects, an immunomodulatory agent is not a chemotherapeutic agent.

Examples of immunomodulatory agents include, but are not limited to, proteinaceous agents such as cytokines, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, cytokine receptor modulators, and modulators mast cell modulators.

As used herein, the term "T cell receptor modulator" refers to an agent which modulates the phosphorylation of a T cell receptor, the activation of a signal transduction pathway associated with a T cell receptor and/or the expression of a particular protein such as a cytokine. Such an agent may directly or indirectly modulate the phosphorylation of a T cell receptor, the activation of a signal transduction pathway associated with a T cell receptor, and/or the expression of a particular protein such as a cytokine. Examples of T cell receptor modulators include, but are not limited to, peptides, polypeptides, proteins, fusion proteins and antibodies which immunospecifically bind to a T cell receptor or a fragment thereof. Further, examples of T cell receptor modulators include, but are not limited to, proteins, peptides, polypeptides (e.g., soluble T cell receptors), fusion proteins and antibodies that immunospecifically bind to a ligand for a T cell receptor or a fragment thereof. Specific examples of T cell receptor modulators include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), and anti-B7 antibodies (e.g., IDEC-114) (IDEC))), CTLA4-immunoglobulin, and LFA-3TIP (Biogen, International Publication No. WO 93/08656 and U.S. Pat. No. 6,162,432).

As used herein, the term "cytokine receptor modulator" refers to an agent which modulates the phosphorylation of a cytokine receptor, the activation of a signal transduction pathway associated with a cytokine receptor, and/or the expression of a particular protein such as a cytokine. Such an agent may directly or indirectly modulate the phosphorylation of a cytokine receptor, the activation of a signal transduction pathway associated with a cytokine receptor, and/or the expression of a particular protein such as a cytokine. Thus, examples of cytokine receptor modulators include, but are not limited to, cytokines, fragments of cytokines, fusion proteins, and antibodies that immunospecifically bind to a cytokine receptor or a fragment thereof. Further, examples of cytokine receptor modulators include, but are not limited to, peptides, polypeptides (e.g., soluble cytokine receptors), fusion proteins and antibodies that immunospecifically binds to a cytokine or a fragment thereof. Specific examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin IL-2, IL-3, IL-4, IL-5, IL-6, IL-7, IL-8, IL-9, IL-10, IL-11, IL-12, IL-13, IL-15, IL-23, TNF-α, TNF-β, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-3 receptor antibodies, anti-IL-4 receptor antibodies, anti-IL-6 receptor antibodies, anti-IL-10 receptor antibodies, anti-IL-12 receptor antibodies, anti-IL-13 receptor antibodies, anti-IL-15 receptor antibodies, and anti-IL-23 receptor antibodies), anti-cytokine antibodies (e.g., anti-IFN antibodies, anti-TNF-α antibodies, anti-IL-1β antibodies, anti-IL-3 antibodies, anti-IL-6 antibodies, anti-IL-8 antibodies (e.g., ABX-IL-8 (Abgenix)), anti-IL-12 antibodies, anti-IL-13 antibodies, anti-IL-15 antibodies, and anti-IL-23 antibodies).

In one aspect, a cytokine receptor modulator is IL-3, IL-4, IL-10, or a fragment thereof. In another aspect, a cytokine receptor modulator is an anti-IL-1β antibody, anti-IL-6 antibody, anti-IL-12 receptor antibody, or anti-TNF-α antibody. In another aspect, a cytokine receptor modulator is the extracellular domain of a TNF-α receptor or a fragment thereof. In certain aspects, a cytokine receptor modulator is not a TNF-α antagonist.

An immunomodulatory agent may be selected to interfere with the interactions between the T helper subsets (TH1 or TH2) and B cells to inhibit neutralizing antibody formation. Antibodies that interfere with or block the interactions necessary for the activation of B cells by TH (T helper) cells, and thus block the production of neutralizing antibodies, are useful as immunomodulatory agents in the methods of the invention. For example, B cell activation by T cells requires certain interactions to occur (Durie et al., Immunol. Today, 15(9):406-410 (1994)), such as the binding of CD40 ligand on the T helper cell to the CD40 antigen on the B cell, and the binding of the CD28 and/or CTLA4 ligands on the T cell to the B7 antigen on the B cell. Without both interactions, the B cell cannot be activated to induce production of the neutralizing antibody.

The CD40 ligand (CD40L)-CD40 interaction is a desirable point to block the immune response because of its broad activity in both T helper cell activation and function as well as the absence of redundancy in its signaling pathway. Thus, in one aspect of the invention, the interaction of CD40L with CD40 is transiently blocked at the time of administration of one or more of the immunomodulatory agents. This can be accomplished by treating with an agent which blocks the CD40 ligand on the TH cell and interferes with the normal binding of CD40 ligand on the T helper cell with the CD40 antigen on the B cell. An antibody to CD40 ligand (anti-CD40L) (available from Bristol-Myers Squibb Co; see, e.g., European patent application 555,880, published Aug. 18, 1993) or a soluble CD40 molecule can be selected and used as an immunomodulatory agent in accordance with the methods of the invention.

An immunomodulatory agent may be selected to inhibit the interaction between TH1 cells and cytotoxic T lymphocytes ("CTLs") to reduce the occurrence of CTL-mediated killing. An immunomodulatory agent may be selected to alter (e.g., inhibit or suppress) the proliferation, differentiation, activity and/or function of the CD4+ and/or CD8+ T cells. For example, antibodies specific for T cells can be used as immunomodulatory agents to deplete, or alter the proliferation, differentiation, activity and/or function of CD4+ and/or CD8+ T cells.

In another aspect, an immunomodulatory agent which reduces or inhibits one or more biological activities (e.g., the differentiation, proliferation, and/or effector functions) of TH0, TH1, and/or TH2 subsets of CD4+ T helper cells is administered to a subject at risk of or with a disorder associated with or characterized by aberrant expression and/or activity of galanin and/or a disorder associated with or characterized by aberrant expression of a galanin receptor in accordance with the methods of the invention. One example of such an immunomodulatory agent is IL-4. IL-4 enhances antigen-specific activity of TH2 cells at the expense of the TH1 cell function (see, e.g., Yokota et al., 1986 Proc. Natl. Acad. Sci., USA, 83:5894-5898; and U.S. Pat. No. 5,017,691). Other examples of immunomodulatory agents that affect the biological activity (e.g., proliferation, differentiation, and/or effector functions) of T-helper cells (in particular, TH1 and/or TH2 cells) include, but are not limited to, IL-2, IL-4, IL-5, IL-6, IL-0, IL-12, IL-13, IL-15, IL-23, and interferon (IFN)-γ.

In another aspect, an immunomodulatory agent administered to a subject at risk of or with a disorder associated with or characterized by aberrant expression and/or activity of galanin and/or a disorder associated with or characterized by aberrant expression of a galanin receptor in accordance with the methods of the invention is a cytokine that prevents antigen presentation. In one aspect, an immunomodulatory agent used in the methods of the invention is IL-10. IL-10 also reduces or inhibits macrophage action which involves bacterial elimination.

In one aspect, proteins, polypeptides or peptides (including antibodies) that are utilized as immunomodulatory agents are derived from the same species as the recipient of the proteins, polypeptides or peptides so as to reduce the likelihood of an immune response to those proteins, polypeptides or peptides. In another aspect, when the subject is a human, the proteins, polypeptides, or peptides that are utilized as immunomodulatory agents are human or humanized.

In accordance with the invention, one or more immunomodulatory agents are administered to a subject at risk of or with a disorder associated with or characterized by aberrant expression and/or activity of galanin and/or a disorder associated with or characterized by aberrant expression of a galanin receptor prior to, subsequent to, or concomitantly with an antibody that immunospecifically binds to a galanin peptide. In one aspect, one or more immunomodulatory agents are administered in combination with an antibody that immunospecifically binds to a galanin peptide to a subject at risk of or with a disorder associated with or characterized by aberrant expression and/or activity of galanin and/or a disorder associated with or characterized by aberrant expression of a galanin receptor to reduce or inhibit one or more aspects of the immune response as deemed necessary by one of skill in the art. Any technique well-known to one skilled in the art can be used to measure one or more aspects of the immune response in a particular subject, and thereby determine when it is necessary to administer an immunomodulatory agent to said subject. In one aspect, a mean absolute lymphocyte count of approximately 500 cells/mm$^3$, preferably 600 cells/mm$^3$, 650 cells/mm$^3$, 700 cells/mm$^3$, 750 cells/mm$^3$, 800 cells/mm$^3$, 900 cells/mm$^3$, 1000 cells/mm$^3$, 1100 cells/mm$^3$, or 1200 cells/mm$^3$ is maintained in a subject. In another aspect, a subject at risk of or with a disorder associated with or characterized by aberrant expression and/or activity of galanin and/or a disorder associated with or characterized by aberrant expression of a galanin receptor is not administered an immunomodulatory agent if their absolute lymphocyte count is 500 cells/mm$^3$ or less, 550 cells/mm$^3$ or less, 600 cells/mm$^3$ or less, 650 cells/mm$^3$ or less, 700 cells/mm$^3$ or less, 750 cells/mm$^3$ or less, or 800 cells/mm$^3$ or less.

In one aspect, one or more immunomodulatory agents are administered in combination with an antibody that immunospecifically binds to a galanin peptide to a subject at risk of or with a disorder associated with or characterized by aberrant expression and/or activity of galanin and/or a disorder associated with or characterized by aberrant expression of a galanin receptor so as to transiently reduce or inhibit one or more aspects of the immune response. Such a transient inhibition or reduction of one or more aspects of the immune system can last for hours, days, weeks, or months. In one aspect, the transient inhibition or reduction in one or more aspects of the immune response lasts for a few hours (e.g., 2 hours, 4 hours, 6 hours, 8 hours, 12 hours, 14 hours, 16 hours, 18 hours, 24 hours, 36 hours, or 48 hours), a few days (e.g., 3 days, 4 days, 5 days, 6 days, 7 days, or 14 days), or a few weeks (e.g., 3 weeks, 4 weeks, 5 weeks or 6 weeks). The transient reduction or inhibition of one or more aspects of the immune response enhances the prophylactic and/or therapeutic effect(s) of an antibody that immunospecifically binds to a galanin peptide.

Nucleic acid molecules encoding proteins, polypeptides, or peptides with immunomodulatory activity or proteins, polypeptides, or peptides with immunomodulatory activity can be administered to a subject at risk of or with a disorder associated with or characterized by aberrant expression and/or activity of galanin and/or a disorder associated with or characterized by aberrant expression of a galanin receptor in accordance with the methods of the invention. Further, nucleic acid molecules encoding derivatives, analogs, or fragments of proteins, polypeptides, or peptides with immunomodulatory activity, or derivatives, analogs, or fragments of proteins, polypeptides, or peptides with immunomodulatory activity can be administered to a subject at risk of or with a disorder associated with or characterized by aberrant expression and/or activity of galanin and/or a disorder associated with or characterized by aberrant expression of a galanin receptor in accordance with the methods of the invention. Preferably, such derivatives, analogs, and fragments retain the immunomodulatory activity of the full-length, wild-type protein, polypeptide, or peptide.

In one apsect, agents that are commercially available and known to function as immunomodulatory agents are used in the methods of the invention. The immunomodulatory activity of an agent can be determined in vitro and/or in vivo by any technique well-known to one skilled in the art, including, e.g., by CTL assays, proliferation assays, and immunoassays (e.g., ELISAs) for the expression of particular proteins such as co-stimulatory molecules and cytokines.

5.2.2 Anti-angiogenic Therapies

Any anti-angiogenic agent well known to one of skill in the art can be used in the compositions and methods of the invention. Non-limiting examples anti-angiogenic agents include proteins, polypeptides, peptides, fusion proteins, antibodies (e.g., human, humanized, chimeric, monoclonal, polyclonal, Fvs, ScFvs, Fab fragments, F(ab)$_2$ fragments, and antigen-binding fragments thereof) such as antibodies that immunospecifically bind to TNF-α, nucleic acid molecules (e.g., antisense molecules or triple helices), organic molecules, inorganic molecules, and small molecules that reduce or inhibit angiogenesis. In particular, examples of anti-angiogenic agents, include, but are not limited to, endostatin, angiostatin, apomigren, anti-angiogenic antithrombin III, the 29 kDa N-terminal and a 40 kDa C-terminal proteolytic fragments of fibronectin, a uPA receptor antagonist, the 16 kDa proteolytic fragment of prolactin, the 7.8 kDa proteolytic fragment of platelet factor-4, the antiangiogenic 24 amino acid fragment of platelet factor-4, the anti-angiogenic factor designated 13.40, the anti-angiogenic 22 amino acid peptide fragment of thrombospondin I, the anti-angiogenic 20 amino acid peptide fragment of SPARC, RGD and NGR containing peptides, the small anti-angiogenic peptides of laminin, fibronectin, procollagen and EGF, integrin $\alpha_v\beta_3$ antagonists (e.g., anti-integrin $\alpha_v\beta_3$ antibodies), acid fibroblast growth factor (aFGF) antagonists, basic fibroblast growth factor (bFGF) antagonists, vascular endothelial growth factor (VEGF) antagonists (e.g., anti-VEGF antibodies), and VEGF receptor (VEGFR) antagonists (e.g., anti-VEGFR antibodies).

Examples of integrin $\alpha_v\beta_3$ antagonists include, but are not limited to, proteinaceous agents such as non-catalytic metalloproteinase fragments, RGD peptides, peptide mimetics, fusion proteins, disintegrins or derivatives or analogs thereof, and antibodies that immunospecifically bind to integrin $\alpha_v\beta_3$, nucleic acid molecules, organic molecules, and inorganic molecules. Non-limiting examples of antibodies that immunospecifically bind to integrin $\alpha_v\beta_3$ include 11D2 (Searle) and LM609 (Scripps). Non-limiting examples of small molecule peptidometric integrin $\alpha_v\beta_3$ antagonists include S836 (Searle) and S448 (Searle). Examples of disintegrins include, but are not limited to, Accutin. The invention also encompasses the use of any of the integrin $\alpha_v\beta_3$ antagonists disclosed in the following U.S. patents and International publications in the compositions and methods of the invention: U.S. Pat. Nos. 5,149,780; 5,196,511; 5,204, 445; 5,262,520; 5,306,620; 5,478,725; 5,498,694; 5,523, 209; 5,578,704; 5,589,570; 5,652,109; 5,652,110; 5,693, 612; 5,705,481; 5,753,230; 5,767,071; 5,770,565; 5,780, 426; 5,817,457; 5,830,678; 5,849,692; 5,955,572; 5,985, 278; 6,048,861; 6,090,944; 6,096,707; 6,130,231; 6,153, 628; 6,160,099; and 6,171,58; and International Publication Nos. WO 95/22543; WO 98/33919; WO 00/78815; and WO 02/070007, each of which is incorporated herein by reference in its entirety.

In one aspect of the invention, an anti-angiogenic agent is endostatin. Naturally occurring endostatin consists of the C-terminal approximately 180 amino acids of collagen XVIII (cDNAs encoding two splice forms of collagen XVIII have GenBank Accession Nos. AF18081 and AF18082). In another aspect of the invention, an anti-angiogenic agent is a plasminogen fragment (the coding sequence for plasminogen can be found in GenBank Accession Nos. NM_000301 and A33096). Angiostatin peptides naturally include the four kringle domains of plasminogen, kringle 1 through kringle 4. It has been demonstrated that recombinant kringle 1, 2 and 3 possess the anti-angiogenic properties of the native peptide, whereas kringle 4 has no such activity (Cao et al., 1996, J. Biol. Chem. 271:29461-29467). Accordingly, the angiostatin peptides comprises at least one and, in one aspect, more than one kringle domain selected from the group consisting of kringle 1, kringle 2 and kringle 3. In one aspect, the anti-angiogenic peptide is the 40 kDa isoform of the human angiostatin molecule, the 42 kDa isoform of the human angiostatin molecule, the 45 kDa isoform of the human angiostatin molecule, or a combination thereof. In another aspect, an anti-angiogenic agent is the kringle 5 domain of plasminogen, which is a more potent inhibitor of angiogenesis than angiostatin (angiostatin comprises kringle domains 1-4). In another aspect of the invention, an anti-angiogenic agent is antithrombin III. Antithrombin III, which is referred to hereinafter as antithrombin, comprises a heparin binding domain that tethers the protein to the vasculature walls, and an active site loop which interacts with thrombin. When antithrombin is tethered to heparin, the protein elicits a conformational change that allows the active loop to interact with thrombin, resulting in the proteolytic cleavage of said loop by thrombin. The proteolytic cleavage event results in another change of conformation of antithrombin, which (i) alters the interaction interface between thrombin and antithrombin and (ii) releases the complex from heparin (Carrell, 1999, Science 285:1861-1862, and references therein). O'Reilly et al. (1999, Science 285:1926-1928) have discovered that the cleaved antithrombin has potent anti-angiogenic activity. Accordingly, in one aspect, an anti-angiogenic agent is the anti-angiogenic form of antithrombin. In another aspect of the invention, an anti-angiogenic agent is the 40 kDa and/or 29 kDa proteolytic fragment of fibronectin.

In another aspect of the invention, an anti-angiogenic agent is a urokinase plasminogen activator (uPA) receptor antagonist. In one mode of the aspect, the antagonist is a dominant negative mutant of uPA (see, e.g., Crowley et al., 1993, Proc. Natl. Acad. Sci. USA 90:5021-5025). In another mode of the aspect, the antagonist is a peptide antagonist or a fusion protein thereof (Goodson et al., 1994, Proc. Natl. Acad. Sci. USA 91:7129-7133). In yet another mode of the aspect, the antagonist is a dominant negative soluble uPA receptor (Min et al., 1996, Cancer Res. 56:2428-2433). In another aspect of the invention, a therapeutic molecule of the invention is the 16 kDa N-terminal fragment of prolactin, comprising approximately 120 amino acids, or a biologically active fragment thereof (the coding sequence for prolactin can be found in GenBank Accession No. NM_000948). In another aspect of the invention, an anti-angiogenic agent is the 7.8 kDa platelet factor-4 fragment. In another aspect of the invention, a therapeutic molecule of the invention is a small peptide corresponding to the anti-angiogenic 13 amino acid fragment of platelet factor-4, the anti-angiogenic factor designated 13.40, the anti-angiogenic 22 amino acid peptide fragment of thrombospondin I, the anti-angiogenic 20 amino acid peptide fragment of SPARC, the small anti-angiogenic peptides of laminin, fibronectin, procollagen, or EGF, or small peptide antagonists of integrin $\alpha_v\beta_3$ or the VEGF receptor. In another aspect, the small peptide comprises an RGD or NGR motif. In certain aspects, an anti-angiogenic agent is a TNF-$\alpha$ antagonist. In other aspects, an anti-angiogenic agent is not a TNF-$\alpha$ antagonist.

Nucleic acid molecules encoding proteins, polypeptides, or peptides with anti-angiogenic activity, or proteins, polypeptides or peptides with anti-angiogenic activity can be administered to a subject at risk of or with a disorder characterized by aberrant expression and/or activity of galanin and/or a disorder characterized by aberrant expression and/or activity of a galanin receptor in accordance with the methods of the invention. Further, nucleic acid molecules encoding derivatives, analogs, fragments, or variants of proteins, polypeptides, or peptides with anti-angiogenic activity, or derivatives, analogs, fragments, or variants of proteins, polypeptides, or peptides with anti-angiogenic activity can be administered to a subject at risk of or with a disorder characterized by aberrant expression and/or activity of galanin and/or a disorder characterized by aberrant expression and/or activity of a galanin receptor in accordance with the methods of the invention. In one aspect, such derivatives, analogs, variants, and fragments retain the anti-angiogenic activity of the full-length, wild-type protein, polypeptide, or peptide.

Proteins, polypeptides, or peptides that can be used as anti-angiogenic agents can be produced by any technique well known in the art or described herein. Proteins, polypeptides or peptides with anti-angiogenic activity can be engineered so as to increase the in vivo half-life of such proteins, polypeptides, or peptides utilizing techniques well-known in the art or described herein. In one aspect, anti-angiogenic agents that are commercially available are used in the compositions and methods of the invention. The anti-angiogenic activity of an agent can be determined in vitro and/or in vivo by any technique well-known to one skilled in the art.

5.2.3 Anti-inflammatory Therapies

Any anti-inflammatory agent well known to one of skill in the art can be used in the compositions and methods of the invention. Non-limiting examples of anti-inflammatory agents include non-steroidal anti-inflammatory drugs (NSAIDs), steroidal anti-inflammatory drugs, anticholinergics (e.g., atropine sulfate, atropine methylnitrate, and ipratropium bromide (ATROVENT™)), beta2-agonists (e.g., abuterol (VENTOLIN® and PROVENTIL®), bitolterol (TORNALATE®), levalbuterol (XOPONEX®), metaproterenol (ALUPENT®), pirbuterol (MAXAIR®), terbutlaine (BRETHAIRE® and BRETHINE®), albuterol (PROVENTIL®, REPETABS®, and VOLMAX®), formoterol (FORADIL AEROLIZER®), and salmeterol (SEREVENT® and SEREVENT DISKUS®)), and methylxanthines (e.g., theophylline (UNIPHYL®, THEO-DUR®, SLO-BID®, AND TEHO-42®)). Examples of NSAIDs include, but are not limited to, aspirin, ibuprofen, celecoxib (CELEBREX®), diclofenac (VOLTAREN®), etodolac (LODINE®), fenoprofen (NALFON®), indomethacin (INDOCIN®), ketorolac (TORADOL®), oxaprozin (DAYPRO®), nabumentone (RELAFEN®), sulindac (CLINORIL®), tolmentin (TOLECTIN®), naproxen (ALEVE®, NAPROSYN®), ketoprofen (ACTRON®) and nabumetone (RELAFEN®). Such NSAIDs function by inhibiting a cyclooxgenase enzyme (e.g., COX-1 and/or COX-2). Examples of steroidal anti-inflammatory drugs include, but are not limited to, glucocorticoids, dexamethasone (DECADRON®), corticosteroids (e.g., methylprednisolone (MEDROL®)), cortisone, hydrocortisone, prednisone (PREDNISONE® and DELTASONE®), prednisolone (PRELONE® and PEDIAPRED®), triamcinolone, azulfidine, and inhibitors of eicosanoids (e.g., prostaglandins and thromboxanes).

Anti-inflammatory therapies and their dosages, routes of administration, and recommended usage are known in the art and have been described in such literature as the *Physician's Desk Reference* (57th ed., 2003).

5.2.4 Anti-cancer Therapies

Any therapy (e.g., therapeutic or prophylactic agent) which is known to be useful, has been used, or is currently being used for the prevention, treatment, management, or amelioration of a hyperproliferative disorder, such as cancer, or one or more symptoms thereof can be used in compositions and method of the invention. Therapies (e.g., therapeutic or prophylactic agents) include, but are not limited to, peptides, polypeptides, fusion proteins, nucleic acid molecules, small molecules, mimetic agents, synthetic drugs, inorganic molecules, and organic molecules. Non-limiting examples of cancer therapies include chemotherapies, radiation therapies, hormonal therapies, and/or biological therapies/immunotherapies.

In certain aspects, the anti-cancer agent is an immunomodulatory agent, such as a chemotherapeutic agent. In certain other aspects, the anti-cancer agent is an immunomodulatory agent other than a chemotherapeutic agent. In other aspects, the anti-cancer agent is not an immunomodulatory agent. In specific aspects, the anti-cancer agent is an anti-angiogenic agent. In other aspects, the anti-cancer agent is not an anti-angiogenic agent. In specific aspects, the anti-cancer agent is an anti-inflammatory agent. In other aspects, the anti-cancer agent is not an anti-inflammatory agent.

In particular aspects, the anti-cancer agent may be, but is not limited to: a chemotherapeutic agent (e.g., acivicin, aclarubicin, acodazole hydrochloride, acronine, adozelesin, aldesleukin, altretamine, ambomycin, ametantrone acetate, aminoglutethimide, amsacrine, anastrozole, anthramycin, asparaginase, azacitidine, azetepa, batimastat, bleomycin, benzodepa, bicalutamide, bisantrene hydrochloride, bisnafide dimesylate, bizelesin, bleomycin sulfate, brequinar sodium, bropirimine, busulfan, cactinomycin, calusterone, campathecin, caracemide, carbetimer, carboplatin, carmustine, carubicin hydrochloride, carzelesin, cedefingol, chlorambucil, cirolemycin, cisplatin, cladribine, crisnatol mesylate, cyclophosphamide, cytarabine, cyclosporin A, combretastatin A4, combretastatin analogue, cytolytic factor, cytostatin, dacliximab, docetaxel, dacarbazine, dactinomycin, daunorubicin hydrochloride, docetaxel, doxorubicin, droloxifene, dromostanolone propionate, duazomycin, edatrexate, eflornithine hydrochloride, elsamitrucin, enloplatin, enpromate, epipropidine, epirubicin hydrochloride, erbulozole, esorubicin hydrochloride, estramustine, etanidazole, etoposide, fazarabine, fenretinide, floxuridine, fluorouracil, flurocitabine, fosquidone, gemcitabine, hydroxyurea, idarubicin, idarubicin hydrochloride, ifosfamide, ilmofosine, iproplatin, ifosfamide, irinotecan hydrochloride, lanreotide acetate, letrozole, leuprolide acetate, liarozole hydrochloride, lometrexol sodium, lomustine, losoxantrone hydrochloride, masoprocol, mercaptopurine, methotrexate, metoprine, meturedepa, mitindomide, mitocarcin, mitocromin, mitomycin, mitoxantrone, mycophenolic acid, nitrosoureas, nocodazole, nogalamycin, ormaplatin, oxisuran, paclitaxel, plicamycin, platinum complex, platinum compounds, platinum-triamine complex, procarbizine, puromycin, taxol, thioguanine, talisomycin, tecogalan sodium, tegafur, teloxantrone hydrochloride, vapreotide, verteporfin, vinblastine sulfate, vincristine sulfate, vindesine, vindesine sulfate, vinepidine sulfate, vinglycinate sulfate, vinleurosine sulfate, vinorelbine tartrate, vinrosidine sulfate, vinzolidine sulfate, vorozole, zeniplatin, and zinostatin), matrix metalloproteinase inhibitors, tyrosine kinase inhibitors, tyrphostins, urokinase receptor antagonists, multiple drug resistance gene inhibitor, multiple tumor suppressor 1-based therapy, plasminogen activator inhibitor, bisphosphonates (e.g., pamidronate (Aredria), sodium clondronate (Bonefos), zoledronic acid (Zometa), alendronate (Fosamax), etidronate, ibandornate, cimadronate, risedromate, and tiludromate), a cytokine (e.g., IL-2, IFN-α, IFN-β, IFN-γ, leukemia inhibiting factor, leukocyte alpha interferon, human chorionic gonadotrophin, and thrombopoietin), a hormone (e.g., thyroid stimulating hormone), an antibody (e.g., an anti-CD2 antibody, an anti-CD20 antibody, and an antibody immunospecific for one or more galanin receptors), vitamin D (e.g., 20-epi-1,25 dihydroxyvitamin D3), an angiogenesis inhibitor, an antisense oligonucleotide, an apoptosis gene modulator, an apoptosis regulator, a BCR/ABL antagonist, a cartilage derived inhibitor, an estrogen agonist, an estrogen antagonist, a gelatinase inhibitor, a glutathione inhibitor, an HMG CoA reductase inhibitor (e.g., atorvastatin, cerivastatin, fluvastatin, lescol, lupitor, lovastatin, rosuvastatin, and simvastatin), an immunostimulant peptide, an insulin-like growth factor-1 receptor inhibitor, an interferon agonist, leuprolide+estrogen+progesterone, leuprorelin, a mismatched double stranded RNA, a proteasome inhibitor, a protein A-based immune modulator, a protein kinase C inhibitor, a protein tyrosine phosphatase inhibitor, a raf antagonist, a ras farnesyl protein transferase inhibitor, a ribozyme, RNAi, a signal transduction modulator, a stem cell inhibitor, a stem-cell division inhibitor, a telomerase inhibitor, a thymopoietin receptor agonist, and a translation inhibitor.

In specific aspects, radiation therapy comprising the use of x-rays, gamma rays and other sources of radiation to destroy the cancer cells is used in combination with the antibodies of the invention. In some aspects, the radiation treatment is administered as external beam radiation or teletherapy, wherein the radiation is directed from a remote source. In other aspects, the radiation treatment is administered as internal therapy or brachytherapy wherein a radioactive source is placed inside the body close to cancer cells or a tumor mass.

Cancer therapies and their dosages, routes of administration and recommended usage are known in the art and have been described in such literature as the *Physician's Desk Reference* (57$^{th}$ ed., 2003).

5.3 Prophylactic and Therapeutic Uses of Antibodies

The present invention is directed to therapies which involve administering one of more antibodies of the invention and compositions comprising said antibodies to a subject, in one aspect, a human subject, for preventing, treating, managing, and/or ameliorating a disorder characterized by or associated with aberrant expression and/or activity of galanin or a symptom thereof and/or a disorder characterized by or associated with aberrant expression and/or activity of a galanin receptor or a symptom thereof. In one aspect, the invention provides a method of preventing, treating, managing, and/or ameliorating a disorder characterized by or associated with aberrant expression and/or activity of galanin or a symptom thereof and/or a disorder characterized by or associated with aberrant expression and/or activity of a galanin receptor or a symptom thereof, said method comprising administering to a subject in need thereof an effective amount of one or more antibodies of the invention. In certain aspects, an effective amount of one or more polypeptides, peptides, and proteins comprising one or more antibodies of the invention is administered to a subject in need thereof to prevent, treat, manage, and/or ameliorate a disorder characterized by or associated with aberrant expression and/or activity of galanin or a symptom thereof and/or a disorder characterized by or associated with aberrant expression and/or activity of a galanin receptor or a symptom thereof.

The invention also provides methods of preventing, treating, managing, and/or ameliorating a disorder characterized by or associated with aberrant expression and/or activity of galanin or a symptom thereof and/or a disorder characterized by or associated with aberrant expression and/or activity of a galanin receptor or a symptom thereof, said methods comprising administering to a subject in need thereof one or more of the antibodies of the invention and one or more therapies (e.g., one or more prophylactic or therapeutic agents) other than antibodies of the invention. The prophylactic or therapeutic agents of the combination therapies of the invention can be administered sequentially or concurrently. In one aspect, the combination therapies of the invention comprise an effective amount of one or more antibodies of the invention and an effective amount of at least one other therapy which has the same mechanism of action as said antibodies. In one aspect, the combination therapies of the invention comprise an effective amount of one or more antibodies of the invention and an effective amount of at least one other therapy (e.g., prophylactic or therapeutic agent), which has a different mechanism of action than said antibodies. In certain aspects, the combination therapies of the present invention improve the prophylactic or therapeutic effect of one or more antibodies of the invention by functioning together with the antibodies to have an additive or synergistic effect. In certain aspects, the combination therapies of the present invention reduce the side effects associated with the therapies (e.g., prophylactic or therapeutic agents).

The prophylactic or therapeutic agents of the combination therapies can be administered to a subject, in one aspect, a human subject, in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

In one aspect, a pharmaceutical composition comprising one or more antibodies of the invention described herein is administered to a subject, in one aspect, a human, to prevent, treat, manage, and/or ameliorate a disorder characterized by or associated with aberrant expression and/or activity of galanin or a symptom thereof and/or a disorder characterized by or associated with aberrant expression and/or activity of a galanin receptor or a symptom thereof. In accordance with the invention, pharmaceutical compositions of the invention may also comprise one or more therapies (e.g., prophylactic or therapeutic agents), other than antibodies of the invention.

5.3.1 Hyperproliferative Disorders

The antibodies of the invention and compositions comprising said antibodies can be used to prevent, treat, manage, and/or ameliorate a hyperproliferative disorder or one or more symptoms thereof. In one aspect, the hyperproliferative disorder is characterized by or associated with aberrant expression and/or activity of galanin and/or a galanin receptor. Examples of such hyperproliferative disorders include, but are not limited to, lung, breast, colon, prostate, and ovarian primary tumors.

The present invention provides methods for preventing, treating, managing, and/or ameliorating a hyperproliferative disorder (e.g., cancer) or one or more symptoms thereof, said methods comprising administering to a subject in need thereof an effective amount of one or more antibodies of the invention. The invention also provides methods for preventing, treating, managing, and/or ameliorating a hyperproliferative disorder (e.g., cancer) in which an effective amount of one or more antibodies of the invention are administered in combination with one or more other therapies (e.g., one or more prophylactic or therapeutic agents) other than antibodies of the invention useful for the prevention, treatment, management, or amelioration of a hyperproliferative disorder (e.g., cancer) or a secondary condition associated therewith (e.g., a viral, bacterial, or fungal infection). Non-limiting examples of such therapies include the agents described in section 5.2, supra, and in particular, the immunomodulatory agents described in section 5.2.1, the antiangiogenic agents described in section 5.2.2, the anti-inflammatory agents described in section 5.2.3., and the anti-cancer agents described in section 5.2.3.

The antibodies of the invention or combination therapies of the invention may be used as the first, second, third, or higher therapy to prevent, manage, treat, and/or ameliorate a hyperproliferative disorder (e.g., cancer) or one or more symptom thereof. The invention also includes methods of preventing, treating, managing, and/or ameliorating a hyperproliferative disorder or one or more symptoms thereof in a patient undergoing therapies for other disease or disorders. The invention encompasses methods of preventing, managing, treating, and/or ameliorating a hyperproliferative disorder (e.g., cancer) or one or more symptoms thereof in a patient before any adverse effects or intolerance to therapies other than antibodies of the invention develops. The invention also encompasses methods of preventing, managing, treating, and/or ameliorating a hyperproliferative disorder (e.g., cancer) or a symptom thereof in patients who are susceptible to adverse reactions to conventional therapies.

The invention encompasses methods for preventing, managing, treating, and/or ameliorating cancer or one or more symptoms thereof in patients with a hyperproliferative disorder (e.g., cancer) that are immunosuppressed as a result of having previously undergone other cancer therapies. The invention also encompasses methods for preventing, managing, treating, and/or ameliorating cancer or one or more symptoms thereof in patients who have proven refractory to other therapies but are no longer on these therapies. The invention also encompasses alternative therapies for preventing, managing, treating, and/or ameliorating a hyperproliferative disorder (e.g., cancer) or one or more symptoms thereof patients in which chemotherapy, radiation therapy, hormonal therapy, and/or biological therapy/immunotherapy has proven or may prove too toxic, i.e., results in unacceptable or unbearable side effects, for the patient undergoing said therapy. The invention also encompasses methods for preventing, managing, treating, and/or ameliorating a hyperproliferative disorder (e.g., cancer) or one or more symptoms thereof in patients predisposed to such hyperproliferative disorder. The invention also encompasses methods for preventing, managing, treating, and/or ameliorating a hyperproliferative disorder (e.g., cancer) or one or more symptoms thereof in patients with mean absolute lymphocyte cell counts of at least 500 cells/mm$^3$, preferably at least 600 cells/mm$^3$, more preferably at least 750 cells/mm$^3$. The invention also encompasses methods for preventing the onset or development of one or more symptoms in patients with a hyperproliferative disorder (e.g., cancer). The invention also encompasses methods to prevent, treat, manage, and/or ameliorate one or more symptoms in patients with an incurable hyperproliferative disorder (e.g., incurable cancer), in particular hospice patients. Further, the invention provides methods for preventing a hyperproliferative disorder (e.g., cancer) in patients who have been treated for such a disorder but have no disease activity.

In one aspect, the invention encompasses methods for managing for preventing, managing, treating, and/or ameliorating a hyperproliferative disorder (e.g., cancer) or one or more symptoms thereof in patients that have undergone or are undergoing chemotherapy. In accordance with this aspect, such patients include patients that have undergone or are undergoing radiation therapy, hormonal therapy, biological therapy/immunotherapy and/or surgery.

In one aspect, the invention encompasses methods for preventing, managing, treating, and/or ameliorating a hyperproliferative disorder (e.g., cancer) or one or more symptoms thereof in cancer patients that have undergone or are undergoing radiation therapy. In accordance with this aspect, such patients include patients that have undergone or are undergoing chemotherapy, hormonal therapy, biological therapy/immunotherapy and/or surgery. In another aspect, the invention encompasses methods for treating or managing patients that have undergone or are undergoing hormonal therapy and/or biological therapy/immunotherapy. In accordance with this aspect, such patients include patients that have undergone or are undergoing chemotherapy, radiation therapy and/or surgery.

The invention encompasses methods for preventing, treating, managing, and/or ameliorating a hyperproliferative disorder or a symptom thereof in a patient who has proven refractory to therapies other than antibodies, compositions, or combination therapies of the invention. In certain aspects, a patient with a hyperproliferative disorder (e.g., cancer) is refractory to a therapy when proliferation disorders has not been eradicated and/or the symptoms have not been alleviated. The determination of whether a patient is refractory can be made in vivo and/or in vitro by any method known in the art for assaying the effectiveness of a treatment of hyperproliferative disorders, using art-accepted meanings of "refractory" such a context. In various aspects, a patient with a hyperproliferative disorder is refractory when the patient's levels of galanin remain aberrant and/or if cellular proliferation has not been decreased.

The present invention provides methods for preventing, treating, managing, and/or ameliorating a hyperproliferative disorder (e.g., cancer) or one or more symptoms thereof as an alternative to other conventional therapies. In specific aspects, the patient being managed or treated in accordance with the methods of the invention is refractory to other therapies or is susceptible to adverse reactions from such therapies. The patient may be a person with a suppressed immune system (e.g., post-operative patients, chemotherapy patients, and patients with immunodeficiency disease), a person with impaired renal or liver function, the elderly, children, infants, persons with neuropsychiatric disorders or those who take psychotropic drugs, persons with histories of seizures, or persons on medication that would negatively interact with conventional agents used to manage or treat a hyperproliferative disorder (e.g., cancer).

The invention encompasses methods for preventing, managing, treating, and/or ameliorating a hyperproliferative disorder (e.g., cancer) or a symptom thereof in a subject refractory to existing single agent therapies for such a disorder. The invention also encompasses methods for preventing, treating, managing, and/or ameliorating a hyperproliferative disorder (e.g., cancer) or a secondary condition associated thereof in patients who have proven refractory to other therapies but are no longer on these therapies. The invention also encompasses methods for the prevention, treatment, management, or amelioration of a hyperproliferative disorder (e.g., cancer) in a patent immunosuppressed by reason of having previously undergone other cancer therapies. The invention provides alternative methods for the prevention, treatment, management, or amelioration of a hyperproliferative disorder (e.g., cancer) where chemotherapy, radiation therapy, hormonal therapy, and/or biological therapy/immunotherapy has proven or may prove too toxic, i.e., results in unacceptable or unbearable side effects, for the subject undergoing therapy. Further, the invention encompasses methods for preventing the recurrence of cancer in patients that have been treated and have no disease.

In certain aspects, the expression level and/or activity of galanin and/or a galanin receptor is determined for a subject predisposed to or with a hyperproliferative disorder prior to the administration of an antibody of the invention. In a specific aspect, a tumor biopsy is obtained from a subject predisposed to or with a hyperproliferative disorder and the amplified status of galanin and/or a galanin receptor (e.g., GALR1, GALR2 or GALR3) is determined prior to administering to said subject an antibody of the invention. See, e.g., International Publication No. WO 03/018770 for methods of determining the amplified status of galanin and/or a galanin receptor.

Cancers that can be treated by the methods encompassed by the invention include, but are not limited to, neoplasms, tumors, metastases, or any disorder characterized by or associated with uncontrolled cell growth. The cancer may be a primary or metastatic cancer. Specific examples of cancers that can be treated by the methods encompassed by the invention include, but are not limited to, cancer of the head, neck, eye, mouth, throat, esophagus, chest, bone, lung, colon, rectum, stomach, prostate, breast, ovaries, kidney, liver, pancreas, and brain. Additional cancers include, but are not limited to, the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenstrom's macroglobulinemia; monoclonal gammopathy of undetermined significance; benign monoclonal gammopathy; heavy chain disease; bone cancer and connective tissue sarcomas such as but not limited to bone sarcoma, myeloma bone disease, multiple myeloma, cholesteatoma-induced bone osteosarcoma, Paget's disease of bone, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, and synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma; breast cancer including but not limited to adenocarcinoma, lobular (small cell) carcinoma, intraductal carcinoma, medullary breast cancer, mucinous breast cancer, tubular breast cancer, papillary breast cancer, Paget's disease (including juvenile Paget's disease) and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to pappillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America). It is also contemplated that cancers caused by aberrations in apoptosis can also be treated by the methods and compositions of the invention. Such cancers may include, but not be limited to, follicular lymphomas, carcinomas with p53 mutations, hormone dependent tumors of the breast, prostate and ovary, and precancerous lesions such as familial adenomatous polyposis, and myelodysplastic syndromes.

In one aspect, the cancer being prevented, managed, treated or ameliorated in accordance with the methods of the invention is breast cancer, lung cancer, ovarian cancer, prostate cancer or colon cancer. In another aspect, the cancer being prevented, managed, treated or ameliorated in accordance with the methods of the invention is a breast, lung, ovarian, prostate or colon primary tumor. In another aspect, the cancer that is being prevented, managed, treated or ameliorated in accordance with the methods of the invention are metastatic tumors including, but not limited to, tumors that have or may metastasize to the bone (non-limiting examples are prostate, breast and lung cancers that have metastasized or have the potential to metastasize to the bone), tumors that have or may metastasize to the lung, tumors that have or may metastasize to the brain, and tumors that have or may metastasize to other organs of a subject. In accordance with these aspects, the cancer can be characterized by or associated with aberrant expression and/or activity of galanin or a galanin receptor.

Therapies and dosages, routes of administration, and recommended usage of therapies for preventing, treating, managing, and/or ameliorating hyperproliferative disorders or one or more symptoms thereof are known in the art and have been described in such literature as the *Physician's Desk Reference* (57th ed., 2003).

5.4 Compositions & Methods of Administering Antibodies

The invention provides for the prevention, treatment, management, and/or amelioration of disorders associated with aberrant expression and/or activity of galanin and/or disorders associated with aberrant expression and/or activity of galanin receptor. In one aspect, a composition comprises one or more antibodies of the invention and optionally, a carrier. In another aspect, a composition comprises one or more antibodies of the invention, one or more prophylactic or therapeutic agents other than the antibodies of the invention, and optionally, a carrier.

In one aspect, a composition comprises one or more peptides, polypeptides, or proteins comprising a fragment of an antibody of the invention that immunospecifically binds to a galanin peptide and optionally, a carrier. In another aspect, a composition comprises one or more peptides, polypeptides, or proteins comprising a fragment of an antibody of the invention that immunospecifically binds to a galanin peptide, one or more other prophylactic or therapeutic agents other than a peptide, polypeptide, or protein comprising a fragment of an antibody of the invention, and optionally, a carrier.

In one aspect, a composition comprises one or more antibodies of the invention, or one or more polypeptides, peptides, or proteins comprising an antibody fragment of the invention, and one or more immunomodulatory agents. In another aspect, a composition comprises one or more antibodies of the invention, or one or more polypeptides, peptides, or proteins comprising an antibody fragment of the invention, and one or more anti-angiogenic agents. In another aspect, a composition comprises one or more antibodies of the invention, or one or more polypeptides, peptides, or proteins comprising an antibody fragment of the invention, and one or more anti-inflammatory agents. In another aspect, a composition comprises one or more antibodies of the invention, or one or more polypeptides, peptides, or proteins comprising an antibody fragment of the invention, and one or more anti-cancer agents. In accordance with this aspect, the anti-cancer agent may or may not be an immunomodulatory agent or an anti-angiogenic agent. In yet another aspect, a composition comprises one or more antibodies of the invention, or one or more polypeptides, peptides, or proteins comprising an antibody fragment of the invention, and any combination of one, two, three, or more of each of the following prophylactic or therapeutic agents: an immunomodulatory agent, an anti-angiogenic agent, an anti-cancer agent other than an immunomodulatory agent or anti-angiogenic agent, an anti-inflammatory agent, an anti-viral agent, antibiotic and/or an anti-fungal agent.

The compositions of the invention include bulk drug compositions useful in the manufacture of pharmaceutical compositions (e.g., compositions that are suitable for administration to a subject), which can be used in the preparation of unit dosage forms. In one aspect, a composition of the invention is a pharmaceutical composition. Such compositions comprise a prophylactically or therapeutically effective amount of one or more prophylactic or therapeutic agents (e.g., an antibody of the invention; polypeptide, peptide, or protein comprising an antibody fragment of the invention, or other prophylactic or therapeutic agent), and a pharmaceutically acceptable carrier. In one aspect, the pharmaceutical compositions are formulated to be suitable for the route of administration to a subject.

In one aspect, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Various delivery systems are known in the art and can be used to administer a prophylactic or therapeutic agent or composition of the invention to prevent, treat, manage, and/or ameliorate a disorder associated with or characterized by aberrant expression and/or activity of galanin and/or a disorder associated with or characterized by aberrant expression and/or activity of a galanin receptor, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a therapy (e.g., prophylactic or therapeutic agent) of the invention include, but are not limited to, parenteral administration (e.g., intradermal, intramuscular, intraperitoneal, intravenous and subcutaneous), epidurala administration, intratumoral administration, and mucosal adminsitration (e.g., intranasal and oral routes). In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and International Publication Nos. WO 92/19244, WO 97/32572, WO 97/44013, WO 98/31346, and WO 99/66903, each of which is incorporated herein by reference their entirety. In one aspect, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In one aspect, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one aspect, an effective amount of one or more antibodies of the invention is administered locally to the affected area to a subject at risk of or with a disorder associated with or characterized by aberrant expression and/or activity of galanin and/or a disorder associated with or characterized by aberrant expression and/or activity of a galanin receptor. In another aspect, an effective amount of one or more antibodies of the invention is administered locally to the affected area in combination with an effective amount of one or more therapies (e.g., one or more prophylactic or therapeutic agents) other than an antibody of the invention to a subject at risk of or with a disorder associated with or characterized by aberrant expression and/or activity of galanin and/or a disorder associated with or characterized by aberrant expression and/or activity of a galanin receptor.

In yet another aspect, a therapy of the invention can be delivered in a controlled release or sustained release system. In one aspect, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another aspect, polymeric materials can be used to achieve controlled or sustained release of the therapies of the invention (see, e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; International Publication No. WO 99/15154; and International Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In one aspect, the polymer used in a sustained release formulation is inert, free of leachable impurities, stable on storage, sterile, and biodegradable. In yet another aspect, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more therapeutic agents of the invention. See, e.g., U.S. Pat. No. 4,526,938, International Publication No. WO 91/05548, International Publication No. WO 96/20698, Ning et al., 1996, "Intratumoral Radioimmunotheraphy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entirety.

In one aspect, where the composition of the invention is a nucleic acid encoding a prophylactic or therapeutic agent, such as an antibody of the invention, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), intratumoral, transdermal (e.g., topical), transmucosal, and rectal administration. In one aspect, the composition is formulated in accordance with routine procedures as a pharmaceutical composition adapted for intravenous, subcutaneous, intramuscular, oral, intranasal, intratumoral or topical administration to human beings. Typically, compositions for intravenous administration are solutions in sterile isotonic aqueous buffer. Where necessary, the composition may also include a solubilizing agent and a local anesthetic such as lidocaine to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well known to one of skill in the art. See, e.g., Remington's Pharmaceutical Sciences and Introduction to Pharmaceutical Dosage Forms, 19$^{th}$ ed., Mack Pub. Co., Easton, Pa. (1995) and Pharmaceutical Dosage Forms and Drug Delivery System, 7$^{th}$ ed., Lippincott Williams & Wilkins (1999). For non-sprayable topical dosage forms, viscous to semi-solid or solid forms comprising a carrier or one or more excipients compatible with topical application and having a dynamic viscosity greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well known in the art. Liquid preparations for oral administration may take the form of, but are not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968, 5,985,320, 5,985,309, 5,934,272, 5,874,064, 5,855,913, 5,290,540, and 4,880,078; and International Publication Nos. WO 92/19244, WO 97/32572, WO 97/44013, WO 98/31346, and WO 99/66903, each of which is incorporated herein by reference their entirety.

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the invention may additionally comprise administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the invention is packaged in a hermetically sealed container such as an ampoule or sachette indicating the quantity of the agent. In one aspect, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. In one aspect, one or more of the prophylactic or therapeutic agents or pharmaceutical compositions of the invention is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative aspect, one or more of the prophylactic or therapeutic agents or pharmaceutical compositions of the invention is supplied in liquid form in a hermetically sealed container indicating the quantity and concentration of the agent. In one aspect, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

Generally, the ingredients of the compositions of the invention are derived from a subject that is the same species origin or species reactivity as recipient of such compositions. Thus, in one aspect, human or humanized antibodies are administered to a human patient for therapy or prophylaxis.

5.4.1 Gene Therapy

In one aspect, nucleotide sequences comprising nucleic acids encoding an antibody of the invention or another prophylactic or therapeutic agent are administered to treat, prevent, manage, and/or ameliorate a disorder associated with or characterized by aberrant expression and/or activity of galanin and/or a disorder associated with or characterized by aberrant expression and/or activity of a galanin receptor by way of gene therapy. Gene therapy refers to therapy performed by the administration to a subject of an expressed or expressible nucleic acid. In this aspect of the invention, the nucleic acids produce their encoded antibody of the invention or prophylactic or therapeutic agent that mediates a prophylactic or therapeutic effect.

Any of the methods for gene therapy available in the art can be used according to the present invention. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, Science 260:926-932 (1993); and Morgan and Anderson, 1993, Ann. Rev. Biochem. 62:191-217; May, 1993, TIBTECH 11(5):155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, N.Y. (1990).

In one aspect, the method of the invention comprises administration of a composition comprising nucleic acids encoding an antibody of the invention or another prophylactic or therapeutic agent, said nucleic acids being part of an expression vector that expresses an antibody of the invention, another prophylactic or therapeutic agent, or fragments or chimeric proteins or heavy or light chains thereof in a suitable host. In particular, such nucleic acids have promoters, for example, heterologous promoters, operably linked to the antibody coding region, said promoter being inducible or constitutive, and, optionally, tissue-specific. In another aspect, nucleic acid molecules are used in which the coding sequences of an antibody of the invention or another prophylactic or therapeutic agent and any other desired sequences are flanked by regions that promote homologous recombination at a desired site in the genome, thus providing for intrachromosomal expression of the antibody encoding nucleic acids (Koller and Smithies, 1989, Proc. Natl. Acad. Sci. USA 86:8932-8935; Zijlstra et al., 1989, Nature 342:435-438). In specific aspects, the expressed antibody of the invention or other prophylactic or therapeutic agent is a single chain antibody; alternatively, the nucleic acid sequences include sequences encoding both the heavy and light chains, or fragments thereof, of the antibody of the invention or another prophylactic or therapeutic agent.

Delivery of the nucleic acids into a subject may be either direct, in which case the subject is directly exposed to the nucleic acid or nucleic acid-carrying vectors, or indirect, in which case, cells are first transformed with the nucleic acids in vitro, then transplanted into the subject. These two approaches are known, respectively, as in vivo or ex vivo gene therapy.

In one aspect, the nucleic acid sequences are directly administered in vivo, where they are expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors). In another aspect, nucleic acid-ligand complexes can be formed in which the ligand comprises a fusogenic viral peptide to disrupt endosomes, allowing the nucleic acid to avoid lysosomal degradation. In yet another aspect, the nucleic acid can be targeted in vivo for cell specific uptake and expression, by targeting a specific receptor (see, e.g., International Publication Nos. WO 92/06180; WO 92/22635; W092/20316; W093/14188; and WO 93/20221). Alternatively, the nucleic acid can be introduced intracellularly and incorporated within host cell DNA for expression, by homologous recombination (Koller and Smithies, 1989, Proc. Natl. Acad. Sci. USA 86:8932-8935; and Zijlstra et al., 1989, Nature 342:435-438).

In one aspect, viral vectors that contains nucleic acid sequences encoding an antibody of the invention, another prophylactic or therapeutic agent, or fragments thereof are used. For example, a retroviral vector can be used (see Miller et al., 1993, Meth. Enzymol. 217:581-599). These retroviral vectors contain the components necessary for the correct packaging of the viral genome and integration into the host cell DNA. The nucleic acid sequences encoding an antibody of the invention or another prophylactic or therapeutic agent to be used in gene therapy are cloned into one or more vectors, which facilitates delivery of the gene into a subject. More detail about retroviral vectors can be found in Boesen et al., 1994, Biotherapy 6:291-302, which describes the use of a retroviral vector to deliver the mdr 1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Klein et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication W094/12649; and Wang et al., 1995, Gene Therapy 2:775-783. In one aspect, adenovirus vectors are used.

Adeno-associated virus (AAV) has also been proposed for use in gene therapy (Walsh et al., 1993, Proc. Soc. Exp. Biol. Med. 204:289-300; and U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a subject.

In this aspect, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599-618; Cohen et al., 1993, Meth. Enzymol. 217:618-644; Clin. Pharma. Ther. 29:69-92 (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and, in one aspect, heritable and expressible by its cell progeny.

The resulting recombinant cells can be delivered to a subject by various methods known in the art. Recombinant blood cells (e.g., hematopoietic stem or progenitor cells) can be administered intravenously. The amount of cells envisioned for use depends on several factors including, but not limited to, the desired effects and the patient state, and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, mast cells, megakaryocytes, granulocytes; various stem or progenitor cells, in particular hematopoietic stem or progenitor cells (e.g., as obtained from bone marrow, umbilical cord blood, peripheral blood, fetal liver, etc.). In one aspect, the cell used for gene therapy is autologous to the subject.

In an aspect in which recombinant cells are used in gene therapy, nucleic acid sequences encoding an antibody are introduced into the cells such that they are expressible by the cells or their progeny, and the recombinant cells are then administered in vivo for therapeutic effect. In one aspect, stem or progenitor cells are used. Any stem and/or progenitor cells which can be isolated and maintained in vitro can potentially be used in accordance with this aspect of the present invention (see, e.g., International Publication No. WO 94/08598; U.S. Pat. Nos. 6,642,049, 6,605,275, 6,589,728, 6,569,427, 6,537,80, and 6,465,247; Stemple and Anderson, 1992, Cell 7 1:973-985; Rheinwald, 1980, Meth. Cell Bio. 21A:229; and Pittelkow and Scott, 1986, Mayo Clinic Proc. 61:771).

In one aspect, the nucleic acid to be introduced for purposes of gene therapy comprises an inducible promoter operably linked to the coding region, such that expression of the nucleic acid is controllable by controlling the presence or absence of the appropriate inducer of transcription.

5.5 Dosage and Frequency of Administration

The amount of a prophylactic or therapeutic agent or a composition of the invention which will be effective in the prevention, treatment, management, and/or amelioration of a disorder associated with or characterized by aberrant expression and/or activity of galanin and/or a disorder associated with or characterized by aberrant expression and/or activity of a galanin receptor can be determined by standard clinical methods. The frequency and dosage will vary also according to factors specific for each patient depending on the specific therapies (e.g., the specific therapeutic or prophylactic agent or agents) administered, the severity of the disorder, disease, or condition, the route of administration, as well as age, body, weight, response, and the past medical history of the patient. For example, the dosage of a prophylactic or therapeutic agent or a composition of the invention which will be effective in the treatment, prevention, management, and/or amelioration of a disorder associated with or characterized by aberrant expression and/or activity of galanin and/or a disorder associated with or characterized by aberrant expression and/or activity of a galanin receptor can be determined by administering the composition to an animal model such as, e.g., the animal models disclosed herein or known to those skilled in the art. In addition, in vitro assays may optionally be employed to help identify optimal dosage ranges. Suitable regimens can be selected by one skilled in the art by considering such factors and by following, for example, dosages reported in literature and recommended in the *Physician's Desk Reference* (57th ed., 2003).

Exemplary doses of a small molecule include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram).

For antibodies, proteins, polypeptides, peptides and fusion proteins encompassed by the invention, the dosage administered to a patient is typically 0.0001 mg/kg to 100 mg/kg of the patient's body weight. In one aspect, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg and 0.25 mg/kg, 0.0001 and 0.15 mg/kg, 0.0001 and 0.10 mg/kg, 0.001 and 0.5 mg/kg, 0.01 and 0.25 mg/kg, 0.01 and 0.10 mg/kg or 0.1 and 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration of the antibodies by modifications such as, for example, lipidation.

In one aspect, the dosage of an antibody of the invention administered to prevent, treat, manage, and/or ameliorate a disorder associated with or characterized by aberrant expression and/or activity of galanin and/or a disorder associated with or characterized by aberrant expression and/or activity of a galanin receptor in a patient is 1500 µg/kg or less, preferably 1250 µg/kg or less, 1000 µg/kg or less, 800 µg/kg or less, 700 µg/kg or less, 600 µg/kg or less, 500 µg/kg or less, 400 µg/kg or less, 300 µg/kg or less 250 µg/kg or less, 200 µg/kg or less, 150 µg/kg or less, 125 µg/kg or less, 100 µg/kg or less, 95 µg/kg or less, 90 µg/kg or less, 85 µg/kg or less, 80 µg/kg or less, 75 µg/kg or less, 70 µg/kg or less, 65 µg/kg or less, 60 µg/kg or less, 55 µg/kg or less, 50 µg/kg or less, 45 µg/kg or less, 40 µg/kg or less, 35 µg/kg or less, 30 µg/kg or less, 25 µg/kg or less, 20 µg/kg or less, 15 µg/kg or less, 10 µg/kg or less or 5 µg/kg or less of a patient's body weight. In another aspect, the dosage of an antibody of the invention administered to prevent, treat, manage, and/or ameliorate a disorder associated with or characterized by aberrant expression and/or activity of galanin and/or a disorder associated with or characterized by aberrant expression and/or activity of a galanin receptor in a patient is a unit dose of 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 mg to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

In some aspects, a subject is administered one or more doses of an effective amount of one or more antibodies of the invention to prevent, treat, manage, and/or ameliorate a disorder associated with or characterized by aberrant expression and/or activity of galanin and/or a disorder associated with or characterized by aberrant expression and/or activity of a galanin receptor, wherein the an effective amount of said antibodies, compositions, or combination therapies prevents at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, at least 80 to 85%, at least 85% to 90%, at least 90% to 95%, or at least 95% to 98% of galanin peptide from binding to one or more of its receptors relative to a control such as PBS. In certain aspects, a subject is administered one or more doses of an effective amount of one or more or more antibodies of the invention to prevent, treat, manage, and/or ameliorate a disorder associated with or characterized by aberrant expression and/or activity of galanin and/or a disorder associated with or characterized by aberrant expression and/or activity of a galanin receptor, wherein the dose of an effective amount of said antibodies, compositions, or combination therapies reduces and/or inhibits proliferation of cancerous cells by at least 20% to 25%, preferably at least 25% to 30%, at least 30% to 35%, at least 35% to 40%, at least 40% to 45%, at least 45% to 50%, at least 50% to 55%, at least 55% to 60%, at least 60% to 65%, at least 65% to 70%, at least 70% to 75%, at least 75% to 80%, at least 80 to 85%, at least 85% to 90%, at least 90% to 95%, or at least 95% to 98% relative to a control such as PBS in an in vitro and/or in vivo assay well-known in the art.

In other aspects, a subject is administered one or more doses of an effective amount of one or more antibodies of the invention to prevent, treat, manage, and/or ameliorate a disorder associated with or characterized by aberrant expression and/or activity of galanin and/or a disorder associated with or characterized by aberrant expression and/or activity of a galanin receptor, wherein the dose of an effective amount achieves a serum titer of at least 0.1 µg/ml, at least 0.5 µg/ml, at least 1 µg/ml, at least 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml of the antibodies of the invention. In yet other aspects, a subject is administered a dose of an effective amount of one or more antibodies of the invention to achieve a serum titer of at least 0.1 µg/ml, at least 0.5 µg/ml, at least 1 µg/ml, at least, 2 µg/ml, at least 5 µg/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml of the antibodies and a subsequent dose of an effective amount of one or more antibodies of the invention is administered to maintain a serum titer of at least 0.1 µg/ml, at least 0.5 µg/ml, at least 1 µg/ml, at least, 2 µg/ml, at least 5 g/ml, at least 6 µg/ml, at least 10 µg/ml, at least 15 µg/ml, at least 20 µg/ml, at least 25 µg/ml, at least 50 µg/ml, at least 100 µg/ml, at least 125 µg/ml, at least 150 µg/ml, at least 175 µg/ml, at least 200 µg/ml, at least 225 µg/ml, at least 250 µg/ml, at least 275 µg/ml, at least 300 µg/ml, at least 325 µg/ml, at least 350 µg/ml, at least 375 µg/ml, or at least 400 µg/ml. In accordance with these aspects, a subject may be administered 1, 2, 3, 4, 5, 6, 7, 8, 9, 10, 11, 12 or more subsequent doses.

In one aspect, the invention provides methods of preventing, treating, managing, or treating a disorder associated with or characterized by aberrant expression and/or activity of galanin and/or a disorder associated with or characterized by aberrant expression and/or activity of a galanin receptor, said method comprising administering to a subject in need thereof a dose of at least 10 µg, preferably at least 25 µg, at least 50 µg, at least 75 µg, at least 100 µg, at least 125 µg, at least 150 µg, at least 200 µg, at least 250 µg, at least 300 µg, at least 350 µg, at least 400 µg, at least 500 µg, at least 550 µg, at least 600 µg, at least 650 µg, at least 700 µg, at least 750 µg, at least 800 µg, at least 850 µg, at least 900 µg, at least 1000 µg, at least 1250 µg or at least 1500 µg of one or more antibodies of the invention. In another aspect, the invention provides a method of preventing, treating, managing, and/or ameliorating a disorder associated with or characterized by aberrant expression and/or activity of galanin and/or a disorder associated with or characterized by aberrant expression and/or activity of a galanin receptor, said methods comprising administering to a subject in need thereof a dose of at least 10 µg, preferably at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, at least 100 µg, at least 105 µg, at least 110 µg, at least 115 µg, or at least 120 µg of one or more antibodies of the invention once every 3 days, preferably, once every 4 days, once every 5 days, once every 6 days, once every 7 days, once every 8 days, once every 10 days, once every two weeks, once every three weeks, or once a month.

The present invention provides methods of preventing, treating, managing, or preventing a disorder associated with or characterized by aberrant expression and/or activity of galanin and/or a disorder associated with or characterized by aberrant expression and/or activity of a galanin receptor, said method comprising: (a) administering to a subject in need thereof one or more doses of a prophylactically or therapeutically effective amount of one or more antibodies of the invention; and (b) monitoring the plasma level/concentration of the said administered antibody or antibodies in said subject after administration of a certain number of doses of the said antibody or antibodies. Moreover, in one aspect, said certain number of doses is 1, 2, 3, 4, 5, 6, 7, 8, 9, 10, 11, or 12 doses of a prophylactically or therapeutically effective amount one or more antibodies of the invention.

In one aspect, the invention provides a method of preventing, treating, managing, and/or ameliorating a disorder associated with or characterized by aberrant expression and/or activity of galanin and/or a disorder associated with or characterized by aberrant expression and/or activity of a galanin receptor, said method comprising: (a) administering to a subject in need thereof a dose of at least 10 µg (preferably at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg) of one or more antibodies of the invention; and (b) administering one or more subsequent doses to said subject when the plasma level of the antibody or antibodies administered in said subject is less than 0.1 µg/ml, preferably less than 0.25 µg/ml, less than 0.5 µg/ml, less than 0.75 µg/ml, or less than 1 µg/ml. In another aspect, the invention provides a method of preventing, treating, managing, and/or ameliorating a disorder associated with or characterized by aberrant expression and/or activity of galanin and/or a disorder associated with or characterized by aberrant expression and/or activity of a galanin receptor, said method comprising: (a) administering to a subject in need thereof one or more doses of at least 10 µg (preferably at least 15 µg, at least 20 µg, at least 25 µg, at least 30 µg, at least 35 µg, at least 40 µg, at least 45 µg, at least 50 µg, at least 55 µg, at least 60 µg, at least 65 µg, at least 70 µg, at least 75 µg, at least 80 µg, at least 85 µg, at least 90 µg, at least 95 µg, or at least 100 µg) of one or more antibodies of the invention; (b) monitoring the plasma level of the administered antibody or antibodies of the invention in said subject after the administration of a certain number of doses; and (c) administering a subsequent dose of the antibody or antibodies of the invention when the plasma level of the administered antibody or antibodies in said subject is less than 0.1 µg/ml, preferably less than 0.25 µg/ml, less than 0.5 µg/ml, less than 0.75 µg/ml, or less than 1 µg/ml. In one aspect, said certain number of doses is 1, 2, 3, 4, 5, 6, 7, 8, 9, 10, 11, or 12 doses of an effective amount of one or more antibodies of the invention.

Therapies (e.g., prophylactic or therapeutic agents), other than antibodies of the invention, which have been or are currently being used to prevent, treat, manage, and/or ameliorate a disorder associated with or characterized by aberrant expression and/or activity of galanin and/or a disorder associated with or characterized by aberrant expression and/or activity of a galanin receptor can be administered in combination with one or more antibodies of the invention according to the methods of the invention to treat, manage, prevent, and/or ameliorate a disorder associated with or characterized by aberrant expression and/or activity of galanin and/or a disorder associated with or characterized by aberrant expression and/or activity of a galanin receptor. In one aspect, the dosages of prophylactic or therapeutic agents used in combination therapies of the invention are lower than those which have been or are currently being used to prevent, treat, manage, and/or ameliorate a disorder associated with or characterized by aberrant expression and/or activity of galanin and/or a disorder associated with or characterized by aberrant expression and/or activity of a galanin receptor. The recommended dosages of agents currently used for the prevention, treatment, management, or amelioration of a disorder associated with or characterized by aberrant expression and/or activity of galanin and/or a disorder associated with or characterized by aberrant expression and/or activity of a galanin receptor can be obtained from any reference in the art including, but not limited to, Hardman et al., eds., 2001, Goodman & Gilman's The Pharmacological Basis Of Basis Of Therapeutics, 10th ed., Mc-Graw-Hill, New York; *Physician's Desk Reference* (*PDR*) 57th ed., 2003, Medical Economics Co., Inc., Montvale, N.J., which are incorporated herein by reference in its entirety.

In various aspects, the therapies (e.g., prophylactic or therapeutic agents) are administered less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In one aspect, two or more therapies are administered within the same patient visit.

In certain aspects, one or more antibodies of the invention and one or more other therapies (e.g., prophylactic or therapeutic agents) are cyclically administered. Cycling therapy involves the administration of a first therapy (e.g., a first prophylactic or therapeutic agent) for a period of time, followed by the administration of a second therapy (e.g., a second prophylactic or therapeutic agent) for a period of time, optionally, followed by the administration of a third therapy (e.g., prophylactic or therapeutic agent) for a period of time and so forth, and repeating this sequential administration, i.e., the cycle in order to reduce the development of resistance to one of the therapies, to avoid or reduce the side effects of one of the therapies, and/or to improve the efficacy of the therapies.

In certain aspects, the administration of the same antibodies of the invention may be repeated and the administrations may be separated by at least 1 day, 2 days, 3 days, 5 days, 10 days, 15 days, 30 days, 45 days, 2 months, 75 days, 3 months, or at least 6 months. In other aspects, the administration of the same therapy (e.g., prophylactic or therapeutic agent) other than an antibody of the invention may be repeated and the administration may be separated by at least at least 1 day, 2 days, 3 days, 5 days, 10 days, 15 days, 30 days, 45 days, 2 months, 75 days, 3 months, or at least 6 months.

5.6 Biological Assays 5.6.1 Immunospecificity of Antibodies of the Invention

Antibodies of the present invention may be characterized in a variety of ways well known to one of skill in the art. In particular, antibodies of the invention may be assayed for the ability to immunospecifically bind to a galanin peptide. Such an assay may be performed in solution (e.g., Houghten, 1992, Bio/Techniques 13:412-421), on beads (Lam, 1991, Nature 354:82-84), on chips (Fodor, 1993, Nature 364:555-556), on bacteria (U.S. Pat. No. 5,223,409), on spores (U.S. Pat. Nos. 5,571,698; 5,403,484; and 5,223,409), on plasmids (Cull et al., 1992, Proc. Natl. Acad. Sci. USA 89:1865-1869) or on phage (Scott and Smith, 1990, Science 249:386-390; Cwirla et al., 1990, Proc. Natl. Acad. Sci. USA 87:6378-6382; and Felici, 1991, J. Mol. Biol. 222:301-310). Antibodies that have been identified to immunospecifically bind to a galanin peptide can then be assayed for their specificity and affinity for a galanin peptide.

The antibodies of the invention may be assayed for immunospecific binding to a galanin peptide and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds., 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1 to 4 hours) at 4° C., adding protein A and/or protein G sepharose beads to the cell lysate, incubating for about an hour or more at 40° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al., eds., 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, incubating the membrane in blocking solution (e.g., PBS with 3% BSA or non-fat milk), washing the membrane in washing buffer (e.g., PBS-Tween 20), incubating the membrane with primary antibody (the antibody of interest) diluted in blocking buffer, washing the membrane in washing buffer, incubating the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs generally comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., $^{3}H$ or $^{125}I$) with the antibody of interest in the presence of increasing amounts of unlabeled antigen, and the detection of the antibody bound to the labeled antigen. The affinity of the antibody of the present invention for a galanin peptide and the binding off-rates can be determined from the data by scatchard plot analysis. Competition with a second antibody can also be determined using radioimmunoassays. In this case, a galanin peptide is incubated with an antibody of the present invention conjugated to a labeled compound (e.g., $^{3}H$ or $^{125}I$) in the presence of increasing amounts of an unlabeled second antibody.

In one aspect, BIAcore kinetic analysis is used to determine the binding on and off rates of antibodies of the invention to a galanin peptide. BIAcore kinetic analysis comprises analyzing the binding and dissociation of antibodies of the invention from chips with immobilized galanin peptide on their surface. A typical BIAcore kinetic study involves the injection of 250 μl of an antibody reagent (mAb, Fab) at varying concentration in HBS buffer containing 0.005% Tween-20 over a sensor chip surface, onto which has been immobilized the antigen. The flow rate is maintained constant at 75 µl/min. Dissociation data is collected for 15 min. or longer as necessary. Following each injection/dissociation cycle, the bound mAb is removed from the antigen surface using brief, 1 min. pulses of dilute acid, typically 10-100 mM HCl, though other regenerants are employed as the circumstances warrant. More specifically, for measurement of the rates of association, $k_{on}$, and dissociation, $k_{off}$, the antigen is directly immobilized onto the sensor chip surface through the use of standard amine coupling chemistries, namely the EDC/NHS method (EDC=N-diethylaminopropyl)-carbodiimide). Briefly, a 5-100 nM solution of the antigen in 10 mM NaOAc, pH4 or pH5 is prepared and passed over the EDC/NHS-activated surface until approximately 30-50 RU's worth of antigen are immobilized. Following this, the unreacted active esters are "capped" off with an injection of 1M Et-NH2. A blank surface, containing no antigen, is prepared under identical immobilization conditions for reference purposes. Once an appropriate surface has been prepared, a suitable dilution series of each one of the antibody reagents is prepared in HBS/Tween-20, and passed over both the antigen and reference cell surfaces, which are connected in series. The range of antibody concentrations that are prepared varies, depending on what the equilibrium binding constant, KD, is estimated to be. As described above, the bound antibody is removed after each injection/dissociation cycle using an appropriate regenerant.

The antibodies of the invention can also be assayed for their ability to inhibit the binding of galanin to one or more of its receptors using techniques known to those of skill in the art. For example, cells expressing a galanin receptor can be contacted with a galanin peptide in the presence or absence of an antibody and the ability of the antibody to inhibit the galanin peptide's binding can measured by, for example, flow cytometry or a scintillation assay. The galanin peptide or the antibody can be labeled with a detectable compound such as a radioactive label (e.g., $^{32}P$, $^{35}S$, and $^{125}I$) or a fluorescent label (e.g., fluorescein isothiocyanate, rhodamine, phycoerythrin, phycocyanin, allophycocyanin, o-phthaldehyde and fluorescamine) to enable detection of an interaction between the galanin peptide and a galanin receptor. Alternatively, the ability of antibodies to inhibit galanin from binding to one or more of its receptors can be determined in cell-free assays. For example, a galanin peptide can be contacted with an antibody and the ability of the antibody to inhibit the galanin peptide from binding to one or more of its host cell receptors can be determined. In one aspect, the antibody is immobilized on a solid support and a galanin peptide is labeled with a detectable compound. Alternatively, a galanin peptide is immobilized on a solid support and the antibody is labeled with a detectable compound. A galanin peptide may be partially or completely isolated (e.g., partially or completely free of other polypeptides) or part of a cell lysate. Further, a galanin peptide may be a fusion protein comprising galanin, a derivative, analog or fragment thereof and a domain such as glutathionine-S-transferase. Alternatively, a galanin peptide can be biotinylated using techniques well known to those of skill in the art (e.g., biotinylation kit, Pierce Chemicals; Rockford, Ill.).

5.6.2 In Vitro Studies

The antibodies, compositions, or combination therapies of the invention can be tested in vitro and then in vivo for the desired therapeutic or prophylactic activity prior to use in humans. For example, assays which can be used to determine whether administration of a specific pharmaceutical composition is indicated include cell culture assays in which a patient tissue sample is grown in culture and exposed to, or otherwise contacted with, a pharmaceutical composition, and the effect of such composition upon the tissue sample is observed. The tissue sample can be obtained by biopsy from the patient. This test allows the identification of the therapeutically most effective therapy (e.g., prophylactic or therapeutic agent) for each individual patient. In various specific aspects, in vitro assays can be carried out with representative cells of cell types involved in a disorder associated with or characterized by aberrant expression and/or activity of galanin and/or a disorder associated with or characterized by aberrant expression and/or activity of a galanin receptor to determine if a pharmaceutical composition of the invention has a desired effect upon such cell types. As an alternative to the use of tissue, tissue samples or cancer cell lines can be used in in vitro assays. Examples of cancer cell lines that can be utilized in in vitro assays include, but are not limited to, the MCF-7 breast cancer cell line, the MCF-7/ADR multi-drug resistant breast cancer cell line, the HT114 human melanoma cell line, the MES/DOX doxorubicenresistant human uterine sarcoma cell line, the HT29 human colorectal cell line, the HCT-116 human colorectal cell line, the A549 human lung carcinoma cell line, the COLO-677 human small cell lung carcinoma cell line, and the BXPC-3 human pancreas primary adenocarcinoma cell line.

The antibodies, compositions or combination therapies of the invention can be assayed for their ability to induce the expression and/or activation of a gene product (e.g., cellular protein or RNA) and/or to induce signal transduction in immune cells, cancer cells, and/or endothelial cells. The induction of the expression or activation of a gene product or the induction of signal transduction pathways in immune cells, cancer cells (in particular tubulin-binding agent resistant cancer cells) and/or endothelial cells can be assayed by techniques known to those of skill in the art including, e.g., ELISAs flow cytometry, Northern blot analysis, Western blot analysis, RT-PCR kinase assays and electrophoretic mobility shift assays. Antibodies, compositions or combination therapies of the invention can also be assayed for their ability to modulate immune cell proliferation, endothelial proliferation and cancer cell proliferation. Techniques known to those in art, include, but are not limited to, $^3H$-thymidine incorporation, trypan blue cell counts, and fluorescence activated cell sorting ("FACS") analysis. The antibodies, compositions or combination therapies of the invention can also be assayed for their ability to induce cytolysis. Cytolysis can be assessed by techniques known to those in art, including, but not limited to, $^{51}CR$-release assays. The antibodies, compositions or combination therapies of the invention can also be assayed for their ability to inhibit cell migration, cell adhesion angiogenesis or tubulin polymerization using techniques well-known to one of skill in the art or described herein. The antibodies, compositions or combination therapies of the invention can also be assayed for their ability to induce cell cycle arrest or apoptosis.

The effect of an antibody, a composition, or a combination therapy of the invention on peripheral blood lymphocyte counts can be monitored/assessed using standard techniques known to one of skill in the art. Peripheral blood lymphocytes counts in a subject can be determined by, e.g., obtaining a sample of peripheral blood from said subject, separating the lymphocytes from other components of peripheral blood such as plasma using, e.g., Ficoll-Hypaque (Pharmacia) gradient centrifugation, and counting the lymphocytes using trypan blue. Peripheral blood T-cell counts in subject can be determined by, e.g., separating the lymphocytes from other components of peripheral blood such as plasma using, e.g., a use of Ficoll-Hypaque (Pharmacia) gradient centrifugation, labeling the T-cells with an antibody directed to a T-cell antigen which is conjugated to FITC or phycoerythrin, and measuring the number of T-cells by FACS.

Further, any in vitro assays known to those skilled in the art can be used to evaluate the prophylactic and/or therapeutic utility of an antibody, a composition or a combination therapy disclosed herein for a disorder disclosed herein or one or more symptoms thereof.

5.6.3 In Vivo Assays

The antibodies, compositions, or combination therapies of the invention can be tested in suitable animal model systems prior to use in humans. Such animal model systems include, but are not limited to, rats, mice, chicken, cows, monkeys, pigs, dogs, rabbits, etc. Any animal system well-known in the art may be used. Several aspects of the procedure may vary; said aspects include, but are not limited to, the temporal regime of administering the therapies (e.g., prophylactic and/or therapeutic agents), whether such therapies are administered separately or as an admixture, and the frequency of administration of the therapies.

Animal models for cancer can be used to assess the efficacy of an antibody, a composition, or a combination therapy of the invention. Examples of animal models for lung cancer include, but are not limited to, lung cancer animal models described by Zhang & Roth (1994, In Vivo 8(5):755-69) and a transgenic mouse model with disrupted p53 function (see, e.g., Morris et al., 1998, J La State Med Soc 150(4):179-85). An example of an animal model for breast cancer includes, but is not limited to, a transgenic mouse that overexpresses cyclin D1 (see, e.g., Hosokawa et al., 2001, Transgenic Res 10(5):471-8). An example of an animal model for colon cancer includes, but is not limited to, a TCR b and p53 double knockout mouse (see, e.g., Kado et al., 2001, Cancer Res 61(6):2395-8). Examples of animal models for pancreatic cancer include, but are not limited to, a metastatic model of Panc02 murine pancreatic adenocarcinoma (see, e.g., Wang et al., 2001, Int J Pancreatol 29(1):37-46) and nu-nu mice generated in subcutaneous pancreatic tumours (see, e.g., Ghaneh et al., 2001, Gene Ther 8(3):199-208). Examples of animal models for non-Hodgkin's lymphoma include, but are not limited to, a severe combined immunodeficiency ("SCID") mouse (see, e.g., Bryant et al., 2000, Lab Invest 80(4):553-73) and an IgHmu-HOX11 transgenic mouse (see, e.g., Hough et al., 1998, Proc Natl Acad Sci USA 95(23):13853-8). An example of an animal model for esophageal cancer includes, but is not limited to, a mouse transgenic for the human papillomavirus type 16 E7 oncogene (see, e.g., Herber et al., 1996, J Virol 70(3):1873-81). Examples of animal models for colorectal carcinomas include, but are not limited to, Apc mouse models (see, e.g., Fodde & Smits, 2001, Trends Mol Med 7(8):369-73 and Kuraguchi et al., 2000, Oncogene 19(50):5755-63).

Further, any assays known to those skilled in the art can be used to evaluate the prophylactic and/or therapeutic utility of an antibody, a composition, a combination therapy disclosed herein for prevention, treatment, management, and/or amelioration of a disorder characterized by aberrant expression and/or activity of galanin and/or a disorder characterized by aberrant expression and/or activity of a galanin receptor.

5.6.4 Toxicity Assays

The toxicity and/or efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Therapies that exhibit large therapeutic indices are preferred. While therapies that exhibit toxic side effects may be used, care should be taken to design a delivery system that targets such agents to the site of affected tissue in order to minimize potential damage to unaffected cells and, thereby, reduce side effects.

The data obtained from the cell culture assays and animal studies can be used in formulating a range of dosage of the prophylactic and/or therapeutic agents for use in humans. The dosage of such agents lies within a range of circulating concentrations that include the $ED_{50}$ with little or no toxicity. The dosage may vary within this range depending upon the dosage form employed and the route of administration utilized. For any therapy used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by ELISA.

5.7 Diagnostic Uses of Antibodies of the Invention

Antibodies of the invention (including molecules comprising, or alternatively consisting of, antibody fragments or variants thereof) that immunospecifically bind to a galanin peptide can be used for diagnostic purposes to detect, diagnose, prognose, or monitor a disorder associated with aberrant expression and/or activity of galanin and/or a disorder associated with aberrant expression and/or activity of a galanin receptor. The invention provides for the detection of aberrant expression of galanin comprising: (a) assaying the expression of galanin in a biological sample from an individual using one or more antibodies of the invention that immunospecifically binds to a galanin peptide; and (b) comparing the level of galanin with a standard level of galanin, e.g., in normal biological samples, whereby an increase or decrease in the assayed level of galanin compared to the standard level of galanin is indicative of a disorder associated with aberrant expression and/or activity of a galanin. In some aspects, aberrant expression level of galanin is indicative of a hyperproliferative disorder or condition associated therewith. In some aspects, the labeled antibodies of the invention that immunospecifically bind to a galanin peptide are used for diagnostic purposes to detect, diagnose, prognose, or monitor a cancer.

Antibodies of the invention can be used to assay galanin levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105: 3087-3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I), carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin.

One aspect of the invention is the detection and diagnosis of a disorder associated with aberrant expression of galanin in an animal, in one aspect, a mammal, and, in one aspect, a human. In one aspect, diagnosis comprises: a) administering (for example, parenterally, subcutaneously, or intraperitoneally) to a subject an effective amount of a labeled antibody of the invention (including molecules comprising, or alternatively consisting of, antibody fragments or variants thereof) that immunospecifically binds to a galanin peptide; b) waiting for a time interval following the administering for permitting the labeled antibody to preferentially concentrate at sites in the subject where galanin is expressed (and for unbound labeled molecule to be cleared to background level); c) determining background level; and d) detecting the labeled antibody in the subject, such that detection of labeled antibody above the background level and above or below the level observed in a subject or population of subjects without the disorder indicates that the subject has a particular disorder associated with aberrant expression of galanin. Background level can be determined by various methods including, comparing the amount of labeled molecule detected to a standard value previously determined for a particular system. A more definitive diagnosis of a hyperproliferative disorder associated with or characterized by aberrant expression of galanin may allow health professionals to employ preventive measures or aggressive treatment earlier and thereby prevent the development or further progression of the disorder.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds, Masson Publishing Inc. (1982). Depending on several variables, including the type of label used and the mode of administration, the time interval following the administration for permitting the labeled molecule to preferentially concentrate at sites in the subject and for unbound labeled molecule to be cleared to background level is 6 to 48 hours, 6 to 24 hours, or 6 to 12 hours. In another aspect the time interval following administration is 5 to 20 days or 5 to 10 days.

In one aspect, monitoring of the disease or disorder is carried out by repeating the method for diagnosing the disease or disorder, for example, one month after initial diagnosis, six months after initial diagnosis, one year after initial diagnosis, etc.

Presence of the labeled galanin antibody can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In one aspect, the galanin antibody is labeled with a radioisotope and is detected in the patient using a radiation responsive surgical instrument (Thurston et al., U.S. Pat. No. 5,441,050). In another aspect, the galanin antibody is labeled with a fluorescent compound and is detected in the patient using a fluorescence responsive scanning instrument. In another aspect, the galanin antibody is labeled with a positron emitting metal and is detected in the patient using positron emission-tomography. In yet another aspect, the galanin antibody is labeled with a paramagnetic label and is detected in a patient using magnetic resonance imaging (MRI).

The antibodies of the invention (including molecules comprising, or alternatively consisting of, antibody fragments or variants thereof) may be utilized for immunophenotyping of cell lines and biological samples by their galanin expression. Various techniques can be utilized using the antibodies, fragments, or variants of the invention to screen for cellular populations (that express galanin, and include magnetic separation using antibody-coated magnetic beads, "panning" with antibody attached to a solid matrix (i.e., plate), and flow cytometry (see, e.g., U.S. Pat. No. 5,985,660; and Morrison et al., Cell, 96:737-49 (1999)).

5.8 Kits

The present invention provides kits that can be used in the above methods. In one aspect, a kit comprises an antibody of the invention, for example, a purified antibody, in one or more containers. In one aspect, the kits of the present invention contain a substantially isolated galanin peptide as a control. In one aspect, the kits of the present invention further comprise a control antibody which does not react with a galanin peptide. In another aspect, the kits of the present invention contain a means for detecting the binding of an antibody to a galanin peptide (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In some aspects, the kit may include a recombinantly produced or chemically synthesized galanin peptide. The galanin peptide provided in the kit may also be attached to a solid support. In one aspect the detecting means of the above-described kit includes a solid support to which a galanin peptide is attached. Such a kit may also include a non-attached reporter-labeled anti-human antibody. In this aspect, binding of the antibody to the galanin peptide can be detected by binding of the said reporter-labeled antibody.

In an additional aspect, the invention includes a diagnostic kit for use in screening serum containing a galanin peptide. The diagnostic kit includes a substantially isolated antibody specifically immunoreactive with a galanin peptide, and means for detecting the binding of the galanin peptide to the antibody. In one aspect, the antibody is attached to a solid support. In one aspect, the antibody may be a monoclonal antibody. The detecting means of the kit may include a second, labeled monoclonal antibody. Alternatively, or in addition, the detecting means may include a labeled, competing antigen.

5.9 Articles of Manufacture

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient, e.g., an antibody of the invention that immunospecifically binds to a galanin peptide, is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, intransal, or topical delivery.

In one aspect, the unit dosage form is suitable for intravenous, intramuscular, intranasal, oral, topical or subcutaneous delivery. Thus, the invention encompasses solutions, for example, sterile, suitable for each delivery route.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures, total lymphocyte, T cell counts, and other monitoring information.

Specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises an antibody that immunospecifically binds to a galanin peptide and wherein said packaging material includes instruction means which indicate that said antibody can be used to prevent, manage, treat, and/or ameliorate a disorder associated with or characterized by aberrant expression and/or activity of galanin or a galanin receptor (in particular, a hyperproliferative disorder) or one or more symptoms thereof by administering specific doses and using specific dosing regimens as described herein.

The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material, wherein one pharmaceutical agent comprises an antibody that immunospecifically binds to a galanin peptide and the other pharmaceutical agent comprises a second, different antibody that immunospecifically binds to a galanin peptide, and wherein said packaging material includes instruction means which indicate that said agents can be used to treat, prevent and/or ameliorate a disorder associated with or characterized by aberrant expression and/or activity of galanin or a galanin receptor (in particular, a hyperproliferative disorder) or one or more symptoms thereof by administering specific doses and using specific dosing regimens as described herein.

The invention also provides an article of manufacture comprising packaging material, such as a box, bottle, tube, vial, container, sprayer, insufflator, intravenous (i.v.) bag, envelope and the like; and at least one unit dosage form of each pharmaceutical agent contained within said packaging material, wherein one pharmaceutical agent comprises an antibody that immunospecifically binds to a galanin peptide and the other pharmaceutical agent comprises a prophylactic or therapeutic agent other than an antibody that immunospecifically binds to a galanin peptide, and wherein said packaging material includes instruction means which indicate that said agents can be used to treat, prevent and/or ameliorate a disorder associated with or characterized by aberrant expression and/or activity of galanin or a galanin receptor (in particular, a hyperproliferative disorder) or one or more symptoms thereof by administering specific doses and using specific dosing regimens as described herein.

The present invention provides that the adverse effects that may be reduced or avoided by the methods of the invention are indicated in informational material enclosed in an article of manufacture for use in preventing, treating and/or ameliorating a hyperproliferative disorder or one or more symptoms thereof. Adverse effects that may be reduced or avoided by the methods of the invention include, but are not limited to, vital sign abnormalities (fever, tachycardia, bardycardia, hypertension, hypotension), hematological events (anemia, lymphopenia, leukopenia, thrombocytopenia), headache, chills, dizziness, nausea, asthenia, back pain, chest pain (chest pressure), diarrhea, myalgia, pain, pruritus, psoriasis, rhinitis, sweating, injection site reaction, and vasodilatation. Since antibodies of the invention that immunospecifically bind to a galanin peptide may be immunosuppressive, prolonged immunosuppression may increase the risk of infection, including opportunistic infections. Prolonged and sustained immunosuppression may also result in an increased risk of developing certain types of cancer.

Further, the information material enclosed in an article of manufacture for use in preventing, treating, managing, and/or ameliorating a hyperproliferatiave disorder or one or more symptoms thereof can indicate that foreign proteins may also result in allergic reactions, including anaphylaxis, or cytosine release syndrome. The information material should indicate that allergic reactions may exhibit only as mild pruritic rashes or they may be severe such as erythroderma, Stevens-Johnson syndrome, vasculitis, or anaphylaxis. The information material should also indicate that anaphylactic reactions (anaphylaxis) are serious and occasionally fatal hypersensitivity reactions. Allergic reactions including anaphylaxis may occur when any foreign protein is injected into the body. They may range from mild manifestations such as urticaria or rash to lethal systemic reactions. Anaphylactic reactions occur soon after exposure, usually within 10 minutes. Patients may experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, or eosinophilia.

5.10 Methods of Producing Antibodies

Antibodies that immunospecifically bind to an antigen can be produced by any method known in the art for the synthesis of antibodies, in particular, by chemical synthesis or, for example, by recombinant expression techniques.

Polyclonal antibodies that immunospecifically bind to an antigen can be produced by various procedures well known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, Cold Spring Harbor Laboratory Press, 2nd ed. (1988); Hammerling, et al., in: *Monoclonal Antibodies and T-Cell Hybridomas* 563-681, Elsevier, N.Y. (1981) and Harlow et al., *Using Antibodies: A Laboratory Manual*, Cold Spring Harbor Laboratory Press (1999) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a galanin peptide and once an immune response is detected, e.g., antibodies specific for galanin are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. Additionally, a RIMMS (repetitive immunization multiple sites) technique can be used to immunize an animal (Kilptrack et al., 1997 *Hybridoma* 16:381-9, incorporated by reference in its entirety). The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating antibodies by culturing a hybridoma cell secreting an antibody of the invention wherein, the hybridoma can be generated by fusing splenocytes isolated from a mouse immunized with a galanin peptide with myeloma cells and then screening the hybridomas resulting from the fusion for hybridoma clones that secrete an antibody able to bind to a galanin peptide.

Antibody fragments which recognize specific galanin epitopes may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743, 5,969,108, 6,333,187, 5,824,520, and 5,702,892; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lamba constant regions. In one aspect, the vectors for expressing the VH or VL domains comprise an EF-1α promoter, a secretion signal, a cloning site for the variable domain, constant domains, and a selection marker such as neomycin. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., PCT publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules. Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415, which are incorporated herein by reference in their entirety.

A humanized antibody is an antibody or its variant thereof which is capable of binding to a predetermined antigen and which comprises a framework region having substantially the amino acid sequence of a human immunoglobulin and a CDR having substantially the amino acid sequence of a non-human immuoglobulin. A humanized antibody comprises substantially all of at least one, and typically two, variable domains (Fab, Fab', F(ab')$_2$, Fv) in which all or substantially all of the CDR regions correspond to those of a non-human immunoglobulin (i.e., donor antibody) and all or substantially all of the framework regions are those of a human immunoglobulin consensus sequence. In one aspect, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG$_1$, IgG$_2$, IgG$_3$ and IgG$_4$. Usually the constant domain is a complement fixing constant domain where it is desired that the humanized antibody exhibit cytotoxic activity, and the class is typically IgG$_1$. Where such cytotoxic activity is not desirable, the constant domain may be of the IgG$_2$ class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental FR and CDR sequences, more often 90%, and most preferably greater than 95%. Humanized antibody can be produced using variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. No. 6,407,213, U.S. Pat. No. 5,766,886, WO 9317105, Tan et al., J. Immunol. 169:1119-25 (2002), Caldas et al., Protein Eng. 13(5):353-60 (2000), Morea et al., Methods 20(3):267-79 (2000), Baca et al., J. Biol. Chem. 272(16):10678-84 (1997), Roguska et al., Protein Eng. 9(10):895-904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). Often, framework residues in the framework regions will be substituted with the corresponding residue from the CDR donor antibody to alter, for example, improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323, which are incorporated herein by reference in their entireties.)

Single domain antibodies, for example, antibodies lacking the light chains, can be produced by methods well-known in the art. See Riechmann et al., 1999, J. Immuno. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety.

Further, the antibodies that immunospecifically bind to an antigen (e.g., a galanin peptide) can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8):2429-2438).

5.10.1 Polynucleotide Sequences Encoding Antibodies

The invention provides polynucleotides comprising a nucleotide sequence encoding an antibody that immunospecifically binds to an antigen (e.g., galanin peptide). The invention also encompasses polynucleotides that hybridize under high stringency, intermediate or lower stringency hybridization conditions, e.g., as defined supra, to polynucleotides that encode an antibody of the invention.

The polynucleotides may be obtained, and the nucleotide sequence of the polynucleotides determined, by any method known in the art. Since the amino acid sequences of murine antibody 4B3, 1D7, 5B4, 2F8, 1A1, 2H9 and 2E11, and humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 are known, nucleotide sequences encoding these antibodies can be determined using methods well known in the art, i.e., nucleotide codons known to encode particular amino acids are assembled in such a way to generate a nucleic acid that encodes the antibody. Such a polynucleotide encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, or variants thereof, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library or a cDNA library generated from, or nucleic acid, for example, poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In one aspect, one or more of the CDRs is inserted within framework regions using routine recombinant DNA techniques. The framework regions may be naturally occurring or consensus framework regions, and, in one aspect, human framework regions (see, e.g., Chothia et al., 1998, J. Mol. Biol. 278:457-479 for a listing of human framework regions). In one aspect, the polynucleotide sequence generated by the combination of the framework regions and CDRs encodes an antibody that immunospecifically binds to a particular antigen (e.g., a galanin peptide). For example, one or more amino acid substitutions may be made within the framework regions, and, in one aspect, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

5.10.2 Recombinant Expression of Antibodies

Recombinant expression of an antibody of the invention (e.g., a heavy or light chain of an antibody of the invention or a single chain antibody of the invention) that immunospecifically binds to a galanin peptide requires construction of an expression vector containing a polynucleotide that encodes the antibody. Once a polynucleotide encoding an antibody molecule, heavy or light chain of an antibody, or antibody fragment (in one aspect, containing the heavy or light chain variable domain) of the invention has been obtained, the vector for the production of the antibody molecule may be produced by recombinant DNA technology using techniques well-known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention thus provides replicable vectors comprising a nucleotide sequence encoding an antibody molecule of the invention, a heavy or light chain of an antibody, a heavy or light chain variable domain of an antibody, or a heavy or light chain CDR, operably linked to a promoter. Such vectors may include the nucleotide sequence encoding the constant region of the antibody molecule (see, e.g., International Publication No. WO 86/05807; International Publication No. WO 89/01036; and U.S. Pat. No. 5,122,464) and the variable domain of the antibody may be cloned into such a vector for expression of the entire heavy, the entire light chain, or both the entire heavy and light chains.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In some aspects, for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NS0, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In one aspect, bacterial cells such as *Escherichia coli*, and, in another aspect, eukaryotic cells, especially for the expression of whole recombinant antibody molecule, csan be used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In one aspect, the expression of nucleotide sequences encoding antibodies of the invention, derivatives or analogs thereof which immunospecifically bind to a galanin peptide is regulated by a constitutive promoter, inducible promoter or tissue specific promoter.

In bacterial systems, a number of expression vectors may be advantageously selected depending upon the use intended for the antibody molecule being expressed. For example, when a large quantity of such an antibody is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, EMBO 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, BT483, Hs578T, HTB2, BT2O and T47D, NS0 (a murine myeloma cell line that does not endogenously produce any immunoglobulin chains), CRL7O3O and HsS78Bst cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoters, enhancers, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk-, hgprt- or aprt-cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIB TECH 11(5):155-2 15); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., 1981, J. Mol. Biol. 150:1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2 197). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention may be fused to heterologous polypeptide sequences described herein or otherwise known in the art to facilitate purification.

5.11 Galanin Peptide

A galanin peptide may be galanin, an analog, derivative or a fragment thereof, or a fusion protein comprising galanin, an analog or a derivative thereof. The galanin peptide may be from any species. The nucleotide and/or amino acid sequences of galanin peptides can be found in the literature or public databases, or the nucleotide and/or amino acid sequences can be determined using cloning and sequencing techniques known to one of skill in the art. For example, the nucleotide sequence of human galanin can be found in the GenBank database (see, e.g., Accession Nos. A28025 and NM_015973). The amino acid sequence of human galanin can be found in the GenBank database (see, e.g., Accession Nos. CAA01907, NP_057057, P22466 and AAH30241). In one aspect, a galanin peptide is mature, processed form of human galanin, an analog, derivative or fragment thereof.

A galanin peptide may be a "free-standing" fragment of galanin, or a fragment of the mature, processed form of galanin within a larger polypeptide of which the fragment forms a part or region, for example, as a single continuous region. Representative examples of galanin fragments that may be bound by antibodies of the present invention, include, for example, fragments that comprise, or alternatively, consist of, from about amino acid residues: 1 to 10, 1-15, 10-25, or 16-30 of the amino acid sequence corresponding to human galanin. Moreover, a galanin peptide that may be bound by antibodies of the present invention can be at least 4, at least 5, at least 6, at least 7, at least 8, at least 9, at least 10, at least 11, at least 12, at least 13, at least 14, at least 15, at least 20, or at least 30 amino acids in length. In this context, "about" means the particularly recited ranges and ranges larger or smaller by 5%, 10%, 15%, 20%, 25%, 30%, 35% or 40%, or 5, 4, 3, 2 or 1 amino acid residues at either or both the amino- and carboxy-termini.

In one aspect, an antibody of the present invention immunospecifically binds to the C-terminus of a mature, processed form of galanin. In certain aspects, an antibody of the invention does not bind to a region of a galanin peptide other than the C-terminus of a mature, processed form of galanin.

A galanin peptide may be fused with the constant domain of immunoglobulins (IgA, IgE, IgG, IgM), or portions thereof (CH1, CH2, CH3, or any combination thereof and portions thereof), or albumin (including but not limited to recombinant human albumin or fragments or variants thereof (see, e.g., U.S. Pat. No. 5,876,969, issued Mar. 2, 1999, EP Patent 0 413 622, and U.S. Pat. No. 5,766,883, issued Jun. 16, 1998), resulting in chimeric polypeptides. Such fusion proteins may facilitate purification and may increase half-life in vivo. This has been shown for chimeric proteins consisting of the first two domains of the human CD4 polypeptide and various domains of the constant regions of the heavy or light chains of mammalian immunoglobulins. See, e.g., EP 394,827; Traunecker et al., Nature, 33 1:84 86 (1998). Enhanced delivery of an antigen across the epithelial barrier to the immune system has been demonstrated for antigens (e.g., insulin) conjugated to an FcRn binding partner such as IgG or Fc fragments (see, e.g., International Publication Nos. WO 96/22024 and WO 99/048 13). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al., allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is transitionally fused to an amino-terminal tag consisting of six histidine residues. The tag serves as a matrix-binding domain for the fusion protein. Extracts from cells infected with the recombinant vaccinia virus are loaded onto $Ni^{2+}$ nitriloacetic acid-agarose column and histidine tagged proteins can be selectively eluted with imidazole-containing buffers.

In one aspect, a galanin peptide is fused with a heterologous antigen (e.g., polypeptide, carbohydrate, phospholipid, or nucleic acid). In one aspect, the heterologous antigen is an immunogen.

In another aspect, a galanin peptide is a derivative of galanin (in one aspect, the mature, processed form of galanin) or the epitope-bearing fragments thereof. Such derivatives can be generated by random mutagenesis of a polynucleotide encoding galanin, by error-prone PCR, random nucleotide insertion or other methods prior to recombination. Alternatively, site-directed mutagenesis techniques can be used to produce derivatives. Amino acids in the galanin peptides that are essential for function can be identified by methods known in the art, such as site-directed mutagenesis or alanine-scanning mutagenesis (Cunningham and Wells, Science 244:1081-1085 (1989)). The latter procedure introduces single alanine mutations at every residue in the molecule. The resulting mutant molecules are then tested for functional activity, such as ligand binding. In one aspect of the invention, a galanin peptide comprises an amino acid sequence which contains at least one conservative amino acid substitution, but not more than 30 conservative amino acid substitutions, in one aspect, not more than 25 conservative amino acid substitutions, in another aspect, not more than 15 conservative amino acid substitutions, and, in yet another aspect, not more than 10 conservative amino acid substitutions relative to the native galanin (for example, the mature, processed form of galanin) amino acid sequence (e.g., the mature, processed form of native human galanin amino acid sequence). In another aspect of the invention, a galanin peptide comprises an amino acid sequence which contains at least one conservative amino acid substitution; but not more than 8, 7, 6, 5, 4, 3, 2 or 1 conservative amino acid substitutions relative to the native galanin (for example, the mature, processed form of galanin) amino acid sequence (e.g., the mature, processed form of native human galanin amino acid sequence). In yet another aspect, a galanin peptide comprises an amino acid sequence which contains one or more conservative substitutions or a combination of non-conservative and conservative amino acid substitutions relative to the native galanin amino acid sequence (for example, the amino acid sequence of the mature, processed form of native galanin).

To improve or alter the characteristics of galanin peptides, protein engineering may be employed. Recombinant DNA technology known to those skilled in the art can be used to create novel mutant proteins or "muteins" including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. For instance, for many proteins, it is known in the art that one or more amino acids may be deleted from the N-terminus or C-terminus without substantial loss of biological function. For instance, Ron et al., J. Biol. Chem., 268:2984-2988 (1993) reported modified KGF proteins that had heparin binding activity even if 3, 8, or 27 amino-terminal amino acid residues were missing. Accordingly, antibodies of the present invention may bind galanin peptide mutants or variants generated by protein engineering.

In another aspect, a galanin peptide is at least 50%, at least 65%, at least 70%, at least 75%, at least 80%, at least 85%, at least 90%, or at least 95% identical to a native galanin (for example, the mature, processed form of galanin) amino acid sequence (e.g., a mature, processed form of native human galanin amino acid sequence).

5.12 Methods of Producing Polypeptides

Polypeptides, peptides, proteins, and fusion proteins can be produced by standard recombinant DNA techniques or by protein synthetic techniques, e.g., by use of a peptide synthesizer. For example, a nucleic acid molecule encoding polypeptides, peptides, proteins, or fusion proteins can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al., eds., John Wiley & Sons, 1992 and *Short Protocols in Molecular Biology: A Compendium of Methods from Current Protocols in Molecular Biology*, 5$^{th}$ ed., Ausubel et al., eds., Wiley, John & Sons, Incorporated, 2002).

The nucleotide sequences encoding a polypeptide, peptide, protein, or fusion protein may be obtained from any information available to those of skill in the art (i.e., from Genbank, the literature, or by routine cloning). The nucleotide sequence coding for a polypeptide, peptide, protein, and fusion protein can be inserted into an appropriate expression vector, i.e., a vector which contains the necessary elements for the transcription and translation of the inserted protein-coding sequence. A variety of host-vector systems may be utilized in the present invention to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

The expression of a polypeptide, peptide, protein, or fusion protein may be controlled by any promoter or enhancer element known in the art. Promoters which may be used to control the expression of the gene encoding fusion protein include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:1441-1445), the regulatory sequences of the metallothionein gene (Brinster et al., 1982, Nature 296:39-42), the tetracycline (Tet) promoter (Gossen et al., 1995, Proc. Nat. Acad. Sci. USA 89:5547-5551); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25; see also "Useful proteins from recombinant bacteria" in Scientific American, 1980, 242:74-94); plant expression vectors comprising the nopaline synthetase promoter region (Herrera-Estrella et al., Nature 303:209-213) or the cauliflower mosaic virus 35S RNA promoter (Gardner, et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286); neuronal-specific enolase (NSE) which is active in neuronal cells (Morelli et al., 1999, Gen. Virol. 80:571-83); brain-derived neurotrophic factor (BDNF) gene control region which is active in neuronal cells (Tabuchi et al., 1998, Biochem. Biophysic. Res. Com. 253:818-823); glial fibrillary acidic protein (GFAP) promoter which is active in astrocytes (Gomes et al., 1999, Braz J Med Biol Res 32(5):619-631; Morelli et al., 1999, Gen. Virol. 80:571-83) and gonadotropic releasing hormone gene control region which is active in the hypothalamus (Mason et al., 1986, Science 234:1372-1378).

In one aspect, the expression of a polypeptide, peptide, protein, or fusion protein is regulated by a constitutive promoter. In another aspect, the expression of a polypeptide, peptide, protein, or a fusion protein is regulated by an inducible promoter. In another aspect, the expression of a polypeptide, peptide, protein, or a fusion protein is regulated by a tissue-specific promoter.

In one aspect, a vector is used that comprises a promoter operably linked to a polypeptide, peptide, protein, or a fusion protein-encoding nucleic acid, one or more origins of replication, and, optionally, one or more selectable markers (e.g., an antibiotic resistance gene).

In mammalian host cells, a number of viral-based expression systems may be utilized. In cases where an adenovirus is used as an expression vector, the polypeptide or fusion protein coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 81:355-359). Specific initiation signals may also be required for efficient translation of inserted fusion protein coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:51-544).

Expression vectors containing inserts of a gene encoding a polypeptide, peptide, protein, or fusion protein can be identified by three general approaches: (a) nucleic acid hybridization, (b) presence or absence of "marker" gene functions, and (c) expression of inserted sequences. In the first approach, the presence of a gene encoding a polypeptide, peptide, protein, or a fusion protein in an expression vector can be detected by nucleic acid hybridization using probes comprising sequences that are homologous to an inserted gene encoding the polypeptide, peptide, protein, or the fusion protein, respectively. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of a nucleotide sequence encoding a polypeptide, peptide, protein, or fusion protein in the vector. For example, if the nucleotide sequence encoding the fusion protein is inserted within the marker gene sequence of the vector, recombinants containing the gene encoding the fusion protein insert can be identified by the absence of the marker gene function. In the third approach, recombinant expression vectors can be identified by assaying the gene product (e.g., fusion protein) expressed by the recombinant. Such assays can be based, for example, on the physical or functional properties of the fusion protein in in vitro assay systems, e.g., binding to an antibody.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells which possess the cellular machinery for proper processing of the primary transcript, glycosylation, and phosphorylation of the gene product may be used. Such mammalian host cells include, but are not limited to, CHO, VERY, BHK, Hela, COS, MDCK, 293, 3T3, WI38, NS0, and in particular, neuronal cell lines such as, for example, SK-N-AS, SK-N-FI, SK-N-DZ human neuroblastomas (Sugimoto et al., 1984, J. Natl. Cancer Inst. 73: 51-57), SK-N-SH human neuroblastoma (Biochim. Biophys. Acta, 1982, 704:450-460), Daoy human cerebellar medulloblastoma (He et al., 1992, Cancer Res. 52:1144-1148) DBTRG-05MG glioblastoma cells (Kruse et al., 1992, In Vitro Cell. Dev. Biol. 28A: 609-614), IMR-32 human neuroblastoma (Cancer Res., 1970, 30: 2110-2118), 1321N1 human astrocytoma (Proc. Natl. Acad. Sci. USA, 1977, 74: 4816), MOG-G-CCM human astrocytoma (Br. J. Cancer, 1984, 49: 269), U87MG human glioblastoma-astrocytoma (Acta Pathol. Microbiol. Scand., 1968, 74: 465-486), A172 human glioblastoma (Olopade et al., 1992, Cancer Res. 52: 2523-2529), C6 rat glioma cells (Benda et al., 1968, Science 161: 370-371), Neuro-2a mouse neuroblastoma (Proc. Natl. Acad. Sci. USA, 1970, 65: 129-136), NB41A3 mouse neuroblastoma (Proc. Natl. Acad. Sci. USA, 1962, 48: 1184-1190), SCP sheep choroid plexus (Bolin et al., 1994, J. Virol. Methods 48: 211-221), G355-5, PG-4 Cat normal astrocyte (Haapala et al., 1985, J. Virol. 53: 827-833), Mpf ferret brain (Trowbridge et al., 1982, In Vitro 18: 952-960), and normal cell lines such as, for example, CTX TNA2 rat normal cortex brain (Radany et al., 1992, Proc. Natl. Acad. Sci. USA 89: 6467-6471) such as, for example, CRL7030 and Hs578Bst. Furthermore, different vector/host expression systems may effect processing reactions to different extents.

For long-term, high-yield production of recombinant polypeptide, peptide, protein, or fusion protein, stable expression is preferred. For example, cell lines which stably express a polypeptide, peptide, protein, or a fusion protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express a polypeptide, peptide, protein, or a fusion protein that immunospecifically binds to a galanin peptide. Such engineered cell lines may be particularly useful in screening and evaluation of compounds that affect the activity of a polypeptide, peptide, protein, or fusion protein that immunospecifically binds to a galanin peptide.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk-, hgprt- or aprt-cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

Once a polypeptide, peptide, protein, or a fusion protein of the invention has been produced by recombinant expression, it may be purified by any method known in the art for purification of a protein, for example, by chromatography (e.g., ion exchange, affinity, particularly by affinity for the specific antigen after Protein A, and sizing column chromatography), centrifugation, differential solubility, or by any other standard technique for the purification of proteins.

6. EXAMPLES

Certain aspects of the invention are illustrated by the following non-limiting examples.

6.1 Generation and Characterization of High Affinity Anti-Galanin Monoclonal Antibodies This example demonstrates that monoclonal antibodies that immunospecifically bind to the C-terminus of galanin exhibit a higher afinity for galanin than monoclonal antibodies that do not bind to the C-terminus of galanin.

Monoclonal antibodies were developed against human galanin by immunizing two groups of six Balb/c mice each with N- or C-terminal fusions of KLH to human galanin. Serum from each mouse was tested in ELISA assays to determine if the mice had a specific immune response against galanin and all were positive. Further, serum from each mouse was tested in a GALR2 filtration binding assay. The binding assay was carried out with 6 μg of a membrane preparation from A9 cells engineered to overexpress GALR2. The GALR2 containing membranes were incubated with 0.25 nM [$^{125}$I]-human galanin (PerkinElmer No. NEX333) plus pre-immune or anti-galanin anti-sera for 1 hour at room temperature and harvested onto a GF/B Unifilter plate (Packard No. 005177). All 12 anti-sera selectively inhibited binding of galanin to GALR2 in the filtration binding assay (FIGS. 36A-B).

Hybridomas were made by fusing splenocytes from mice from each group with the myeloma fusion partner, P3X63Ag8.653. Thirty-seven out of 500 hybridomas were positive by ELISA using galanin-KLH. Of these 37 clones, 21 were able to inhibit binding of human galanin to GALR2 using the filtration binding assay described above. A binding assay using labeled MCH binding to MCHR1 was used as a selectivity control (FIG. 37). These 21 hybridomas were recloned resulting in the survival of 16 clones. Ascites production was carried out for all 16 clones.

Simultaneously, monoclonal antibodies (MAb) were ranked based on relative affinities using an immunoprecipitation method (Van Heyningen, 1986. Methods in Emzymology 121: 472-81). Hybridoma supematants from confluent cultures were serially diluted, pre-incubated with 0.8 nM [$^{125}$I]-human galanin, and precipitated with an excess of Protein G Sepharose (Amersham No. 17-0618). Based on these results, the MAbs fell into two groups—7 high affinity and 9 lower affinity (FIG. 38).

All 7 high and 2 lower affinity MAbs were purified from ascites over a Protein G Sepharose column. Ascites were delipidated by filtration through miracloth, using a binding/wash buffer (50 mM Tris.Cl, pH 7.9, 150 mM NaCl), an elution buffer (50 mM Glycine.Cl, pH 2.7, 150 mM NaCl), and a neutralizing buffer (0.5 M Sodium Phosphate, pH 8.0). Purified MAbs were again ranked in three additional assays: (1) a galanin binding assay; (2) the GALR2 filtration binding assay described above; and (3) a plasmon surface resonance assay using the BIAcore instrument.

The galanin binding assay uses the ORIGEN technology (IGEN, Gaithersburg, Md.) and measures solution state binding. 0.75 μg/ml biotinylated galanin and 2 μg/ml ORI-TAG anti-mouse IgG were preincubated with serially diluted MAbs. 0.4 mg/ml streptavidin-coated Dyna beads were added, incubated, and read on an IGEN M8 Analyzer. In the plasmon surface resonance assay, biotinylated galanin was bound to a streptavidin-coated sensor chip and MAbs allowed to pass through the flow cells in order to generate on and off rates. In every assay tested, the MAbs ranked in virtually the same order.

The dissociation constants calculated from the BIAcore measurements are shown in Table 4, infra.

TABLE 4

| Rank | Clone | Isotype | $K_a$ ($e^9$) | $K_{d(e^{-10})}$ |
|---|---|---|---|---|
| 1 | 4B3 | IgG$_1$, k | 14 | 0.7 |
| 2 | 1D7 | IgG$_1$, k | 15 | 0.9 |
| 3 | 1G12 | IgG$_1$, k | 9.3 | 1.1 |
| 4 | 5B4 | IgG$_{2a}$, k | 7.5 | 1.3 |
| 5 | 2F8 | IgG$_1$, k | 6.8 | 1.5 |
| 6 | 2H9 | IgG$_1$, k | 6.7 | 1.5 |
| 7 | 1A1 | IgG$_1$, k | 2.5 | 4.0 |
| 8 | 4C10 | IgG$_1$, k | 0.6 | 18 |
| 9 | 2E11 | IgG$_1$, k | 0.5 | 21 |

Epitope mapping studies were performed using the monoclonal antibodies produced by the clones 5B4, 1G12, 2F8, 1D7, 4B3, 2H9 and 2E11. The MAbs produced by clones 5B4, 1G12, 2F8, 1D7, 4B3 and 2H9 were found to recognize an epitope near the C-terminus of galanin. In particular, the MAbs produced by these clones were found to recognize amino acid residues 21 through 27 of the mature, processed form of human and murine galanin. In contrast, the MAb produced by clone 2E11 was found to recognize an epitope in the center of the mature, processed form of human and murine galanin, in particular amino acid residues 10 through 15. Those MAbs that recognize an epitope near the C-terminus of galanin were consistently found to have a higher affinity for galanin than 2E11 or the commercially available anti-galanin antibodies, that do not bind to the C-terminus.

6.2 Inhibition of Tumorigenesis by Anti-Galanin Monoclonal Antibody

This example demonstrates the effectiveness of a high affinity, C-terminal binding monoclonal antibody in the reduction of the volume of a tumor in a murine model for human small cell lung carcinoma.

COLO-677 (DSMZ #ACC 248) is a human small cell lung carcinoma cell line with amplified and overexpressed galanin, GALR2, and GALR3 (3.1, 3.8, 3.0 and 7.4, 12, 92 respectively by QPCR normalized to levels observed in normal human bronchial epithelial cells). These cells were maintained in RPMI 1640 supplemented with 10% FBS, 100 iu/ml penicillin, 100 mg/mlstreptomycin, and 2 mM glutamine at 37° C., 5% $CO_2$, 95% humidity. Cultures were harvested by combining the non-adherent cell population with adherent cells detached using trypsin/EDTA into one tube, centrifuging, resuspending in medium, and passing cells through a 70 mM cell strainer (BD Falcon #352350). Cells were counted by hemacytometer, washed 1× with PBS (without $Ca^{2+}$ or $Mg^{2+}$), and resuspended in PBS to a final concentration of 25×10$^6$ cells/ml. 5×10$^6$ cells or 0.2 ml were injected per athymic nude mouse (Harlan #4814901) subcutaneous/interdermal. In one set of experiments, mice were injected with antibodies beginning at Day 0. In another set of experiments designed to test the ability of anti-galanin to block the growth of pre-existing tumors, mice were injected when tumor volumes reached 50-80 mm$^3$. Each mouse per group number received IP injections every other day containing either one of the following: 1) vehicle ([⅘ Glycine.Cl Buffer, pH 2.7+⅕ Sodium Phosphate Neutralizing Buffer, pH 8.0] plus 10% glycerol), 2) 200 µg mouse IgG (Zymed No. 02-6502 re-purified over Protein G Sepharose), or 3) 200 µg anti-Galanin monoclonal IgG, clone 5B4. Tumor volumes were routinely measured with a caliper in three dimensions and recorded. An approximate 60% reduction in tumor volume was observed in the 5B4 group compared to the vehicle and IgG controls in both the prophylactic and therapeutic treatments (FIG. 39).

6.3. Generation and Characterization of High Affinity Anti-Galanin Humanized Antibodies This example demonstrates a method for creating humanized anti-galanin antibodies.

6.3.1. Selection of Human Frameworks and CDR Grafting

In order to select human frameworks, the amino acid sequences of the variable domains of the 5B4 and 1D7 antibodies were used to form a TBLASTN query (Altschul, S. F. et al. 1990. J. Mol. Biol. 215:403-410) to search the human EST database (available at the National Center for Biotechnology information). Sequence alignments were produced using the software MacVector 7.0 (Oxford Molecular Group PLC., 2000). The EST DNA sequences predicted to encode a protein with the greatest amino acid identity to the 1D7 and 5B4 light and heavy variable regions were selected as human donor sequences with the following Genbank accession numbers: AW405977 for the 5B4 heavy variable sequence; AW406448 for the 5B4 light variable sequence; AW405772 for the 1D7 heavy variable sequence; and U00586 for the 1D7 light variable sequence.

To humanize the mouse 1D7 and 5B4 variable regions, the peptide sequence of the complimentarity determining regions (CDRs) of the mouse Fab fragments and of the donor human sequences were identified (Al-Lazikani, B. et al. 1997: J Mol Biol. 273:927-48). This information was used to create theoretical proteins for humanized versions of the 1D7 and 5B4 antibodies. To make DNA expression constructs for these humanized proteins, theoretical DNA coding sequences were created by replacing the DNA sequences encoding the CDR regions of the human donor sequences with the DNA sequences encoding the CDR regions of the 5B4 and 1D7 antibodies.

6.3.2. Generation of Humanized Fab Expression Constructs

To make a bacterial construct for expressing humanized Fab fragments, five independent DNA fragments were generated. Two of these fragments contained coding sequences for the humanized variable domain and were generated with synthetic oligonucleotides. One fragment contained coding sequences for the constant region for light (kappa) chain ($C_L$), and another contained coding sequences for IgG2 heavy chain constant region one ($C_H1$). The fifth fragment contained coding sequences for a PelB bacterial periplasmic localization signal. Generation of these five fragments is described below. Next, these fragments were linked together to create expression constructs identical to the constructs used for expressing mouse Fab fragments in bacteria except the mouse coding sequences were replaced with human or humanized coding sequences.

Humanized Variable Domain Construction

To generate DNA fragments containing the coding sequences of the humanized variable domains, oligonucleotides containing the sense and anti-sense DNA sequences were synthesized by Integrated DNA Technologies (Coralville, Iowa). These oligonucleotides, pre-dissolved at a concentration of 10 µM, were processed as follows. In a half-milliliter PCR tube, 5 µl of each sense and antisense oligo for each coding sequence (i.e., humanized 1D7 light variable region, humanized 1D7 heavy variable region, humanized 5B4 light variable region, or humanized 5B4 heavy variable region) were added except for oligonucleotides at the extreme 5' end of the sense and anti-sense positions. 10 µl of 10×T4 DNA Ligase buffer (New England Biolabs, Beverly, Mass.) and 5 to 10 µl of water were added to achieve a final volume of 95 µl. To add 5' phosphate groups to the oligonucleotides, 5 µl of T4 polynucleotide kinase (New England Biolabs) were added to each tube, and the resulting reactions were incubated at 37° C. for 30 to 60 min. The T4 polynucleotide kinase was then inactivated by incubating the reactions at 95° C. for five minutes. 5 µl of the oligonucleotides for the extreme 5' end of the sense and anti-sense strands were added to the appropriate reactions. To anneal the oligonucleotides, each reaction tube was incubated at 95° C. for five minutes, then 75° C. for five minutes, then was cooled at a rate of 1° C. per minute until a temperature of 25° C. was achieved. The annealed oligonucleotides were ligated to each other by addition of 21 µl of 10×T4 Ligase Buffer and 5 µl of T4 DNA ligase (New England Biolabs) and incubating the resulting reactions at room temperature for thirty minutes. The resulting annealed products were concentrated using a Qiaquick PCR purification kit (Qiagen, Valencia, Calif.) and were electrophoresed on a 1.5% agarose gel. The agarose gel was stained with ethidium bromide and illuminated with UV light. The annealed and ligated oligonucleotides formed a product approximately 320 base pairs in size; this product was excised from the agarose gel and was purified using a Qiaquick Gel Purification Kit (Qiagen) eluting in 30 µl of 10 mM Tris, pH 8.5.

To introduce restriction endonuclease sites for subcloning and to enrich for nick-free DNA fragments, polymerase chain reactions were performed using the ligation products as templates. Briefly, 100 µl PCR reactions were set up containing 1 µl of the purified ligation product, 1×Pfu Polymerase buffer (Stratagene, La Jolla, Calif.), 5 units of Pfu Polymerase (Stratagen), 0.2 mM dNTPs, and 1 µM of each of primers that specifically hybridize to the 5' and 3' ends of each ligation product. In addition, the PCR primers included DNA sequences that resulted from the introduction of restriction endonuclease sites at the end of the PCR products: sites for Sfi I and Nhe I were introduced, respectively, into the 5' and 3' ends of the heavy chain sense strand; and sites for Rsr II and Kpn I were introduced into the 5' and 3' ends of the light chain sense strand. Twenty cycles of PCR amplification were performed using the following temperature cycles: 1 minute at 95° C., 1 minute at 55° C., and 1 minute at 72° C. The resulting PCR products were purified by agarose gel electrophoresis as described above.

Pel B Linker Construction

Oligonucleotides synthesized for a pel B secretion signal and were dissolved at a concentration of 100 µM. A procedure identical to that used for annealing and ligating the humanized variable domain coding sequences was used to anneal and ligate these oligonucleotides with the following exceptions. Starting reactions for adding 5' phosphate groups to oligonucleotides contained 1 µl of each of oligonucleotides RApelB-S2, RApelB-S3, RApelB-A1, RApelB-A2, 5 µl of 10×T4 DNA ligase buffer, and 87 µl of water. After incubating at 95° C. to inactivate the T4 Polynucleotide kinase, 1 µl of oligonucleotides RApelB-S1 and RApelB-A3 were added. The resulting product was purified by agarose gel electrophoresis and was approximately 100 base pairs in size. The 5' end of the sense strand of this product contained a DNA site recognized by the Asc I restriction endonuclease and the 3' end of the sense strand of this product incorporated a restriction site for the Rsr II restriction endonuclease.

Amplification of Coding Sequences of Human Constant Regions

Coding sequences for the constant region of the human light (kappa) chain ($C_L$) and the constant region 1 of human IgG2 heavy chain ($C_H1$) were amplified from a Marathon-Ready Human Spleen cDNA (BD Biosciences Clontech, Palo Alto, Calif.) using the polymerase chain reaction. The primers designed for these PCR reactions introduce DNA sites recognized by restriction endonucleases Nhe I and Asc I, respectively, for the 5' and 3' ends of the $C_H1$ fragment; and Kpn I and Not I, respectively, for the 5' and 3' ends of the $C_L$ fragment. The primers also introduced a stop codon at the 3' end of the $C_H1$ fragment but not the $C_L$ fragment. Briefly, PCR reactions contained 5 µl of cDNA, 1 µl of each of 5' and 3' primers, 36 µl of water, one µl of 10 mM dNTPs, 5 µl of 10×PCR Advatage2 Buffer (BD Biosciences Clontech), and 1 µl of Advatage2 Polymerase mix (BD Biosciences Clontech). Thirty-five cycles of PCR amplification were performed using the following temperature cycles: 1 minute at 95° C., 1 minute at 57° C., and 1 minute at 72° C. PCR reactions were loaded directly onto a 1.5% agarose gel, visualized by ethidium bromide staining and UV light illumination, and excised from the agarose gel. The excised products were purified from the agarose using a Qiaquick gel purification kit (Qiagen).

Creation of a Fab Expression Cassette

A series of PCR reactions were performed to create a DNA cassette that consisted of, in order from 5' to 3' end of the sense strand sequences, the humanized heavy variable regions, the CH1 region of IgG2, the pel B leader coding sequence, the humanized light variable regions, and the $C_L$ region. The resulting cassette was subcloned into the pBADSfiNot expression vector.

The first PCR reaction joined the heavy variable fragments to the heavy constant region and the pel B fragment. Briefly, 100 µl PCR reactions were set up containing 1 µl of the heavy variable region PCR product for humanized 5B4 or humanized 1D7, 1 µl of the CH1 fragment, 1 µl of the pel B ligation product, 1×Pfu Polymerase buffer (Stratagene, La Jolla, Calif.), 5 units of Pfu Polymerase (Stratagene), 0.2 mM dNTPs, 1 µM of primer recognizing the 5' end of the humanized 5B4 or 1D7 variable region (5'hG12H or 5'h1D7H), and 1 µM oligonucleotide RApelB-A3. Twenty-one cycles of PCR amplification were performed using the following temperature cycles: 1 minute at 95° C., 1 minute at 53° C., and 1 minute at 72° C. The joining of the fragments during PCR was mediated by 18 bases of sequence identity between the 5' end of the $C_H1$ fragment and the 3' of the heavy variable PCR products for both humanized 1D7 and 5B4 and by 14 bases of sequence identity between the 3' end of the $C_H1$ fragment and the 5' end of the pel B ligation product. A PCR product was produced that was consistent with the predicted size of 753 base pairs: this product was purified by agarose gel electrophoresis and extracted from the agarose gel using a Qiaquick purification kit (Qiagen).

A second PCR reaction was performed to join the humanized light variable regions to the $C_L$ fragment. Reactions were performed as described above except the 5' primers used were 5'h1D7Lv2 and 5' h5B4Lv3, oligonucleotide 3'G12LC1 was used as a 3' primer, and DNA fragments included in the reaction were 1 µl of humanized light variable region and 1 µl of $C_L$ fragment. Joining of the DNA fragments during PCR was mediated between first 21 bases pairs of sequence identity shared between the 5' end of the $C_L$ fragment and the 3' end of the light variable PCR product. A PCR product was produced that was consistent with the predicted size of 681 base pairs; this product was purified by agarose gel electrophoresis and extracted from the agarose gel using a Qiaquick purification kit (Qiagen).

A third PCR reaction joined together the heavy variable-$C_H1$-pel B PCR products with the light variable-$C_L$ PCR products. This PCR reaction was performed as described above except the 5' primers used were 5'h1D7H and 5'h5B4H (as appropriate), and oligonucleotide 3'G12LC1 was used as a 3' primer. Nineteen base pairs of sequence identity existed between the 3' end first round PCR product (i.e., the 3' end of the pel B sequence) and the 5' end of the second round PCR product (i.e., the 5' end of the light variable product), allowing these two products to prime off of each other and allowing a full-length expression cassette to be generated. Agarose gel electrophoresis showed that a PCR product was formed consistent with the predicted size of 1422 base pairs. This PCR product was excised from the agarose gel and purified using a Qiaquick purification kit. As described above, the resulting PCR product was digested with the Sfi I and Not I restriction endonucleases and was ligated into the pBADSfiNot vector digested with the same enzymes.

Expression of humanized Fab fragments in bacteria and preparation of periplasmic extracts were performed as described previously for the bacterial expression of mouse Fab fragments (Example 1.1). The periplasmic extracts containing the humanized Fabs were tested in the galanin ELISA assay. The humanized Fabs were inactive in this assay, indicating that grafting of the mouse CDRs onto a human framework was not sufficient to create a humanized antibody with anti-galanin binding activity and that amino acids outside of the CDR regions would probably need to be changed from human to mouse to create active Fab fragments.

6.3.4. Structural Comparison of Mouse and Humanized Fab Fragments

To optimize humanized antibodies, crystal structures were obtained for the Fab fragments of the murine antibodies 5B4, 4B3 and 1D7. Mouse hybridoma protein was isolated by Protein G chromatography and cleaved in vitro using the protease papain, resulting in the production of Fab and fragments. The Fc fragments were removed by Protein A chromatography, and the Fab fragments were purified by ion exchange chromatography using a Mono Q column. Crystal structures were obtained for unliganded Fab protein and for Fab protein complexed with a peptide of the 14 C-terminal amino acids of human galanin that was made on a peptide synthesizer. In addition to the CDRs on the VH and VL domains of murine antibodies, other amino acids in these domains appear to be important for maintaining the galanin-binding affinity of the antibody. Thus, additional mutations to the VH and VL domains of the humanized antibody 5B4 were necessary in order to regain the highest level of affinity for human galanin. Similar mutations would be required for other humanized antibodies that are generated by grafting the murine CDRs of the VH and VL domains of 5B4, 1G12, 2F8, 1D7, 4B3, 2H9, 1A1 or 2E11 onto an appropriate human antibody.

The non-CDR residues of the VH and VL domains that are essential for human galanin-binding activity but may not be present on the humanized antibody, include, but are not limited to the following positions: VH-48, VH-68, VH-77, VH-81, VH-98, VL-41, VL-42, and VL-51. Below are examples of representative substitutions at these positions:

VH-48I. The side-chain of VH-48I makes hydrophobic contacts to the side-chains of VH-64, VH-68 and VH-81.

VH-68A. The side-chain of VH-68A makes hydrophobic contacts to the side-chains of VH-48, VH-81 and VH-83.

VH-77N. VH-77N stabilizes the positioning of CDR1 on the VH domain by making two hydrogen bonds to it. The amide nitrogen of the residue side-chain makes a hydrogen bond to the carbonyl oxygen of VH-27F and the oxygen of the residue side-chain makes a hydrogen bond to the main-chain amide nitrogen of VH-29I.

VH-81L. The side-chain of VH-81L makes hydrophobic contacts to the side-chains of VH-36W and VH-83L.

VH-98R. One of the terminal amino groups of the residue side-chain makes a water-mediated hydrogen bond to the main-chain carbonyl oxygen of human galanin Gly27.

VL-41Y. VL-41Y stabilizes the positioning of CDR3 on the VH domain by making a hydrogen bond to it. The phenolic hydroxyl of VL-41Y makes a hydrogen bond to the main-chain carbonyl oxygen of VH-100Y.

VL-42L. The side-chain of VL-42L makes hydrophobic contacts to the side-chains of VL-52L and VL-91Y.

VL-51L. The side-chain of VL-51L makes hydrophobic contacts to the side-chains of VL-41Y and VL-60F.

6.3.5. Creation of a Library of Humanized Variable Region Coding Sequences with Back Mutations Using standard molecular biology techniques, a library of humanized 5B4 expression constructs was designed targeting the 8 non-CDR residues that, based on the crystal structure of mouse antibody, might be critical for activity of the humanized antibody. The library was designed to contain all 256 possible combinations of human or mouse residues for these 8 amino acid positions. To construct the library, three oligonucleotide pairs were ordered with degenerate nucleotides in the codons corresponding to selected 8 amino acids, and allowed for either a mouse or human amino acid to be expressed at each of these eight codons. Each oligo nucleotide pair contained approximately 20 base pairs of complementarity. These oligonucleotides were subcloned into pBAD_zu5B4_v02, the DNA construct for expression of 5B4 Fab in bacteria. For this subcloning, each oligonucleotide was first annealed to its partner (Hu5B4_Mu1a to Hu5B4_Mu1b; Hu5B4_Mu2a to Hu5B4_Mu2b; and Hu5B4_Mu3a to Hu5B4_Mu3b). Each annealed oligonucleotide pair contained approximately 20 base pairs of complementarity, and each pair was extended with Taq DNA polymerase in the presence of dNTPs to create double stranded DNA fragments termed Mu1, Mu2, and Mu3. Fragment Mu1 was digested with the restriction endonucleases PpuM and Pst I and was ligated to pBAD_zu5B4 digested with the same enzymes. Fragment Mu2 was digested with restriction endonucleases Sac II and Sal I and was ligated into pBAD_zu5B4 digested with the same enzymes. Fragment Mu3 was digested with restriction endonucleases Sac II and Dra III and was ligated into pBAD_zu5B4 digested with the same enzymes. Each ligation reaction was transformed into competent TOP10 E. coli (Invitrogen Inc.) and was plated onto LB-amp plates. The next day, all of the colonies from each transformation were scraped off the plates, and DNA was isolated from these colonies using a miniprep kit (Qiagen Inc), to create three DNA libraries. To combine the three Mu 1, Mu2, and Mu3 fragments, fragments from the Mu2 and Mu3 libraries were Mu1 DNA library. This combination was effected by digesting the Mu1 library with the restriction enzymes Sal I and Dra III followed by treatment with calf intestinal alkaline phosphatase and gel purification of the 5304 base pair vector DNA fragment. The Mu2 and Mu3 libraries were, respectively digested with Dra III and Sac II or Sac II and Sal I, and the respective 107 base pair and 86 base pair fragments were gel purified. A 3-way ligation was set up to ligate the Mu2 and Mu3 library fragments into the Mu1 library vector. These resulting colonies were screened for production of functional Fab fragments as described below.

6.3.6. Screening Active Backmutated Humanized 5B4 Fab Fragments

Colonies from the library created by the ligation of the Mu1, Mu2, and Mu3 fragments were individually tested for their ability to make Fab fragments with galanin binding activity. Expression of humanized Fab fragments in bacteria and preparation of periplasmic extracts in 96 well plates was performed as described above. The periplasmic extracts containing the humanized Fabs were tested in the galanin ELISA assay as described above. A total of 288 colonies were grown and tested in this assay. DNA sequences were obtained for the 57 Fab coding sequences that produced weak to strong ELISA signals. Thirty clones were selected at random for DNA sequencing to determine the frequency at which each mouse residue was present in the library. The results of this work indicated that backmutation of three residues, H77, H98, and L41, was significant in restoring activity to the humanized antibody. In addition, other residues may be important.

6.3.7. Mammalian Expression of Humanized 5B4 Variants as Human IgG1 and their Affinity Characterization Using BIAcore In terms of ELISA signal, the top 17 Fab fragments consisted of various combinations of three light chains and five heavy chains. For example, the heavy variable region of Fab P1A7 was identical to the heavy variable regions of Fabs R2E9 and R2E8. The five heavy variable regions were amplified by PCR and the PCR products were subcloned into a human IgG1 heavy chain mammalian expression vector, pVE414N. The three light variable region products were amplified by PCR and were subcloned into a human kappa light chain mammalian expression vector, pDC414N. The sequences of the heavy and light chains constructs were confirmed by DNA sequencing. Fab fragment P1A7 yielded the strongest ELISA signal. To determine which heavy or light variable regions might yield the highest affinity antibody, each heavy chain was co-expressed with the P1A7 light chain, and each light chain was co-expressed with the P1A7 heavy chain. These IgG heavy and light chain combinations were expressed in E5 cells and were purified from the cell culture medium using protein A affinity chromatography. Affinities of these purified antibodies were measured on a BIAcore 3000. Goat anti-human IgG Fc antibody immobilized on CM5 sensor chips was used to capture P1A7 and the variants. Human galanin peptide was flowed over the chip surface with captured anti galanin antibody. The binding kinetics was analyzed using the model fit of 1:1 Langmuir+local Rmax+Mass Transfer. Pairing P1A7 light chain with three different heavy chains revealed that the P1A7 heavy chain yields the highest affinity antibody compared to the other two light chains (Table 5). Antibodies with P1A7 light chain paired with the five different heavy chains yield nearly identical dissociation constants.

TABLE 5

Galanin Binding Characteristics Of Humanized Antibodies Expressed In Mammalian Cells

| Light Chain | Heavy Chain | ka (1/M) | kd (1/s) | $K_D$ (nM) |
|---|---|---|---|---|
| zu5B4 v04 | zu5B4 v04 | 3.30E+06 | 5.90E−03 | 1.8 |
| zu5B4 v04 | zu5B4 v06 | 3.20E+06 | 5.10E−03 | 1.6 |
| zu5B4 v04 | zu5B4 v12 | 3.20E+06 | 4.80E−03 | 1.5 |
| zu5B4 v04 | zu5B4 v13 | 2.80E+06 | 5.00E−03 | 1.8 |
| zu5B4 v04 | zu5B4 v11 | 3.20E+06 | 5.60E−03 | 1.7 |
| zu5B4 v13 | zu5B4 v04 | 3.50E+06 | 7.00E−03 | 2.0 |
| zu5B4 v05 | zu5B4 v04 | 4.20E+06 | 9.50E−03 | 2.3 |

7. DEPOSIT INFORMATION

The murine hybridomas listed below were deposited with the American Type Culture Collection (ATCC), 10801 University Blvd., Manassas, Va. 20110, under the provisions of the Budapest Treaty on the International Recognition of the Deposit of Microorganisms for the Purposes of Patent Procedure, and compliance with the criteria set forth in 37 C.F.R. § 1.801-1.809 regarding availability and permanency of deposits. The deposits were made on the date indicated and assigned the indicated accession number:

| Deposit | Accession Number | Date |
|---|---|---|
| 1D7D1 | PTA-5650 | Nov. 21, 2003 |
| 5B4C1 | PTA-5651 | Nov. 21, 2003 |

8. EQUIVALENTS

Those skilled in the art will recognize, or be able to ascertain using no more than routine experimentation, many equivalents to the specific aspects of the invention described herein. Such equivalents are intended to be encompassed by the following claims.

All publications, patents and patent applications mentioned in this specification are herein incorporated by reference into the specification to the same extent as if each individual publication, patent or patent application was specifically and individually indicated to be incorporated herein by reference.

What is claimed is:

1. An isolated antibody that immunospecifically binds to an epitope comprising amino acid residues 21 through 27 of SEQ ID NO:150 with a $k_a$ of at least $1 \times 10^8$ $M^{-1}$, wherein the antibody comprises a variable heavy (VH) domain having the amino acid sequence of a VH domain of the murine antibody 5B4, 1G12, 2F8, 1D7, 4B3, 2H9 or 1A1, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13.

2. An isolated antibody that immunospecifically binds to an epitope comprising amino acid residues 21 through 27 of SEQ ID NO:150 with a $k_a$ of at least $1 \times 10^8$ $M^{-1}$, wherein the antibody comprises a variable light (VL) domain having the amino acid sequence of a VL domain of the murine antibody 5B4, 1G12, 2F8, 1D7, 4B3, 2H9 or 1A1, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13.

3. The antibody of claim 1, wherein the antibody further comprises a VL domain having the amino acid sequence of a VL domain of the murine antibody 5B4, 1G12, 2F8, 1D7, 4B3, 2H9 or 1A1, respectively, or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13, respectively.

4. An isolated antibody that immunospecifically binds to an epitope comprising amino acid residues 21 through 27 of SEQ ID NO:150 with a $k_a$ of at least $1 \times 10^8$ $M^{-1}$, wherein the antibody competes with the murine antibody produced by the murine hybridoma clone 5B4C1 (ATCC Accession No. PTA-5651) or 1D7D1 (ATCC Accession No. PTA-5650), or the humanized antibody 5B4-v2, 5B4-v4, 5B4-v5, 5B4-v6, 5B4-v7, 5B4-v8, 5B4-v9, 5B4-v10, 5B4-v11, 5B4-v12, or 5B4-v13 for binding to the epitope.

5. An isolated antibody comprising a VH domain having the amino acid sequence of the VH domain of the murine antibody 5B4, 1G12, 2F8, 1D7, 4B3, 2H9, or 1A1, or the humanized antibody 5B4-v2, 5B4-v4, 5B4-v5, 5B4-v6, 5B4-V7, 5B4-v8, 5B4v9, 5B4-v10, 5B4-v11, 5B4-v12, or 5B4-v13, wherein said antibody immunospecifically binds to an epitope comprising amino acid residues 21 through 27 of SEQ ID NO:150.

6. An isolated antibody comprising a VL domain having the amino acid sequence of the VL domain of the murine antibody 5B4, 1G12, 2F8, 1D7, 4B3, 2H9, or 1A1, or the humanized antibody 5B4-v2, 5B4-v4, 5B4v5, 5B4-v6, 5B4-v7, 5B4-v8, 5B4-v9, 5B4-v10, 5B4-v11, 5B4-v12, or 5B4-v13, wherein said antibody immunospecifically binds to an epitope comprising amino acid residues 21 through 27 of SEQ ID NO:150.

7. An isolated antibody that immunospecifically binds to SEQ ID NO:150, wherein the antibody comprises:
  (a) a VH domain having the amino acid sequence of the VH domain of the murine antibody 5B4 and a VL domain having the amino acid sequence of the VL domain of the murine antibody 5B4;
  (b) a VH domain having the amino acid sequence of the VH domain of the murine antibody 1G2 and a VL domain having the amino acid sequence of the VL domain of the murine antibody 1G2;
  (c) a VH domain having the amino acid sequence of the VH domain of the murine antibody 2F8 and a VL domain having the amino acid sequence of the VL domain of the murine antibody 2F8;
  (d) a VH domain having the amino acid sequence of the VH domain of the murine antibody 1D7 and a VL domain having the amino acid sequence of the VL domain of the murine antibody 1D7;
  (e) a VH domain having the amino acid sequence of the VH domain of the murine antibody 4B3 and a VL domain having the amino acid sequence of the VL domain of the murine antibody 4B3;
(f) a VH domain having the amino acid sequence of the VH domain of the murine antibody 2H9 and a VL domain having the amino acid sequence of the VL domain of the murine antibody 2H9;
(g) a VH domain having the amino acid sequence of the VH domain of the murine antibody 1A2 and a VL domain having the amino acid sequence of the VL domain of the murine antibody 1A2;
(h) a VH domain having the amino acid sequence of the VH domain of the humanized antibody 5B4-V2 and a VL domain having the amino acid sequence of the VL domain of the humanized antibody 5B4-V2;
(i) a VH domain having the amino acid sequence of the VH domain of the humanized antibody 5B4-V4 and a VL domain having the amino acid sequence of the VL domain of the humanized antibody 5B4-V4;
(j) a VH domain having the amino acid sequence of the VH domain of the humanized antibody 5B4-V5 and a VL domain having the amino acid sequence of the VL domain of the humanized antibody 5B4-V5;
(k) a VH domain having the amino acid sequence of the VH domain of the humanized antibody 5B4-V6 and a VL domain having the amino acid sequence of the VL domain of the humanized antibody 5B4-V6;
(l) a VH domain having the amino acid sequence of the VH domain of the humanized antibody 5B4-V7 and a VL domain having the amino acid sequence of the VL domain of the humanized antibody 5B4-V7;
(m) a VH domain having the amino acid sequence of the VH domain of the humanized antibody 5B4-V8 and a VL domain having the amino acid sequence of the VL domain of the humanized antibody 5B4-V8;
(n) a VH domain having the amino acid sequence of the VH domain of the humanized antibody 5B4-V9 and a VL domain having the amino acid sequence of the VL domain of the humanized antibody 5B4-V9;
(o) a VH domain having the amino acid sequence of the VH domain of the humanized antibody 5B4-V10 and a VL domain having the amino acid sequence of the VL domain of the humanized antibody 5B4-V10;
(p) a VH domain having the amino acid sequence of the VH domain of the humanized antibody 5B4-V11 and a VL domain having the amino acid sequence of the VL domain of the humanized antibody 5B4-V11;
(q) a VH domain having the amino acid sequence of the VH domain of the humanized antibody 5B4-V12 and a VL domain having the amino acid sequence of the VL domain of the humanized antibody 5B4-V12; or
(r) a VH domain having the amino acid sequence of the VH domain of the humanized antibody 5B4-V13 and a VL domain having the amino acid sequence of the VL domain of the humanized antibody 5B4-V13.

8. The antibody of claim 5 or 6, wherein the antibody is selected from the group consisting of:
(a) a monoclonal antibody;
(b) a human antibody;
(c) a humanized antibody;
(d) a Fab fragment; and
(e) a single chain antibody.

9. A monoclonal antibody produced by hybridoma clone 1D7D1 (ATCC Accession No.: PTA-5650) or hybridoma clone 5B4C1 (ATCC Accession No.: PTA-5651).

10. Hybridoma clone 1D7D1 (ATCC Accession No.: PTA-5650).

11. Hybridoma clone 5B4C1 (ATCC Accession No.: PTA-5651).

12. An isolated antibody that competes with the monoclonal antibody produced by hybridoma clone 1D7D1 (ATCC Accession No.: PTA-5650) or hybridoma clone 5B4C1 (ATCC Accession No.: PTA-5651) for epitope binding.

13. The antibody of claim 12, wherein the antibody is selected from the group consisting of:
(a) a monoclonal antibody;
(b) a human antibody;
(c) a humanized antibody;
(d) a Fab fragment; and
(e) a single chain antibody.

14. A pharmaceutical composition comprising the antibody of claim 7, 9 or 12, and a pharmaceutically acceptable carrier.

15. A pharmaceutical composition comprising the antibody of claim 5 or 6 and a pharmaceutically acceptable carrier.

16. A kit comprising the antibody of claim 7, 9 or 12, in one or more containers.

17. An isolated antibody that immunospecifically binds to an epitope comprising amino acid residues 21 through 27 of SEQ ID NO:150, wherein the antibody comprises:
(a) a VH CDR1, a VH CDR2, a VH CDR3, VL CDR1, a VL CDR2 and a VL CDR3 having the amino acid sequences of the VH CDR1, VH CDR2, VH CDR3, VL CDR1, VL CDR2, and VL CDR3 of the murine antibody 5B4;
(b) a VH CDR1, a VH CDR2, a VH CDR3, a VL CDR1, a VL CDR2 and a VL CDR3 having the amino acid sequences of the VH CDR1, VH CDR2, VH CDR3, VL CDR1, VL CDR2, and VL CDR3 of the murine antibody 1G12;
(c) a VH CDR1, a VH CDR2, a VH CDR3, a VL CDR1, a VL CDR2 and a VL CDR3 having the amino acid sequences of the VH CDR1, VH CDR2, VH CDR3, VL CDR1, VL CDR2, and VL CDR3 of the murine antibody 2F8;
(d) a VH CDR1, a VH CDR2, a VH CDR3, a VL CDR1, a VL CDR2 and a VL CDR3 having the amino acid sequences of the VH CDR1, VH CDR2, VH CDR3, VL CDR1, VL CDR2, and VL CDR3 of the murine antibody 1D7;
(e) a VH CDR1, a VH CDR2, a VH CDR3, a VL CDR1, a VL CDR2 and a VL CDR3 having the amino acid sequences of the VH CDR1, VH CDR2, VH CDR3, VL CDR1, VL CDR2, and VL CDR3 of the murine antibody 4B3;
(f) a VH CDR1, a VH CDR2, a VH CDR3, a VL CDR1, a VL CDR2 and a VL CDR3 having the amino acid sequences of the VH CDR1, VH CDR2, VH CDR3, VL CDR1, VL CDR2, and VL CDR3 of the murine antibody 2H9; or
(g) a VH CDR1, a VH CDR2, a VH CDR3, a VL CDR1, a VL CDR2 and a VL CDR3 having the amino acid sequences of the VH CDR1, VH CDR2, VH CDR3, VL CDR1, VL CDR2, and VL CDR3 of the murine antibody 1A1.

18. An isolated antibody that immunospecifically binds to SEQ ID NO:150, wherein the antibody comprises:
(a) a VH CDR1, a VH CDR2, a VH CDR3, VL CDR1, a VL CDR2 and a VL CDR3 having the amino acid sequences of the VH CDR1, VH CDR2, VH CDR3, VL CDR1, VL CDR2, and VL CDR3 of the murine antibody 5B4;

(b) a VH CDR1, a VH CDR2, a VH CDR1, a VL CDR1, a VL CDR2 and a VL CDR3 having the amino acid sequences of the VH CDR1, VH CDR2, VH CDR3, VL CDR1, VL CDR2, and VL CDR3 of the murine antibody 1G12;

(c) a VH CDR1, a VH CDR2, a VH CDR3, a VL CDR1, a VL CDR2 and a VL CDR3 having the amino acid sequences of the VH CDR1, VH CDR2, VH CDR3, VL CDR1, VL CDR2, and VL CDR3 of the murine antibody 2F8;

(d) a VH CDR1, a VH CDR2, a VH CDR3, a VL CDR1, a VL CDR2 and a VL CDR3 having the amino acid sequences of the VH CDR1, VH CDR2, VH CDR3, VL CDR1, VL CDR2, and VL CDR3 of the murine antibody 1D7;

(e) a VH CDR1, a VH CDR2, a VH CDR3, a VL CDR1, a VL CDR2 and a VL CDR3 having the amino acid sequences of the VH CDR1, VH CDR2, VH CDR3, VL CDR1, VL CDR2, and VL CDR3 of the murine antibody 4B3;

(f) a VH CDR1, a VH CDR2, a VH CDR3, a VL CDR1, a VL CDR2 and a VL CDR3 having the amino acid sequences of the VH CDR1, VH CDR2, VH CDR3, VL CDR1, VL CDR2, and VL CDR3 of the murine antibody 2H9; or (g) a VH CDR1, a VH CDR2, a VH CDR3, a VL CDR1, a VL CDR2 and a VL CDR3 having the amino acid sequences of the VH CDR1, VH CDR2, VH CDR3, VL CDR1, VL CDR2, and VL CDR3 of the murine antibody 1A1.

19. An isolated antibody that immunospecifically binds to an epitope within amino acid residues 1 to 15 of SEQ ID NO:150, wherein the antibody comprises:

(a) a VH domain having the amino acid sequence of the VH domain of the murine antibody 2E11;

(b) a VL domain having the amino acid sequence of the VL domain of the murine antibody 2E11;

(c) a VH domain having the amino acid sequence of the VH domain of the murine antibody 2E11 and a VL domain having the amino acid sequence of the VL domain of the murine antibody 2E11; or (d) a VH CDR1, a VH CDR2, a VH CDR3, a VL CDR1, a VL CDR2, and a VL CDR3 having the amino acid sequence of the VH CDR1, VH CDR2, VH CDR3, VL CDR1, VL CDR2, and VL CDR3 of the murine antibody 2E11.

20. The antibody of claim 7, 9, 12, 18 or 19, wherein the antibody is conjugated to a detectable agent or a therapeutic moiety.

21. A pharmaceutical composition comprising the antibody of claim 18 or 19, and a pharmaceutically acceptable carrier.

22. A kit comprising the antibody of claim 18 or 19, in one or more containers.

23. The antibody of claim 7, 18 or 19, wherein the antibody is selected from the group consisting of:

(a) a monoclonal antibody;

(b) a human antibody;

(c) a humanized antibody;

(d) a Fab fragment; and (e) a single chain antibody.

24. The antibody of claim 5, or 6, wherein the antibody is conjugated to a detectable agent or a therapeutic moiety.

25. A kit comprising the antibody of claim 5, or 6, in one or more containers.

\* \* \* \* \*

UNITED STATES PATENT AND TRADEMARK OFFICE
CERTIFICATE OF CORRECTION

PATENT NO.       : 7,371,381 B2                                        Page 1 of 1
APPLICATION NO.  : 11/009443
DATED            : May 13, 2008
INVENTOR(S)      : Wade Aaron et al.

It is certified that error appears in the above-identified patent and that said Letters Patent is hereby corrected as shown below:

Title page item 75 under the inventors change "Anthony J. Slavin, Redwood City, CA (US)" to --Anthony J. Slavin, Redwood City, CA (AU)--

Signed and Sealed this

Twenty-sixth Day of August, 2008

JON W. DUDAS
*Director of the United States Patent and Trademark Office*

SEQUENCE LISTING

<160> NUMBER OF SEQ ID NOS: 149

<210> SEQ ID NO 1
<211> LENGTH: 10
<212> TYPE: PRT
<213> ORGANISM: Mus musculus

<400> SEQUENCE: 1

Gly Phe Asn Ile Glu Asp Tyr Tyr Met His
1               5                   10

```
<210> SEQ ID NO 2
<211> LENGTH: 10
<212> TYPE: PRT
<213> ORGANISM: Mus musculus

<400> SEQUENCE: 2

Arg Ile Asp Pro Glu Asn Gly Asn Thr Ile
1               5                   10

<210> SEQ ID NO 3
<211> LENGTH: 4
<212> TYPE: PRT
<213> ORGANISM: Mus musculus

<400> SEQUENCE: 3

Gly Tyr Val Asp
1

<210> SEQ ID NO 4
<211> LENGTH: 16
<212> TYPE: PRT
<213> ORGANISM: Mus musculus

<400> SEQUENCE: 4

Arg Ser Ser Gln Ser Ile Val His Ser Asp Gly Asp Thr Tyr Leu Glu
1               5                   10                  15

<210> SEQ ID NO 5
<211> LENGTH: 7
<212> TYPE: PRT
<213> ORGANISM: Mus musculus

<400> SEQUENCE: 5

Lys Val Ser Asn Arg Phe Ser
1               5

<210> SEQ ID NO 6
<211> LENGTH: 9
<212> TYPE: PRT
<213> ORGANISM: Mus musculus

<400> SEQUENCE: 6

Phe Gln Gly Ser His Val Pro Tyr Thr
1               5

<210> SEQ ID NO 7
<211> LENGTH: 10
<212> TYPE: PRT
<213> ORGANISM: Mus musculus

<400> SEQUENCE: 7

Gly Phe Asn Ile Lys Asp Tyr Tyr Ile His
1               5                   10

<210> SEQ ID NO 8
<211> LENGTH: 10
<212> TYPE: PRT
<213> ORGANISM: Mus musculus

<400> SEQUENCE: 8

Arg Ile Asp Pro Glu Asp Gly Glu Ile Glu
1               5                   10
```

```
<210> SEQ ID NO 9
<211> LENGTH: 4
<212> TYPE: PRT
<213> ORGANISM: Mus musculus

<400> SEQUENCE: 9

Gly Tyr Ala Ser
1

<210> SEQ ID NO 10
<211> LENGTH: 16
<212> TYPE: PRT
<213> ORGANISM: Mus musculus

<400> SEQUENCE: 10

Arg Ser Ser Gln Thr Phe Val His Ser Asp Gly Asn Thr Tyr Leu Glu
1               5                   10                  15

<210> SEQ ID NO 11
<211> LENGTH: 10
<212> TYPE: PRT
<213> ORGANISM: Mus musculus

<400> SEQUENCE: 11

Gly Phe Asn Ile Glu Asp Tyr Tyr Ile His
1               5                   10

<210> SEQ ID NO 12
<211> LENGTH: 10
<212> TYPE: PRT
<213> ORGANISM: Mus musculus

<400> SEQUENCE: 12

Arg Ile Asp Pro Glu Asp Gly Glu Thr Glu
1               5                   10

<210> SEQ ID NO 13
<211> LENGTH: 16
<212> TYPE: PRT
<213> ORGANISM: Mus musculus

<400> SEQUENCE: 13

Arg Ser Ser Gln Ser Phe Val His Ser Asp Gly Asn Thr Tyr Leu Glu
1               5                   10                  15

<210> SEQ ID NO 14
<211> LENGTH: 10
<212> TYPE: PRT
<213> ORGANISM: Mus musculus

<400> SEQUENCE: 14

Arg Ile Asp Pro Glu Asp Gly Glu Thr Glu
1               5                   10

<210> SEQ ID NO 15
<211> LENGTH: 10
<212> TYPE: PRT
<213> ORGANISM: Mus musculus

<400> SEQUENCE: 15

Gly Phe Asn Ile Lys Asp Tyr Tyr Met His
1               5                   10

<210> SEQ ID NO 16
<211> LENGTH: 10
```

```
<212> TYPE: PRT
<213> ORGANISM: Mus musculus

<400> SEQUENCE: 16

Arg Ile Asp Pro Glu Asn Asp Asn Ser Ile
1               5                   10

<210> SEQ ID NO 17
<211> LENGTH: 7
<212> TYPE: PRT
<213> ORGANISM: Mus musculus

<400> SEQUENCE: 17

Lys Val Ser Asn Arg Phe Ser
1               5

<210> SEQ ID NO 18
<211> LENGTH: 113
<212> TYPE: PRT
<213> ORGANISM: Mus musculus

<400> SEQUENCE: 18

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Glu Asp Tyr
                20                  25                  30

Tyr Met His Trp Val Arg Gln Arg Pro Glu Gln Gly Leu Glu Trp Ile
            35                  40                  45

Gly Arg Ile Asp Pro Glu Asn Gly Asn Thr Ile Tyr Asp Pro Lys Phe
        50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Val Arg Gly Tyr Val Asp Trp Gly Gln Gly Thr Leu Val Thr Val Ser
                100                 105                 110

Ala

<210> SEQ ID NO 19
<211> LENGTH: 114
<212> TYPE: PRT
<213> ORGANISM: Mus musculus

<400> SEQUENCE: 19

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asp Gly Asp Thr Tyr Leu Glu Trp Tyr Leu Gln Lys Ala Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Leu Tyr Tyr Cys Phe Gln Gly
                85                  90                  95

Ser His Val Pro Tyr Thr Phe Gly Gly Gly Thr Lys Leu Glu Ile Lys
                100                 105                 110
```

Arg Ala

<210> SEQ ID NO 20
<211> LENGTH: 339
<212> TYPE: DNA
<213> ORGANISM: Mus musculus

<400> SEQUENCE: 20

```
gaagttcagt tgcagcagtc tggggctgag cttgtgaggc caggggcctt agtcaagttg      60
tcctgcaaag cttctggctt caacattgaa gactactata tgcactgggt gaggcagagg     120
cctgaagagg gcctggagtg gattggaagg attgatcctg agaatggtaa tactatatat     180
gacccgaagt tccagggcaa ggccagtata acagcagaca catcctccaa cacagcctac     240
ctgcagctca gcagcctgac atctgaggac actgccgtct attactgtgt tagagggtat     300
gttgactggg gccaagggac tctggtcact gtctctgca                            339
```

<210> SEQ ID NO 21
<211> LENGTH: 30
<212> TYPE: DNA
<213> ORGANISM: Mus musculus

<400> SEQUENCE: 21

```
ggattcaaca tcgaggacta ctacatgcac                                       30
```

<210> SEQ ID NO 22
<211> LENGTH: 30
<212> TYPE: DNA
<213> ORGANISM: Mus musculus

<400> SEQUENCE: 22

```
cgtatcgatc ctgaaaatgg taatacaatc                                       30
```

<210> SEQ ID NO 23
<211> LENGTH: 12
<212> TYPE: DNA
<213> ORGANISM: Mus musculus

<400> SEQUENCE: 23

```
ggatatgtcg ac                                                          12
```

<210> SEQ ID NO 24
<211> LENGTH: 343
<212> TYPE: DNA
<213> ORGANISM: Mus musculus

<400> SEQUENCE: 24

```
gatgttttga tgacccagac tccactctcc ctgcctgtca gtcttggaga tcaagcctcc      60
atctcttgca gatctagtca gagcattgta catagtgatg agacaccta ttttagaatg      120
gtacctgcag aaagcaggcc agtctcctaa gctcctgatc tacaaagttt ccaaccgatt     180
ttctggggtc ccagacaggt tcagtggcag tggatcaggg acagatttca cactcaagat     240
cagcagagtg gaggctgagg atctgggact ttattactgc tttcaaggtt cacatgttcc     300
gtacacgttc ggaggggga ccaagctgga aataaaacgg gct                        343
```

<210> SEQ ID NO 25
<211> LENGTH: 48
<212> TYPE: DNA
<213> ORGANISM: Mus musculus

<400> SEQUENCE: 25

-continued aggtctagtc aaagcatcgt acacagtgat ggagacacct acttggag        48

<210> SEQ ID NO 26
<211> LENGTH: 21
<212> TYPE: DNA
<213> ORGANISM: Mus musculus

<400> SEQUENCE: 26
aaggtttcta accggttctc t        21

<210> SEQ ID NO 27
<211> LENGTH: 27
<212> TYPE: DNA
<213> ORGANISM: Mus musculus

<400> SEQUENCE: 27
ttccaaggta gccacgtgcc gtacact        27

<210> SEQ ID NO 28
<211> LENGTH: 114
<212> TYPE: PRT
<213> ORGANISM: Mus musculus

<400> SEQUENCE: 28

Glu Val Gln Leu Gln Gln Ser Gly Ala Glu Leu Val Lys Pro Gly Ala
1               5                   10                  15

Ser Val Gln Leu Ser Cys Thr Ala Ser Gly Phe Asn Ile Lys Asp Tyr
            20                  25                  30

Tyr Ile His Trp Val Gln Gln Arg Thr Glu Gln Gly Leu Glu Trp Ile
        35                  40                  45

Gly Arg Ile Asp Pro Glu Asp Gly Glu Ile Glu Tyr Ala Pro Lys Phe
    50                  55                  60

Gln Asp Lys Ala Thr Ile Thr Ala Asp Thr Ser Ser Asn Thr Ala Tyr
65                  70                  75                  80

Leu Gln Leu Ser Ser Leu Thr Ser Glu Asp Ser Ala Val Tyr Tyr Cys
                85                  90                  95

Thr Arg Gly Tyr Ala Ser Trp Gly Gln Gly Thr Thr Leu Thr Val Ser
            100                 105                 110

Ser Ala

<210> SEQ ID NO 29
<211> LENGTH: 114
<212> TYPE: PRT
<213> ORGANISM: Mus musculus

<400> SEQUENCE: 29

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Phe Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

-continued

Ser His Val Pro Tyr Thr Phe Gly Gly Gly Thr Lys Leu Glu Ile Lys
            100                 105                 110

Arg Ala

<210> SEQ ID NO 30
<211> LENGTH: 342
<212> TYPE: DNA
<213> ORGANISM: Mus musculus

<400> SEQUENCE: 30
gaggtgcagt tgcagcagtc tggggcagag cttgtgaagc caggggcctc agtccagttg      60
tcctgcacag cctctggctt caacattaaa gactactata cactgggt gcaacagagg     120 actgaacagg gcctggagtg gattggaagg attgatcctg aggatggtga aattgaatat     180
gccccgaaat tccaggacaa ggccactata acagcagaca catcctccaa cacagcctac     240
ctgcagctca gcagcctgac atctgaggac tctgccgtct attactgtac tagaggctat     300
gcctcctggg gccaaggcac cactctcaca gtctcctcag cc                         342

<210> SEQ ID NO 31
<211> LENGTH: 30
<212> TYPE: DNA
<213> ORGANISM: Mus musculus

<400> SEQUENCE: 31
ggcttcaaca ttaaagacta ctatatacac                                       30

<210> SEQ ID NO 32
<211> LENGTH: 30
<212> TYPE: DNA
<213> ORGANISM: Mus musculus

<400> SEQUENCE: 32
aggattgatc ctgaggatgg tgaaattgaa                                       30

<210> SEQ ID NO 33
<211> LENGTH: 12
<212> TYPE: DNA
<213> ORGANISM: Mus musculus

<400> SEQUENCE: 33
ggctatgcct cc                                                          12

<210> SEQ ID NO 34
<211> LENGTH: 342
<212> TYPE: DNA
<213> ORGANISM: Mus musculus

<400> SEQUENCE: 34
gacgtgctga tgactcagac cccactctcc ctgcctgtca gtcttggaga tcaagcctcc      60
atctcttgca gatctagtca gacctttgta catagtgatg aaacaccta tttagaatgg     120 tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggwtc acatgttccg     300
tacacgttcg gagggggac caagctggaa ataaaacggg ct                          342

<210> SEQ ID NO 35
<211> LENGTH: 48

```
<212> TYPE: DNA
<213> ORGANISM: Mus musculus

<400> SEQUENCE: 35
agatctagtc agacctttgt acatagtgat ggaaacacct atttagaa              48

<210> SEQ ID NO 36
<211> LENGTH: 21
<212> TYPE: DNA
<213> ORGANISM: Mus musculus

<400> SEQUENCE: 36
aaagtttcca accgattttc t                                           21

<210> SEQ ID NO 37
<211> LENGTH: 27
<212> TYPE: DNA
<213> ORGANISM: Mus musculus

<400> SEQUENCE: 37
tttcaaggwt cacatgttcc gtacacg                                     27

<210> SEQ ID NO 38
<211> LENGTH: 114
<212> TYPE: PRT
<213> ORGANISM: Mus musculus

<400> SEQUENCE: 38
```

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Glu Asp Tyr
            20                  25                  30

Tyr Ile His Trp Val Arg Gln Arg Pro Glu Glu Gly Leu Glu Trp Ile
        35                  40                  45

Gly Arg Ile Asp Pro Glu Asn Gly Asn Thr Ile Tyr Asp Pro Lys Phe
    50                  55                  60

Gln Gly Lys Ala Ser Leu Thr Ala Asp Thr Ser Ser Asn Thr Ala Tyr
65                  70                  75                  80

Leu Gln Leu Ser Ser Leu Thr Ser Glu Asp Thr Ala Val Tyr Phe Cys
                85                  90                  95

Ala Arg Gly Tyr Val Asp Trp Gly Gln Gly Thr Leu Val Thr Val Ser
            100                 105                 110

Ala Ala

```
<210> SEQ ID NO 39
<211> LENGTH: 342
<212> TYPE: DNA
<213> ORGANISM: Mus musculus

<400> SEQUENCE: 39
gaggtacagt tgcagcagtc tggggctgag cttgtgaggc caggggcctt agtcaagttg    60
tcctgcaaag cttctggctt caacattgaa gactactata cactgggt gaggcagagg    120 cctgaagagg gcctggagtg gattggaagg attgatcctg agaatggtaa tactatatat   180
gacccgaagt tccagggcaa ggccagtcta acagcagaca catcctccaa cacagcctac   240
ctgcagctca gcagcctgac atctgaggac actgccgtct atttctgtgc tagagggtat   300
gttgactggg gccaagggac tctggtcact gtctctgcag cc                     342
```

```
<210> SEQ ID NO 40
<211> LENGTH: 30
<212> TYPE: DNA
<213> ORGANISM: Mus musculus

<400> SEQUENCE: 40
ggcttcaaca ttgaagacta ctatatacac                                30

<210> SEQ ID NO 41
<211> LENGTH: 30
<212> TYPE: DNA
<213> ORGANISM: Mus musculus

<400> SEQUENCE: 41
aggattgatc ctgagaatgg taatactata                                30

<210> SEQ ID NO 42
<211> LENGTH: 12
<212> TYPE: DNA
<213> ORGANISM: Mus musculus

<400> SEQUENCE: 42
gggtatgttg ac                                                   12

<210> SEQ ID NO 43
<211> LENGTH: 342
<212> TYPE: DNA
<213> ORGANISM: Mus musculus

<400> SEQUENCE: 43
gacgtgttga tgactcagac cccgctctcc ctgcctgtca gtcttggaga tcaagcctcc   60
atctcttgca gatctagtca gagcattgta catagtgatg gagacaccta tttagaatgg  120
tacctgcaga aaccaggcca gtctcctaag ctcctgatct acaaagtttc caaccgattt  180
tctggggtcc cagacaggtt cagtggcagt ggatcaggga cagatttcac actcaagatc  240
atcagagtgg aggctgagga tctgggactt tatttctgct ttcaaggwtc acatgttccg  300
tacacgttcg gagggggggac caagctggaa ataaaacggg ct                    342

<210> SEQ ID NO 44
<211> LENGTH: 48
<212> TYPE: DNA
<213> ORGANISM: Mus musculus

<400> SEQUENCE: 44
agatctagtc agagcattgt acatagtgat ggagacacct atttagaa              48

<210> SEQ ID NO 45
<211> LENGTH: 21
<212> TYPE: DNA
<213> ORGANISM: Mus musculus

<400> SEQUENCE: 45
aaagtttcca accgattttc t                                          21

<210> SEQ ID NO 46
<211> LENGTH: 27
<212> TYPE: DNA
<213> ORGANISM: Mus musculus

<400> SEQUENCE: 46
tttcaaggwt cacatgttcc gtacacg                                    27
```

```
<210> SEQ ID NO 47
<211> LENGTH: 114
<212> TYPE: PRT
<213> ORGANISM: Mus musculus

<400> SEQUENCE: 47

Glu Ile Gln Leu Gln Gln Ser Glu Ala Glu Leu Val Lys Pro Gly Ala
1               5                   10                  15

Ser Val Arg Leu Ser Cys Ala Thr Ser Gly Phe Asn Ile Lys Asp Tyr
            20                  25                  30

Tyr Ile His Trp Val Lys Gln Thr Thr Glu Gln Gly Leu Glu Trp Ile
        35                  40                  45

Gly Arg Ile Asp Pro Glu Asp Gly Glu Thr Glu Tyr Ala Pro Lys Phe
    50                  55                  60

Gln Gly Lys Ala Thr Ile Ala Ala Asp Thr Ser Ser Asn Thr Ala Tyr
65                  70                  75                  80

Leu Leu Leu Asn Ser Leu Ser Ser Glu Asp Thr Ala Val Tyr Tyr Cys
                85                  90                  95

Thr Arg Gly Tyr Ala Ser Trp Gly Gln Gly Thr Thr Leu Thr Val Ser
            100                 105                 110

Ser Ala

<210> SEQ ID NO 48
<211> LENGTH: 114
<212> TYPE: PRT
<213> ORGANISM: Mus musculus

<400> SEQUENCE: 48

Asp Val Leu Met Thr Gln Thr Pro Leu Ser Leu Ser Val Ser Leu Gly
1               5                   10                  15

Asp Gln Ala Ser Ile Ser Cys Arg Ser Ser Gln Ser Phe Val His Ser
            20                  25                  30

Asp Gly Asn Thr Tyr Leu Glu Trp Tyr Leu Gln Lys Ser Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Ala

<210> SEQ ID NO 49
<211> LENGTH: 342
<212> TYPE: DNA
<213> ORGANISM: Mus musculus

<400> SEQUENCE: 49
gaaattcagt tgcagcagtc tgaggcagag cttgtgaagc caggggcctc agtcaggttg      60
tcctgcgcta cttctggctt caacattaaa gactactata cactgggt gaagcagacg       120 actgaacagg gcctggagtg gattggaagg attgatcctg aggatggtga aactgagtat     180
gccccgaaat tccagggcaa ggccactata gcagcagaca catcttccaa tacagcctac     240
cttctactca acagcctgtc atctgaggac actgccgtct attactgtac tagaggctat     300
```

```
gcctcctggg gccaaggcac cactctcaca gtctcctcag cc                    342

<210> SEQ ID NO 50
<211> LENGTH: 30
<212> TYPE: DNA
<213> ORGANISM: Mus musculus

<400> SEQUENCE: 50
ggcttcaaca ttaaagacta ctatatacac                                  30

<210> SEQ ID NO 51
<211> LENGTH: 30
<212> TYPE: DNA
<213> ORGANISM: Mus musculus

<400> SEQUENCE: 51
aggattgatc ctgaggatgg tgaaactgag                                  30

<210> SEQ ID NO 52
<211> LENGTH: 12
<212> TYPE: DNA
<213> ORGANISM: Mus musculus

<400> SEQUENCE: 52
ggctatgcct cc                                                     12

<210> SEQ ID NO 53
<211> LENGTH: 342
<212> TYPE: DNA
<213> ORGANISM: Mus musculus

<400> SEQUENCE: 53
gacgtactga tgacccagac tccactctcc ctgtctgtca gtcttggaga tcaagcctcc  60
atctcttgta gatctagtca gagttttgta catagtgatg gaaacaccta tttagaatgg  120
tacctgcaga aatcaggcca gtctccaaag ctcctgatct acaaagtttc caaccgattt  180
tctggggtcc cagacaggtt cagtggcagt ggatcaggga cagatttcac actcaagatc  240
aacagagtgg aggctgagga tctgggagtt tattactgct ttcaaggttc acatgttccg  300
tacacgttcg gaggggggac caagttggaa ataaaacggg ct                    342

<210> SEQ ID NO 54
<211> LENGTH: 48
<212> TYPE: DNA
<213> ORGANISM: Mus musculus

<400> SEQUENCE: 54
agatctagtc agagttttgt acatagtgat ggaaacacct atttagaa              48

<210> SEQ ID NO 55
<211> LENGTH: 21
<212> TYPE: DNA
<213> ORGANISM: Mus musculus

<400> SEQUENCE: 55
aaagtttcca accgattttc t                                           21

<210> SEQ ID NO 56
<211> LENGTH: 27
<212> TYPE: DNA
<213> ORGANISM: Mus musculus
```

<400> SEQUENCE: 56
tttcaaggtt cacatgttcc gtacacg                                27

<210> SEQ ID NO 57
<211> LENGTH: 339
<212> TYPE: DNA
<213> ORGANISM: Homo sapiens

<400> SEQUENCE: 57
gaaattcagt tgcagcagtc cgaggcagag cttgtgaagc caggggcctc agtcaggttg    60
tcctgcgcta cttctggctt caacattaaa gactactata tacactgggt gaagcagacg   120
actgaacagg gcctggagtg gattggaagg attgatcctg aggatggtga aactgagtat   180
gccccgaaat tccagggcaa ggccactata gcagcagaca catcttccaa tacagcctac   240
cttctactca acagcctgtc atctgaggac actgccgtct attactgtac tagaggctat   300
gcctcctggg gccaaggcac cactctcaca gtctcctca                          339

<210> SEQ ID NO 58
<211> LENGTH: 30
<212> TYPE: DNA
<213> ORGANISM: Homo sapiens

<400> SEQUENCE: 58
ggcttcaaca ttaaagacta ctatatacac                                    30

<210> SEQ ID NO 59
<211> LENGTH: 30
<212> TYPE: DNA
<213> ORGANISM: Homo sapiens

<400> SEQUENCE: 59
aggattgatc ctgaggatgg tgaaactgag                                    30

<210> SEQ ID NO 60
<211> LENGTH: 12
<212> TYPE: DNA
<213> ORGANISM: Homo sapiens

<400> SEQUENCE: 60
ggctatgcct cc                                                       12

<210> SEQ ID NO 61
<211> LENGTH: 342
<212> TYPE: DNA
<213> ORGANISM: Homo sapiens

<400> SEQUENCE: 61
gacgtactga tgactcagac tccgctctcc ctgtctgtca gtcttggaga tcaagcctcc    60
atctcttgta gatctagtca gagttttgta catagtgatg aaacaccta tttagaatgg   120 tacctgcaga aatcaggcca gtctccaaag ctcctgatct acaaagtttc caaccgattt   180
tctggggtcc cagacaggtt cagtggcagt ggatcaggga cagatttcac actcaagatc   240
aacagagtgg aggctgagga tctgggagtt tattactgct ttcaaggwtc acatgttccg   300
tacacgttcg gagggggggac caagttggaa ataaaacggg ct                     342

<210> SEQ ID NO 62
<211> LENGTH: 48
<212> TYPE: DNA
<213> ORGANISM: Homo sapiens

<400> SEQUENCE: 62
agatctagtc agagttttgt acatagtgat ggaaacacct atttagaa  48

<210> SEQ ID NO 63
<211> LENGTH: 21
<212> TYPE: DNA
<213> ORGANISM: Homo sapiens

<400> SEQUENCE: 63
aaagtttcca accgattttc t  21

<210> SEQ ID NO 64
<211> LENGTH: 27
<212> TYPE: DNA
<213> ORGANISM: Homo sapiens

<400> SEQUENCE: 64
tttcaaggwt cacatgttcc gtacacg  27

<210> SEQ ID NO 65
<211> LENGTH: 113
<212> TYPE: PRT
<213> ORGANISM: Homo sapiens

<400> SEQUENCE: 65

Glu Ile Gln Leu Gln Gln Ser Glu Ala Glu Leu Val Lys Pro Gly Ala
1               5                   10                  15

Ser Val Arg Leu Ser Cys Ala Thr Ser Gly Phe Asn Ile Lys Asp Tyr
            20                  25                  30

Tyr Ile His Trp Val Lys Gln Thr Thr Glu Gln Gly Leu Glu Trp Ile
        35                  40                  45

Gly Arg Ile Asp Pro Glu Asp Gly Glu Thr Glu Tyr Ala Pro Lys Phe
    50                  55                  60

Gln Gly Lys Ala Thr Ile Ala Ala Asp Thr Ser Ser Asn Thr Ala Tyr
65                  70                  75                  80

Leu Leu Leu Asn Ser Leu Ser Ser Glu Asp Thr Ala Val Tyr Tyr Cys
                85                  90                  95

Thr Arg Gly Tyr Ala Ser Trp Gly Gln Gly Thr Thr Leu Thr Val Ser
            100                 105                 110

Ser

<210> SEQ ID NO 66
<211> LENGTH: 339
<212> TYPE: DNA
<213> ORGANISM: Homo sapiens

<400> SEQUENCE: 66
gaaattcagt tgcagcagtc cgaggcagag cttgtgaagc caggggcctc agtcaggttg  60
tcctgcgcta cttctggctt caacattaaa gactactata cactgggt gaagcagacg  120 actgaacagg gcctggagtg gattggaagg attgatcctg aggatggtga aactgagtat  180
gccccgaaat tccagggyaa ggccactata gcagcagaca catcttccaa tacagcctac  240
cttctactca acagcctgtc atctgaggac actgccgtct attactgtac tagaggctat  300
gcctcctggg gccaaggcac cactctcaca gtctcctca  339

<210> SEQ ID NO 67
<211> LENGTH: 30

```
<212> TYPE: DNA
<213> ORGANISM: Homo sapiens

<400> SEQUENCE: 67
ggcttcaaca ttaaagacta ctatatacac                                    30

<210> SEQ ID NO 68
<211> LENGTH: 30
<212> TYPE: DNA
<213> ORGANISM: Homo sapiens

<400> SEQUENCE: 68
aggattgatc ctgaggatgg tgaaactgag                                    30

<210> SEQ ID NO 69
<211> LENGTH: 12
<212> TYPE: DNA
<213> ORGANISM: Homo sapiens

<400> SEQUENCE: 69
ggctatgcct cc                                                       12

<210> SEQ ID NO 70
<211> LENGTH: 342
<212> TYPE: DNA
<213> ORGANISM: Homo sapiens

<400> SEQUENCE: 70
gacgttttga tgacccagac tccactctcc ctgtctgtca gtcttggaga tcaagcctcc   60
atctcttgta gatctagtca gagttttgta catagtgatg gaaacaccta tttagaatgg  120
tacctgcaga aatcaggcca gtctccaaag ctcctgatct acaaagtttc caaccgattt  180
tctggggtcc cagacaggtt cagtggcagt ggatcaggga cagatttcac actcaagatc  240
aacagagtgg aggctgagga tctgggagtt tattactgct ttcaaggttc acatgttccg  300
tacacgttcg gaggggggac caagttggaa ataaaacggg ct                     342

<210> SEQ ID NO 71
<211> LENGTH: 48
<212> TYPE: DNA
<213> ORGANISM: Homo sapiens

<400> SEQUENCE: 71
agatctagtc agagttttgt acatagtgat ggaaacacct atttagaa               48

<210> SEQ ID NO 72
<211> LENGTH: 21
<212> TYPE: DNA
<213> ORGANISM: Homo sapiens

<400> SEQUENCE: 72
aaagtttcca accgattttc t                                             21

<210> SEQ ID NO 73
<211> LENGTH: 27
<212> TYPE: DNA
<213> ORGANISM: Homo sapiens

<400> SEQUENCE: 73
tttcaaggtt cacatgttcc gtacacg                                       27

<210> SEQ ID NO 74
```

<211> LENGTH: 113
<212> TYPE: PRT
<213> ORGANISM: Homo sapiens

<400> SEQUENCE: 74

Glu Ile Gln Leu Gln Gln Ser Glu Ala Glu Leu Val Arg Pro Gly Ala
1               5                   10                  15

Leu Val Lys Leu Ser Cys Lys Thr Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Arg Ile Asp Pro Glu Asn Asp Asn Ser Ile Tyr Asp Pro Asn Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Val Arg Gly Tyr Val Asp Trp Gly Gln Gly Thr Leu Val Thr Val Ser
            100                 105                 110

Ala

<210> SEQ ID NO 75
<211> LENGTH: 114
<212> TYPE: PRT
<213> ORGANISM: Homo sapiens

<400> SEQUENCE: 75

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asp Gly Asp Thr Tyr Leu Glu Trp Tyr Leu Gln Lys Pro Gly Gln Ser
        35                  40                  45

Pro Lys Leu Leu Ile Phe Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Ala

<210> SEQ ID NO 76
<211> LENGTH: 339
<212> TYPE: DNA
<213> ORGANISM: Homo sapiens

<400> SEQUENCE: 76
gagatccagt tgcagcagtc tgaggctgag cttgtgaggc caggggcctt agtcaagttg      60
tcctgcaaaa cttctggctt caacattaaa gactactata tgcactgggt gaagcagagg     120
cctgaacagg gcctggagtg gataggacgg attgatcctg agaatgataa tagtatatat     180
gacccgaact tccagggcaa ggccagtata acagcagaca catcctccaa cacagcctat     240
ctgcagctca gcagcctgac atctgaggac actgccgtct attattgtgt tagagggtat     300
gttgactggg gccaagggac tctggtcact gtctctgca                            339

<210> SEQ ID NO 77
<211> LENGTH: 30
<212> TYPE: DNA
<213> ORGANISM: Homo sapiens

<400> SEQUENCE: 77
ggcttcaaca ttaaagacta ctatatgcac                              30

<210> SEQ ID NO 78
<211> LENGTH: 30
<212> TYPE: DNA
<213> ORGANISM: Homo sapiens

<400> SEQUENCE: 78
cggattgatc ctgagaatga taatagtata                              30

<210> SEQ ID NO 79
<211> LENGTH: 12
<212> TYPE: DNA
<213> ORGANISM: Homo sapiens

<400> SEQUENCE: 79
gggtatgttg ac                                                 12

<210> SEQ ID NO 80
<211> LENGTH: 342
<212> TYPE: DNA
<213> ORGANISM: Homo sapiens

<400> SEQUENCE: 80
gatgttctga tgacccagac tccactctcc ctgcctgtca gtcttggaga tcaagcctcc    60
atctcttgca gatctagtca gagcattgta catagtgatg gagacaccta tttagaatgg   120
tacctgcaga aaccaggcca gtctccaaaa ctcctgatct tcaaagtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatgttccg   300
tacacgttcg agggggggac taagctggaa ataaaacggg ct                     342

<210> SEQ ID NO 81
<211> LENGTH: 48
<212> TYPE: DNA
<213> ORGANISM: Homo sapiens

<400> SEQUENCE: 81
agatctagtc agagcattgt acatagtgat ggagacacct atttagaa             48

<210> SEQ ID NO 82
<211> LENGTH: 21
<212> TYPE: DNA
<213> ORGANISM: Homo sapiens

<400> SEQUENCE: 82
aaagtttcca accgattttc g                                        21

<210> SEQ ID NO 83
<211> LENGTH: 27
<212> TYPE: DNA
<213> ORGANISM: Homo sapiens

<400> SEQUENCE: 83

-continued tttcaaggtt cacatgttcc gtacacg                    27

<210> SEQ ID NO 84
<211> LENGTH: 117
<212> TYPE: PRT
<213> ORGANISM: Homo sapiens

<400> SEQUENCE: 84

Glu Ile Gln Leu Gln Gln Ser Gly Ala Glu Val Met Lys Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Ile Lys Gln Arg Pro Gly His Gly Leu Glu Trp Ile
        35                  40                  45

Gly Glu Ile Leu Pro Gly Ser Glu Ser Thr Lys Tyr Asn Glu Lys Phe
    50                  55                  60

Lys Gly Lys Ala Thr Phe Thr Thr Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Thr Phe Tyr Gly Gly Phe Asp Tyr Trp Gly Gln Gly Thr Thr Leu
            100                 105                 110

Thr Val Ser Ser Ala
        115

<210> SEQ ID NO 85
<211> LENGTH: 10
<212> TYPE: PRT
<213> ORGANISM: Mus musculus

<400> SEQUENCE: 85

Gly Tyr Thr Phe Ser Asn Tyr Trp Ile Glu
1               5                   10

<210> SEQ ID NO 86
<211> LENGTH: 10
<212> TYPE: PRT
<213> ORGANISM: Mus musculus

<400> SEQUENCE: 86

Glu Ile Leu Pro Gly Ser Glu Ser Thr Lys
1               5                   10

<210> SEQ ID NO 87
<211> LENGTH: 7
<212> TYPE: PRT
<213> ORGANISM: Mus musculus

<400> SEQUENCE: 87

Phe Tyr Gly Gly Phe Asp Tyr
1               5

<210> SEQ ID NO 88
<211> LENGTH: 114
<212> TYPE: PRT
<213> ORGANISM: Homo sapiens

<400> SEQUENCE: 88

Asp Val Leu Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser

```
                20                  25                  30
Asp Gly Lys Ile Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Arg Thr Phe Gly Gly Gly Thr Lys Leu Glu Ile Lys
            100                 105                 110

Arg Ala

<210> SEQ ID NO 89
<211> LENGTH: 16
<212> TYPE: PRT
<213> ORGANISM: Mus musculus

<400> SEQUENCE: 89

Lys Ser Ser Gln Ser Leu Leu Tyr Ser Asp Gly Lys Ile Tyr Leu Asn
1               5                   10                  15

<210> SEQ ID NO 90
<211> LENGTH: 7
<212> TYPE: PRT
<213> ORGANISM: Mus musculus

<400> SEQUENCE: 90

Leu Val Ser Lys Leu Asp Ser
1               5

<210> SEQ ID NO 91
<211> LENGTH: 9
<212> TYPE: PRT
<213> ORGANISM: Mus musculus

<400> SEQUENCE: 91

Val Gln Gly Thr His Phe Pro Arg Thr
1               5

<210> SEQ ID NO 92
<211> LENGTH: 351
<212> TYPE: DNA
<213> ORGANISM: Homo sapiens

<400> SEQUENCE: 92
gagatccagt tgcagcagtc tggagctgag gtgatgaagc ctggggcctc agtgaagata      60
tcctgcaagg ctactggcta cacattcagt aactactgga tagagtggat aaaacagagg     120
cctggacatg gccttgagtg gattggagag atttttacctg gaagtgaaag tactaaatat    180
aatgagaagt tcaagggcaa ggccacattt actacagata catcctccaa cacagcgtac     240
atgcaactca gcagcctgac atctgaggac tctgccgtct attactgtgc aaccttctac     300
ggaggttttg actactgggg ccaaggcacc actctcacag tctcctcagc c               351

<210> SEQ ID NO 93
<211> LENGTH: 30
<212> TYPE: DNA
<213> ORGANISM: Homo sapiens

<400> SEQUENCE: 93
```

```
ggctacacat tcagtaacta ctggatagag                                          30

<210> SEQ ID NO 94
<211> LENGTH: 30
<212> TYPE: DNA
<213> ORGANISM: Homo sapiens

<400> SEQUENCE: 94
gagattttac ctggaagtga aagtactaaa                                          30

<210> SEQ ID NO 95
<211> LENGTH: 21
<212> TYPE: DNA
<213> ORGANISM: Homo sapiens

<400> SEQUENCE: 95
ttctacggag gttttgacta c                                                   21

<210> SEQ ID NO 96
<211> LENGTH: 342
<212> TYPE: DNA
<213> ORGANISM: Homo sapiens

<400> SEQUENCE: 96
gacgttctga tgacccagac tccactgact ttgtcggtta ccattggaca accagcctct         60
atctcttgca agtcaagtca gagcctccta tatagtgatg gaaaaatcta tttgaattgg        120
ttattacaga ggccaggcca gtctccaaag cgcctaattt atctggtgtc taaattggac        180
tctggagtcc ctgacaggtt cactggcagt ggatcaggaa cagattttac actgaaaatc        240
agcagagtgg aggctgagga tttgggagtt tattactgcg tgcaaggtac acattttcct        300
cggacgttcg gtggaggcac caagctggaa atcaaacggg ct                           342

<210> SEQ ID NO 97
<211> LENGTH: 48
<212> TYPE: DNA
<213> ORGANISM: Homo sapiens

<400> SEQUENCE: 97
aagtcaagtc agagcctcct atatagtgat ggaaaaatct atttgaat                     48

<210> SEQ ID NO 98
<211> LENGTH: 21
<212> TYPE: DNA
<213> ORGANISM: Homo sapiens

<400> SEQUENCE: 98
ctggtgtcta aattggactc t                                                   21

<210> SEQ ID NO 99
<211> LENGTH: 27
<212> TYPE: DNA
<213> ORGANISM: Homo sapiens

<400> SEQUENCE: 99
gtgcaaggta cacattttcc tcggacg                                             27

<210> SEQ ID NO 100
<211> LENGTH: 113
<212> TYPE: PRT
<213> ORGANISM: Homo sapiens
```

<400> SEQUENCE: 100

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Glu Asp Tyr
            20                  25                  30

Tyr Met His Trp Val Gln Gln Ala Pro Gly Lys Gly Leu Glu Trp Met
        35                  40                  45

Gly Arg Ile Asp Pro Glu Asn Gly Asn Thr Ile Tyr Asp Pro Lys Phe
    50                  55                  60

Gln Gly Arg Val Thr Ile Thr Ala Asp Thr Ser Thr Asp Thr Ala Tyr
65                  70                  75                  80

Met Asp Leu Ser Ser Leu Arg Ser Glu Asp Thr Ala Val Tyr Tyr Cys
                85                  90                  95

Ala Thr Gly Tyr Val Asp Trp Gly Gln Gly Thr Leu Val Thr Val Ser
            100                 105                 110

Ser

<210> SEQ ID NO 101
<211> LENGTH: 114
<212> TYPE: PRT
<213> ORGANISM: Homo sapiens

<400> SEQUENCE: 101

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asp Gly Asp Thr Tyr Leu Glu Trp Phe Gln Gln Arg Pro Gly Gln Ser
        35                  40                  45

Pro Met Ser Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg Thr

<210> SEQ ID NO 102
<211> LENGTH: 339
<212> TYPE: DNA
<213> ORGANISM: Homo sapiens

<400> SEQUENCE: 102
gaggtccagc tggtacagtc tggggctgag gtgaagaagc ctggggctac agtgaaaatc      60
tcctgcaagg tttctggatt caacatcgag gactactaca tgcactgggt gcaacaggcc     120
cctggaaaag gccttgagtg gatgggacgt atcgatcctg aaaatggtaa tacaatctac     180
gacccgaagt tccagggcag agtcaccata accgcggaca cgtctacaga cacagcctac     240
atggacctga gcagcctgag atctgaggac acggccgtgt attactgtgc aacaggatat     300
gtcgactggg gccagggaac cctggtcacc gtctcctca                            339

<210> SEQ ID NO 103
<211> LENGTH: 342

-continued

```
<212> TYPE: DNA
<213> ORGANISM: Homo sapiens

<400> SEQUENCE: 103
gatgtagtaa tgactcagtc tccactctcc ctgcccgtca cccttggaca gccggcctcc      60
atctcctgca ggtctagtca aagcatcgta cacagtgatg agacaccta cttggagtgg     120 tttcagcaga ggccaggcca atctccaatg agcctaattt ataaggtttc taaccggttc    180
tctggggtcc cagacagatt cagcggcagt gggtcaggca ctgacttcac actgaaaatc    240 accaggtgg aggctgagga tgttggggtt tattactgct tccaaggtag ccacgtgccg     300
tacactttcg gcggaggtac caaggtggaa atcaaacgaa ct                       342

<210> SEQ ID NO 104
<211> LENGTH: 113
<212> TYPE: PRT
<213> ORGANISM: Mus musculus

<400> SEQUENCE: 104

Glu Ile Gln Leu Gln Gln Ser Glu Ala Glu Leu Val Lys Pro Gly Ala
1               5                   10                  15

Ser Val Arg Leu Ser Cys Ala Thr Ser Gly Phe Asn Ile Lys Asp Tyr
            20                  25                  30

Tyr Ile His Trp Val Lys Gln Thr Thr Glu Gln Gly Leu Glu Trp Ile
        35                  40                  45

Gly Arg Ile Asp Pro Glu Asp Gly Glu Thr Glu Tyr Ala Pro Lys Phe
    50                  55                  60

Gln Gly Lys Ala Thr Ile Ala Ala Asp Thr Ser Ser Asn Thr Ala Tyr
65                  70                  75                  80

Leu Leu Leu Asn Ser Leu Ser Ser Glu Asp Thr Ala Val Tyr Tyr Cys
                85                  90                  95

Thr Arg Gly Tyr Ala Ser Trp Gly Gln Gly Thr Thr Leu Thr Val Ser
            100                 105                 110

Ser

<210> SEQ ID NO 105
<211> LENGTH: 114
<212> TYPE: PRT
<213> ORGANISM: Mus musculus

<400> SEQUENCE: 105

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asp Gly Asp Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ile Arg Val Glu Ala Glu Asp Leu Gly Leu Tyr Phe Cys Phe Gln Gly
                85                  90                  95

Ser His Val Pro Tyr Thr Phe Gly Gly Gly Thr Lys Leu Glu Ile Lys
            100                 105                 110

Arg Ala
```

```
<210> SEQ ID NO 106
<211> LENGTH: 114
<212> TYPE: PRT
<213> ORGANISM: Mus musculus

<400> SEQUENCE: 106

Asp Val Leu Met Thr Gln Thr Pro Leu Ser Leu Ser Val Ser Leu Gly
1               5                   10                  15

Asp Gln Ala Ser Ile Ser Cys Arg Ser Ser Gln Ser Phe Val His Ser
            20                  25                  30

Asp Gly Asn Thr Tyr Leu Glu Trp Tyr Leu Gln Lys Ser Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Ala

<210> SEQ ID NO 107
<211> LENGTH: 114
<212> TYPE: PRT
<213> ORGANISM: Homo sapiens

<400> SEQUENCE: 107

Asp Val Leu Met Thr Gln Thr Pro Leu Ser Leu Ser Val Ser Leu Gly
1               5                   10                  15

Asp Gln Ala Ser Ile Ser Cys Arg Ser Ser Gln Ser Phe Val His Ser
            20                  25                  30

Asp Gly Asn Thr Tyr Leu Glu Trp Tyr Leu Gln Lys Ser Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg Ala

<210> SEQ ID NO 108
<211> LENGTH: 113
<212> TYPE: PRT
<213> ORGANISM: Homo sapiens

<400> SEQUENCE: 108

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Glu Asp Tyr
            20                  25                  30

Tyr Met His Trp Val Gln Gln Ala Pro Gly Lys Gly Leu Glu Trp Met
        35                  40                  45
```

Gly Arg Ile Asp Pro Glu Asn Gly Asn Thr Ile Tyr Asp Pro Lys Phe
 50                  55                  60

Gln Gly Arg Val Thr Ile Thr Ala Asp Thr Ser Thr Asn Thr Ala Tyr
 65                  70                  75                  80

Leu Asp Leu Ser Ser Leu Arg Ser Glu Asp Thr Ala Val Tyr Tyr Cys
                 85                  90                  95

Ala Arg Gly Tyr Val Asp Trp Gly Gln Gly Thr Leu Val Thr Val Ser
             100                 105                 110

Ser

<210> SEQ ID NO 109
<211> LENGTH: 114
<212> TYPE: PRT
<213> ORGANISM: Homo sapiens

<400> SEQUENCE: 109

Asp Val Val Met Thr Gln Ser Pro Leu Ser Leu Pro Val Thr Leu Gly
 1               5                  10                  15

Gln Pro Ala Ser Ile Ser Cys Arg Ser Ser Gln Ser Ile Val His Ser
             20                  25                  30

Asp Gly Asp Thr Tyr Leu Glu Trp Tyr Leu Gln Arg Pro Gly Gln Ser
         35                  40                  45

Pro Met Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Thr Arg Val Glu Ala Glu Asp Val Gly Val Tyr Tyr Cys Phe Gln Gly
                 85                  90                  95

Ser His Val Pro Tyr Thr Phe Gly Gly Gly Thr Lys Val Glu Ile Lys
             100                 105                 110

Arg Thr

<210> SEQ ID NO 110
<211> LENGTH: 339
<212> TYPE: DNA
<213> ORGANISM: Homo sapiens

<400> SEQUENCE: 110
gaggtccagc tggtacagtc tggggctgag gtgaagaagc ctggggctac agtgaaaatc      60
tcctgcaagg tttctggatt caacatcgag gactactaca tgcactgggt gcaacaggcc     120
cctggaaaag ggctcgagtg gatgggacgt atcgatcctg aaaatggtaa tacaatctac     180
gacccgaagt tccagggcag agtcaccata accgcggaca cgtctacaaa cacagcctac     240
ctggacctga gcagcctgag atctgaggac acggccgtgt attactgtgc aagaggatat     300
gtcgactggg gccagggaac cctggtcacc gtctcctca                            339

<210> SEQ ID NO 111
<211> LENGTH: 342
<212> TYPE: DNA
<213> ORGANISM: Homo sapiens

<400> SEQUENCE: 111
gatgtagtaa tgactcagtc tccactctcc ctgcccgtca cccttggaca gccggcctcc      60
atctcctgca ggtctagtca agcatcgta cacagtgatg gagacaccta cttggagtgg     120
tatctgcaga ggcccgggca atctccaatg ttgctaattt ataaggtttc taaccggttc     180

```
tctggggtcc cagacagatt cagcggcagt gggtcaggca ctgacttcac actgaaaatc    240
accagggtgg aggctgagga tgttggggtt tattactgct tccaaggtag ccacgtgccg    300
tacactttcg gcggaggtac caaggtggaa atcaaacgaa ct                       342
```

<210> SEQ ID NO 112
<211> LENGTH: 113
<212> TYPE: PRT
<213> ORGANISM: Homo sapiens

<400> SEQUENCE: 112

```
Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Glu Asp Tyr
            20                  25                  30

Tyr Met His Trp Val Gln Gln Ala Pro Gly Lys Gly Leu Glu Trp Met
        35                  40                  45

Gly Arg Ile Asp Pro Glu Asn Gly Asn Thr Ile Tyr Asp Pro Lys Phe
    50                  55                  60

Gln Gly Arg Val Thr Ile Thr Ala Asp Thr Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Gly Tyr Val Asp Trp Gly Gln Gly Thr Leu Val Thr Val Ser
            100                 105                 110

Ser
```

<210> SEQ ID NO 113
<211> LENGTH: 114
<212> TYPE: PRT
<213> ORGANISM: Homo sapiens

<400> SEQUENCE: 113

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asp Gly Asp Thr Tyr Leu Glu Trp Tyr Gln Gln Arg Pro Gly Gln Ser
        35                  40                  45

Pro Met Ser Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg Thr
```

<210> SEQ ID NO 114
<211> LENGTH: 339
<212> TYPE: DNA
<213> ORGANISM: Homo sapiens

<400> SEQUENCE: 114

```
gaggtccagc tggtacagtc tggggctgag gtgaagaagc ctggggctac agtgaaaatc     60
tcctgcaagg tttctggatt caacatcgag gactactaca tgcactgggt gcaacaggcc    120
```

```
cctggaaaag ggctcgagtg gatgggacgt atcgatcctg aaaatggtaa tacaatctac    180
gacccgaagt tccagggcag agtcaccata accgcggaca cgtctacaaa cacagcctac    240
atggacctga gcagcctgag atctgaggac acggccgtgt attactgtgc aagaggatat    300
gtcgactggg gccagggaac cctggtcacc gtctcctca                           339
```

```
<210> SEQ ID NO 115
<211> LENGTH: 342
<212> TYPE: DNA
<213> ORGANISM: Homo sapiens

<400> SEQUENCE: 115
```

```
gatgtagtaa tgactcagtc tccactctcc ctgcccgtca cccttggaca gccggcctcc    60
atctcctgca ggtctagtca agcatcgta cacagtgatg agacaccta cttggagtgg     120 tatcagcaga ggcccgggca atctccaatg tcgctaattt ataaggtttc taaccggttc   180
tctggggtcc cagacagatt cagcggcagt gggtcaggca ctgacttcac actgaaaatc   240
accagggtgg aggctgagga tgttggggtt tattactgct tccaaggtag ccacgtgccg   300
tacactttcg gcggaggtac caaggtggaa atcaaacgaa ct                      342
```

```
<210> SEQ ID NO 116
<211> LENGTH: 113
<212> TYPE: PRT
<213> ORGANISM: Homo sapiens

<400> SEQUENCE: 116
```

Glu Val Gln Leu Val Gln Ser Gly Ala Glu Val Lys Lys Pro Gly Ala
1               5                  10                  15

Thr Val Lys Ile Ser Cys Lys Val Ser Gly Phe Asn Ile Glu Asp Tyr
            20                  25                  30

Tyr Met His Trp Val Gln Gln Ala Pro Gly Lys Gly Leu Glu Trp Ile
        35                  40                  45

Gly Arg Ile Asp Pro Glu Asn Gly Asn Thr Ile Tyr Asp Pro Lys Phe
    50                  55                  60

Gln Gly Arg Ala Thr Ile Thr Ala Asp Thr Ser Thr Asn Thr Ala Tyr
65                  70                  75                  80

Leu Asp Leu Ser Ser Leu Arg Ser Glu Asp Thr Ala Val Tyr Tyr Cys
                85                  90                  95

Ala Arg Gly Tyr Val Asp Trp Gly Gln Gly Thr Leu Val Thr Val Ser
            100                 105                 110

Ser

```
<210> SEQ ID NO 117
<211> LENGTH: 114
<212> TYPE: PRT
<213> ORGANISM: Homo sapiens

<400> SEQUENCE: 117
```

Asp Val Val Met Thr Gln Ser Pro Leu Ser Leu Pro Val Thr Leu Gly
1               5                  10                  15

Gln Pro Ala Ser Ile Ser Cys Arg Ser Ser Gln Ser Ile Val His Ser
            20                  25                  30

Asp Gly Asp Thr Tyr Leu Glu Trp Tyr Gln Gln Arg Pro Gly Gln Ser
        35                  40                  45

Pro Met Ser Leu Ile Tyr Lys Val Ser Asn Arg Phe Ser Gly Val Pro
    50                  55                  60

```
Asp Arg Phe Ser Gly Ser Gly Ser Gly Thr Asp Phe Thr Leu Lys Ile
65                  70                  75                  80

Thr Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg Thr
```

<210> SEQ ID NO 118
<211> LENGTH: 339
<212> TYPE: DNA
<213> ORGANISM: Homo sapiens

<400> SEQUENCE: 118

```
gaggtccagc tggtacagtc tggggctgag gtgaagaagc ctggggctac agtgaaaatc    60
tcctgcaagg tttctggatt caacatcgag gactactaca tgcactgggt gcaacaggcc   120
cctggaaaag ggctcgagtg gatcggacgt atcgatcctg aaaatggtaa tacaatctac   180
gacccgaagt tccagggcag agccaccata accgcggaca cgtctacaaa cacagcctac   240
ctggacctga gcagcctgag atctgaggac acggccgtgt attactgtgc aagaggatat   300
gtcgactggg gccagggaac cctggtcacc gtctcctca                          339
```

<210> SEQ ID NO 119
<211> LENGTH: 342
<212> TYPE: DNA
<213> ORGANISM: Homo sapiens

<400> SEQUENCE: 119

```
gatgtagtaa tgactcagtc tccactctcc ctgcccgtca cccttggaca gccggcctcc    60
atctcctgca ggtctagtca aagcatcgta cacagtgatg agacacccta cttggagtgg   120
tatcagcaga ggcccgggca atctccaatg tcgctaattt ataaggtttc taaccggttc   180
tctggggtcc cagacagatt cagcggcagt gggtcaggca ctgacttcac actgaaaatc   240
accagggtgg aggctgagga tgttggggtt tattactgct tccaaggtag ccacgtgccg   300
tacactttcg gcggaggtac caaggtggaa atcaaacgaa ct                      342
```

<210> SEQ ID NO 120
<211> LENGTH: 113
<212> TYPE: PRT
<213> ORGANISM: Homo sapiens

<400> SEQUENCE: 120

```
Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Glu Asp Tyr
                20                  25                  30

Tyr Met His Trp Val Gln Gln Ala Pro Gly Lys Gly Leu Glu Trp Met
            35                  40                  45

Gly Arg Ile Asp Pro Glu Asn Gly Asn Thr Ile Tyr Asp Pro Lys Phe
        50                  55                  60

Gln Gly Arg Val Thr Ile Thr Ala Asp Thr Ser Thr Asn Thr Ala Tyr
65                  70                  75                  80

Leu Asp Leu Ser Ser Leu Arg Ser Glu Asp Thr Ala Val Tyr Tyr Cys
                85                  90                  95

Ala Arg Gly Tyr Val Asp Trp Gly Gln Gly Thr Leu Val Thr Val Ser
```

```
                  100                 105                 110
Ser

<210> SEQ ID NO 121
<211> LENGTH: 114
<212> TYPE: PRT
<213> ORGANISM: Homo sapiens

<400> SEQUENCE: 121

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asp Gly Asp Thr Tyr Leu Glu Trp Tyr Gln Gln Arg Pro Gly Gln Ser
        35                  40                  45

Pro Met Ser Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg Thr

<210> SEQ ID NO 122
<211> LENGTH: 339
<212> TYPE: DNA
<213> ORGANISM: Homo sapiens

<400> SEQUENCE: 122
gaggtccagc tggtacagtc tggggctgag gtgaagaagc tggggctac agtgaaaatc      60 tcctgcaagg tttctggatt caacatcgag gactactaca tgcactgggt gcaacaggcc   120
cctggaaaag ggctcgagtg gatgggacgt atcgatcctg aaaatggtaa tacaatctac   180
gacccgaagt tccagggcag agtcaccata accgcggaca cgtctacaaa cacagcctac   240
ctggacctga gcagcctgag atctgaggac acggccgtgt attactgtgc aagaggatat   300
gtcgactggg gccagggaac cctggtcacc gtctcctca                           339

<210> SEQ ID NO 123
<211> LENGTH: 342
<212> TYPE: DNA
<213> ORGANISM: Homo sapiens

<400> SEQUENCE: 123
gatgtagtaa tgactcagtc tccactctcc ctgcccgtca cccttggaca gccggcctcc      60
atctcctgca ggtctagtca agcatcgta cacagtgatg gagacaccta cttggagtgg    120
tatcagcaga ggcccgggca atctccaatg tcgctaattt ataaggtttc taaccggttc    180
tctggggtcc cagacagatt cagcggcagt gggtcaggca ctgacttcac actgaaaatc    240
accagggtgg aggctgagga tgttggggtt tattactgct tccaaggtag ccacgtgccg    300
tacactttcg gcggaggtac caaggtggaa atcaaacgaa ct                       342

<210> SEQ ID NO 124
<211> LENGTH: 113
<212> TYPE: PRT
```

```
<213> ORGANISM: Homo sapiens

<400> SEQUENCE: 124

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Glu Asp Tyr
            20                  25                  30

Tyr Met His Trp Val Gln Ala Pro Gly Lys Gly Leu Glu Trp Met
        35                  40                  45

Gly Arg Ile Asp Pro Glu Asn Gly Asn Thr Ile Tyr Asp Pro Lys Phe
50                  55                  60

Gln Gly Arg Ala Thr Ile Thr Ala Asp Thr Ser Thr Asp Thr Ala Tyr
65                  70                  75                  80

Leu Asp Leu Ser Ser Leu Arg Ser Glu Asp Thr Ala Val Tyr Tyr Cys
                85                  90                  95

Ala Arg Gly Tyr Val Asp Trp Gly Gln Gly Thr Leu Val Thr Val Ser
            100                 105                 110

Ser

<210> SEQ ID NO 125
<211> LENGTH: 114
<212> TYPE: PRT
<213> ORGANISM: Homo sapiens

<400> SEQUENCE: 125

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asp Gly Asp Thr Tyr Leu Glu Trp Tyr Gln Gln Arg Pro Gly Gln Ser
        35                  40                  45

Pro Met Ser Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Thr Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg Thr

<210> SEQ ID NO 126
<211> LENGTH: 339
<212> TYPE: DNA
<213> ORGANISM: Homo sapiens

<400> SEQUENCE: 126
gaggtccagc tggtacagtc tggggctgag gtgaagaagc ctggggctac agtgaaaatc     60
tcctgcaagg tttctggatt caacatcgag gactactaca tgcactgggt gcaacaggcc    120
cctggaaaag gctcgagtg atgggacgt atcgatcctg aaaatggtaa tacaatctac       180
gacccgaagt tccagggcag agccaccata accgcggaca cgtctacaga cacagcctac    240
ctggacctga gcagcctgag atctgaggac acggccgtgt attactgtgc aagaggatat    300
gtcgactggg gccagggaac cctggtcacc gtctcctca                            339
```

<210> SEQ ID NO 127
<211> LENGTH: 342
<212> TYPE: DNA
<213> ORGANISM: Homo sapiens

<400> SEQUENCE: 127

```
gatgtagtaa tgactcagtc tccactctcc ctgcccgtca cccttggaca gccggcctcc      60
atctcctgca ggtctagtca aagcatcgta cacagtgatg agacaccta cttggagtgg     120 tatcagcaga ggcccgggca atctccaatg tcgctaattt ataaggtttc taaccggttc     180
tctggggtcc cagacagatt cagcggcagt gggtcaggca ctgacttcac actgaaaatc     240
accagggtgg aggctgagga tgttggggtt tattactgct tccaaggtag ccacgtgccg     300
tacactttcg gcggaggtac caaggtggaa atcaaacgaa ct                       342
```

<210> SEQ ID NO 128
<211> LENGTH: 113
<212> TYPE: PRT
<213> ORGANISM: Homo sapiens

<400> SEQUENCE: 128

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Glu Asp Tyr
            20                  25                  30

Tyr Met His Trp Val Gln Gln Ala Pro Gly Lys Gly Leu Glu Trp Ile
        35                  40                  45

Gly Arg Ile Asp Pro Glu Asn Gly Asn Thr Ile Tyr Asp Pro Lys Phe
    50                  55                  60

Gln Gly Arg Val Thr Ile Thr Ala Asp Thr Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Gly Tyr Val Asp Trp Gly Gln Gly Thr Leu Val Thr Val Ser
            100                 105                 110

Ser

<210> SEQ ID NO 129
<211> LENGTH: 114
<212> TYPE: PRT
<213> ORGANISM: Homo sapiens

<400> SEQUENCE: 129

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asp Gly Asp Thr Tyr Leu Glu Trp Tyr Gln Gln Arg Pro Gly Gln Ser
        35                  40                  45

Pro Met Ser Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

-continued

Arg Thr

<210> SEQ ID NO 130
<211> LENGTH: 339
<212> TYPE: DNA
<213> ORGANISM: Homo sapiens

<400> SEQUENCE: 130

```
gaggtccagc tggtacagtc tggggctgag gtgaagaagc ctggggctac agtgaaaatc      60
tcctgcaagg tttctggatt caacatcgag gactactaca tgcactgggt gcaacaggcc     120
cctggaaaag gctcgagtg gatcggacgt atcgatcctg aaaatggtaa tacaatctac     180
gacccgaagt tccagggcag agtcaccata accgcggaca cgtctacaaa cacagcctac     240
atggacctga gcagcctgag atctgaggac acggccgtgt attactgtgc aagaggatat     300
gtcgactggg gccagggaac cctggtcacc gtctcctca                            339
```

<210> SEQ ID NO 131
<211> LENGTH: 342
<212> TYPE: DNA
<213> ORGANISM: Homo sapiens

<400> SEQUENCE: 131

```
gatgtagtaa tgactcagtc tccactctcc ctgcccgtca cccttggaca gccggcctcc      60
atctcctgca ggtctagtca agcatcgta cacagtgatg agacaccta cttggggtgg     120
tatcagcaga ggcccgggca atctccaatg tcgctaattt ataaggtttc taaccggttc     180
tctggggtcc cagacagatt cagcggcagt gggtcaggca ctgacttcac actgaaaatc     240
accagggtgg aggctgagga tgttgggggtt tattactgct tccaaggtag ccacgtgccg     300
tacactttcg gcggaggtac caaggtggaa atcaaacgaa ct                        342
```

<210> SEQ ID NO 132
<211> LENGTH: 113
<212> TYPE: PRT
<213> ORGANISM: Homo sapiens

<400> SEQUENCE: 132

```
Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Glu Asp Tyr
            20                  25                  30

Tyr Met His Trp Val Gln Gln Ala Pro Gly Lys Gly Leu Glu Trp Ile
        35                  40                  45

Gly Arg Ile Asp Pro Glu Asn Gly Asn Thr Ile Tyr Asp Pro Lys Phe
    50                  55                  60

Gln Gly Arg Ala Thr Ile Thr Ala Asp Thr Ser Thr Asn Thr Ala Tyr
65                  70                  75                  80

Leu Asp Leu Ser Ser Leu Arg Ser Glu Asp Thr Ala Val Tyr Tyr Cys
                85                  90                  95

Ala Arg Gly Tyr Val Asp Trp Gly Gln Gly Thr Leu Val Thr Val Ser
            100                 105                 110

Ser
```

<210> SEQ ID NO 133
<211> LENGTH: 114
<212> TYPE: PRT
<213> ORGANISM: Homo sapiens

<400> SEQUENCE: 133

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asp Gly Asp Thr Tyr Leu Glu Trp Tyr Gln Gln Arg Pro Gly Gln Ser
        35                  40                  45

Pro Met Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg Thr

<210> SEQ ID NO 134
<211> LENGTH: 339
<212> TYPE: DNA
<213> ORGANISM: Homo sapiens

<400> SEQUENCE: 134
gaggtccagc tggtacagtc tggggctgag gtgaagaagc ctggggctac agtgaaaatc      60
tcctgcaagg tttctggatt caacatcgag gactactaca tgcactgggt gcaacaggcc    120
cctggaaaag ggctcgagtg gatcggacgt atcgatcctg aaaatggtaa tacaatctac    180
gacccgaagt tccagggcag agccaccata accgcgaca cgtctacaaa cacagcctac     240
ctggacctga gcagcctgag atctgaggac acggccgtgt attactgtgc aagaggatat    300
gtcgactggg gccagggaac cctggtcacc gtctcctca                            339

<210> SEQ ID NO 135
<211> LENGTH: 342
<212> TYPE: DNA
<213> ORGANISM: Homo sapiens

<400> SEQUENCE: 135
gatgtagtaa tgactcagtc tccactctcc ctgcccgtca cccttggaca gccggcctcc      60
atctcctgca ggtctagtca aagcatcgta cacagtgatg agacaccta cttggagtgg     120 tatcagcaga ggcccgggca atctccaatg ttgctaattt ataaggtttc taaccggttc    180
tctggggtcc cagacagatt cagcggcagt gggtcaggca ctgacttcac actgaaaatc    240
accagggtgg aggctaagga tgttggggtt tattactgct tccaaggtag ccacgtgccg    300
tacactttcg gcggaggtac caaggtggaa atcaaacgaa ct                        342

<210> SEQ ID NO 136
<211> LENGTH: 113
<212> TYPE: PRT
<213> ORGANISM: Homo sapiens

<400> SEQUENCE: 136

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Glu Asp Tyr
            20                  25                  30

```
Tyr Met His Trp Val Gln Gln Ala Pro Gly Lys Gly Leu Glu Trp Met
            35                  40                  45

Gly Arg Ile Asp Pro Glu Asn Gly Asn Thr Ile Tyr Asp Pro Lys Phe
        50                  55                  60

Gln Gly Arg Val Thr Ile Thr Ala Asp Thr Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Gly Tyr Val Asp Trp Gly Gln Gly Thr Leu Val Thr Val Ser
            100                 105                 110

Ser

<210> SEQ ID NO 137
<211> LENGTH: 114
<212> TYPE: PRT
<213> ORGANISM: Homo sapiens

<400> SEQUENCE: 137

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asp Gly Asp Thr Tyr Leu Glu Trp Tyr Gln Gln Arg Pro Gly Gln Ser
        35                  40                  45

Pro Met Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg Thr

<210> SEQ ID NO 138
<211> LENGTH: 113
<212> TYPE: PRT
<213> ORGANISM: Homo sapiens

<400> SEQUENCE: 138

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Glu Asp Tyr
            20                  25                  30

Tyr Met His Trp Val Gln Gln Ala Pro Gly Lys Gly Leu Glu Trp Met
        35                  40                  45

Gly Arg Ile Asp Pro Glu Asn Gly Asn Thr Ile Tyr Asp Pro Lys Phe
    50                  55                  60

Gln Gly Arg Ala Thr Ile Thr Ala Asp Thr Ser Thr Asp Thr Ala Tyr
65                  70                  75                  80

Leu Asp Leu Ser Ser Leu Arg Ser Glu Asp Thr Ala Val Tyr Tyr Cys
                85                  90                  95

Ala Arg Gly Tyr Val Asp Trp Gly Gln Gly Thr Leu Val Thr Val Ser
            100                 105                 110

Ser
```

```
<210> SEQ ID NO 139
<211> LENGTH: 114
<212> TYPE: PRT
<213> ORGANISM: Homo sapiens

<400> SEQUENCE: 139

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asp Gly Asp Thr Tyr Leu Glu Trp Tyr Leu Gln Arg Pro Gly Gln Ser
        35                  40                  45

Pro Met Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Thr Arg Val Glu Ala Glu Asp Val Gly Val Tyr Tyr Cys Phe Gln Gly
                85                  90                  95

Ser His Val Pro Tyr Thr Phe Gly Gly Gly Thr Lys Val Glu Ile Lys
            100                 105                 110

Arg Thr

<210> SEQ ID NO 140
<211> LENGTH: 113
<212> TYPE: PRT
<213> ORGANISM: Homo sapiens

<400> SEQUENCE: 140

Glu Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Glu Asp Tyr
            20                  25                  30

Tyr Met His Trp Val Gln Gln Ala Pro Gly Lys Gly Leu Glu Trp Ile
        35                  40                  45

Gly Arg Ile Asp Pro Glu Asn Gly Asn Thr Ile Tyr Asp Pro Lys Phe
    50                  55                  60

Gln Gly Arg Val Thr Ile Thr Ala Asp Thr Ser Thr Asn Thr Ala Tyr
65                  70                  75                  80

Met Asp Leu Ser Ser Leu Arg Ser Glu Asp Thr Ala Val Tyr Tyr Cys
                85                  90                  95

Ala Arg Gly Tyr Val Asp Trp Gly Gln Gly Thr Leu Val Thr Val Ser
            100                 105                 110

Ser

<210> SEQ ID NO 141
<211> LENGTH: 114
<212> TYPE: PRT
<213> ORGANISM: Homo sapiens

<400> SEQUENCE: 141

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asp Gly Asp Thr Tyr Leu Glu Trp Tyr Gln Gln Arg Pro Gly Gln Ser
        35                  40                  45
```

```
Pro Met Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Thr Arg Val Glu Ala Glu Asp Val Gly Val Tyr Tyr Cys Phe Gln Gly
                85                  90                  95
Ser His Val Pro Tyr Thr Phe Gly Gly Gly Thr Lys Val Glu Ile Lys
            100                 105                 110
Arg Thr
```

<210> SEQ ID NO 142
<211> LENGTH: 339
<212> TYPE: DNA
<213> ORGANISM: Homo sapiens

<400> SEQUENCE: 142

| | | | | | |
|---|---|---|---|---|---|
| gaagttcagt | tgcagcagtc | tggggctgag | cttgtgaggc | caggggcctt | agtcaagttg | 60 |
| tcctgcaaag | cttctggctt | caacattgaa | gactactata | tgcactgggt | gaggcagagg | 120 |
| cctgaagagg | gcctggagtg | gattggaagg | attgatcctg | agaatggtaa | tactatatat | 180 |
| gacccgaagt | tccagggcaa | ggccagtata | acagcagaca | catcctccaa | cacagcctac | 240 |
| ctgcagctca | gcagcctgac | atctgaggac | actgccgtct | attactgtgt | tagagggtat | 300 |
| gttgactggg | gccaagggac | tctggtcact | gtctctgca | | | 339 |

<210> SEQ ID NO 143
<211> LENGTH: 30
<212> TYPE: DNA
<213> ORGANISM: Homo sapiens

<400> SEQUENCE: 143
ggcttcaaca ttgaagacta ctatatgcac                                     30

<210> SEQ ID NO 144
<211> LENGTH: 30
<212> TYPE: DNA
<213> ORGANISM: Homo sapiens

<400> SEQUENCE: 144
aggattgatc ctgagaatgg taatactata                                     30

<210> SEQ ID NO 145
<211> LENGTH: 12
<212> TYPE: DNA
<213> ORGANISM: Homo sapiens

<400> SEQUENCE: 145
gggtatgttg ac                                                        12

<210> SEQ ID NO 146
<211> LENGTH: 342
<212> TYPE: DNA
<213> ORGANISM: Homo sapiens

<400> SEQUENCE: 146

| | | | | | |
|---|---|---|---|---|---|
| gatgttttga | tgacccagac | tccactctcc | ctgcctgtca | gtcttggaga | tcaagcctcc | 60 |
| atctcttgca | gatctagtca | gagcattgta | catagtgatg | gagacaccta | tttagaatgg | 120 |
| tacctgcaga | aagcaggcca | gtctcctaag | ctcctgatct | acaaagtttc | caaccgattt | 180 |
| tctggggtcc | cagacaggtt | cagtggcagt | ggatcaggga | cagatttcac | actcaagatc | 240 |

-continued

```
agcagagtgg aggctgagga tctgggactt tattactgct ttcaaggttc acatgttccg      300
tacacgttcg gagggggac caagctggaa ataaaacggg ct                          342

<210> SEQ ID NO 147
<211> LENGTH: 48
<212> TYPE: DNA
<213> ORGANISM: Homo sapiens

<400> SEQUENCE: 147
agatctagtc agagcattgt acatagtgat ggagacacct atttagaa                    48

<210> SEQ ID NO 148
<211> LENGTH: 21
<212> TYPE: DNA
<213> ORGANISM: Homo sapiens

<400> SEQUENCE: 148
aaagtttcca accgattttc t                                                 21

<210> SEQ ID NO 149
<211> LENGTH: 27
<212> TYPE: DNA
<213> ORGANISM: Homo sapiens

<400> SEQUENCE: 149
tttcaaggtt cacatgttcc gtacacg                                           27
```